(12) United States Patent
Stintzi et al.

(10) Patent No.: US 10,023,918 B2
(45) Date of Patent: Jul. 17, 2018

(54) METHODS FOR THE DIAGNOSIS AND TREATMENT OF INFLAMMATORY BOWEL DISEASE

(71) Applicant: UNIVERSITY OF OTTAWA, Ottawa (CA)

(72) Inventors: Alain Stintzi, Ottawa (CA); David R. Mack, Ottawa (CA); Daniel Figeys, Ottawa (CA); Walid Abdelfattah Elsayed Mottawea, Ottawa (CA); Turki Saleh A. Abujamel, Jeddah (SA); Cheng-kang Chiang, Ottawa (CA)

(73) Assignee: UNIVERSITY OF OTTAWA, Ottawa, ON (CA)

( * ) Notice: Subject to any disclaimer, the term of this patent is extended or adjusted under 35 U.S.C. 154(b) by 0 days.

(21) Appl. No.: 14/774,838

(22) PCT Filed: Mar. 14, 2014

(86) PCT No.: PCT/CA2014/050245
§ 371 (c)(1),
(2) Date: Sep. 11, 2015

(87) PCT Pub. No.: WO2014/138999
PCT Pub. Date: Sep. 18, 2014

(65) Prior Publication Data
US 2016/0032363 A1   Feb. 4, 2016

Related U.S. Application Data

(60) Provisional application No. 61/781,564, filed on Mar. 14, 2013.

(51) Int. Cl.
| | |
|---|---|
| C12Q 1/68 | (2018.01) |
| C12P 19/34 | (2006.01) |
| C12Q 1/689 | (2018.01) |
| C12Q 1/04 | (2006.01) |
| G01N 33/569 | (2006.01) |
| C12Q 1/6883 | (2018.01) |
| A61K 45/06 | (2006.01) |
| A61K 31/00 | (2006.01) |
| A61K 33/24 | (2006.01) |
| A61K 31/555 | (2006.01) |
| C12Q 1/06 | (2006.01) |

(52) U.S. Cl.
CPC ............. *C12Q 1/689* (2013.01); *A61K 31/00* (2013.01); *A61K 31/555* (2013.01); *A61K 33/245* (2013.01); *A61K 45/06* (2013.01); *C12Q 1/04* (2013.01); *C12Q 1/06* (2013.01); *C12Q 1/6883* (2013.01); *G01N 33/56911* (2013.01); *C12Q 2600/112* (2013.01); *C12Q 2600/158* (2013.01); *G01N 2800/065* (2013.01)

(58) Field of Classification Search
None
See application file for complete search history.

(56) References Cited

U.S. PATENT DOCUMENTS

| | | |
|---|---|---|
| 5,225,329 A | 7/1993 | Marks |
| 2007/0269813 A1 | 11/2007 | Dewhirst et al. |

FOREIGN PATENT DOCUMENTS

| | | |
|---|---|---|
| WO | WO 2007/056680 A2 | 5/2007 |
| WO | WO 2013/133298 A1 | 9/2013 |

OTHER PUBLICATIONS

N. Katarzyna et al., Visfatin/PBEF/Nampt and Other Adipocytokines in Inflammatory Bowel Disease, Advances in Clinical and Experimental Medicine 19(3):399-404 • Apr. 2010.
PCT/CA2015/050992 international search report with related claims.
PCT/CA2015/050992 written opinion.
Alessandro Armuzzi et al., Results of the 2nd scientific workshop of the ECCO (IV): Therapeutic strategies to enhance intestinal healing in inflammatory bowel disease, Journal of Crohn's and Colitis (2012) 6, 492-502.
Bhupinder K. Sandhu et al., Guidelines for the Management of Inflammatory Bowel Disease in Children in the United Kingdom, JPGN 2010;50: S1-S13.
Cary G. Sauer et al., Pediatric Inflammatory Bowel Disease: Highlighting Pediatric Differences in IBD, Gastroenterol Clin N Am 38 (2009) 611-628.
Daniel N. Frank et al., Molecular-phylogenetic characterization of microbial community imbalances in human inflammatory bowel diseases, 13780-13785 ☐ PNAS ☐ Aug. 21, 2007 ☐ vol. 104 ☐ No. 34.
Dermot P.B. McGovern et al., Genome-wide association identifies multiple ulcerative colitis susceptibility loci, Nat Genet. Apr. 2010; 42(4): 332-337.
E Bentley et al., How could pathologists improve the initial diagnosis of colitis? Evidence from an international workshop, J Clin Pathol 2002;55:955-960.
Francesca Fava, Silvio Danese, Intestinal microbiota in inflammatory bowel disease: Friend of foe?, World J Gastroenterol Feb. 7, 2011; 17(5): 557-566.
Ilseung Cho et al., The human microbiome: at the interface of health and disease, Nature review 13, 260-270 2012.
Jeffrey C. Barrett et al., Genome-wide association defines more than thirty distinct susceptibility loci for Crohn's disease, Nat Genet. Aug. 2008; 40(8): 955-962.
Jimmy et al., Fecal Hydrogen sulfide production in ulcerative colitis, American journal of gastraoenterology, vol. 93 No. 1 1998, 83-87.
Jose C. Clemente et al., The Impact of the Gut Microbiota on Human Health: An Integrative View, Cell 148, Mar. 16, 2012, 1258-1269.

(Continued)

*Primary Examiner* — Jehanne S Sitton
(74) *Attorney, Agent, or Firm* — Anglehart et al.

(57) ABSTRACT

There is provided methods and compositions to diagnose, classify and treat inflammatory bowel disease including ulcerative colitis and Crohn's disease by measuring the levels of certain bacterial taxa and proteins collected from the gut.

6 Claims, 40 Drawing Sheets

(56) References Cited

OTHER PUBLICATIONS

Junjie Qin et al., A human gut microbial gene catalog established by metagenomic sequencing, Nature. Mar. 4, 2010; 464(7285): 59-65.
Kaminska B et al., Colonic microflora in inflammatory bowel disease, Pediatria Wspolozesna, vol. 7 issue 3 2005 167-170.
Kim SC et al., Dual-association of gnotobiotic IL-10-/- mice with 2 nonpathogenic commensal bacteria induces aggressive pancolitis, Inflammatory Bowel Diseases [2007, 13(12):1457-1466].
Manichanh C et al., The gut microbiota in IBD, Nat Rev Gastroenterol Hepatol. Oct. 2012;9(10):599-608, abstract.
Marcin Imielinski et al., Common variants at five new loci associated with early-onset inflammatory bowel disease, Nat Genet. Dec. 2009; 41(12): 1335-1340.
Mekki Medani et al., Emerging Role of Hydrogen Sulfide in Colonic Physiology and Pathophysiology, Inflamm Bowel Dis • vol. 17. No. 7. Jul. 2011.
Nicholas J. Talley et al., An Evidence-Based Systematic Review on Medical Therapies for Infl ammatory Bowel Disease, Am J Gastroenterol 2011; 106:S2-S25; doi: 10.1038/ajg.2011.58.
PCT/CA2014/050245 international preliminary report.
PCT/CA2014/050245 international search report.
PCT/CA2014/050245 search strategy.
Rajaratnam Rameshshanker et al., Endoscopy in inflammatory bowel disease when and why ,World J Gastrointest Endosc Jun. 16, 2012; 4(6): 201-211.
Susanna Nikolaus et al., Diagnostics of Inflammatory Bowel Disease, Gastroenterology 2007;133:1670-1689.
Tighe MP et al., Nutrition and inflammatory bowel disease: primary or adjuvant therapy, Current Opinion in Clinical Nutrition and Metabolic Care [2011, 14(5):491-496] Abstract.
Wendy S. Garrett et al., Communicable ulcerative colitis induced by T-bet deficiency in the innate immune system, Cell. Oct. 5, 2007; 131(1): 33-45.

\+ *A. parvulum*
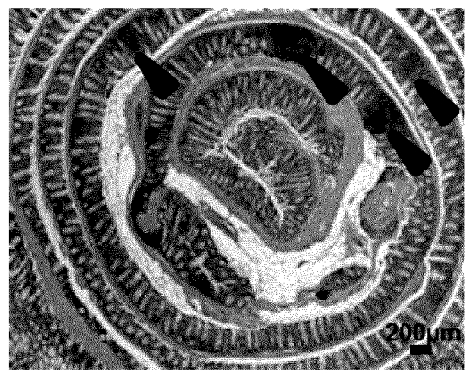
\+ *A. parvulum* + bismuth
\- *A. parvulum* + bismuth
Figure 4D

SEQUENCE LISTING

<160> NUMBER OF SEQ ID NOS: 47

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
ggggagtatt tcttccgtgc cg                                    22

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
cttcacctaa atgtcaagcc ctgg                                  24

<210> SEQ ID NO 3
<211> LENGTH: 73
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(43)
<223> OTHER INFORMATION: n is Inosine
<220> FEATURE:
<221> NAME/KEY: misc_feature
<222> LOCATION: (46)..(46)
<223> OTHER INFORMATION: n is Inosine
<220> FEATURE:
<221> NAME/KEY: misc_feature
<222> LOCATION: (55)..(55)
<223> OTHER INFORMATION: n is Inosine
<220> FEATURE:
<221> NAME/KEY: misc_feature
<222> LOCATION: (64)..(64)
<223> OTHER INFORMATION: n is Inosine

<400> SEQUENCE: 3
ccatctcatc cctgcgtgtc tccgactcag acgagtgcgt gcngancatt tcacntggaa    60
ywsntggcay atg                                                      73

<210> SEQ ID NO 4
<211> LENGTH: 73
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(43)
<223> OTHER INFORMATION: n is Inosine
<220> FEATURE:
<221> NAME/KEY: misc_feature
<222> LOCATION: (46)..(46)
<223> OTHER INFORMATION: n is Inosine
<220> FEATURE:
<221> NAME/KEY: misc_feature
<222> LOCATION: (55)..(55)
<223> OTHER INFORMATION: n is Inosine
<220> FEATURE:
<221> NAME/KEY: misc_feature
<222> LOCATION: (64)..(64)
<223> OTHER INFORMATION: n is Inosine

<400> SEQUENCE: 4
ccatctcatc cctgcgtgtc tccgactcag acgctcgaca gcngancatt tcacntggaa    60
ywsntggcay atg                                                      73

<210> SEQ ID NO 5
<211> LENGTH: 73
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 5
ccatctcatc cctgcgtgtc tccgactcag agacgcactc gcngancatt tcacntggaa    60
ywsntggcay atg                                                      73

<210> SEQ ID NO 6
<211> LENGTH: 73
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 6
ccatctcatc cctgcgtgtc tccgactcag agcactgtag gcngancatt tcacntggaa    60
ywsntggcay atg                                                      73

<210> SEQ ID NO 7
<211> LENGTH: 73
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(43)
<223> OTHER INFORMATION: n is a, c, g, or t

```
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 7
ccatctcatc cctgcgtgtc tccgactcag atcagacacg gcngancatt tcacntggaa      60
ywsntggcay atg                                                         73

<210> SEQ ID NO 8
<211> LENGTH: 73
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 8
ccatctcatc cctgcgtgtc tccgactcag atatcgcgag gcngancatt tcacntggaa      60
ywsntggcay atg                                                         73

<210> SEQ ID NO 9
<211> LENGTH: 73
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 9
ccatctcatc cctgcgtgtc tccgactcag cgtgtctcta gcngancatt tcacntggaa      60
ywsntggcay atg                                                         73
```

<210> SEQ ID NO 10
<211> LENGTH: 73
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 10
ccatctcatc cctgcgtgtc tccgactcag ctcgcgtgtc gcngancatt tcacntggaa    60
ywsntggcay atg                                                      73

<210> SEQ ID NO 11
<211> LENGTH: 73
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 11
ccatctcatc cctgcgtgtc tccgactcag tctctatgcg gcngancatt tcacntggaa    60
ywsntggcay atg                                                      73

<210> SEQ ID NO 12
<211> LENGTH: 73
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

```
<220> FEATURE:
<221> NAME/KEY: misc_feature
<222> LOCATION: (64)..(64)
<223> OTHER INFORMATION: n is a, c, g, or t

<400> SEQUENCE: 12
ccatctcatc cctgcgtgtc tccgactcag tgatacgtct gcngancatt tcacntggaa      60
ywsntggcay atg                                                        73

<210> SEQ ID NO 13
<211> LENGTH: 73
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 13
ccatctcatc cctgcgtgtc tccgactcag catagtagtg gcngancatt tcacntggaa      60
ywsntggcay atg                                                        73

<210> SEQ ID NO 14
<211> LENGTH: 73
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(43)
<223> OTHER INFORMATION: n is Inosine
<220> FEATURE:
<221> NAME/KEY: misc_feature
<222> LOCATION: (46)..(46)
<223> OTHER INFORMATION: n is Inosine
<220> FEATURE:
<221> NAME/KEY: misc_feature
<222> LOCATION: (55)..(55)
<223> OTHER INFORMATION: n is Inosine
<220> FEATURE:
<221> NAME/KEY: misc_feature
<222> LOCATION: (64)..(64)
<223> OTHER INFORMATION: n is Inosine

<400> SEQUENCE: 14
ccatctcatc cctgcgtgtc tccgactcag cgagagatac gcngancatt tcacntggaa      60
ywsntggcay atg                                                        73

<210> SEQ ID NO 15
<211> LENGTH: 56
<212> TYPE: DNA
<213> ORGANISM: Artificial Sequence
<220> FEATURE:
<223> OTHER INFORMATION: primer
```

```
<220> FEATURE:
<221> NAME/KEY: misc_feature
<222> LOCATION: (48)..(48)
<223> OTHER INFORMATION: n is Inosine
<220> FEATURE:
<221> NAME/KEY: misc_feature
<222> LOCATION: (54)..(54)
<223> OTHER INFORMATION: n is a, c, g, or t

<400> SEQUENCE: 15
cctatcccct gtgtgccttg gcagtctcag cctgcctttg caatrtcnac raangc        56

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
aaactcaaak gaattgacgg                                                20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
acgagctgac gacarccatg                                                20

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
tcctacggga ggcagcagt                                                 19

<210> SEQ ID NO 19
<211> LENGTH: 26
<212> TYPE: DNA
<213> ORGANISM: Artificial Sequence
<220> FEATURE:
<223> OTHER INFORMATION: Primer

<400> SEQUENCE: 19
ggactaccag ggtatctaat cctgtt                                         26

<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
tggaatcctg tggcatccat gaaac                                          25

<210> SEQ ID NO 21
<211> LENGTH: 25
<212> TYPE: DNA
<213> ORGANISM: Artificial Sequence
```

```
<220> FEATURE:
<223> OTHER INFORMATION: Primer

<400> SEQUENCE: 21
taaaacgcag ctcagtaaca gtccg                                          25

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
gctgggattc acctcaagaa                                                20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
tctccgttac ttggggacac                                                20

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
atgagcacag aaagcatgat c                                              21

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
tacaggcttg tcactcgaat t                                              21

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
ggaagcacgg cagcagcaga ata                                            23

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
aacttgaggg agaagtagga atgg                                           24
```

```
<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
gcccatcctc tgtgactcat                                              20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
aggccacagg tattttgtcg                                              20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
tccagaaggc cctcagacta                                              20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
acacccacca gcatcttctc                                              20

<210> SEQ ID NO 32
<211> LENGTH: 29
<212> TYPE: DNA
<213> ORGANISM: Artificial Sequence
<220> FEATURE:
<223> OTHER INFORMATION: Primer

<400> SEQUENCE: 32
gcgacatttc actggaayws tggcayatg                                    29

<210> SEQ ID NO 33
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (23)..(23)
<223> OTHER INFORMATION: n is a, c, g or t

<400> SEQUENCE: 33
cctgcctttg caatrtcacr aangc                                        25
```

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
gtgstgcayg gyygtcgtca                                                    20

<210> SEQ ID NO 35
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (12)..(12)
<223> OTHER INFORMATION: n is a, c, g or t

<400> SEQUENCE: 35
acgtcrtccm cnccttcctc                                                    20

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36
actcctacgg gaggcagc                                                      18

<210> SEQ ID NO 37
<211> LENGTH: 23
<212> TYPE: DNA
<213> ORGANISM: Artificial Sequence
<220> FEATURE:
<223> OTHER INFORMATION: Primer

<400> SEQUENCE: 37
gcttcttagt caggtaccgt cat                                                23

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
ccatgaattg ccttcaaaac tgtt                                               24

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
gagcctcagc gtcagttggt                                                    20

```
<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
gcggtrcggc aagtctga                                                    18

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
cctccgacac tctagtmcga c                                                21

<210> SEQ ID NO 42
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is Inosine
<220> FEATURE:
<221> NAME/KEY: misc_feature
<222> LOCATION: (6)..(6)
<223> OTHER INFORMATION: n is Inosine
<220> FEATURE:
<221> NAME/KEY: misc_feature
<222> LOCATION: (15)..(15)
<223> OTHER INFORMATION: n is Inosine
<220> FEATURE:
<221> NAME/KEY: misc_feature
<222> LOCATION: (24)..(24)
<223> OTHER INFORMATION: n is Inosine

<400> SEQUENCE: 42
gcngancatt tcacntggaa ywsntggcay atg                                   33

<210> SEQ ID NO 43
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: n is Inosine
<220> FEATURE:
<221> NAME/KEY: misc_feature
<222> LOCATION: (24)..(24)
<223> OTHER INFORMATION: n is a, c, g or t

<400> SEQUENCE: 43
cctgcctttg caatrtcnac raangc                                           26

<210> SEQ ID NO 44
<211> LENGTH: 22
<212> TYPE: DNA
<213> ORGANISM: Artificial Sequence
<220> FEATURE:
<223> OTHER INFORMATION: Primer
```

```
<220> FEATURE:
<221> NAME/KEY: misc_feature
<222> LOCATION: (11)..(11)
<223> OTHER INFORMATION: n is Inosine

<400> SEQUENCE: 44
tcaaatcmgg ngactgggtw ga                                              22

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45
tcataaccgc ccatatgcca tgag                                            24

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gacaagggcc gtcaggtcta                                                 20

<210> SEQ ID NO 47
<211> LENGTH: 23
<212> TYPE: DNA
<213> ORGANISM: Artificial Sequence
<220> FEATURE:
<223> OTHER INFORMATION: Primer

<400> SEQUENCE: 47
ggacaggcag ataagctct tgc                                              23
```

METHODS FOR THE DIAGNOSIS AND TREATMENT OF INFLAMMATORY BOWEL DISEASE

This application is a nonprovisional of U.S. provisional patent application 61/781,564 filed Mar. 14, 2013, the specification of which is hereby incorporated by reference.

TECHNICAL FIELD

This invention relates generally to methods and compounds for the diagnosis and treatment of inflammatory bowel disease (IBD).

BACKGROUND

An intricate and essential partnership is established early in life between the host and the intestinal microbiome, assuring the maintenance of microbiota homeostasis. Disturbance of this partnership is often associated with various pathological conditions including inflammatory bowel diseases (IBD) (Cho, I. & Blaser, M. J. The human microbiome: at the interface of health and disease. Nature reviews. Genetics 13, 260-270, doi:10.1038/nrg3182 (2012)). The microbiota of IBD patients are characterized by a decreased prevalence of protective microorganisms (i.e. Clostridium IXa and IV groups) and an expansion of detrimental bacteria (i.e. Enterobacteriaceae/Escherichia coli) (Manichanh, C., Borruel, N., Casellas, F. & Guarner, F. The gut microbiota in IBD. Nature reviews. Gastroenterology & hepatology 9, 599-608, doi:10.1038/nrgastro.2012.152 (2012).

Inflammatory Bowel Disease encompasses two principal conditions: ulcerative colitis (UC) and Crohn's disease (CD). Some patients have features of both subtypes and are classified as IBD-undefined (IBD-U) (Gastroenterology, 2007. 133(5): p. 1670-89). UC is defined by continuous mucosal inflammation starting in the rectum and restricted to the colon while CD inflammation can occur anywhere in the gastrointestinal tract, involves full thickness of the bowel wall and often with skip lesions (Gastroenterol Clin North Am, 2009. 38(4): p. 611-28; Gastroenterology, 2007. 133(5): p. 1670-89). Recent attempts to find new markers for IBD subtypes, such as conventional antibodies, have fared very poorly at differentiating colonic CD versus UC. As treatments and responses to medical therapies differ between CD and UC (J Pediatr Gastroenterol Nutr, 2010, S1-S13. The American journal of gastroenterology, 2011. 106 Suppl 1: p. S2-25; quiz S26. Gastroenterol Clin North Am, 2009. 38(4): p. 611-28) there is an urgent need for biomarkers to differentiate between CD and UC.

The primary tool used for both diagnosis and IBD management is endoscopy (World J Gastrointest Endosc, 2012. 4(6): p. 201-11). Endoscopy enables both visualization of the mucosa and access for mucosal biopsies to diagnose disease, to define disease extent and activity, and to monitor disease progression. The diagnostic accuracy from colonoscopy ranges from 60 to 74% (J Clin Pathol, 2002. 55: p. 955-60). Accurate and early diagnosis is essential for proper disease management. The goal of IBD treatment is to bring active disease into remission and to prevent follow-up relapse (flare-ups). The choice of treatment depends on disease type (CD versus UC), disease location, severity of disease, disease complications and individual host factors (e.g. nutritional and growth status, pubertal status, child's age and size, medication allergies) (J Pediatr Gastroenterol Nutr, 2010, S1-S13. The American journal of gastroenterology, 2011. 106 Suppl 1: p. S2-25; quiz S26. Gastroenterol Clin North Am, 2009. 38(4): p. 611-28). Current drug therapies consist of aminosalycylates, immune-modulators, corticosteroids, antibiotics and biological therapies (i.e. anti-TNFα monoclonal antibodies). The optimum therapeutic regimen for maintaining a disease free state still remains to be determined and the effectiveness of these drugs significantly differs between CD and UC (J Pediatr Gastroenterol Nutr, 2010, S1-S13. The American journal of gastroenterology, 2011. 106 Suppl 1: p. S2-25; quiz S26. Gastroenterol Clin North Am, 2009. 38(4): p. 611-28). For example, 5-aminosalicylic acid (5-ASA) drugs are moderately effective at inducing remission and preventing relapse in mild-to-moderate-active UC, while they are not recommended in the management of active CD (The American journal of gastroenterology, 2011. 106 Suppl 1: p. S2-25; quiz S26). Methotrexate is good evidence for use as maintenance therapy to prevent relapse in CD however, there is no evidence for its use in UC (The American journal of gastroenterology, 2011. 106 Suppl 1: p. S2-25; quiz S26). Greater doses of anti-TNFα therapies at more frequent intervals are being just now recognized to be required for successful treatment of severe UC as compared to standard treatment protocols in use for CD. One third of the cost associated with IBD is due to medical therapies (CCFC. 2008, report. p. 1-101) stressing the economic importance of an effective treatment and thereby an accurate diagnosis.

While the etiology of IBD is unknown, the gut microbiota is emerging as a key player in disease development and/or chronicity. Genome wide association studies in both adults and pediatric patients have identified novel IBD-associated genes but only define 25% of the genetic risk for developing IBD and excepting for very young infants (i.e. <2 years of age), no unique genes have been discovered that define pediatric IBD from adult-onset IBD. IBD is a complex polygenic disease involving multiple risk gene loci (Nature genetics, 2008. 40(8): p. 955-62. Nature genetics, 2009. 41(12): p. 1335-40. Nature genetics, 2010. 42(4): p. 332-7). These loci encode genes involved in innate and adaptive immunity, autophagy, and maintenance of epithelial barrier integrity for those genes that have known function. While these studies have shown us that multiple pathways are involved in the pathogenesis of IBD, we remain surprisingly ignorant on the root cause(s) and pathogenesis of IBD. A prevailing hypothesis is that IBD development is a consequence of functional abnormalities in the interplay between the intestinal microbiota and the host (World journal of gastroenterology: WJG, 2011. 17(5): p. 557-66). Some of the best evidence that the gut microbiota plays a key role in IBD comes from animal model studies (World journal of gastroenterology: WJG, 2011. 17(5): p. 557-66. Cell, 2007. 131(1): p. 33-45. Inflamm Bowel Dis, 2007. 13(12): p. 1457-66). Although the experimental animal models of IBD do not exactly mimic human IBD, these studies have shown that the development of the disease is dependent on the presence of resident bacteria (Cell, 2007. 131(1): p. 33-45. Inflamm Bowel Dis, 2007. 13(12): p. 1457-66). The loss of the transcriptional factor T-bet in mice, which regulates the differentiation and function of immune system cells, was shown to promote the microbiota to become colitogenic. Moreover, the induced colitis could be transmitted to other genetically intact hosts by vertical transfer of the colitogenic microbiota (Cell, 2007. 131(1): p. 33-45). Numerous studies have revealed alterations in the composition of the gut microbiota of patients with IBD (Proc Natl Acad Sci USA, 2007. 104(34): p. 13780-5. (9) Nature, 2010. 464(7285): p. 59-65. (10) Cell, 2012. 148(6): p. 1258-70; World journal of gastroenterology: WJG, 2011. 17(5): p. 557-66). However, we do not know what triggers IBD and the resulting gut microbiota dysbiosis and we have only a rudimentary understanding of the interplay between the gut microbiota and the host. Clearly, studies that longitudinally follow gut microbiota dysbiosis in humans during flare-ups and remissions could contribute important insights into the clinical significance of the gut microbiota composition.

IBD symptoms may include bloody diarrhea, abdominal pain, cramping, fatigue, various nutritional deficiencies including iron deficiency anemia, bone health problems and weight loss (Archives of disease in childhood, 2006). In children poor linear growth is also common. The onset of symptoms is slow, indolent and non-specific and so the disease may be present in certain regions of the bowel for very long periods of time prior to diagnosis. Following diagnosis, this chronic, life-long disease is characterized by episodes of flare-up and remission (quiescent, symptom-free state) (Gastroenterol Clin North Am, 2009. 38(4): p. 611-28; Archives of disease in childhood, 2006). The current therapeutic treatments aim to stop mucosal inflammation so as to maintain the quiescent period and to reduce flare-ups to reduce permanent bowel damage and alleviate the complications of disease. Corticosteroids (prednisone) remain a mainstay of treatment for IBD despite the well-known side effects of this medication (Journal of Crohn's & colitis, 2012. 6(4): p. 492-502). Alternatively, enteral nutrition (EN) is more commonly being used as a primary therapy in lieu of prednisone to induce CD remission (Current opinion in clinical nutrition and metabolic care, 2011. 14(5): p. 491-6). However, it is more difficult for most patients to adhere to these protocols that involve enteral formulas alone without eating foods for many weeks at a time. It is apparent that the microbiota composition correlates with disease and that an "abnormal" microbiota contributes to (if not triggers) mucosa alterations and immune system malfunctions (World journal of gastroenterology: WJG, 2011. 17(5): p. 557-66). It follows that interventions aimed at restoring microbiota equilibrium could promote health and/or prevent flare-up. Moreover, given that each patient is have a unique gut microbiota composition it follows that any interventions aimed at manipulating the gut microbiota should preferably be disease and patient-specific.

In view of the above there is a need for better diagnostic assays and treatments for the management of IBD.

SUMMARY

There is provided assays and methods to diagnose and treat IBD as well as to classify gut samples into IBD, UC or CD samples. There is also provided a device for classifying gut samples into IBD, UC or CD samples.

In an embodiment there is provided an assay comprising the steps of measuring a level of proteobacteria or $H_2S$ producing bacteria or both in a gut microbioata sample from a human subject to identify the likelihood of the human subject having inflammatory bowel disease (IBD), and comparing the level of proteobacteria or $H_2S$ producing bacteria or both to a reference level of proteobacteria or $H_2S$ producing bacteria or both from gut microbiota samples of healthy human subjects, wherein a level of proteobacteria or $H_2S$ producing bacteria or both higher than the reference level is indicative of disease.

In another embodiment there is provided an assay comprising the steps of measuring a level of *A. parvulum* in a gut microbiota sample from a human subject to identify the likelihood of the human subject having IBD, and comparing the level of *A. parvulum* to a reference level of *A. parvulum* from gut microbiota samples of healthy human subjects, wherein a level of *A. parvulum* higher than the reference level is indicative of disease.

In a further embodiment there is provided an assay comprising the steps of measuring a level of butyrate producing bacteria in a gut microbiota sample from a human subject to identify the likelihood of the human subject having IBD, and comparing the level of butyrate producing bacteria to a reference level of butyrate producing bacteria from gut microbiota samples of healthy human subjects, wherein a level of butyrate producing bacteria lower than the reference level is indicative of disease.

Advantageously, the invention provides a method for distinguishing between patients with UC or CD.

In yet a further embodiment there is provided an assay for determining a severity of CD disease comprising measuring a level of one or more bacterial taxa selected from *Carnobacteriaceae, Granulicatella, Mogibacterium, Proprionibacterium, Bacillaceae* and *Atopobium* in a gut microbioata sample from the human subject wherein a level higher than a predetermined level is indicative of moderate or severe inflammation.

There is further provided an assay comprising the steps of measuring a level of sulfur dioxygenase (ETHE1), thiosulfate sulfur transferase (TST), cytochrome c oxidase subunit IV, sulfide dehydrogenase (SQR) and complexes III and IV of mithochondrial respiratory chain in a gut mucus sample from a human subject to identify the likelihood of the human subject having IBD, and wherein a lower level relative to a reference level from a healthy subject is indicative of disease.

In another aspect there is provided a method of treating IBD in a patient the method comprising: performing an assay to determine the presence of disease (IBD or UC or CD) and administering to the patient a pharmaceutically effective amount of a compound selected from aminosalycylates, immunomodulators, anti-integrins, anti-cytokines, enteral feed programs, steroids, corticosteroids, antibiotics, anti-TNFα, bismuth or a combination thereof.

These and other embodiments of the invention are further described below with reference to the Drawings and the Detailed Description.

BRIEF DESCRIPTION OF THE DRAWINGS

The invention is better understood by way of the following detailed description of embodiments of the invention with reference to the appended drawings, in which:

FIG. 1 B is a biplot analysis of the first two components of the PLS-DA model in panel A showing the significant taxa relative to disease activity (arrows).

FIG. 1 C is a graph showing the Abundance of *A. parvulum* relative to total bacteria as determined by quantitative PCR as a function of CD severity (n=13 for controls and severe CD; n=6 for mild and moderate CD; statistical comparison by Kruskal-Wallis test; diamond indicates minimum or maximum; cross indicates mean; horizontal bar indicates median).

FIG. 2 B is a photomicrograph showing inflammation monitored macroscopically with a murine endoscope.

FIG. 2 C is a photomicrograph showing representative histological sections of the distal colon and cecum.

FIG. 2 D is a graph showing a blinded histological score of inflammation (n=6 to 7 per group; horizontal lines indicate mean and crosses indicate median; comparison by Mann-Whitney two tailed test).

FIG. 3 B is a PLS-DA analysis of CD patients as a function of disease activity and controls (10 fold external validation of the model was performed on separate holdout validation sets of 5 randomly selected samples showing prediction accuracy of 75%).

FIG. 3 C qRT-PCR analysis of TST normalized to control, n=5 for UC, 13 to 15 for CD and 10 to 15 for controls Ns, not significant statistical significance was assessed using a two-tailed Mann-Whitney test.

FIG. 3 D qRT-PCR analysis cytochrome c oxidase subunit IV (hCOX41) normalized to control, n=5 for UC, 13 to 15 for CD and 10 to 15 for controls Ns, not significant statistical significance was assessed using a two-tailed Mann-Whitney test.

FIG. 3 E qRT-PCR analysis sulfide dehydrogenase (SQR) normalized to control, n=5 for UC, 13 to 15 for CD and 10 to 15 for controls Ns, not significant statistical significance was assessed using a two-tailed Mann-Whitney test.

FIG. 4 B are blinded inflammation scores (n=7 to 8 per group) for Il10$^{-/-}$ mice under SPF conditions, horizontal lines indicate means and crosses indicate median statistical significance was assessed using a Kruskal-Wallis test with a Dunn's post hoc test using the Conover-Iman procedure.

FIG. 4 C is a graph of number of GALT foci of Il10$^{-/-}$ mice associated or not with *A. parvulum* and treated or not with bismuth, and kept under gnotobiotic or SPF conditions (n=6 to 11 per group) horizontal lines indicate means and crosses indicate median. Statistical significance was assessed using a Kruskal-Wallis test with a Dunn's post hoc test.

FIG. 4 D are representative histological Swiss-rolled sections of the colon showing GALT foci in gnotobiotic mice arrows indicate GALT foci.

FIG. 4 E is PCA analysis of microbiota from Il10$^{-/-}$ mice kept under SPF conditions (light blue), bismuth-treated (blue), associated with *A. parvulum* (red), and associated with *A. parvulum* and treated with bismuth (green).

FIG. 5 B is phylogenetic tree of the microbial taxa detected in at least 75% of the samples within each group wherein a total of 241 core OTUs were detected, which represent 90.2%±8.3% of the microbial population, the figure was generated using the iTOL (Interactive Tree of Life) web package in which taxa marked with inner circle were identified as members of the core microbiota of the control subjects, taxa marked with middle and outer circles were identified as members of the core microbiota of the UC or CD patients respectively, CD and UC microbial communities are characterized by a smaller core microbiota as compared to control with 179, 172 and 214 core OTUs for CD, UC and control subjects respectively.

FIG. 6 B represents the change in relative abundance of Proteobacteria (mean±SEM) in controls, CD and UC patients; Mann-Whitney two-tailed test was applied for statistical pairwise comparison.

FIG. 7 B is a histogram of the LDA effect size score for UC-specific differentially abundant taxa (n=9 for control and n=8 for UC), as shown in panel A, *Atopobium* was identified as a biomarker of CD; 454-pyrosequencing reads assigned as *Atopobium* by QIIME analysis were retrieved and found to match to *A. parvulum* following alignment of the reads against the RDB and NCBI databases (the aligned region covered the entire 454 sequence length with >99% sequence identity to *A. parvulum* and did not align to any other known bacterial species).

FIG. 8 B is a Functional annotation analysis of the differentially expressed proteins for MF: molecular functions in which the 10 most significantly enriched functional groups (GO terms) are shown ($p<10^{-13}$); all classifications were significantly enriched compared to the whole proteomic dataset with $P<0.05$ (Fisher's exact test).

FIG. 8 C is a Functional annotation analysis of the differentially expressed proteins for KEGG pathways in which the 10 most significantly enriched functional groups (GO terms) are shown ($p<10^{-13}$); all classifications were significantly enriched compared to the whole proteomic dataset with $P<0.05$ (Fisher's exact test).

FIG. 9 B is a PLS-DA analysis of the 96 differentially expressed mitochondrial proteins from CD patients classified as a function of disease activity (mild, moderate and severe), arobust model with good predictive power was generated with four components (Predictive ability parameter [$Q^2$ cum]=0.44, goodness-of-fit parameter [$R^2Y$ cum]= 0.94).

FIG. 11 B is a graph of Il-17 cytokine expression in conventionalized $Il10^{-/-}$ mice (129/SvEv $Il10^{-/-}$ mice), measured by qRT-PCR, which were associated or not with $A. parvulum$ and kept under SPF conditions (n=7 to 8 per group), total RNA was extracted from colonic intestinal tissues 6 weeks post-association and A Mann-Whitney U test was performed to assess statistical significance, the horizontal lines indicate the mean and error bars the SD, n.s., non-significant.

FIG. 11 C is a graph of Il-12 cytokine expression in conventionalized $Il10^{-/-}$ mice (129/SvEv $Il10^{-/-}$ mice), measured by qRT-PCR, which were associated or not with $A. parvulum$ and kept under SPF conditions (n=7 to 8 per group), total RNA was extracted from colonic intestinal tissues 6 weeks post-association and A Mann-Whitney U test was performed to assess statistical significance, the horizontal lines indicate the mean and error bars the SD, n.s., non-significant.

FIG. 11 D is a graph of Il10 cytokine expression in conventionalized $Il10^{-/-}$ mice (129/SvEv $Il10^{-/-}$ mice), measured by qRT-PCR, which were associated or not with $A. parvulum$ and kept under SPF conditions (n=7 to 8 per group), total RNA was extracted from colonic intestinal tissues 6 weeks post-association and A Mann-Whitney U test was performed to assess statistical significance, the horizontal lines indicate the mean and error bars the SD, n.s., non-significant.

FIG. 12 B represents levels of chromosomal DNA was extracted from stool pellets obtained 6 week after mono-association or not of 129/SvEv $Il10^{-/-}$ mice with $A. parvulum$, colonization level was estimated using real-time qPCR and reported as the number of 16S rDNA gene copies per mg of stool, error bars indicate SEM, for panels A and B, horizontal lines indicate means. Statistical significance was assessed using a Mann-Whitney U-test.

FIG. 14 B shows Alpha diversity represented by Chao1 estimated OTUs (left panel) and Shannon diversity index (right panel). Number of reads was equalized between samples at 4,600 reads. Control (blue bar), CD (red bar), and UC (orange bar).

FIG. 14 C shows Beta diversity presented by two-dimensional principal coordinates analysis (PCoA) plot of weighted UniFrac distance. Left plot represents control group and CD patients beta diversity, and right plot is showing control group and UC patients beta diversity. Percentage of variance explained by each component is presented under each axis. Control samples (green squares), CD samples (red triangle), and UC samples (blue circles).

FIG. 19 B shows Ct for total bacteria 16S rRNA is similar between groups. Error bars represent the standard error of the mean.

DETAILED DESCRIPTION

Figure 1A:
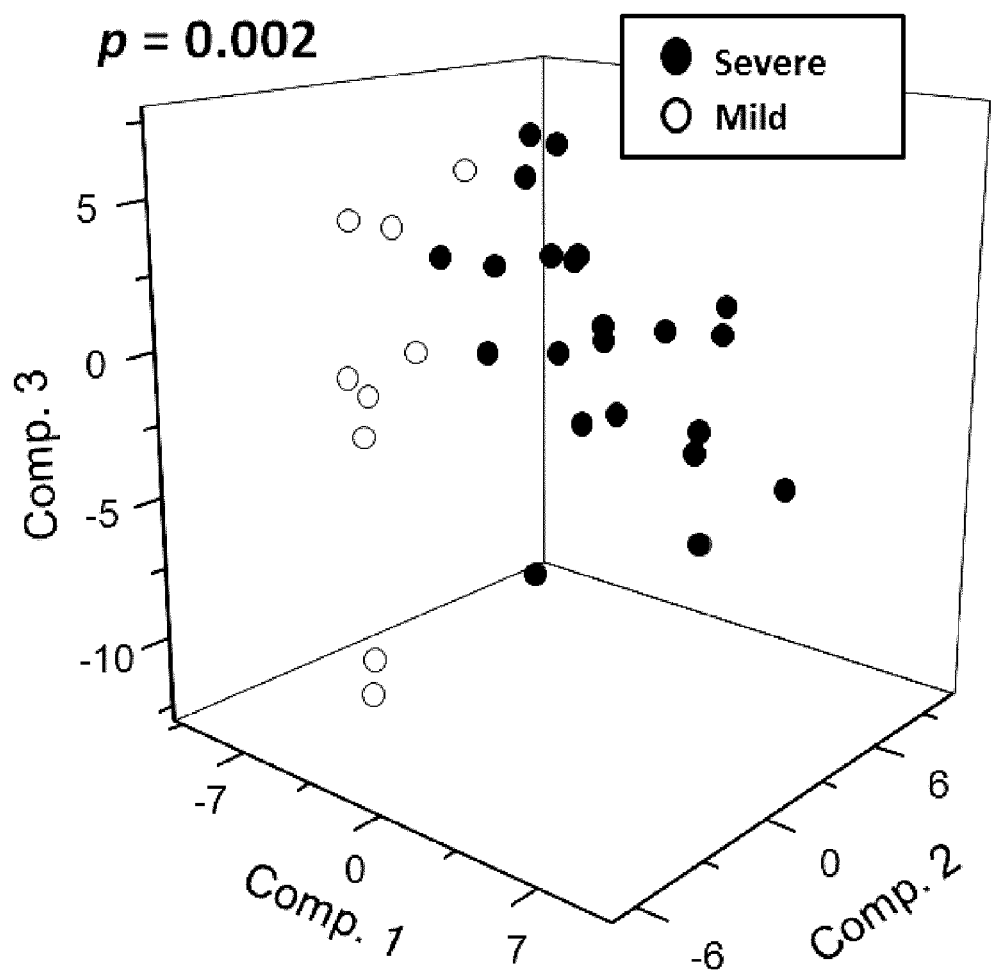
FIG. 1 A is a PLS-DA of CD patients with severe inflammation (n=23) against CD patients with mild inflammation (n=9), to confirm the validation of the PLS-DA models, permutation tests (n=1000) were performed and the corresponding p value for prediction accuracy calculated.

In the present description by microbiota it is meant an ensemble of microorganisms residing in an environment and in particular by gut microbiota it is meant microorganisms found in any part of the alimentary canal from lips to the anus.

By patients having Inflammatory bowel disease (IBD) it is meant patients with ulcerative colitis (UC) or patients with Crohn's disease (CD) or IBD-undefined (IBD-U).

By level or abundance of bacteria or bacterial taxa it is meant a level or abundance obtained by a means to quantify bacteria such as culture based methods, flow cytometry, microscopy, quantitative DNA analysis and any other means that would be obvious to a person skilled in the art.

By severity of the disease it is meant a level of symptoms as described in disease activity index such Crohn's disease activity index (CDAI), Pediatric Crohn's disease activity index (PCDAI) Harvey-Bradshaw index, Ulcerative colitis activity index (UCAI), Pediatric Ulcerative colitis activity index (PUCAI), Paris classification of pediatric Crohn's disease and the like. For example severe CD corresponds to a score of 450 in the CDAI index.

By "core" it is meant the bacterial taxa that are conserved between individuals (that are present in two or more individuals).

In an aspect of the invention there is provided a method in which IBD can be detected by measuring the levels (or relative abundance) of certain bacterial taxa in samples from the gut of patients. Microbiota samples from the gut may be obtained from stools, intestinal mucosal biopsies, gut lavage or combination thereof. In an embodiment of the invention, microbiota samples are collected such as to comprise the microbiota from the mucosa-luminal interface of the gut.

In one embodiment of the invention, the collection can be performed during endoscopy by flushing a physiological solution, such as sterile saline solution or sterile water, onto the mucosa to remove the strongly adherent mucus layer overlying the intestinal mucosal epithelial cells and the microbial community embedded within the mucus layer. Aspirates are then collected directly through a colonoscope at a specific location in the gut as for example from the terminal ileum right colon and left colon and the samples are preferably immediately put on ice right in the endoscopy suite. For example the following steps can be performed: 1) a regular protocol of bowel clean out in preparation for colonoscopy is first applied to the patient, 2) then the colonoscope ("scope") is advanced to the ascending colon or a region of the colon distal to that of interest, 3) suction out fluid and particulate matter, using either the scope's wash system or with a syringe through biopsy port, 4) flush sterile water onto mucosa until shards of mucus are dislodged, 5) aspirate mucus containing fluid into sterile trap through scope aspiration system, 6) remove the trap from scope suction and cap it and immediately place on ice, 7) advance the scope to more proximal region of interest and repeat steps 3-6, 8) transport traps with mucus to lab within 15 minutes of collection. The sample can then be analyzed at the point of care or transferred to a laboratory. The samples can also be further processed and then stored at −80° C.

Collection of the gut microbiota can also be performed on stools. Collection of bacteria from stools is known in the art. In the case of fecal microbiota collection/analysis, fresh stools may be collected and immediately processed and stored at −80° C. for DNA extraction and sequence/quantification as part of a bacterial analysis as further described below.

Samples containing gut microbiota collected as described above can be assayed for determining their microbial composition. Identification of the bacteria present in samples can be performed using DNA sequencing techniques as described in the examples below. In one embodiment, total DNA can be extracted from intestinal aspirates or stool samples. The protocol may comprise the extraction of total DNA using an extraction step with mechanical disruption. The extracted DNA can then be subjected to sequencing to identify bacteria by comparing the sequences to sequences contained in databases. In a preferred embodiment metagenomic DNA can be subjected to multiplexed massively parallel sequencing on the hypervariable V6 region of the 16S rRNA gene. It is appreciated that the sequencing of regions other than the hypervariable V6 region of the 16S rRNA gene can be used provided that such regions provide discriminating power (taxonomic resolution) for at least some bacterial taxa or operational taxonomic units (OTU's) and in particular for bacterial taxa that are preferentially associated with IBD as is further described below.

It will also be appreciated that other methods can be used to identify bacteria from the gut samples including but not limited to microscopy, metabolites identification, Gram staining, flow cytometry, immunological techniques (antibodies), culture-based methods such a colony forming unit counting and the like as would be known to a person skilled in the art.

Figure 5A:
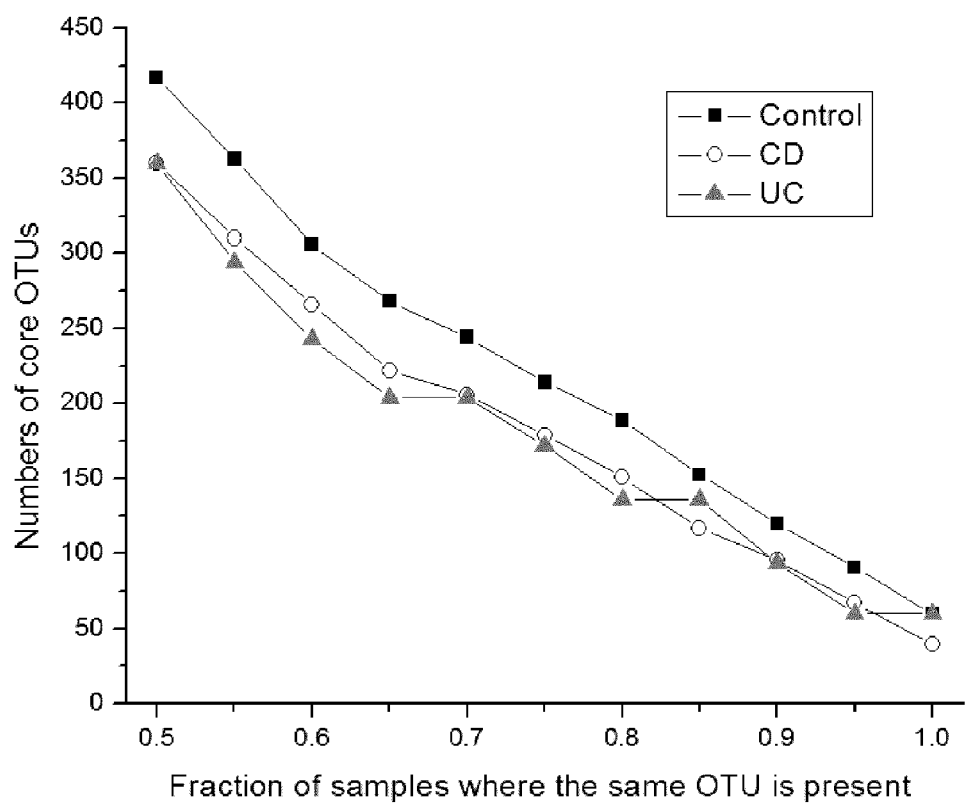
FIG. 5 A is a plot of the size of the core microbiota of control subjects, and CD and UC patients; (OTU: operating taxonomic unit).
Figure 5B:
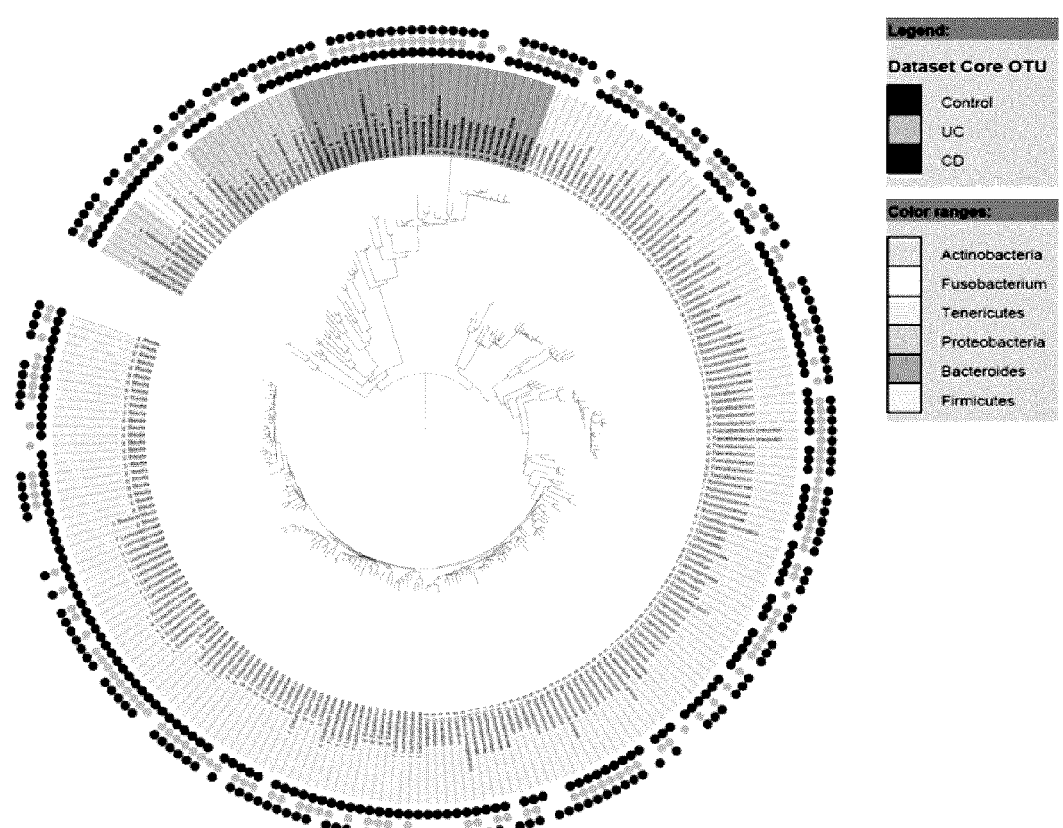
Figure 6A:
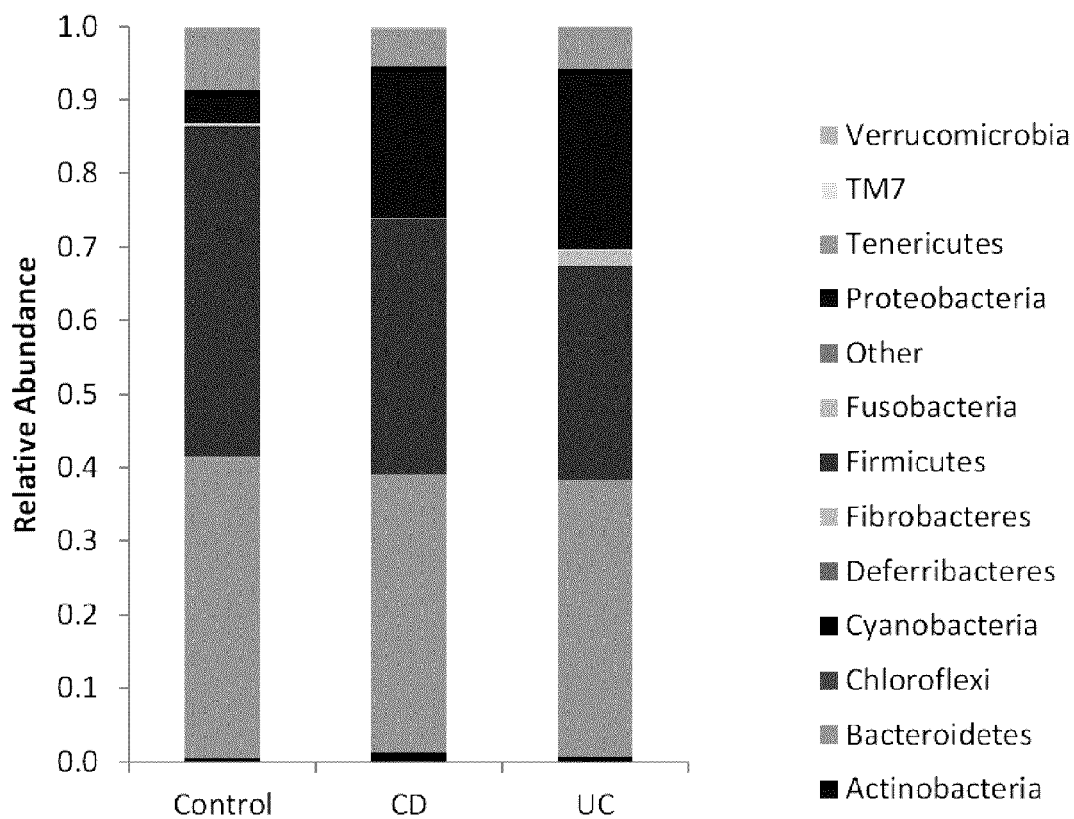
FIG. 6 A represents the average relative abundance of bacterial phyla identified in patients with Crohn's disease (CD; n=9) and Ulcerative Colitis (UC; n=8) and control subjects (n=9); similar profiles were obtained with reads generated using Hiseq2500 sequencing.
Figure 6B:
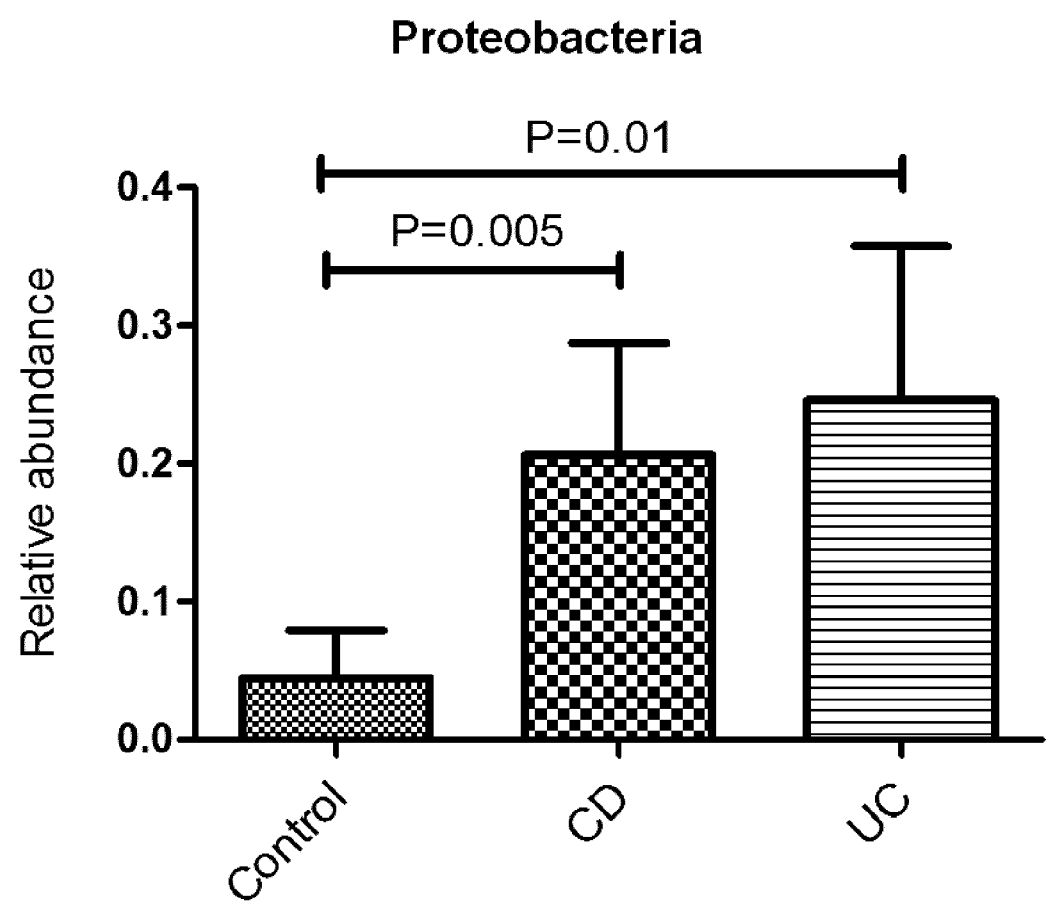

In an aspect of the invention the relative abundance of certain bacterial taxa namely phylum, class, order, family, genus or species or combination thereof in the gut (gut microbiota profile) of patients is used to assess the presence or absence of IBD disease. It has been found that the IBD microbiota is characterized by a smaller core as compared to controls (FIG. 5A-B and Table 1), indicating a loss of microbiota homeostasis. Also, the IBD microbiota is characterized by a depletion of butyrate producing microbes together with an increased abundance of $H_2S$-generating bacteria. For example, increase in the levels of $H_2S$ producers such as *Fusobacterium nucleatum*, *Veillonella parvula*, and *Atopobium parvulum* is indicative of disease.

Assessment of the presence of CD and UC disease in a human subject can be achieved by measuring the relative abundance of taxa as exemplified in table 1. In this particular example, microbial operational taxonomic units (OTUs) that were detected in all the samples within each group and that vary significantly in abundance between CD, UC and/or controls are listed. The number of 16S rDNA reads in each sample was normalized by random subsampling to 500,000. Minimum and maximum correspond to the minimum and maximum number of reads obtained; mean corresponds to the mean of the number of reads obtained. P values were generated using a Kruskal-Wallis test with a Dunn's post hoc test. "p|Control" indicates the P values obtained by comparison to the controls; "p|UC" and "p|CD" indicate the P values obtained by comparison to the UC and CD patients respectively. Values in bold indicate significance (P<0.05). From the table it can be seen that certain taxa are more or less abundant in patients with disease than in healthy controls. Furthermore there it is also possible to distinguish between CD and UC based on the relative abundance.

TABLE 1

Core OTUs that varies significantly in abundance in at least one of the three pairwise comparisons performed (controls vs. CD; controls vs. UC; and CD vs. UC).

| OTU \| Variable | Taxonomy \| Variable | Min | Max | Mean | Std. deviation | p \| Control | p \| UC | p \| CD |
|---|---|---|---|---|---|---|---|---|
| 177005 \| Control | k__Bacteria; p__Firmicutes; c__Clostridia; o__Clostridiales; f__Lachnospiraceae; g__Blautia; s__ \| Control | 0.000 | 12876.000 | 1590.857 | 3303.847 | 1 | 0.304 | 0.022 |

TABLE 1-continued

Core OTUs that varies significantly in abundance in at least one of the three pairwise comparisons performed (controls vs. CD; controls vs. UC; and CD vs. UC).

| OTU \| Variable | Taxonomy \| Variable | Min | Max | Mean | Std. deviation | p \| Control | p \| UC | p \| CD |
| --- | --- | --- | --- | --- | --- | --- | --- | --- |
| 177005 \| UC | k__Bacteria; p__Firmicutes; c__Clostridia; o__Clostridiales; f__Lachnospiraceae; g__Blautia; s__ \| UC | 1.000 | 8538.000 | 829.071 | 2266.987 | 0.304 | 1 | 0.388 |
| 177005 \| CD | k__Bacteria; p__Firmicutes; c__Clostridia; o__Clostridiales; f__Lachnospiraceae; g__Blautia; s__ \| CD | 0.000 | 24758.000 | 870.135 | 4086.298 | 0.022 | 0.388 | 1 |
| 541301 \| Control | k__Bacteria; p__Bacteroidetes; c__Bacteroidia; o__Bacteroidales; f__Porphyromonadaceae; g__Parabacteroides; s__ \| Control | 0.000 | 34876.000 | 2923.571 | 7856.412 | 1 | 0.265 | 0.332 |
| 541301 \| UC | k__Bacteria; p__Bacteroidetes; c__Bacteroidia; o__Bacteroidales; f__Porphyromonadaceae; g__Parabacteroides; s__ \| UC | 2.000 | 4594.000 | 400.357 | 1221.873 | 0.265 | 1 | 0.038 |
| 541301 \| CD | k__Bacteria; p__Bacteroidetes; c__Bacteroidia; o__Bacteroidales; f__Porphyromonadaceae; g__Parabacteroides; s__ \| CD | 1.000 | 10433.000 | 1166.622 | 2439.874 | 0.332 | 0.038 | 1 |
| 258691 \| Control | k__Bacteria; p__Bacteroidetes; c__Bacteroidia; o__Bacteroidales; f__Bacteroidaceae; g__Bacteroides; s__Bacteroidesovatus \| Control | 0.000 | 40719.000 | 2275.238 | 8846.849 | 1 | 0.812 | 0.038 |
| 258691 \| UC | k__Bacteria; p__Bacteroidetes; c__Bacteroidia; o__Bacteroidales; f__Bacteroidaceae; g__Bacteroides; s__Bacteroidesovatus \| UC | 1.000 | 86361.000 | 6325.500 | 23037.262 | 0.812 | 1 | 0.122 |
| 258691 \| CD | k__Bacteria; p__Bacteroidetes; c__Bacteroidia; o__Bacteroidales; f__Bacteroidaceae; g__Bacteroides; s__Bacteroidesovatus \| CD | 1.000 | 37102.000 | 3148.459 | 7654.185 | 0.038 | 0.122 | 1 |
| 182122 \| Control | k__Bacteria; p__Firmicutes; c__Clostridia; o__Clostridiales; f__Lachnospiraceae; g__; s__ \| Control | 3.000 | 13653.000 | 1649.619 | 3463.599 | 1 | 0.034 | 0.077 |
| 182122 \| UC | k__Bacteria; p__Firmicutes; c__Clostridia; o__Clostridiales; f__Lachnospiraceae; g__; s__ \| UC | 0.000 | 5379.000 | 518.643 | 1417.505 | 0.034 | 1 | 0.427 |

TABLE 1-continued

Core OTUs that varies significantly in abundance in at least one of the three pairwise comparisons performed (controls vs. CD; controls vs. UC; and CD vs. UC).

| OTU \| Variable | Taxonomy \| Variable | Min | Max | Mean | Std. deviation | p \| Control | p \| UC | p \| CD |
|---|---|---|---|---|---|---|---|---|
| 182122 \| CD | k_Bacteria; p_Firmicutes; c_Clostridia; o_Clostridiales; f_Lachnospiraceae; g_; s_ \| CD | 1.000 | 7805.000 | 691.216 | 1475.854 | 0.077 | 0.427 | 1 |
| 261912 \| Control | k_Bacteria; p_Firmicutes; c_Clostridia; o_Clostridiales; f_Lachnospiraceae; g_Dorea; s_Doreaformicigenerans \| Control | 12.000 | 23969.000 | 7682.238 | 8341.342 | 1 | 0.043 | 0.540 |
| 261912 \| UC | k_Bacteria; p_Firmicutes; c_Clostridia; o_Clostridiales; f_Lachnospiraceae; g_Dorea; s_Doreaformicigenerans \| UC | 24.000 | 7473.000 | 1846.143 | 2506.511 | 0.043 | 1 | 0.091 |
| 261912 \| CD | k_Bacteria; p_Firmicutes; c_Clostridia; o_Clostridiales; f_Lachnospiraceae; g_Dorea; s_Doreaformicigenerans \| CD | 4.000 | 92806.000 | 10038.811 | 17773.654 | 0.540 | 0.091 | 1 |
| 585419 \| Control | k_Bacteria; p_Firmicutes; c_Clostridia; o_Clostridiales; f_Veillonellaceae; g_Veillonella; s_ \| Control | 2.000 | 860.000 | 111.000 | 201.434 | 1 | 0.003 | 0.114 |
| 585419 \| UC | k_Bacteria; p_Firmicutes; c_Clostridia; o_Clostridiales; f_Veillonellaceae; g_Veillonella; s_ \| UC | 17.000 | 29801.000 | 4900.714 | 9206.483 | 0.003 | 1 | 0.059 |
| 585419 \| CD | k_Bacteria; p_Firmicutes; c_Clostridia; o_Clostridiales; f_Veillonellaceae; g_Veillonella; s_ \| CD | 5.000 | 14260.000 | 1293.811 | 3473.360 | 0.114 | 0.059 | 1 |
| 566952 \| Control | k_Bacteria; p_Firmicutes; c_Clostridia; o_Clostridiales; f_Lachnospiraceae; g_Clostridium; s_ \| Control | 1.000 | 559.000 | 152.381 | 171.608 | 1 | 0.011 | 0.137 |
| 566952 \| UC | k_Bacteria; p_Firmicutes; c_Clostridia; o_Clostridiales; f_Lachnospiraceae; g_Clostridium; s_ \| UC | 0.000 | 378.000 | 41.429 | 101.442 | 0.011 | 1 | 0.137 |
| 566952 \| CD | k_Bacteria; p_Firmicutes; c_Clostridia; o_Clostridiales; f_Lachnospiraceae; g_Clostridium; s_ \| CD | 0.000 | 720.000 | 106.108 | 165.187 | 0.137 | 0.137 | 1 |

TABLE 1-continued

Core OTUs that varies significantly in abundance in at least one of the three pairwise comparisons performed (controls vs. CD; controls vs. UC; and CD vs. UC).

| OTU \| Variable | Taxonomy \| Variable | Min | Max | Mean | Std. deviation | p \| Control | p \| UC | p \| CD |
|---|---|---|---|---|---|---|---|---|
| 303772 \| Control | k_Bacteria; p_Firmicutes; c_Clostridia; o_Clostridiales; f_Lachnospiraceae; g_; s_ \| Control | 0.000 | 149466.000 | 8653.333 | 32546.409 | 1 | 0.163 | 0.177 |
| 303772 \| UC | k_Bacteria; p_Firmicutes; c_Clostridia; o_Clostridiales; f_Lachnospiraceae; g_; s_ \| UC | 1.000 | 16984.000 | 1460.286 | 4486.377 | 0.163 | 1 | 0.007 |
| 303772 \| CD | k_Bacteria; p_Firmicutes; c_Clostridia; o_Clostridiales; f_Lachnospiraceae; g_; s_ \| CD | 0.000 | 2852.000 | 193.811 | 613.649 | 0.177 | 0.007 | 1 |
| 145149 \| Control | k_Bacteria; p_Firmicutes; c_Clostridia; o_Clostridiales; f_Veillonellaceae; g_Veillonella; s_ \| Control | 1.000 | 350.000 | 75.524 | 107.340 | 1 | 0.012 | 0.170 |
| 145149 \| UC | k_Bacteria; p_Firmicutes; c_Clostridia; o_Clostridiales; f_Veillonellaceae; g_Veillonella; s_ \| UC | 2.000 | 15569.000 | 4072.786 | 6042.303 | 0.012 | 1 | 0.119 |
| 145149 \| CD | k_Bacteria; p_Firmicutes; c_Clostridia; o_Clostridiales; f_Veillonellaceae; g_Veillonella; s_ \| CD | 1.000 | 9591.000 | 811.892 | 1841.236 | 0.170 | 0.119 | 1 |
| 362168 \| Control | k_Bacteria; p_Bacteroidetes; c_Bacteroidia; o_Bacteroidales; f_Bacteroidaceae; g_Bacteroides; s_ \| Control | 1.000 | 10035.000 | 709.286 | 2194.846 | 1 | 0.540 | 0.039 |
| 362168 \| UC | k_Bacteria; p_Bacteroidetes; c_Bacteroidia; o_Bacteroidales; f_Bacteroidaceae; g_Bacteroides; s_ \| UC | 2.000 | 17437.000 | 1507.500 | 4604.990 | 0.540 | 1 | 0.261 |
| 362168 \| CD | k_Bacteria; p_Bacteroidetes; c_Bacteroidia; o_Bacteroidales; f_Bacteroidaceae; g_Bacteroides; s_ \| CD | 2.000 | 35846.000 | 1950.054 | 6025.223 | 0.039 | 0.261 | 1 |
| 470973 \| Control | k_Bacteria; p_Firmicutes; c_Clostridia; o_Clostridiales; f_Lachnospiraceae; g_Ruminococcus; s_Ruminococcustorques \| Control | 3.000 | 73975.000 | 5461.905 | 16369.874 | 1 | 0.106 | 0.637 |

TABLE 1-continued

Core OTUs that varies significantly in abundance in at least one of the three pairwise comparisons performed (controls vs. CD; controls vs. UC; and CD vs. UC).

| OTU \| Variable | Taxonomy \| Variable | Min | Max | Mean | Std. deviation | p \| Control | p \| UC | p \| CD |
|---|---|---|---|---|---|---|---|---|
| 470973 \| UC | k__Bacteria; p__Firmicutes; c__Clostridia; o__Clostridiales; f__Lachnospiraceae; g__Ruminococcus; s__Ruminococcustorques \| UC | 3.000 | 55265.000 | 4591.643 | 14678.969 | 0.106 | 1 | 0.029 |
| 470973 \| CD | k__Bacteria; p__Firmicutes; c__Clostridia; o__Clostridiales; f__Lachnospiraceae; g__Ruminococcus; s__Ruminococcustorques \| CD | 0.000 | 109867.000 | 8736.757 | 20949.142 | 0.637 | 0.029 | 1 |
| 138006 \| Control | k__Bacteria; p__Bacteroidetes; c__Bacteroidia; o__Bacteroidales; f__Rikenellaceae; g__Alistipes; s__ \| Control | 0.000 | 2913.000 | 464.476 | 900.379 | 1 | 0.117 | 0.229 |
| 138006 \| UC | k__Bacteria; p__Bacteroidetes; c__Bacteroidia; o__Bacteroidales; f__Rikenellaceae; g__Alistipes; s__ \| UC | 0.000 | 1393.000 | 193.286 | 411.329 | 0.117 | 1 | 0.006 |
| 138006 \| CD | k__Bacteria; p__Bacteroidetes; c__Bacteroidia; o__Bacteroidales; f__Rikenellaceae; g__Alistipes; s__ \| CD | 1.000 | 7020.000 | 795.243 | 1586.474 | 0.229 | 0.006 | 1 |
| 188900 \| Control | k__Bacteria; p__Firmicutes; c__Clostridia; o__Clostridiales; f__Ruminococcaceae; g__Faecalibacterium; s__ \| Control | 11.000 | 9087.000 | 1275.952 | 2844.824 | 1 | 0.266 | 0.042 |
| 188900 \| UC | k__Bacteria; p__Firmicutes; c__Clostridia; o__Clostridiales; f__Ruminococcaceae; g__Faecalibacterium; s__ \| UC | 3.000 | 87401.000 | 7661.214 | 23050.226 | 0.266 | 1 | 0.585 |
| 188900 \| CD | k__Bacteria; p__Firmicutes; c__Clostridia; o__Clostridiales; f__Ruminococcaceae; g__Faecalibacterium; s__ \| CD | 2.000 | 98077.000 | 8299.324 | 20200.719 | 0.042 | 0.585 | 1 |
| 64396 \| Control | k__Bacteria; p__Fusobacteria; c__Fusobacteria; o__Fusobacteriales; f__Fusobacteriaceae; g__Fusobacterium; s__ \| Control | 0.000 | 674.000 | 86.952 | 185.286 | 1 | 0.050 | 0.013 |
| 64396 \| UC | k__Bacteria; p__Fusobacteria; c__Fusobacteria; o__Fusobacteriales; f__Fusobacteriaceae; g__Fusobacterium; s__ \| UC | 0.000 | 41529.000 | 3892.429 | 11049.181 | 0.050 | 1 | 0.993 |

TABLE 1-continued

Core OTUs that varies significantly in abundance in at least one of the three pairwise
comparisons performed (controls vs. CD; controls vs. UC; and CD vs. UC).

| OTU \| Variable | Taxonomy \| Variable | Min | Max | Mean | Std. deviation | p \| Control | p \| UC | p \| CD |
|---|---|---|---|---|---|---|---|---|
| 64396 \| CD | k__Bacteria; p__Fusobacteria; c__Fusobacteria; o__Fusobacteriales; f__Fusobacteriaceae; g__Fusobacterium; s__ \| CD | 1.000 | 164748.000 | 6092.135 | 27224.424 | 0.013 | 0.993 | 1 |
| 196731 \| Control | k__Bacteria; p__Firmicutes; c__Clostridia; o__Clostridiales; f__Lachnospiraceae; g__; s__ \| Control | 1.000 | 787.000 | 174.333 | 238.985 | 1 | <0.0001 | 0.346 |
| 196731 \| UC | k__Bacteria; p__Firmicutes; c__Clostridia; o__Clostridiales; f__Lachnospiraceae; g__; s__ \| UC | 0.000 | 0.000 | 0.000 | 0.000 | <0.0001 | 1 | <0.0001 |
| 196731 \| CD | k__Bacteria; p__Firmicutes; c__Clostridia; o__Clostridiales; f__Lachnospiraceae; g__; s__ \| CD | 0.000 | 8748.000 | 666.892 | 1933.413 | 0.346 | <0.0001 | 1 |
| 469709 \| Control | k__Bacteria; p__Bacteroidetes; c__Bacteroidia; o__Bacteroidales; f__Bacteroidaceae; g__Bacteroides; s__Bacteroidesdorei \| Control | 4.000 | 113796.000 | 12561.190 | 32939.260 | 1 | 0.274 | 0.035 |
| 469709 \| UC | k__Bacteria; p__Bacteroidetes; c__Bacteroidia; o__Bacteroidales; f__Bacteroidaceae; g__Bacteroides; s__Bacteroidesdorei \| UC | 11.000 | 123061.000 | 14096.286 | 34346.257 | 0.274 | 1 | 0.529 |
| 469709 \| CD | k__Bacteria; p__Bacteroidetes; c__Bacteroidia; o__Bacteroidales; f__Bacteroidaceae; g__Bacteroides; s__Bacteroidesdorei \| CD | 2.000 | 221413.000 | 22583.189 | 42793.771 | 0.035 | 0.529 | 1 |
| 183879 \| Control | k__Bacteria; p__Firmicutes; c__Clostridia; o__Clostridiales; f__Lachnospiraceae; g__; s__ \| Control | 0.000 | 25451.000 | 2080.381 | 5620.095 | 1 | 0.097 | 0.005 |
| 183879 \| UC | k__Bacteria; p__Firmicutes; c__Clostridia; o__Clostridiales; f__Lachnospiraceae; g__; s__ \| UC | 1.000 | 26097.000 | 2375.786 | 6987.836 | 0.097 | 1 | 0.533 |
| 183879 \| CD | k__Bacteria; p__Firmicutes; c__Clostridia; o__Clostridiales; f__Lachnospiraceae; g__; s__ \| CD | 0.000 | 2104.000 | 220.324 | 486.771 | 0.005 | 0.533 | 1 |
| 514611 \| Control | k__Bacteria; p__Firmicutes; c__Clostridia; o__Clostridiales; f__Clostridiaceae; g__Clostridium; s__ \| Control | 3.000 | 44090.000 | 2806.333 | 9573.507 | 1 | 0.154 | 0.019 |

TABLE 1-continued

Core OTUs that varies significantly in abundance in at least one of the three pairwise comparisons performed (controls vs. CD; controls vs. UC; and CD vs. UC).

| OTU \| Variable | Taxonomy \| Variable | Min | Max | Mean | Std. deviation | p \| Control | p \| UC | p \| CD |
|---|---|---|---|---|---|---|---|---|
| 514611 \| UC | k_Bacteria; p_Firmicutes; c_Clostridia; o_Clostridiales; f_Clostridiaceae; g_Clostridium; s_ \| UC | 0.000 | 3656.000 | 599.643 | 1154.057 | 0.154 | 1 | 0.633 |
| 514611 \| CD | k_Bacteria; p_Firmicutes; c_Clostridia; o_Clostridiales; f_Clostridiaceae; g_Clostridium; s_ \| CD | 0.000 | 173925.000 | 6113.162 | 29294.960 | 0.019 | 0.633 | 1 |
| 288565 \| Control | k_Bacteria; p_Fusobacteria; c_Fusobacteria; o_Fusobacteriales; f_Fusobacteriaceae; g_Fusobacterium; s_ \| Control | 1.000 | 204469.000 | 18673.762 | 57773.500 | 1 | 0.343 | <0.0001 |
| 288565 \| UC | k_Bacteria; p_Fusobacteria; c_Fusobacteria; o_Fusobacteriales; f_Fusobacteriaceae; g_Fusobacterium; s_ \| UC | 0.000 | 21535.000 | 2582.714 | 6677.428 | 0.343 | 1 | <0.0001 |
| 288565 \| CD | k_Bacteria; p_Fusobacteria; c_Fusobacteria; o_Fusobacteriales; f_Fusobacteriaceae; g_Fusobacterium; s_ \| CD | 0.000 | 0.000 | 0.000 | 0.000 | <0.0001 | <0.0001 | 1 |
| 171559 \| Control | k_Bacteria; p_Bacteroidetes; c_Bacteroidia; o_Bacteroidales; f_Bacteroidaceae; g_Bacteroides; s_ \| Control | 1.000 | 697.000 | 109.762 | 201.308 | 1 | <0.0001 | <0.0001 |
| 171559 \| UC | k_Bacteria; p_Bacteroidetes; c_Bacteroidia; o_Bacteroidales; f_Bacteroidaceae; g_Bacteroides; s_ \| UC | 0.000 | 0.000 | 0.000 | 0.000 | <0.0001 | 1 | 1.000 |
| 171559 \| CD | k_Bacteria; p_Bacteroidetes; c_Bacteroidia; o_Bacteroidales; f_Bacteroidaceae; g_Bacteroides; s_ \| CD | 0.000 | 0.000 | 0.000 | 0.000 | <0.0001 | 1.000 | 1 |

In table 2 results for relative abundance of taxa are presented. Taxa that varie significantly in abundance in at least one of the three pairwise comparisons performed (controls vs. CD; controls vs. UC; and CD vs. UC) are shown. In table 2, microbial OTUs that were detected in at least 75% of the samples within each group and that vary significantly in abundance between CD, UC and/or controls are listed. The number of 16S rDNA reads in each sample was normalized by random subsampling to 500,000. Minimum and maximum correspond to the minimum and maximum number of reads obtained; mean corresponds to the mean of the number of reads obtained. P values were generated using a Kruskal-Wallis test with a Dunn's post hoc test. "p|Control" indicates the P values obtained by comparison to the controls; "p|UC" and "p|CD" indicate the P values obtained by comparison to the UC and CD patients respectively. Values in bold indicate significance (P<0.05).

TABLE 2

| Variable | Minimum | Maximum | Mean | Std. dev. | p|Control | p|UC | p|CD |
|---|---|---|---|---|---|---|---|
| PHYLUM | | | | | | | |
| Firmicutes|Control | 177570.000 | 471151.000 | 300049.381 | 95087.202 | 1 | 0.011 | 0.246 |
| Firmicutes|UC | 39474.000 | 359555.000 | 204394.000 | 82968.346 | 0.011 | 1 | 0.075 |
| Firmicutes|CD | 66149.000 | 447067.000 | 259197.486 | 102279.924 | 0.246 | 0.075 | 1 |
| CLASS | | | | | | | |
| Negativicutes|Control | 23.000 | 16688.000 | 1555.333 | 3588.392 | 1 | 0.020 | 0.008 |
| Negativicutes|UC | 95.000 | 39966.000 | 10613.357 | 14349.888 | 0.020 | 1 | 0.799 |
| Negativicutes|CD | 27.000 | 74088.000 | 8759.081 | 15370.608 | 0.008 | 0.799 | 1 |
| Clostridia|Control | 172358.000 | 466967.000 | 290267.667 | 92133.532 | 1 | 0.006 | 0.054 |
| Clostridia|UC | 37917.000 | 356417.000 | 186560.357 | 84887.686 | 0.006 | 1 | 0.173 |
| Clostridia|CD | 9293.000 | 413730.000 | 227236.162 | 109051.179 | 0.054 | 0.173 | 1 |
| Verrucomicrobiae|Control | 0.000 | 1098.000 | 85.381 | 251.309 | 1 | 0.014 | 0.296 |
| Verrucomicrobiae|UC | 0.000 | 13.000 | 1.071 | 3.452 | 0.014 | 1 | 0.075 |
| Verrucomicrobiae|CD | 0.000 | 2103.000 | 95.811 | 357.421 | 0.296 | 0.075 | 1 |
| Betaproteobacteria|Control | 14.000 | 44407.000 | 4215.810 | 10576.956 | 1 | 0.120 | 0.002 |
| Betaproteobacteria|UC | 27.000 | 74113.000 | 12641.071 | 23053.369 | 0.120 | 1 | 0.306 |
| Betaproteobacteria|CD | 26.000 | 129123.000 | 14407.270 | 26352.478 | 0.002 | 0.306 | 1 |
| ORDER | | | | | | | |
| Pasteurellales|Control | 0.000 | 446.000 | 24.238 | 96.821 | 1 | 0.003 | 0.002 |
| Pasteurellales|UC | 0.000 | 6141.000 | 661.857 | 1682.557 | 0.003 | 1 | 0.544 |
| Pasteurellales|CD | 0.000 | 998.000 | 75.135 | 190.092 | 0.002 | 0.544 | 1 |
| Chromatiales|Control | 0.000 | 1.000 | 0.048 | 0.218 | 1 | 0.003 | 0.009 |
| Chromatiales|UC | 0.000 | 12.000 | 2.071 | 3.407 | 0.003 | 1 | 0.331 |
| Chromatiales|CD | 0.000 | 30.000 | 2.054 | 5.637 | 0.009 | 0.331 | 1 |
| Burkholderiales|Control | 9.000 | 44407.000 | 4150.000 | 10590.948 | 1 | 0.764 | 0.015 |
| Burkholderiales|UC | 5.000 | 52910.000 | 6830.000 | 14990.496 | 0.764 | 1 | 0.073 |
| Burkholderiales|CD | 9.000 | 128561.000 | 13994.270 | 26364.706 | 0.015 | 0.073 | 1 |
| Selenomonadales|Control | 23.000 | 16688.000 | 1555.333 | 3588.392 | 1 | 0.020 | 0.008 |
| Selenomonadales|UC | 95.000 | 39966.000 | 10613.357 | 14349.888 | 0.020 | 1 | 0.799 |
| Selenomonadales|CD | 27.000 | 74088.000 | 8759.081 | 15370.608 | 0.008 | 0.799 | 1 |
| Clostridiales|Control | 172357.000 | 466967.000 | 290267.619 | 92133.596 | 1 | 0.006 | 0.054 |
| Clostridiales|UC | 37917.000 | 356417.000 | 186558.857 | 84887.572 | 0.006 | 1 | 0.173 |
| Clostridiales|CD | 9292.000 | 413730.000 | 227233.919 | 109052.061 | 0.054 | 0.173 | 1 |
| Hydrogenophilales|Control | 0.000 | 0.000 | 0.000 | 0.000 | 1 | 0.008 | 0.660 |
| Hydrogenophilales|UC | 0.000 | 2.000 | 0.286 | 0.611 | 0.008 | 1 | 0.011 |
| Hydrogenophilales|CD | 0.000 | 2.000 | 0.054 | 0.329 | 0.660 | 0.011 | 1 |
| Oceanospirillales|Control | 0.000 | 4777.000 | 381.000 | 1090.456 | 1 | 0.007 | 0.127 |
| Oceanospirillales|UC | 1.000 | 8453.000 | 1310.500 | 2596.743 | 0.007 | 1 | 0.100 |
| Oceanospirillales|CD | 0.000 | 2349.000 | 180.459 | 413.881 | 0.127 | 0.100 | 1 |
| Rhizobiales|Control | 0.000 | 2.000 | 0.238 | 0.539 | 1 | 0.001 | 0.537 |
| Rhizobiales|UC | 0.000 | 170.000 | 23.786 | 55.134 | 0.001 | 1 | 0.002 |
| Rhizobiales|CD | 0.000 | 67.000 | 4.243 | 14.245 | 0.537 | 0.002 | 1 |
| Verrucomicrobiales|Control | 0.000 | 1098.000 | 85.381 | 251.309 | 1 | 0.014 | 0.296 |
| Verrucomicrobiales|UC | 0.000 | 13.000 | 1.071 | 3.452 | 0.014 | 1 | 0.075 |
| Verrucomicrobiales|CD | 0.000 | 2103.000 | 95.811 | 357.421 | 0.296 | 0.075 | 1 |
| FAMILY | | | | | | | |
| Verrucomicrobiaceae|Control | 0.000 | 1098.000 | 85.381 | 251.309 | 1 | 0.014 | 0.296 |
| Verrucomicrobiaceae|UC | 0.000 | 13.000 | 1.071 | 3.452 | 0.014 | 1 | 0.075 |
| Verrucomicrobiaceae|CD | 0.000 | 2103.000 | 95.811 | 357.421 | 0.296 | 0.075 | 1 |

TABLE 2-continued

| Variable | Minimum | Maximum | Mean | Std. dev. | p\|Control | p\|UC | p\|CD |
|---|---|---|---|---|---|---|---|
| Staphylococcaceae\|Control | 0.000 | 4079.000 | 355.333 | 910.119 | 1 | 0.345 | 0.009 |
| Staphylococcaceae\|UC | 0.000 | 229.000 | 59.000 | 80.285 | 0.345 | 1 | 0.216 |
| Staphylococcaceae\|CD | 0.000 | 5529.000 | 222.270 | 934.404 | 0.009 | 0.216 | 1 |
| Lachnospiraceae\|Control | 1485.000 | 244085.000 | 73731.762 | 57312.252 | 1 | 0.006 | 0.058 |
| Lachnospiraceae\|UC | 1094.000 | 83206.000 | 26960.929 | 25720.429 | 0.006 | 1 | 0.178 |
| Lachnospiraceae\|CD | 388.000 | 160635.000 | 47128.243 | 45439.902 | 0.058 | 0.178 | 1 |
| Halomonadaceae\|Control | 0.000 | 55.000 | 2.667 | 11.993 | 1 | 0.014 | 0.263 |
| Halomonadaceae\|UC | 0.000 | 711.000 | 52.857 | 189.465 | 0.014 | 1 | 0.083 |
| Halomonadaceae\|CD | 0.000 | 12.000 | 0.811 | 2.246 | 0.263 | 0.083 | 1 |
| Pasteurellaceae\|Control | 0.000 | 446.000 | 24.238 | 96.821 | 1 | 0.003 | 0.002 |
| Pasteurellaceae\|UC | 0.000 | 6141.000 | 661.857 | 1682.557 | 0.003 | 1 | 0.544 |
| Pasteurellaceae\|CD | 0.000 | 998.000 | 75.135 | 190.092 | 0.002 | 0.544 | 1 |
| Paenibacillaceae\|Control | 0.000 | 181.000 | 32.000 | 44.159 | 1 | 0.014 | 0.009 |
| Paenibacillaceae\|UC | 0.000 | 53.000 | 8.286 | 14.435 | 0.014 | 1 | 0.658 |
| Paenibacillaceae\|CD | 0.000 | 617.000 | 23.730 | 100.869 | 0.009 | 0.658 | 1 |
| Listeriaceae\|Control | 0.000 | 11.000 | 1.381 | 3.008 | 1 | 0.310 | 0.011 |
| Listeriaceae\|UC | 0.000 | 3.000 | 0.286 | 0.825 | 0.310 | 1 | 0.272 |
| Listeriaceae\|CD | 0.000 | 2.000 | 0.054 | 0.329 | 0.011 | 0.272 | 1 |
| Bradyrhizobiaceae\|Control | 0.000 | 2.000 | 0.190 | 0.512 | 1 | 0.006 | 0.604 |
| Bradyrhizobiaceae\|UC | 0.000 | 32.000 | 3.714 | 8.914 | 0.006 | 1 | 0.010 |
| Bradyrhizobiaceae\|CD | 0.000 | 57.000 | 3.216 | 11.814 | 0.604 | 0.010 | 1 |
| Methylococcaceae\|Control | 0.000 | 2.000 | 0.190 | 0.512 | 1 | 0.004 | 0.243 |
| Methylococcaceae\|UC | 0.000 | 351.000 | 30.929 | 94.613 | 0.004 | 1 | 0.032 |
| Methylococcaceae\|CD | 0.000 | 4.000 | 0.243 | 0.830 | 0.243 | 0.032 | 1 |
| Hydrogenophilaceae\|Control | 0.000 | 0.000 | 0.000 | 0.000 | 1 | 0.008 | 0.660 |
| Hydrogenophilaceae\|UC | 0.000 | 2.000 | 0.286 | 0.611 | 0.008 | 1 | 0.011 |
| Hydrogenophilaceae\|CD | 0.000 | 2.000 | 0.054 | 0.329 | 0.660 | 0.011 | 1 |
| GENUS | | | | | | | |
| *Porphyromonas*\|Control | 0.000 | 1.000 | 0.143 | 0.359 | 1 | 0.002 | 0.443 |
| *Porphyromonas*\|UC | 0.000 | 42.000 | 6.286 | 12.073 | 0.002 | 1 | 0.007 |
| *Porphyromonas*\|CD | 0.000 | 16.000 | 1.000 | 2.963 | 0.443 | 0.007 | 1 |
| *Lautropia*\|Control | 0.000 | 1.000 | 0.048 | 0.218 | 1 | 0.001 | 0.555 |
| *Lautropia*\|UC | 0.000 | 57.000 | 5.286 | 15.097 | 0.001 | 1 | <0.0001 |
| *Lautropia*\|CD | 0.000 | 0.000 | 0.000 | 0.000 | 0.555 | <0.0001 | 1 |
| *Methylobacterium*\|Control | 0.000 | 1.000 | 0.048 | 0.218 | 1 | 0.004 | 0.243 |
| *Methylobacterium*\|UC | 0.000 | 103.000 | 12.786 | 31.740 | 0.004 | 1 | 0.032 |
| *Methylobacterium*\|CD | 0.000 | 11.000 | 1.000 | 2.759 | 0.243 | 0.032 | 1 |
| *Akkermansia*\|Control | 0.000 | 1098.000 | 85.381 | 251.309 | 1 | 0.014 | 0.296 |
| *Akkermansia*\|UC | 0.000 | 13.000 | 1.071 | 3.452 | 0.014 | 1 | 0.075 |
| *Akkermansia*\|CD | 0.000 | 2103.000 | 95.811 | 357.421 | 0.296 | 0.075 | 1 |
| *Tannerella*\|Control | 0.000 | 60.000 | 2.857 | 13.093 | 1 | 0.042 | 0.431 |
| *Tannerella*\|UC | 0.000 | 1.000 | 0.214 | 0.426 | 0.042 | 1 | 0.004 |
| *Tannerella*\|CD | 0.000 | 0.000 | 0.000 | 0.000 | 0.431 | 0.004 | 1 |
| *Haemophilus*\|Control | 0.000 | 11.000 | 1.381 | 2.941 | 1 | 0.007 | 0.010 |
| *Haemophilus*\|UC | 0.000 | 722.000 | 79.714 | 190.874 | 0.007 | 1 | 0.478 |
| *Haemophilus*\|CD | 0.000 | 600.000 | 30.568 | 101.515 | 0.010 | 0.478 | 1 |
| *Finegoldia*\|Control | 0.000 | 1.000 | 0.048 | 0.218 | 1 | 0.014 | 0.941 |
| *Finegoldia*\|UC | 0.000 | 303.000 | 30.643 | 84.514 | 0.014 | 1 | 0.009 |
| *Finegoldia*\|CD | 0.000 | 1.000 | 0.054 | 0.229 | 0.941 | 0.009 | 1 |

TABLE 2-continued

| Variable | Minimum | Maximum | Mean | Std. dev. | p|Control | p|UC | p|CD |
|---|---|---|---|---|---|---|---|
| *Turicibacter*|Control | 0.000 | 866.000 | 70.190 | 198.733 | 1 | 0.007 | 0.006 |
| *Turicibacter*|UC | 0.000 | 2.000 | 0.286 | 0.611 | 0.007 | 1 | 0.569 |
| *Turicibacter*|CD | 0.000 | 1456.000 | 39.919 | 239.274 | 0.006 | 0.569 | 1 |
| *Nitrincola*|Control | 0.000 | 88.000 | 6.762 | 20.630 | 1 | 0.008 | 0.021 |
| *Nitrincola*|UC | 0.000 | 4354.000 | 397.071 | 1158.944 | 0.008 | 1 | 0.360 |
| *Nitrincola*|CD | 0.000 | 1068.000 | 38.676 | 175.578 | 0.021 | 0.360 | 1 |
| *Hydrogenophilus*|Control | 0.000 | 0.000 | 0.000 | 0.000 | 1 | 0.008 | 0.660 |
| *Hydrogenophilus*|UC | 0.000 | 2.000 | 0.286 | 0.611 | 0.008 | 1 | 0.011 |
| *Hydrogenophilus*|CD | 0.000 | 2.000 | 0.054 | 0.329 | 0.660 | 0.011 | 1 |
| *Listeria*|Control | 0.000 | 11.000 | 1.381 | 3.008 | 1 | 0.310 | 0.011 |
| *Listeria*|UC | 0.000 | 3.000 | 0.286 | 0.825 | 0.310 | 1 | 0.272 |
| *Listeria*|CD | 0.000 | 2.000 | 0.054 | 0.329 | 0.011 | 0.272 | 1 |
| *Actinobacillus*|Control | 0.000 | 6.000 | 0.571 | 1.535 | 1 | 0.005 | 0.018 |
| *Actinobacillus*|UC | 0.000 | 1806.000 | 138.786 | 480.704 | 0.005 | 1 | 0.307 |
| *Actinobacillus*|CD | 0.000 | 243.000 | 15.649 | 45.935 | 0.018 | 0.307 | 1 |
| *Anaerococcus*|Control | 0.000 | 20.000 | 1.095 | 4.358 | 1 | 0.001 | 0.054 |
| *Anaerococcus*|UC | 0.000 | 23670.000 | 1740.571 | 6312.547 | 0.001 | 1 | 0.065 |
| *Anaerococcus*|CD | 0.000 | 1602.000 | 46.324 | 263.052 | 0.054 | 0.065 | 1 |
| *Catonella*|Control | 0.000 | 8.000 | 0.524 | 1.750 | 1 | 0.133 | 0.231 |
| *Catonella*|UC | 0.000 | 13.000 | 2.071 | 3.990 | 0.133 | 1 | 0.007 |
| *Catonella*|CD | 0.000 | 19.000 | 0.595 | 3.149 | 0.231 | 0.007 | 1 |
| *Mobiluncus*|Control | 0.000 | 0.000 | 0.000 | 0.000 | 1 | 0.007 | 0.677 |
| *Mobiluncus*|UC | 0.000 | 3.000 | 0.500 | 1.092 | 0.007 | 1 | 0.009 |
| *Mobiluncus*|CD | 0.000 | 1.000 | 0.027 | 0.164 | 0.677 | 0.009 | 1 |
| *Pantoea*|Control | 0.000 | 0.000 | 0.000 | 0.000 | 1 | 0.058 | 0.002 |
| *Pantoea*|UC | 0.000 | 8.000 | 1.071 | 2.401 | 0.058 | 1 | 0.523 |
| *Pantoea*|CD | 0.000 | 99.000 | 3.432 | 16.194 | 0.002 | 0.523 | 1 |
| *Enterobacter*|Control | 0.000 | 17.000 | 1.810 | 3.829 | 1 | 0.003 | 0.109 |
| *Enterobacter*|UC | 0.000 | 10592.000 | 778.786 | 2824.745 | 0.003 | 1 | 0.057 |
| *Enterobacter*|CD | 0.000 | 3590.000 | 105.892 | 588.904 | 0.109 | 0.057 | 1 |
| *Paenibacillus*|Control | 0.000 | 181.000 | 31.952 | 44.147 | 1 | 0.013 | 0.007 |
| *Paenibacillus*|UC | 0.000 | 53.000 | 8.214 | 14.412 | 0.013 | 1 | 0.699 |
| *Paenibacillus*|CD | 0.000 | 617.000 | 23.595 | 100.894 | 0.007 | 0.699 | 1 |
| *Staphylococcus*|Control | 0.000 | 4079.000 | 353.762 | 910.667 | 1 | 0.224 | 0.010 |
| *Staphylococcus*|UC | 0.000 | 229.000 | 58.357 | 80.759 | 0.224 | 1 | 0.370 |
| *Staphylococcus*|CD | 0.000 | 5529.000 | 214.649 | 925.461 | 0.010 | 0.370 | 1 |
| *Vitreoscilla*|Control | 0.000 | 37.000 | 2.286 | 8.057 | 1 | 0.009 | 0.319 |
| *Vitreoscilla*|UC | 0.000 | 1667.000 | 128.357 | 443.285 | 0.009 | 1 | 0.044 |
| *Vitreoscilla*|CD | 0.000 | 15.000 | 1.622 | 3.192 | 0.319 | 0.044 | 1 |
| *Alcanivorax*|Control | 0.000 | 0.000 | 0.000 | 0.000 | 1 | 0.012 | 1.000 |
| *Alcanivorax*|UC | 0.000 | 5.000 | 0.643 | 1.646 | 0.012 | 1 | 0.006 |
| *Alcanivorax*|CD | 0.000 | 0.000 | 0.000 | 0.000 | 1.000 | 0.006 | 1 |
| *Veillonella*|Control | 6.000 | 1213.000 | 187.571 | 292.401 | 1 | 0.003 | 0.106 |
| *Veillonella*|UC | 23.000 | 38298.000 | 8985.571 | 13795.955 | 0.003 | 1 | 0.063 |
| *Veillonella*|CD | 7.000 | 17002.000 | 2107.243 | 4464.809 | 0.106 | 0.063 | 1 |
| *Tatumella*|Control | 0.000 | 61.000 | 3.381 | 13.347 | 1 | 0.014 | 0.090 |
| *Tatumella*|UC | 0.000 | 1836.000 | 175.643 | 501.883 | 0.014 | 1 | 0.224 |
| *Tatumella*|CD | 0.000 | 71.000 | 5.054 | 13.894 | 0.090 | 0.224 | 1 |
| *Afipia*|Control | 0.000 | 1.000 | 0.095 | 0.301 | 1 | 0.027 | 0.913 |
| *Afipia*|UC | 0.000 | 30.000 | 2.429 | 7.949 | 0.027 | 1 | 0.012 |
| *Afipia*|CD | 0.000 | 3.000 | 0.135 | 0.536 | 0.913 | 0.012 | 1 |

Certain bacterial taxa exhibit higher levels (abundance) in UC or CD or IBD patients and some taxa exhibit lower levels in UC or CD or IBD patients. Therefore, an assay on a gut sample from a patient can be performed to measure an abundance (or level) of a bacterial taxa and by comparing this abundance to that of a predetermined abundance or an average abundance (as in tables 1 or 2) of the taxa derived from sample of patients with UC or CD or IBD. The result allows one to determine whether a patient has UC or CD or IBD.

The abundance or level of bacterial taxa can be determined for example by quantitative DNA analysis such as quantitative polymerase chain reaction. As described above the data can be normalized (example subsampling normalization) as would be known in the art. Therefore the results discussed in the present application can represent relative abundance. It will be appreciated that a person skilled in the art would know to interpret these values to determine the relative levels of bacteria.

A method is also provided in which a diagnosis of UC or CD or IBD is achieved by collecting a gut sample from a patient and from which bacterial taxa levels will be determined using an assay as described above. The gut sample may be from the flushing of the colon wall as described above and still further described below or from stools.

Certain taxa exhibit a statistically significant difference in their abundance between UC patients and CD patients. Therefore by comparing the relative abundance of one or more of these taxa between UC and CD patients it is possible to determine whether the patient has CD or UC disease. For example, Hydrogenophilus is more abundant in both CD and UC patients relative to healthy individuals and furthermore it is more abundant in UC patients than CD patients.

In another aspect of the invention the severity of the disease can also be assessed from the bacterial profile of the gut microbiota. Thus, the severity of CD can be established by measuring the relative abundance of certain bacterial taxa in a gut microbiota sample. In this respect, the relative abundance of one or more microbial taxa from the gut can be compared/correlated with a standard disease activity index. The resulting classification allows the use of relative abundance of bacterial taxa as an indicator of disease severity (Table 3). It will be appreciated that abundance measurements from one or more bacterial taxa can be used for that purpose.

Supplementary Table 6: Taxa that varies significantly in abundance in CD patients in at least one of the three pairwise comparisons performed (mild vs. moderate; mild vs. sever; and moderate vs. severe). In table 3 the number of 16S rDNA reads in each sample was normalized by random subsampling to 500,000. Minimum and maximum correspond to the minimum and maximum number of reads obtained; mean corresponds to the mean of the number of reads obtained. P values were generated using a Kruskal-Wallis test with a Dunn's post hoc test and a Bonferroni correction for multiple hypotheses. "p|mild" indicates the P values obtained by comparison to the CD patients with a mild inflammation; "p|moderate" and "p|severe" indicate the P values obtained by comparison to CD patients with a moderate and severe inflammation respectively. Values in bold indicate significance (P<0.05).

TABLE 3

| Variable | Minimum | Maximum | Mean | Std. deviation | p\| mild | p\| severe | p\| moderate |
|---|---|---|---|---|---|---|---|
| PHYLUM | | | | | | | |
| None | | | | | | | |
| CLASS | | | | | | | |
| Clostridia\|Mild | 174469.000 | 413730.000 | 312892.000 | 87462.076 | 1 | 0.012 | 0.105 |
| Clostridia\|Severe | 9293.000 | 407027.000 | 198223.435 | 105908.496 | 0.012 | 1 | 0.860 |
| Clostridia\|Moderate | 59849.000 | 289226.000 | 206514.200 | 90299.691 | 0.105 | 0.860 | 1 |
| Betaproteobacteria\|Mild | 26.000 | 29550.000 | 4640.333 | 9490.562 | 1 | 0.170 | 0.013 |
| Betaproteobacteria\|Severe | 60.000 | 54643.000 | 10878.696 | 15121.993 | 0.170 | 1 | 0.084 |
| Betaproteobacteria\|Moderate | 2685.000 | 129123.000 | 48219.200 | 55650.162 | 0.013 | 0.084 | 1 |
| ORDER | | | | | | | |
| Clostridiales\|Mild | 174469.000 | 413730.000 | 312892.000 | 87462.076 | 1 | 0.012 | 0.105 |
| Clostridiales\|Severe | 9292.000 | 407027.000 | 198219.870 | 105908.987 | 0.012 | 1 | 0.860 |
| Clostridiales\|Moderate | 59849.000 | 289225.000 | 206514.000 | 90299.462 | 0.105 | 0.860 | 1 |
| FAMILY | | | | | | | |
| Staphylococcaceae\|Mild | 4.000 | 1507.000 | 255.222 | 507.068 | 1 | 0.025 | 0.002 |
| Staphylococcaceae\|Severe | 0.000 | 5529.000 | 257.522 | 1149.930 | 0.025 | 1 | 0.089 |
| Staphylococcaceae\|Moderate | 0.000 | 2.000 | 0.800 | 0.837 | 0.002 | 0.089 | 1 |
| Propionibacteriaceae\|Mild | 0.000 | 1.000 | 0.556 | 0.527 | 1 | 0.016 | 0.484 |
| Propionibacteriaceae\|Severe | 0.000 | 363.000 | 33.652 | 88.327 | 0.016 | 1 | 0.007 |
| Propionibacteriaceae\|Moderate | 0.000 | 1.000 | 0.200 | 0.447 | 0.484 | 0.007 | 1 |
| Acidaminococcaceae\|Mild | 0.000 | 4.000 | 1.111 | 1.691 | 1 | 0.003 | 0.030 |
| Acidaminococcaceae\|Severe | 0.000 | 36271.000 | 2476.261 | 7722.681 | 0.003 | 1 | 0.965 |
| Acidaminococcaceae\|Moderate | 0.000 | 8395.000 | 1712.000 | 3736.459 | 0.030 | 0.965 | 1 |
| Bacillaceae\|Mild | 0.000 | 136.000 | 16.000 | 45.008 | 1 | 0.137 | 0.281 |
| Bacillaceae\|Severe | 0.000 | 6167.000 | 427.174 | 1339.746 | 0.137 | 1 | 0.016 |
| Bacillaceae\|Moderate | 0.000 | 3.000 | 0.600 | 1.342 | 0.281 | 0.016 | 1 |
| Carnobacteriaceae\|Mild | 13.000 | 643.000 | 155.222 | 229.710 | 1 | 0.206 | 0.148 |
| Carnobacteriaceae\|Severe | 5.000 | 76920.000 | 3723.870 | 15973.648 | 0.206 | 1 | 0.008 |
| Carnobacteriaceae\|Moderate | 4.000 | 78.000 | 26.200 | 30.136 | 0.148 | 0.008 | 1 |
| Sutterellaceae\|Mild | 2.000 | 1157.000 | 136.889 | 382.665 | 1 | 0.004 | 0.004 |
| Sutterellaceae\|Severe | 1.000 | 54546.000 | 7005.435 | 15182.702 | 0.004 | 1 | 0.342 |
| Sutterellaceae\|Moderate | 9.000 | 128471.000 | 42805.000 | 59466.785 | 0.004 | 0.342 | 1 |
| GENUS | | | | | | | |
| *Atopobium*\|Mild | 1.000 | 257.000 | 60.778 | 81.208 | 1 | 0.704 | 0.056 |
| *Atopobium*\|Severe | 0.000 | 1273.000 | 118.652 | 263.676 | 0.704 | 1 | 0.014 |
| *Atopobium*\|Moderate | 0.000 | 7.000 | 4.800 | 2.775 | 0.056 | 0.014 | 1 |
| *Propionibacterium*\|Mild | 0.000 | 1.000 | 0.556 | 0.527 | 1 | 0.016 | 0.484 |
| *Propionibacterium*\|Severe | 0.000 | 363.000 | 33.652 | 88.327 | 0.016 | 1 | 0.007 |
| *Propionibacterium*\|Moderate | 0.000 | 1.000 | 0.200 | 0.447 | 0.484 | 0.007 | 1 |
| *Trichococcus*\|Mild | 0.000 | 3.000 | 0.556 | 1.014 | 1 | 0.002 | 0.031 |
| *Trichococcus*\|Severe | 0.000 | 0.000 | 0.000 | 0.000 | 0.002 | 1 | 1.000 |
| *Trichococcus*\|Moderate | 0.000 | 0.000 | 0.000 | 0.000 | 0.031 | 1.000 | 1 |
| *Pectobacterium*\|Mild | 0.000 | 0.000 | 0.000 | 0.000 | 1 | 1.000 | 0.029 |
| *Pectobacterium*\|Severe | 0.000 | 0.000 | 0.000 | 0.000 | 1.000 | 1 | 0.014 |

TABLE 3-continued

| Variable | Minimum | Maximum | Mean | Std. deviation | p\| mild | p\| severe | p\| moderate |
|---|---|---|---|---|---|---|---|
| Pectobacterium\|Moderate | 0.000 | 80.000 | 16.000 | 35.777 | 0.029 | 0.014 | 1 |
| Granulicatella\|Mild | 13.000 | 581.000 | 145.444 | 215.009 | 1 | 0.229 | 0.167 |
| Granulicatella\|Severe | 5.000 | 74250.000 | 3494.130 | 15434.318 | 0.229 | 1 | 0.012 |
| Granulicatella\|Moderate | 3.000 | 78.000 | 25.000 | 30.406 | 0.167 | 0.012 | 1 |
| Jonquetella\|Mild | 0.000 | 0.000 | 0.000 | 0.000 | 1 | 1.000 | 0.029 |
| Jonquetella\|Severe | 0.000 | 0.000 | 0.000 | 0.000 | 1.000 | 1 | 0.014 |
| Jonquetella\|Moderate | 0.000 | 83.000 | 16.600 | 37.119 | 0.029 | 0.014 | 1 |
| Riemerella\|Mild | 0.000 | 0.000 | 0.000 | 0.000 | 1 | 1.000 | 0.002 |
| Riemerella\|Severe | 0.000 | 0.000 | 0.000 | 0.000 | 1.000 | 1 | 0.000 |
| Riemerella\|Moderate | 0.000 | 3.000 | 0.800 | 1.304 | 0.002 | 0.000 | 1 |
| Mogibacterium\|Mild | 0.000 | 45.000 | 7.556 | 14.934 | 1 | 0.187 | 0.207 |
| Mogibacterium\|Severe | 0.000 | 376.000 | 34.478 | 82.168 | 0.187 | 1 | 0.013 |
| Mogibacterium\|Moderate | 0.000 | 1.000 | 0.200 | 0.447 | 0.207 | 0.013 | 1 |
| Staphylococcus\|Mild | 4.000 | 1247.000 | 226.333 | 428.093 | 1 | 0.024 | 0.002 |
| Staphylococcus\|Severe | 0.000 | 5529.000 | 256.565 | 1150.035 | 0.024 | 1 | 0.090 |
| Staphylococcus\|Moderate | 0.000 | 2.000 | 0.800 | 0.837 | 0.002 | 0.090 | 1 |
| Sutterella\|Mild | 2.000 | 1157.000 | 136.889 | 382.665 | 1 | 0.004 | 0.004 |
| Sutterella\|Severe | 1.000 | 54546.000 | 7005.435 | 15182.702 | 0.004 | 1 | 0.342 |
| Sutterella\|Moderate | 9.000 | 128471.000 | 42805.000 | 59466.785 | 0.004 | 0.342 | 1 |
| Phascolarctobacterium\|Mild | 0.000 | 4.000 | 1.111 | 1.691 | 1 | 0.003 | 0.030 |
| Phascolarctobacterium\|Severe | 0.000 | 36271.000 | 2476.261 | 7722.681 | 0.003 | 1 | 0.965 |
| Phascolarctobacterium\|Moderate | 0.000 | 8395.000 | 1712.000 | 3736.459 | 0.030 | 0.965 | 1 |
| Comamonas\|Mild | 0.000 | 3.000 | 0.667 | 1.118 | 1 | 0.016 | 0.054 |
| Comamonas\|Severe | 0.000 | 1.000 | 0.043 | 0.209 | 0.016 | 1 | 0.792 |
| Comamonas\|Moderate | 0.000 | 0.000 | 0.000 | 0.000 | 0.054 | 0.792 | 1 |
| Hylemonella\|Mild | 0.000 | 0.000 | 0.000 | 0.000 | 1 | 1.000 | 0.029 |
| Hylemonella\|Severe | 0.000 | 0.000 | 0.000 | 0.000 | 1.000 | 1 | 0.014 |
| Hylemonella\|Moderate | 0.000 | 1.000 | 0.200 | 0.447 | 0.029 | 0.014 | 1 |
| Xenorhabdus\|Mild | 0.000 | 0.000 | 0.000 | 0.000 | 1 | 1.000 | 0.029 |
| Xenorhabdus\|Severe | 0.000 | 0.000 | 0.000 | 0.000 | 1.000 | 1 | 0.014 |
| Xenorhabdus\|Moderate | 0.000 | 1.000 | 0.200 | 0.447 | 0.029 | 0.014 | 1 |
| Averyella\|Mild | 0.000 | 0.000 | 0.000 | 0.000 | 1 | 1.000 | 0.029 |
| Averyella\|Severe | 0.000 | 0.000 | 0.000 | 0.000 | 1.000 | 1 | 0.014 |
| Averyella\|Moderate | 0.000 | 11.000 | 2.200 | 4.919 | 0.029 | 0.014 | 1 |

It will be appreciated that it is possible to refine the assessment of the stage or severity of the disease by combining the measurement(s) of the abundance of bacterial taxa with the observation of a choice of symptoms underlying the classic disease indexes to arrive at the establishment of a diagnosis. For example it may be desirable or sometimes only possible to measure only a limited set of standard symptoms associated with disease indexes. This limited set of symptoms may not be sufficient to pose a diagnostic. In such cases it may be possible to combine an assay involving the measurement of bacterial taxa to provide additional information on the nature or stage of the disease.

Figure 1B:
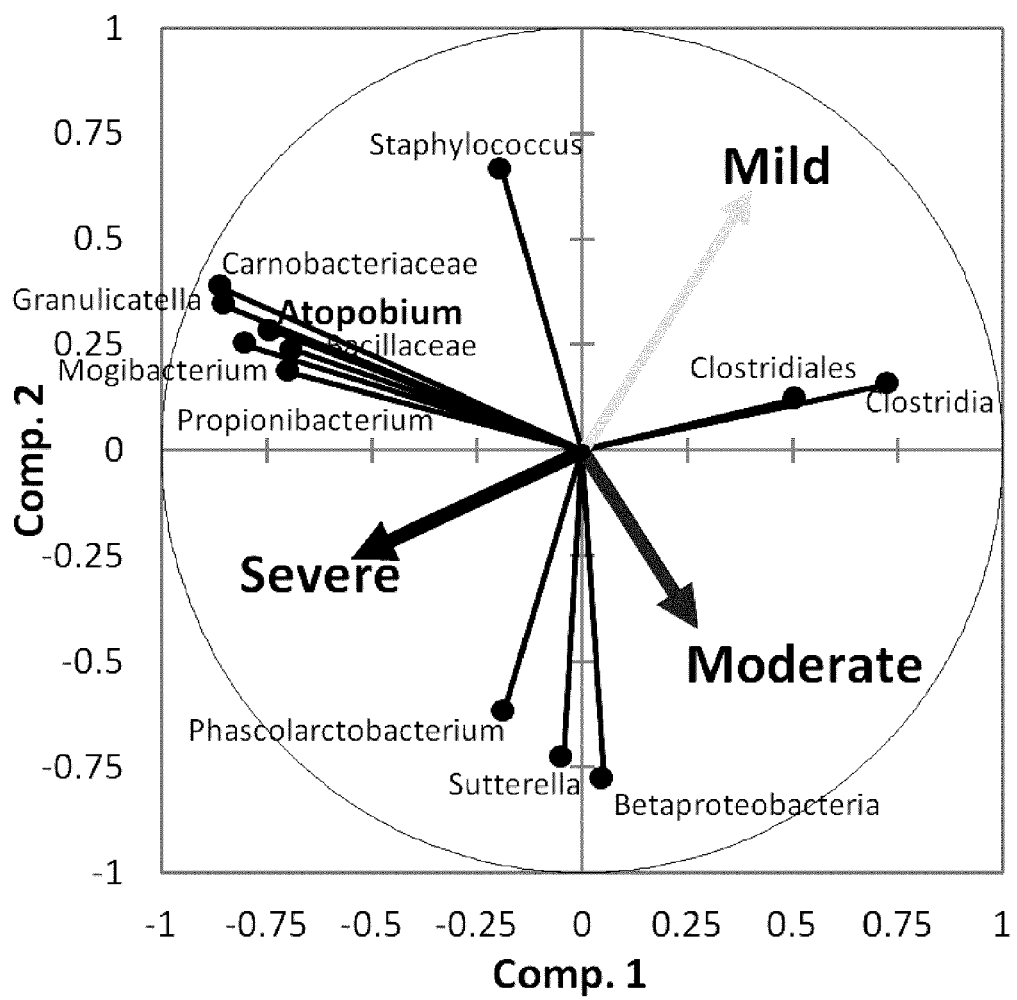
Figure 1C:
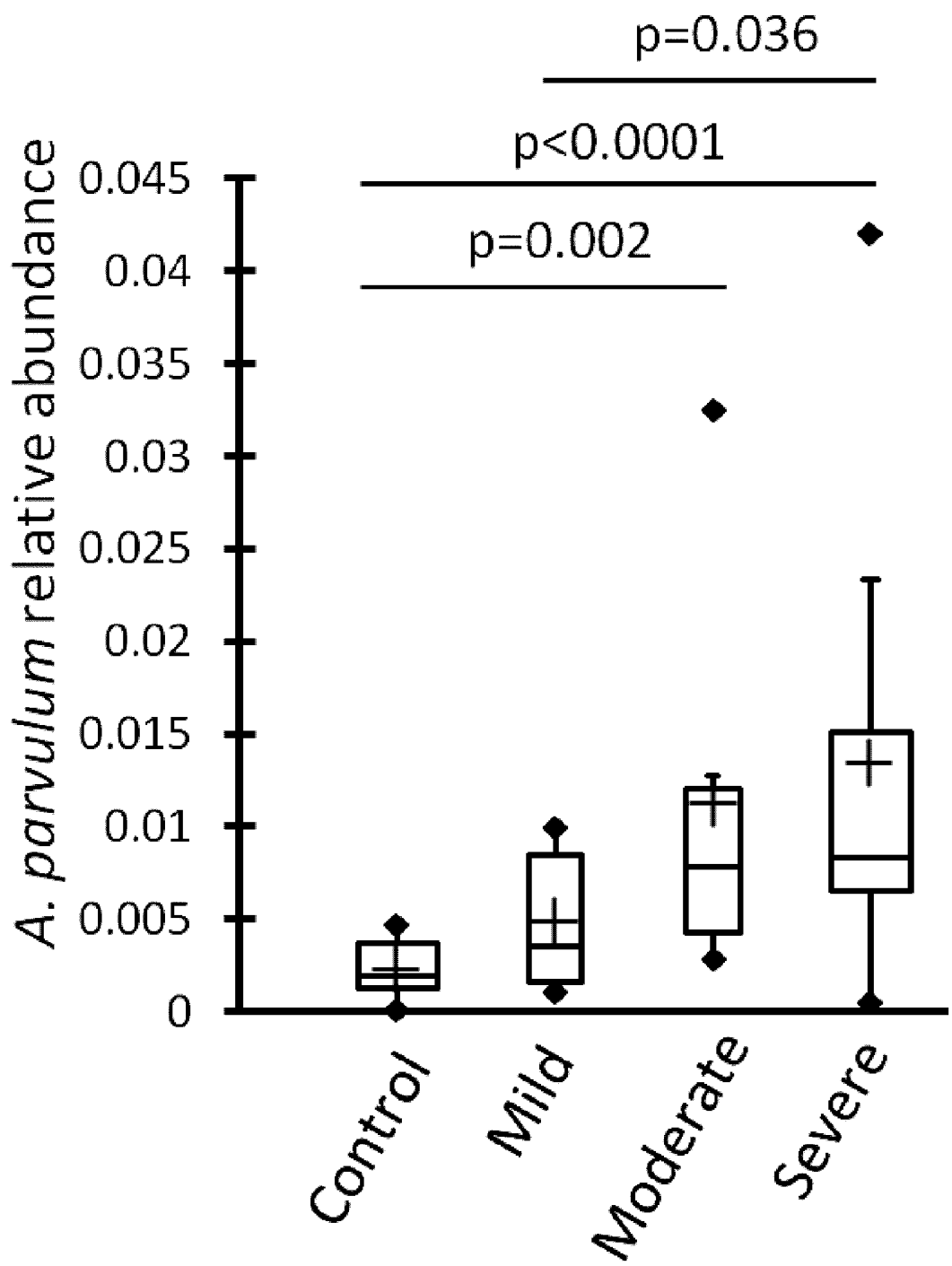

In an aspect of the invention A. parvulum, an $H_2S$ producer, is a good marker of CD exhibiting a higher relative abundance in patient with CD than in controls. Furthermore, the relative abundance of A. parvulum compared to core bacterial taxa abundance is also a measure of the presence and severity of the disease. For example an abundance of A. parvulum relative to the core greater than 0.005% is indicative of moderate or severe stage of the disease (FIG. 1C). Furthermore severity of CD can also be characterized by a significant increased abundance of Proteobacteria microbes. Severe CD and UC can also be characterized by an increased in the relative abundance of $H_2S$ producers compared to controls. It will be appreciated that specific taxa can be used to assess the severity of disease as described in Table 3.

In yet another aspect of the invention a decrease in the relative abundance of butyrate producers such as Firmicutes, Clostridia, Clostridiales and Lachnopiraceae Eubacterium and Faecalibacterium is indicative of the presence of disease (CD or UC).

The measurements of the abundance of bacterial taxa using DNA quatification can generally be done by methods that are known in the art. However in one aspect of the invention there is provided a method for determining the abundance of A. parvulum by absolute quantitative DNA measurement by performing PCR on the extracted metagenomic DNA. The following primers for the quantitative measurements of A. parvulum were developed: Aparv-711F 5'-GGGGAGTATTTCTTCCGTGCCG-3' (SEQ ID NO. 1) and Aparv-881R 5'-CTTCACCTAAATGTCAA GCCCTGG-3' (SEQ ID NO. 2). The development of these primers enables the use of an assay for measuring the abundance of A. parvulum that is highly specific, rapid and reliable. Thus in an another aspect of the invention there is also provided kits that would comprise these primers and other reagents as would be known in the art to detect A. parvulum or other taxa useful for the diagnosis, assessment or staging of UC, CD or IBD as described herein.

In further embodiment of the invention, the presence of UC and CD disease can be assessed by the presence, absence and/or relative abundance of certain host proteins. Proteins can be identified and measured by techniques known in the art such as shotgun mass-spectrometry in conjunction with protein fractionation. Other method for detecting specific proteins such as, immunology based methods (antibodies), western blots, spectrophotometry, enzyme assays, ELISA and any other method as would be known to one skilled in the art may also be used.

Table 4 provides a list of all differentially expressed proteins and their variable importance in projection scores (VIP) derived from the calculated PLS-DA. (Control v. CD with increasing inflammation severity)

TABLE 4

| Variable | Comp 1 VIP | Comp 2 VIP | Comp 3 VIP |
| --- | --- | --- | --- |
| General transcription factor IIA subunit 1; TFIIA p19 subunit; TFIIA p35 subunit; TFIIAL; Transcription initiation factor IIA alpha chain; Transcription initiation factor IIA beta chain; Transcription initiation factor IIA subunit 1; Transcription initiation factor TFIIA 42 kDa subunit | 2.513 | 1.975 | 1.814 |
| Angiotensin-binding protein; Microsomal endopeptidase; Mitochondrial oligopeptidase M; Neurolysin, mitochondrial; Neurotensin endopeptidase | 2.296 | 1.901 | 1.745 |
| Defensin, alpha 5; Defensin-5 | 2.013 | 1.575 | 1.399 |
| Mineral dust-induced gene protein; MYC-induced nuclear antigen; Nucleolar protein 52 | 1.942 | 1.793 | 1.585 |
| Glutaminase kidney isoform, mitochondrial; K-glutaminase; L-glutamine amidohydrolase | 1.880 | 1.538 | 1.358 |
| Ethanolaminephosphotransferase 1; Selenoprotein I; Putative uncharacterized protein ENSP00000385426; Putative uncharacterized protein ENSP00000391804 | 1.853 | 1.918 | 1.702 |
| 18S rRNA dimethylase; DIM1 dimethyladenosine transferase 1-like; Probable dimethyladenosine transferase; S-adenosylmethionine-6-N,N-adenosyl(rRNA) dimethyltransferase | 1.790 | 1.524 | 1.435 |
| 6PF-2-K/Fru-2,6-P2ase heart-type isozyme; 6-phosphofructo-2-kinase; 6-phosphofructo-2-kinase/fructose-2,6-biphosphatase 2; Fructose-2,6-bisphosphatase | 1.717 | 1.442 | 1.275 |
| Armadillo repeat-containing protein 8; cDNA FLJ56387, highly similar to Mus musculus armadillo repeat containing 8 (Armc8), mRNA; Putative uncharacterized protein ARMC8; Armadillo repeat containing 8, isoform CRA_g; cDNA FLJ53383, highly similar to Homo sapiens armadillo repeat containing 8 (ARMC8), transcript variant 2, mRNA | 1.692 | 1.548 | 1.376 |
| Aconitase 2, mitochondrial; Aconitate hydratase, mitochondrial; Citrate hydro-lyase; cDNA FLJ60429, highly similar to Aconitate hydratase, mitochondrial (EC 4.2.1.3); cDNA FLJ50886, highly similar to Aconitate hydratase, mitochondrial(EC 4.2.1.3) | 1.645 | 1.338 | 1.191 |
| 2C4D; Class II mMOB1; Mob1 homolog 3; Mps one binder kinase activator-like 3; Preimplantation protein 3; cDNA FLJ52887, highly similar to Preimplantation protein 3 | 1.634 | 1.359 | 1.203 |
| Iron-sulfur subunit of complex II; Succinate dehydrogenase [ubiquinone] iron-sulfur subunit, mitochondrial | 1.612 | 1.266 | 1.216 |
| Reticulocalbin-1; cDNA FLJ55835, highly similar to Reticulocalbin-1 | 1.593 | 1.238 | 1.093 |
| DRB sensitivity-inducing factor 14 kDa subunit; DRB sensitivity-inducing factor small subunit; Transcription elongation factor SPT4 | 1.592 | 1.247 | 1.102 |
| Rhodanese; Thiosulfate sulfurtransferase | 1.590 | 1.257 | 1.112 |
| 22 kDa protein; CP-22; Sorcin; V19; Putative uncharacterized protein SRI; cDNA FLJ60640, highly similar to Sorcin; cDNA FLJ54267, moderately similar to Sorcin | 1.589 | 1.282 | 1.144 |
| Flavoprotein subunit of complex II; Succinate dehydrogenase [ubiquinone] flavoprotein subunit, mitochondrial | 1.576 | 1.225 | 1.169 |
| Acetylneuraminyl hydrolase; G9 sialidase; Lysosomal sialidase; N-acetyl-alpha-neuraminidase 1; Sialidase-1 | 1.562 | 1.955 | 1.773 |
| Beta-IV spectrin; Spectrin beta chain, brain 3; Spectrin, non-erythroid beta chain 3; Putative uncharacterized protein SPTBN4 | 1.557 | 1.291 | 1.194 |
| Translocation protein SEC63 homolog | 1.542 | 1.555 | 1.373 |
| Epidermal-type fatty acid-binding protein; Fatty acid-binding protein 5; Fatty acid-binding protein, epidermal; Psoriasis-associated fatty acid-binding protein homolog | 1.540 | 1.206 | 1.071 |
| Complex I-51 kd; NADH dehydrogenase [ubiquinone] flavoprotein 1, mitochondrial; NADH dehydrogenase flavoprotein 1; NADH-ubiquinone oxidoreductase 51 kDa subunit; cDNA FLJ57949, highly similar to NADH-ubiquinone oxidoreductase 51 kDa subunit, mitochondrial (EC 1.6.5.3); cDNA, FLJ79021, highly similar to NADH-ubiquinone oxidoreductase 51 kDa subunit, mitochondrial (EC 1.6.5.3) | 1.530 | 1.205 | 1.205 |
| Calregulin; Calreticulin; CRP55; Endoplasmic reticulum resident protein 60; grp60; HACBP; cDNA FLJ58668, highly similar to Calreticulin | 1.528 | 1.220 | 1.077 |
| UDP-glucose 6-dehydrogenase; cDNA FLJ60093, highly similar to UDP-glucose 6-dehydrogenase (EC 1.1.1.22) | 1.522 | 1.183 | 1.052 |
| 4-alpha-glucanotransferase; Amylo-alpha-1,6-glucosidase; Dextrin 6-alpha-D-glucosidase; Glycogen debrancher; Glycogen debranching enzyme; Oligo-1,4-1,4-glucantransferase | 1.516 | 1.200 | 1.072 |
| Malic enzyme 2; NAD-dependent malic enzyme, mitochondrial | 1.514 | 1.225 | 1.081 |
| Delta(3),delta(2)-enoyl-CoA isomerase; Diazepam-binding inhibitor-related protein 1; Dodecenoyl-CoA isomerase; DRS-1; Hepatocellular carcinoma-associated antigen 88; Peroxisomal 3,2-trans-enoyl-CoA isomerase; Renal carcinoma antigen NY-REN-1; Putative uncharacterized protein PECI | 1.513 | 1.178 | 1.046 |
| Complex I-75 kD; NADH-ubiquinone oxidoreductase 75 kDa subunit, mitochondrial; cDNA FLJ60586, highly similar to NADH-ubiquinone oxidoreductase 75 kDa subunit, mitochondrial (EC 1.6.5.3) | 1.510 | 1.324 | 1.181 |
| cDNA FLJ53665, highly similar to Four and a half LIM domains protein 1; Four and a half LIM domains 1; Four and a half LIM domains protein 1; Skeletal muscle LIM-protein 1 | 1.500 | 1.168 | 1.031 |
| Putative adenosylhomocysteinase 3; S-adenosylhomocysteine hydrolase-like protein 2; S-adenosyl-L-homocysteine hydrolase 3 | 1.499 | 1.165 | 1.031 |
| 28S ribosomal protein S9, mitochondrial | 1.489 | 1.198 | 1.121 |
| 150 kDa oxygen-regulated protein; 170 kDa glucose-regulated protein; Hypoxia up-regulated protein 1; cDNA FLJ54708, highly similar to 150 kDa oxygen-regulated protein (Orp150) | 1.480 | 1.179 | 1.041 |
| Complex I-39 kD; NADH dehydrogenase [ubiquinone] 1 alpha subcomplex subunit 9, mitochondrial; NADH-ubiquinone oxidoreductase 39 kDa subunit | 1.466 | 1.152 | 1.083 |
| DDAHI; Dimethylargininase-1; N(G),N(G)-dimethylarginine dimethylaminohydrolase 1; cDNA FLJ54083, highly similar to NG,NG-dimethylarginine dimethylaminohydrolase 1 (EC 3.5.3.18); cDNA FLJ54119, highly similar to NG,NG-dimethylarginine dimethylaminohydrolase 1 (EC 3.5.3.18) | 1.465 | 1.177 | 1.072 |

TABLE 4-continued

| Variable | Comp 1 VIP | Comp 2 VIP | Comp 3 VIP |
|---|---|---|---|
| Phenylalanine--tRNA ligase beta chain; Phenylalanyl-tRNA synthetase beta chain | 1.462 | 1.154 | 1.080 |
| ABP-278; ABP-280 homolog; Actin-binding-like protein; Beta-filamin; Filamin homolog 1; Filamin-3; Filamin-B; Thyroid autoantigen; Truncated actin-binding protein | 1.462 | 1.166 | 1.032 |
| GTP-specific succinyl-CoA synthetase subunit beta; Succinyl-CoA ligase [GDP-forming] subunit beta, mitochondrial; Succinyl-CoA synthetase beta-G chain | 1.459 | 1.151 | 1.018 |
| TPPP/p20; Tubulin polymerization-promoting protein family member 3 | 1.455 | 1.376 | 1.275 |
| F8W031; F8VXJ7; F8VP03 | 1.450 | 1.187 | 1.058 |
| Protein NipSnap homolog 1 | 1.438 | 1.119 | 0.993 |
| 78 kDa gastrin-binding protein; Long chain 3-hydroxyacyl-CoA dehydrogenase; Long-chain enoyl-CoA hydratase; TP-alpha; Trifunctional enzyme subunit alpha, mitochondrial | 1.434 | 1.118 | 1.032 |
| Antioxidant enzyme AOE372; Peroxiredoxin IV; Peroxiredoxin-4; Thioredoxin peroxidase AO372; Thioredoxin-dependent peroxide reductase A0372 | 1.421 | 1.144 | 1.011 |
| Calumenin; Crocalbin; IEF SSP 9302 | 1.418 | 1.286 | 1.136 |
| GTPase IMAP family member 4; Immunity-associated nucleotide 1 protein; Immunity-associated protein 4; cDNA FLJ51351, highly similar to GTPase, IMAP family member 4 | 1.418 | 1.105 | 0.975 |
| Plakophilin-2; Truncated plakophilin-2 | 1.417 | 1.103 | 1.000 |
| Adaptor protein complex AP-1 mu-2 subunit; Adaptor-related protein complex 1 mu-2 subunit; AP-1 complex subunit mu-2; AP-mu chain family member mu1B; Clathrin assembly protein complex 1 medium chain 2; Golgi adaptor HA1/AP1 adaptin mu-2 subunit; Mu1B-adaptin; Mu-adaptin 2 | 1.417 | 1.262 | 1.117 |
| Complex III subunit 1; Core protein I; Cytochrome b-c1 complex subunit 1, mitochondrial; Ubiquinol-cytochrome-c reductase complex core protein 1 | 1.413 | 1.209 | 1.071 |
| 90 kDa ribosomal protein S6 kinase 3; Insulin-stimulated protein kinase 1; MAP kinase-activated protein kinase 1b; pp90RSK2; Ribosomal protein S6 kinase alpha-3; Ribosomal S6 kinase 2; cDNA, FLJ79381, highly similar to Ribosomal protein S6 kinase alpha-3 (EC 2.7.11.1); cDNA FLJ56618, highly similar to Ribosomal protein S6 kinase alpha-3 (EC 2.7.11.1) | 1.410 | 1.200 | 1.080 |
| 3-5 RNA exonuclease OLD35; PNPase old-35; Polynucleotide phosphorylase 1; Polynucleotide phosphorylase-like protein; Polyribonucleotide nucleotidyltransferase 1, mitochondrial | 1.407 | 1.255 | 1.155 |
| Complex I-B15; NADH dehydrogenase [ubiquinone] 1 beta subcomplex subunit 4; NADH-ubiquinone oxidoreductase B15 subunit; Putative uncharacterized protein NDUFB4 | 1.397 | 1.113 | 1.010 |
| Carnitine O-palmitoyltransferase 2, mitochondrial; Carnitine palmitoyltransferase II | 1.396 | 1.089 | 0.976 |
| Aldehyde dehydrogenase 5; Aldehyde dehydrogenase family 1 member B1; Aldehyde dehydrogenase X, mitochondrial; cDNA FLJ51238, highly similar to Aldehyde dehydrogenase X, mitochondrial (EC 1.2.1.3) | 1.393 | 1.120 | 0.988 |
| Coatomer subunit epsilon; Epsilon-coat protein; Coatomer protein complex, subunit epsilon, isoform CRA_e; Putative uncharacterized protein COPE | 1.388 | 1.080 | 0.959 |
| Ethylmalonic encephalopathy protein 1; Hepatoma subtracted clone one protein; Protein ETHE1, mitochondrial | 1.383 | 1.090 | 0.974 |
| SRA stem-loop-interacting RNA-binding protein, mitochondrial | 1.382 | 1.075 | 0.960 |
| 15-hydroxyprostaglandin dehydrogenase [NADP+]; Carbonyl reductase [NADPH] 1; NADPH-dependent carbonyl reductase 1; Prostaglandin 9-ketoreductase; Prostaglandin-E(2) 9-reductase; Putative uncharacterized protein CBR1; Carbonyl reductase 1, isoform CRA_c; cDNA FLJ60474, highly similar to Carbonyl reductase | 1.379 | 1.085 | 1.043 |
| ER-Golgi intermediate compartment 53 kDa protein; Gp58; Intracellular mannose-specific lectin MR60; Lectin mannose-binding 1; Protein ERGIC-53 | 1.374 | 1.129 | 1.046 |
| Intestinal trefoil factor; Polypeptide P1.B; Trefoil factor 3 | 1.369 | 1.093 | 0.971 |
| 78 kDa glucose-regulated protein; Endoplasmic reticulum lumenal Ca(2+)-binding protein grp78; Heat shock 70 kDa protein 5; Immunoglobulin heavy chain-binding protein | 1.366 | 1.104 | 1.046 |
| Complex I-13 kD-A; NADH dehydrogenase [ubiquinone] iron-sulfur protein 6, mitochondrial; NADH-ubiquinone oxidoreductase 13 kDa-A subunit | 1.365 | 1.090 | 0.968 |
| 3-ketoacyl-CoA thiolase, mitochondrial; Acetyl-CoA acyltransferase; Beta-ketothiolase; Mitochondrial 3-oxoacyl-CoA thiolase; T1 | 1.365 | 1.097 | 1.028 |
| Endoplasmic reticulum resident protein 46; Thioredoxin domain-containing protein 5; Thioredoxin-like protein p46; TXNDC5 protein; cDNA, FLJ96678, Homo sapiens thioredoxin domain containing 5 (TXNDC5), mRNA; HCG1811539, isoform CRA_b | 1.363 | 1.103 | 0.994 |
| Elongation factor Tu, mitochondrial; P43 | 1.361 | 1.065 | 0.985 |
| Outer mitochondrial membrane protein porin 2; Voltage-dependent anion-selective channel protein 2; Voltage-dependent anion channel 2; cDNA FLJ60120, highly similar to Voltage-dependent anion-selective channel protein 2; cDNA, FLJ78818, highly similar to Voltage-dependent anion-selective channel protein 2 | 1.361 | 1.060 | 0.938 |
| 63 kDa membrane protein; Cytoskeleton-associated protein 4 | 1.361 | 1.102 | 0.975 |
| Cytovillin; Ezrin; p81; Villin-2 | 1.360 | 1.057 | 0.937 |
| Myosin I beta; Myosin-Ic | 1.359 | 1.071 | 0.948 |
| 250/210 kDa paraneoplastic pemphigus antigen; Desmoplakin | 1.356 | 1.126 | 1.002 |
| Very long-chain specific acyl-CoA dehydrogenase, mitochondrial | 1.355 | 1.089 | 0.983 |
| 15-oxoprostaglandin 13-reductase; Prostaglandin reductase 2; Zinc-binding alcohol dehydrogenase domain-containing protein 1 | 1.353 | 1.160 | 1.057 |
| Complex III subunit 2; Core protein II; Cytochrome b-c1 complex subunit 2, mitochondrial; Ubiquinol-cytochrome-c reductase complex core protein 2 | 1.345 | 1.200 | 1.182 |
| Aspartate aminotransferase, mitochondrial; Fatty acid-binding protein; Glutamate oxaloacetate transaminase 2; Plasma membrane-associated fatty acid-binding protein; Transaminase A | 1.339 | 1.041 | 0.919 |
| CML33; Phenylalanine-tRNA ligase alpha chain; Phenylalanyl-tRNA synthetase alpha chain; cDNA FLJ50378, highly similar to Phenylalanyl-tRNA synthetase alpha chain (EC 6.1.1.20) | 1.337 | 1.179 | 1.051 |

TABLE 4-continued

| Variable | Comp 1 VIP | Comp 2 VIP | Comp 3 VIP |
|---|---|---|---|
| Sodium pump subunit alpha-1; Sodium/potassium-transporting ATPase subunit alpha-1; ATPase, Na+/K+ transporting, alpha 1 polypeptide, isoform CRA_a; cDNA FLJ52430, highly similar to Sodium/potassium-transporting ATPase alpha-1 chain (EC 3.6.3.9) | 1.335 | 1.042 | 0.927 |
| Putative uncharacterized protein MLLT4; Afadin; ALL1-fused gene from chromosome 6 protein; Myeloid/lymphoid or mixed-lineage leukemia (Trithorax homolog, *Drosophila*); translocated to, 4 | 1.334 | 1.277 | 1.207 |
| Cytochrome c oxidase polypeptide Vb; Cytochrome c oxidase subunit 5B, mitochondrial | 1.332 | 1.229 | 1.092 |
| 35 kDa lectin; Carbohydrate-binding protein 35; Galactose-specific lectin 3; Galactoside-binding protein; Galectin-3; IgE-binding protein; L-31; Laminin-binding protein; Lectin L-29; Mac-2 antigen | 1.328 | 1.057 | 0.972 |
| Complex I-B22; LYR motif-containing protein 3; NADH dehydrogenase [ubiquinone] 1 beta subcomplex subunit 9; NADH-ubiquinone oxidoreductase B22 subunit | 1.327 | 1.179 | 1.045 |
| 3-ketoacyl-CoA thiolase; Acetyl-CoA acyltransferase; Beta-ketothiolase; TP-beta; Trifunctional enzyme subunit beta, mitochondrial; cDNA FLJ56214, highly similar to Trifunctional enzyme subunit beta, mitochondrial; Putative uncharacterized protein HADHB | 1.325 | 1.030 | 0.972 |
| Endoplasmic reticulum resident protein 28; Endoplasmic reticulum resident protein 29; Endoplasmic reticulum resident protein 31 | 1.322 | 1.061 | 0.938 |
| Alu corepressor 1; Antioxidant enzyme B166; Liver tissue 2D-page spot 71B; Peroxiredoxin V; Peroxiredoxin-5, mitochondrial; Peroxisomal antioxidant enzyme; PLP; Thioredoxin peroxidase PMP20; Thioredoxin reductase; TPx type VI; Putative uncharacterized protein PRDX5 | 1.316 | 1.071 | 0.947 |
| ER-Golgi SNARE of 24 kDa; SEC22 vesicle-trafficking protein homolog B; SEC22 vesicle-trafficking protein-like 1; Vesicle-trafficking protein SEC22b | 1.315 | 1.023 | 0.937 |
| Calcium-binding mitochondrial carrier protein Aralar2; Citrin; Mitochondrial aspartate glutamate carrier 2; Solute carrier family 25 member 13 | 1.314 | 1.021 | 0.944 |
| RRP12-like protein | 1.311 | 1.083 | 0.961 |
| Endoplasmic reticulum resident protein 70; Endoplasmic reticulum resident protein 72; Protein disulfide-isomerase A4 | 1.311 | 1.110 | 0.980 |
| Myosin-Id | 1.308 | 1.070 | 0.944 |
| Actin-depolymerizing factor; Destrin | 1.306 | 1.027 | 0.918 |
| Complex I-B14.5a; NADH dehydrogenase [ubiquinone] 1 alpha subcomplex subunit 7; NADH-ubiquinone oxidoreductase subunit B14.5a | 1.305 | 1.115 | 1.169 |
| Beta-G1; Beta-glucuronidase | 1.297 | 1.019 | 0.921 |
| Chymotrypsin-like elastase family member 3A; Elastase IIIA; Elastase-3A; Protease E | 1.297 | 1.020 | 0.910 |
| 17-beta-hydroxysteroid dehydrogenase 11; 17-beta-hydroxysteroid dehydrogenase XI; Cutaneous T-cell lymphoma-associated antigen HD-CL-03; Dehydrogenase/reductase SDR family member 8; Estradiol 17-beta-dehydrogenase 11; Retinal short-chain dehydrogenase/reductase 2 | 1.294 | 1.013 | 0.895 |
| Interleukin-25; Stromal cell-derived growth factor SF20; UPF0556 protein C19orf10 | 1.292 | 1.121 | 0.990 |
| Complex III subunit 3; Complex III subunit III; Cytochrome b; Cytochrome b-c1 complex subunit 3; Ubiquinol-cytochrome-c reductase complex cytochrome b subunit | 1.287 | 1.237 | 1.209 |
| Cellular thyroid hormone-binding protein; p55; Prolyl 4-hydroxylase subunit beta; Protein disulfide-isomerase; cDNA FLJ59430, highly similar to Protein disulfide-isomerase (EC 5.3.4.1) | 1.285 | 1.018 | 0.995 |
| Importin-4; Importin-4b; Ran-binding protein 4 | 1.280 | 1.268 | 1.137 |
| 94 kDa glucose-regulated protein; Endoplasmin; gp96 homolog; Heat shock protein 90 kDa beta member 1; Tumor rejection antigen 1 | 1.277 | 1.040 | 1.005 |
| Amine oxidase [flavin-containing] A; Monoamine oxidase type A; cDNA FLJ61220, highly similar to Amine oxidase (flavin-containing) A (EC 1.4.3.4) | 1.276 | 1.023 | 0.903 |
| Ubiquitin-fold modifier 1 | 1.269 | 1.042 | 1.089 |
| Antigen NY-CO-4; Elongation factor 1-delta | 1.267 | 1.160 | 1.025 |
| 3-phosphoadenosine-5-phosphosulfate synthase; Adenosine-5-phosphosulfate 3-phosphotransferase; Adenylylsulfate 3-phosphotransferase; Adenylyl-sulfate kinase; APS kinase; ATP-sulfurylase; Bifunctional 3-phosphoadenosine 5-phosphosulfate synthase 2; Sulfate adenylate transferase; Sulfate adenylyltransferase; Sulfurylase kinase 2 | 1.263 | 0.990 | 0.874 |
| Alpha-adducin; Erythrocyte adducin subunit alpha; Adducin 1 (Alpha); Adducin 1 (Alpha), isoform CRA_e; ADD1 protein | 1.259 | 1.110 | 0.981 |
| Microsomal signal peptidase 25 kDa subunit; Signal peptidase complex subunit 2 | 1.257 | 0.978 | 0.863 |
| Quiescin Q6; Sulfhydryl oxidase 1 | 1.257 | 1.111 | 1.053 |
| Acetoacetyl-CoA thiolase; Acetyl-CoA acetyltransferase, mitochondrial; T2 | 1.255 | 0.994 | 0.887 |
| 2-oxoglutarate dehydrogenase complex component E1; 2-oxoglutarate dehydrogenase, mitochondrial; Alpha-ketoglutarate dehydrogenase | 1.254 | 0.996 | 0.933 |
| Complex III subunit 7; Complex III subunit VII; Cytochrome b-c1 complex subunit 7; QP-C; Ubiquinol-cytochrome c reductase complex 14 kDa protein; cDNA FLJ52271, moderately similar to Ubiquinol-cytochrome c reductase complex 14 kDa protein (EC 1.10.2.2) | 1.251 | 1.078 | 0.966 |
| Calcium-activated chloride channel family member 1; Calcium-activated chloride channel protein 1; Calcium-activated chloride channel regulator 1 | 1.250 | 0.983 | 0.905 |
| Complement component 4A (Rodgers blood group); Putative uncharacterized protein C4A; Complement component C4B (Childo blood group); Complement component C4B (Childo blood group) 2; C4B1; Complement component 4B (Childo blood group) | 1.249 | 0.982 | 0.981 |
| Actin-interacting protein 1; NORI-1; WD repeat-containing protein 1; cDNA FLJ58303, highly similar to WD repeat protein 1 | 1.249 | 1.050 | 1.050 |
| Catalase | 1.245 | 0.986 | 0.951 |
| Proteasome subunit alpha type-7; Proteasome subunit RC6-1; Proteasome subunit XAPC7; Proteasome subunit alpha type | 1.244 | 0.988 | 1.122 |

TABLE 4-continued

| Variable | Comp 1 VIP | Comp 2 VIP | Comp 3 VIP |
|---|---|---|---|
| Heat shock-related 70 kDa protein 2; cDNA FLJ40505 fis, clone TESTI2045562, highly similar to HEAT SHOCK-RELATED 70 kDa PROTEIN 2 | 1.244 | 1.032 | 0.922 |
| Endopeptidase SP18; Microsomal signal peptidase 18 kDa subunit; SEC11 homolog A; SEC11-like protein 1; Signal peptidase complex catalytic subunit SEC11A; SPC18; cDNA FLJ51313, highly similar to Microsomal signal peptidase 18 kDa subunit(EC 3.4.—.—); SEC11-like 1 (S. cerevisiae), isoform CRA_d | 1.240 | 1.009 | 1.057 |
| Inorganic pyrophosphatase; Pyrophosphate phospho-hydrolase; Pyrophosphatase (Inorganic) 1 | 1.238 | 0.962 | 0.998 |
| Myosin heavy chain 11; Myosin heavy chain, smooth muscle isoform; Myosin-11; SMMHC; Myosin heavy chain 11 smooth muscle isoform | 1.234 | 0.963 | 0.862 |
| Clathrin heavy chain 1; Clathrin heavy chain on chromosome 17 | 1.232 | 0.982 | 0.869 |
| Villin-1; cDNA FLJ57609, highly similar to Villin-1 | 1.228 | 0.979 | 0.871 |
| Centromere protein V; Nuclear protein p30; Proline-rich protein 6 | 1.227 | 1.172 | 1.067 |
| Cathepsin C; Cathepsin J; Dipeptidyl peptidase 1; Dipeptidyl peptidase 1 exclusion domain chain; Dipeptidyl peptidase 1 heavy chain; Dipeptidyl peptidase 1 light chain; Dipeptidyl peptidase I; Dipeptidyl peptidase I exclusion domain chain; Dipeptidyl peptidase I heavy chain; Dipeptidyl peptidase I light chain; Dipeptidyl transferase | 1.224 | 0.962 | 0.855 |
| Hydroxyacyl-coenzyme A dehydrogenase, mitochondrial; Medium and short-chain L-3-hydroxyacyl-coenzyme A dehydrogenase; Short-chain 3-hydroxyacyl-CoA dehydrogenase | 1.224 | 1.009 | 0.903 |
| Aldo-keto reductase family 1 member B10; Aldose reductase-like; Aldose reductase-related protein; ARL-1; Small intestine reductase | 1.223 | 0.954 | 0.851 |
| Carbonate dehydratase II; Carbonic anhydrase 2; Carbonic anhydrase C; Carbonic anhydrase II | 1.223 | 1.031 | 0.910 |
| Putative uncharacterized protein PRRC1; Protein PRRC1 | 1.223 | 0.951 | 0.938 |
| Cytosolic malate dehydrogenase; Malate dehydrogenase, cytoplasmic; Malate dehydrogenase; Putative uncharacterized protein MDH1 | 1.222 | 0.988 | 0.875 |
| Cadherin-associated Src substrate; Catenin delta-1; p120 catenin; p120(cas); Putative uncharacterized protein CTNND1 | 1.222 | 1.013 | 0.894 |
| Metavinculin; Vinculin | 1.221 | 0.977 | 0.955 |
| Amphiregulin-associated protein; Midgestation and kidney protein; Midkine; Neurite outgrowth-promoting factor 2; Neurite outgrowth-promoting protein | 1.220 | 1.206 | 1.070 |
| Putative uncharacterized protein APEH; Acylamino-acid-releasing enzyme; Acylaminoacyl-peptidase; Acyl-peptide hydrolase; Oxidized protein hydrolase | 1.219 | 0.973 | 0.871 |
| Kallikrein inhibitor; Kallistatin; Peptidase inhibitor 4; Serpin A4 | 1.218 | 1.258 | 1.166 |
| Dihydrolipoamide dehydrogenase; Dihydrolipoyl dehydrogenase, mitochondrial; Glycine cleavage system L protein; cDNA FLJ50515, highly similar to Dihydrolipoyl dehydrogenase, mitochondrial (EC 1.8.1.4); Dihydrolipoyl dehydrogenase | 1.213 | 0.980 | 0.911 |
| 5-aminoimidazole-4-carboxamide ribonucleotide formyltransferase; AICAR transformylase; ATIC; Bifunctional purine biosynthesis protein PURH; IMP cyclohydrolase; IMP synthase; Inosinicase; Phosphoribosylaminoimidazolecarboxamide formyltransferase | 1.212 | 0.943 | 0.864 |
| Glioma pathogenesis-related protein 2; Golgi-associated plant pathogenesis-related protein 1; GLI pathogenesis-related 2 | 1.210 | 1.027 | 0.947 |
| Signal transducer and activator of transcription 1-alpha/beta; Transcription factor ISGF-3 components p91/p84 | 1.209 | 1.167 | 1.046 |
| PDHE1-A type I; Pyruvate dehydrogenase E1 component subunit alpha, somatic form, mitochondrial | 1.205 | 0.948 | 0.932 |
| Glucose phosphomutase 1; Phosphoglucomutase-1; cDNA FLJ50606, highly similar to Phosphoglucomutase-1 (EC 5.4.2.2) | 1.202 | 0.935 | 0.998 |
| 18 kDa Alu RNA-binding protein; Signal recognition particle 14 kDa protein | 1.200 | 1.015 | 0.912 |
| Isovaleryl-CoA dehydrogenase, mitochondrial; cDNA FLJ16602 fis, clone TESTI4007816, highly similar to Isovaleryl-CoA dehydrogenase, mitochondrial (EC 1.3.99.10); Isovaleryl Coenzyme A dehydrogenase, isoform CRA_b | 1.198 | 1.177 | 1.045 |
| Cullin-associated and neddylation-dissociated protein 1; Cullin-associated NEDD8-dissociated protein 1; p120 CAND1; TBP-interacting protein of 120 kDa A | 1.197 | 1.039 | 0.994 |
| Cytochrome c oxidase polypeptide VIc; Cytochrome c oxidase subunit 6C | 1.196 | 1.056 | 0.935 |
| Beta-hexosaminidase subunit alpha; Beta-N-acetylhexosaminidase subunit alpha; N-acetyl-beta-glucosaminidase subunit alpha | 1.194 | 1.105 | 1.110 |
| HCNPpp; Hippocampal cholinergic neurostimulating peptide; Neuropolypeptide h3; Phosphatidylethanolamine-binding protein 1; Prostatic-binding protein; Raf kinase inhibitor protein; cDNA FLJ51535, highly similar to Phosphatidylethanolamine-binding protein 1 | 1.193 | 0.958 | 0.996 |
| 59 kDa serine/threonine-protein kinase; ILK-1; ILK-2; Integrin-linked protein kinase; p59ILK; cDNA FLJ50979, moderately similar to Integrin-linked protein kinase (EC 2.7.11.1); cDNA FLJ53825, highly similar to Integrin-linked protein kinase 1 (EC 2.7.11.1) | 1.192 | 1.090 | 0.965 |
| Collagen alpha-1 (XV) chain; Endostatin; Endostatin-XV; Related to endostatin; Restin | 1.188 | 0.994 | 0.894 |
| Desmoyokin; Neuroblast differentiation-associated protein AHNAK | 1.187 | 0.968 | 0.893 |
| HBeAg-binding protein 2 binding protein A; Mannose-P-dolichol utilization defect 1 protein; Suppressor of Lec15 and Lec35 glycosylation mutation homolog; My008 protein; cDNA FLJ57793, moderately similar to Mannose-P-dolichol utilization defect 1 protein; cDNA FLJ14836 fis, clone OVARC1001702 | 1.183 | 0.933 | 0.904 |
| Outer mitochondrial membrane protein porin 1; Plasmalemmal porin; Porin 31HL; Porin 31HM; Voltage-dependent anion-selective channel protein 1 | 1.182 | 0.920 | 0.858 |
| Alpha E-catenin; Cadherin-associated protein; Catenin alpha-1; Renal carcinoma antigen NY-REN-13; cDNA FLJ54047, highly similar to Alpha-1 catenin (Cadherin-associated protein); Catenin (Cadherin-associated protein), alpha 1, 102 kDa, isoform CRA_c; CTNNA1 protein | 1.180 | 0.933 | 0.847 |

TABLE 4-continued

| Variable | Comp 1 VIP | Comp 2 VIP | Comp 3 VIP |
|---|---|---|---|
| Antigen KI-67 | 1.180 | 1.623 | 1.483 |
| Glutamate dehydrogenase 1, mitochondrial; cDNA FLJ55203, highly similar to Glutamate dehydrogenase 1, mitochondrial (EC 1.4.1.3); cDNA FLJ16138 fis, clone BRALZ2017531, highly similar to Glutamate dehydrogenase 1, mitochondrial (EC 1.4.1.3); Glutamate dehydrogenase 1, isoform CRA_a; Glutamate dehydrogenase 2, mitochondrial | 1.179 | 0.981 | 0.896 |
| Complex I-PDSW; NADH dehydrogenase [ubiquinone] 1 beta subcomplex subunit 10; NADH-ubiquinone oxidoreductase PDSW subunit; NADH dehydrogenase (Ubiquinone) 1 beta subcomplex, 10, 22 kDa, isoform CRA_a; NDUFB10 protein | 1.176 | 1.263 | 1.126 |
| Hydroxysteroid dehydrogenase-like protein 2; cDNA FLJ61200, highly similar to Homo sapiens hydroxysteroid dehydrogenase like 2 (HSDL2), mRNA | 1.175 | 0.941 | 0.868 |
| Elongation factor Ts, mitochondrial; Elongation factor Ts | 1.169 | 1.294 | 1.165 |
| 5H9 antigen; CD9 antigen; Cell growth-inhibiting gene 2 protein; Leukocyte antigen MIC3; Motility-related protein; p24; Tetraspanin-29; Putative uncharacterized protein CD9; cDNA FLJ51032, highly similar to CD9 antigen | 1.169 | 0.916 | 0.826 |
| 180 kDa ribosome receptor homolog; ES/130-related protein; Ribosome receptor protein; Ribosome-binding protein 1 | 1.168 | 0.928 | 1.046 |
| Hematopoietic cell-specific LYN substrate 1; Hematopoietic lineage cell-specific protein; LckBP1; p75 | 1.167 | 1.083 | 1.017 |
| DDAHII; Dimethylargininase-2; N(G),N(G)-dimethylarginine dimethylaminohydrolase 2; Protein G6a; S-phase protein; Dimethylarginine dimethylaminohydrolase 2 | 1.166 | 0.968 | 0.901 |
| Glutathione S-transferase omega-1; Glutathione S-transferase omega 1, isoform CRA_a; Glutathione S-transferase omega 1 | 1.162 | 0.906 | 0.890 |
| Apoptotic chromatin condensation inducer in the nucleus | 1.160 | 1.040 | 0.920 |
| Aldehyde dehydrogenase family 6 member A1; Methylmalonate-semialdehyde dehydrogenase [acylating], mitochondrial | 1.158 | 0.938 | 0.845 |
| Protein disulfide isomerase P5; Protein disulfide-isomerase A6; Thioredoxin domain-containing protein 7; cDNA FLJ58502, highly similar to Protein disulfide-isomerase A6 (EC 5.3.4.1) | 1.158 | 0.924 | 0.953 |
| Nuclear transport factor 2; Placental protein 15 | 1.157 | 1.016 | 0.914 |
| Complex I-23 kD; NADH dehydrogenase [ubiquinone] iron-sulfur protein 8, mitochondrial; NADH-ubiquinone oxidoreductase 23 kDa subunit; TYKY subunit | 1.151 | 1.148 | 1.025 |
| Complex III subunit 5; Complex III subunit IX; Cytochrome b-c1 complex subunit 11; Cytochrome b-c1 complex subunit 5; Cytochrome b-c1 complex subunit Rieske, mitochondrial; Rieske iron-sulfur protein; Ubiquinol-cytochrome c reductase 8 kDa protein; Ubiquinol-cytochrome c reductase iron-sulfur subunit; Putative cytochrome b-c1 complex subunit Rieske-like protein 1 | 1.150 | 1.059 | 0.936 |
| Nicotinamide phosphoribosyltransferase; Pre-B-cell colony-enhancing factor 1; Visfatin; Novel protein similar to Pre-B cell enhancing factor (PBEF) | 1.148 | 0.893 | 0.823 |
| Basic leucine zipper and W2 domain-containing protein 2; Putative uncharacterized protein BZW2; Basic leucine zipper and W2 domains 2, isoform CRA_b | 1.147 | 0.987 | 0.974 |
| ATP-specific succinyl-CoA synthetase subunit beta; Renal carcinoma antigen NY-REN-39; Succinyl-CoA ligase [ADP-forming] subunit beta, mitochondrial; Succinyl-CoA synthetase beta-A chain; Succinate-CoA ligase, ADP-forming, beta subunit | 1.147 | 0.928 | 0.922 |
| 3-hydroxyisobutyryl-CoA hydrolase, mitochondrial; 3-hydroxyisobutyryl-coenzyme A hydrolase | 1.145 | 1.152 | 1.058 |
| E3 UFM1-protein ligase 1 | 1.143 | 1.066 | 1.053 |
| UPF0197 transmembrane protein C11orf10 | 1.140 | 0.886 | 0.782 |
| Interferon-induced protein 53; T1-TrpRS; T2-TrpRS; Tryptophan--tRNA ligase; Tryptophanyl-tRNA synthetase, cytoplasmic | 1.139 | 1.201 | 1.084 |
| Tumor protein D52-like 2; Tumor protein D52-like 2, isoform CRA_e; Tumor protein D54 | 1.136 | 1.002 | 0.885 |
| Glycogen phosphorylase, brain form | 1.131 | 0.884 | 0.787 |
| Cytosolic thyroid hormone-binding protein; Opa-interacting protein 3; p58; Pyruvate kinase 2/3; Pyruvate kinase isozymes M1/M2; Pyruvate kinase muscle isozyme; Thyroid hormone-binding protein 1; Tumor M2-PK | 1.131 | 1.043 | 0.931 |
| 58 kDa glucose-regulated protein; 58 kDa microsomal protein; Disulfide isomerase ER-60; Endoplasmic reticulum resident protein 57; Endoplasmic reticulum resident protein 60; Protein disulfide-isomerase A3; cDNA PSEC0175 fis, clone OVARC1000169, highly similar to Protein disulfide-isomerase A3 (EC 5.3.4.1) | 1.129 | 0.910 | 1.022 |
| Glutathione S-transferase kappa 1; Glutathione S-transferase subunit 13; GST 13-13; GST class-kappa; GSTK1-1 | 1.128 | 0.978 | 0.995 |
| Enoyl-CoA hydratase 1; Enoyl-CoA hydratase, mitochondrial; Short-chain enoyl-CoA hydratase | 1.125 | 0.890 | 0.787 |
| Active breakpoint cluster region-related protein; cDNA FLJ54747, highly similar to Active breakpoint cluster region-related protein | 1.124 | 0.918 | 0.913 |
| HLA-DR-associated protein II; Inhibitor of granzyme A-activated DNase; PHAPII; Phosphatase 2A inhibitor I2PP2A; Protein SET; Template-activating factor I; SET nuclear oncogene; Putative uncharacterized protein SET | 1.118 | 1.145 | 1.099 |
| Tubulin beta-2 chain; Tubulin beta-2C chain | 1.117 | 0.900 | 0.805 |
| Beta-II spectrin; Fodrin beta chain; Spectrin beta chain, brain 1; Spectrin, non-erythroid beta chain 1 | 1.117 | 0.905 | 0.800 |
| Cyclophilin B; CYP-S1; Peptidyl-prolyl cis-trans isomerase B; Rotamase B; S-cyclophilin | 1.115 | 0.920 | 0.903 |
| ATP synthase subunit a; F-ATPase protein 6 | 1.112 | 0.888 | 0.826 |
| Putative uncharacterized protein ARPC4; Actin-related protein 2/3 complex subunit 4; Arp2/3 complex 20 kDa subunit | 1.106 | 0.931 | 0.919 |
| Carboxymethylenebutenolidase homolog | 1.106 | 0.927 | 0.820 |
| Vasodilator-stimulated phosphoprotein | 1.106 | 1.087 | 0.995 |

TABLE 4-continued

| Variable | Comp 1 VIP | Comp 2 VIP | Comp 3 VIP |
|---|---|---|---|
| 47 kDa mannose 6-phosphate receptor-binding protein; Cargo selection protein TIP47; Mannose-6-phosphate receptor-binding protein 1; Perilipin-3; Placental protein 17 | 1.102 | 0.978 | 0.917 |
| All-trans-13,14-dihydroretinol saturase; All-trans-retinol 13,14-reductase | 1.099 | 1.249 | 1.121 |
| Beta-coat protein; Coatomer subunit beta; p102; cDNA FLJ56271, highly similar to Coatomer subunit beta; Coatomer protein complex, subunit beta 2 (Beta prime), isoform CRA_b | 1.097 | 0.880 | 0.905 |
| BPG-dependent PGAM 1; Phosphoglycerate mutase 1; Phosphoglycerate mutase isozyme B | 1.096 | 1.042 | 0.940 |
| Cadherin family member 5; Desmoglein-2; HDGC | 1.096 | 1.083 | 1.010 |
| Superoxide dismutase [Mn], mitochondrial; Superoxide dismutase | 1.095 | 0.871 | 0.872 |
| Interferon-induced 15 kDa protein; Interferon-induced 17 kDa protein; Ubiquitin cross-reactive protein | 1.093 | 0.918 | 0.810 |
| Transmembrane and coiled-coil domain-containing protein 1; Transmembrane and coiled-coil domains protein 4; Xenogeneic cross-immune protein PCIA3; Putative uncharacterized protein TMCO1 | 1.092 | 0.849 | 0.786 |
| Actin-binding protein 280; Alpha-filamin; Endothelial actin-binding protein; Filamin-1; Filamin-A; Non-muscle filamin; Filamin A, alpha (Actin binding protein 280) | 1.091 | 0.939 | 0.851 |
| ABP-280-like protein; ABP-L; Actin-binding-like protein; Filamin-2; Filamin-C; Gamma-filamin | 1.089 | 0.855 | 0.761 |
| 1-acylglycerophosphocholine O-acyltransferase; 1-acylglycerophosphoserine O-acyltransferase; Lysophosphatidylcholine acyltransferase; Lysophosphatidylcholine acyltransferase 3; Lysophosphatidylserine acyltransferase; Lysophospholipid acyltransferase 5; Membrane-bound O-acyltransferase domain-containing protein 5; cDNA FLJ55747, highly similar to Membrane bound O-acyltransferase domain-containing protein 5 (EC 2.3.—.—) | 1.088 | 1.242 | 1.118 |
| Alcohol dehydrogenase 1C; Alcohol dehydrogenase subunit gamma | 1.086 | 0.976 | 0.875 |
| Beta-hexosaminidase subunit beta; Beta-hexosaminidase subunit beta chain A; Beta-hexosaminidase subunit beta chain B; Beta-N-acetylhexosaminidase subunit beta; Cervical cancer proto-oncogene 7 protein; N-acetyl-beta-glucosaminidase subunit beta; ENC-1AS | 1.081 | 0.841 | 0.811 |
| E3 ubiquitin/ISG15 ligase TRIM25; Estrogen-responsive finger protein; RING finger protein 147; Tripartite motif-containing protein 25; Ubiquitin/ISG15-conjugating enzyme TRIM25; Zinc finger protein 147 | 1.079 | 0.982 | 0.925 |
| p195; Ras GTPase-activating-like protein IQGAP1 | 1.078 | 0.877 | 0.859 |
| Cytochrome c oxidase polypeptide IV; Cytochrome c oxidase subunit 4 isoform 1, mitochondrial; Cytochrome c oxidase subunit IV isoform 1; COX4I1 protein | 1.074 | 1.097 | 0.969 |
| Intramembrane protease 1; Minor histocompatibility antigen H13; Presenilin-like protein 3; Signal peptide peptidase | 1.074 | 0.847 | 0.768 |
| Complex I-ASHI; NADH dehydrogenase [ubiquinone] 1 beta subcomplex subunit 8, mitochondrial; NADH-ubiquinone oxidoreductase ASHI subunit; NADH dehydrogenase (Ubiquinone) 1 beta subcomplex, 8, 19 kDa; NADH dehydrogenase (Ubiquinone) 1 beta subcomplex, 8, 19 kDa, isoform CRA_a; cDNA FLJ52503, highly similar to NADH dehydrogenase (ubiquinone) 1 beta subcomplex subunit 8, mitochondrial (EC 1.6.5.3) (EC 1.6.99.3) (NADH-ubiquinone oxidoreductase ASHI subunit) (Complex I-ASHI) (CI-ASHI) | 1.073 | 0.986 | 1.194 |
| Cathepsin D; Cathepsin D heavy chain; Cathepsin D light chain | 1.070 | 0.864 | 0.790 |
| Golgi transport 1 homolog B; hGOT1a; Putative NF-kappa-B-activating protein 470; Vesicle transport protein GOT1B | 1.069 | 0.834 | 0.763 |
| ADP-ribosylation factor 4; Putative uncharacterized protein ARF4 | 1.069 | 0.890 | 0.832 |
| Calnexin; IP90; Major histocompatibility complex class I antigen-binding protein p88; p90; cDNA FLJ54242, highly similar to Calnexin | 1.068 | 0.857 | 0.983 |
| Macropain subunit C8; Multicatalytic endopeptidase complex subunit C8; Proteasome component C8; Proteasome subunit alpha type-3 | 1.066 | 0.845 | 0.953 |
| Endoplasmic oxidoreductin-1-like protein; ERO1-like protein alpha; Oxidoreductin-1-L-alpha | 1.066 | 0.875 | 0.912 |
| Elastin microfibril interface-located protein 1; EMILIN-1 | 1.064 | 0.846 | 0.788 |
| Membrane protein p24A; Transmembrane emp24 domain-containing protein 2; cDNA FLJ52153, highly similar to Transmembrane emp24 domain-containing protein 2 | 1.059 | 0.828 | 0.826 |
| 60 kDa SS-A/Ro ribonucleoprotein; Ro 60 kDa autoantigen; Sjoegren syndrome antigen A2; Sjoegren syndrome type A antigen; TROVE domain family member 2; TROVE domain family, member 2; TROVE domain family, member 2, isoform CRA_c; TROVE domain family, member 2, isoform CRA_e; TROVE domain family, member 2, isoform CRA_d | 1.057 | 1.024 | 0.928 |
| Serine/threonine-protein phosphatase PP1-beta catalytic subunit | 1.049 | 0.850 | 0.916 |
| Complex I-49 kD; NADH dehydrogenase [ubiquinone] iron-sulfur protein 2, mitochondrial; NADH-ubiquinone oxidoreductase 49 kDa subunit; cDNA, FLJ78876, highly similar to NADH-ubiquinone oxidoreductase 49 kDa subunit, mitochondrial (EC 1.6.5.3) | 1.048 | 0.883 | 0.931 |
| Glycoprotein GP36b; Lectin mannose-binding 2; Vesicular integral-membrane protein VIP36; cDNA FLJ52285, highly similar to Vesicular integral-membrane protein VIP36 | 1.039 | 0.809 | 0.779 |
| Azoreductase; DT-diaphorase; Menadione reductase; NAD(P)H dehydrogenase [quinone] 1; NAD(P)H: quinone oxidoreductase 1; Phylloquinone reductase; Quinone reductase 1; cDNA FLJ50573, highly similar to Homo sapiens NAD(P)H dehydrogenase, quinone 1 (NQO1), transcript variant 3, mRNA | 1.039 | 0.880 | 0.848 |
| Fortilin; Histamine-releasing factor; p23; Translationally-controlled tumor protein; TPT1 protein; Tumor protein, translationally-controlled 1; Tumor protein, translationally-controlled 1, isoform CRA_a | 1.037 | 0.854 | 0.770 |
| Adapter protein CMS; Cas ligand with multiple SH3 domains; CD2-associated protein | 1.033 | 1.063 | 0.962 |
| Oxysterol-binding protein 1 | 1.032 | 1.125 | 1.001 |
| B5; Dolichyl-diphosphooligosaccharide-protein glycosyltransferase subunit STT3A; Integral membrane protein 1; Transmembrane protein TMC | 1.029 | 0.966 | 0.888 |

TABLE 4-continued

| Variable | Comp 1 VIP | Comp 2 VIP | Comp 3 VIP |
| --- | --- | --- | --- |
| 11S regulator complex subunit alpha; Activator of multicatalytic protease subunit 1; Interferon gamma up-regulated I-5111 protein; Proteasome activator 28 subunit alpha; Proteasome activator complex subunit 1; Putative uncharacterized protein PSME1 | 1.028 | 1.069 | 0.953 |
| CFR-1; Cysteine-rich fibroblast growth factor receptor; E-selectin ligand 1; Golgi apparatus protein 1; Golgi sialoglycoprotein MG-160 | 1.028 | 0.879 | 0.890 |
| Ubiquitin carrier protein D3; Ubiquitin-conjugating enzyme E2 D3; Ubiquitin-conjugating enzyme E2(17)KB 3; Ubiquitin-conjugating enzyme E2-17 kDa 3; Ubiquitin-protein ligase D3; Ubiquitin carrier protein D2; Ubiquitin-conjugating enzyme E2 D2; Ubiquitin-conjugating enzyme E2(17)KB 2; Ubiquitin-conjugating enzyme E2-17 kDa 2; Ubiquitin-protein ligase D2; Ubiquitin carrier protein | 1.028 | 0.940 | 0.831 |
| Activated RNA polymerase II transcriptional coactivator p15; p14; Positive cofactor 4; SUB1 homolog | 1.024 | 0.913 | 0.818 |
| HLA-B-associated transcript 3; Large proline-rich protein BAT3; Protein G3; HLA-B associated transcript 3; HLA-B associated transcript 3, isoform CRA_a | 1.024 | 0.942 | 0.836 |
| Cytochrome c oxidase polypeptide II; Cytochrome c oxidase subunit 2 | 1.024 | 1.008 | 1.048 |
| Histone H1; Histone H1(0); Histone H1.0 | 1.022 | 0.846 | 0.748 |
| Echinoderm microtubule-associated protein-like 4; Restrictedly overexpressed proliferation-associated protein; Ropp 120; Putative uncharacterized protein EML4 | 1.021 | 0.899 | 0.822 |
| Fructose-bisphosphate aldolase A; Lung cancer antigen NY-LU-1; Muscle-type aldolase | 1.019 | 0.828 | 0.750 |
| High density lipoprotein-binding protein; Vigilin | 1.018 | 0.791 | 0.705 |
| 32 kDa accessory protein; Vacuolar proton pump subunit d 1; V-ATPase 40 kDa accessory protein; V-ATPase AC39 subunit; V-type proton ATPase subunit d 1 | 1.015 | 0.810 | 0.900 |
| NADH dehydrogenase [ubiquinone] flavoprotein 2, mitochondrial; NADH-ubiquinone oxidoreductase 24 kDa subunit | 1.015 | 0.833 | 0.956 |
| Maternal-embryonic 3; Vacuolar protein sorting-associated protein 35; Vesicle protein sorting 35 | 1.013 | 0.795 | 0.951 |
| Histone H3 | 1.013 | 0.825 | 0.729 |
| 17-beta-hydroxysteroid dehydrogenase type 2; 20 alpha-hydroxysteroid dehydrogenase; E2DH; Estradiol 17-beta-dehydrogenase 2; Microsomal 17-beta-hydroxysteroid dehydrogenase; Testosterone 17-beta-dehydrogenase | 1.013 | 1.457 | 1.303 |
| 56 kDa selenium-binding protein; Selenium-binding protein 1; cDNA FLJ61035, highly similar to Selenium-binding protein 1; Selenium binding protein 1 | 1.013 | 0.789 | 0.706 |
| Cell proliferation-inducing gene 19 protein; LDH muscle subunit; L-lactate dehydrogenase A chain; Renal carcinoma antigen NY-REN-59 | 1.006 | 0.936 | 1.001 |
| Tight junction protein 1; Tight junction protein ZO-1; Zona occludens protein 1; Zonula occludens protein 1 | 1.002 | 1.323 | 1.170 |
| Ras-related protein Rab-18; RAB18, member RAS oncogene family | 1.000 | 0.849 | 1.001 |
| Epithelial protein lost in neoplasm; LIM domain and actin-binding protein 1; cDNA FLJ55990, highly similar to LIM domain and actin-binding protein 1 | 1.000 | 0.980 | 0.875 |
| Iron regulatory protein 2; Iron-responsive element-binding protein 2 | 0.999 | 0.786 | 0.761 |
| G protein subunit beta-2; Guanine nucleotide-binding protein G(I)/G(S)/G(T) subunit beta-2; Transducin beta chain 2; Putative uncharacterized protein GNB2 | 0.995 | 0.799 | 0.785 |
| 40S ribosomal protein S13 | 0.991 | 0.857 | 0.891 |
| Heat shock 70 kDa protein 1/2; Heat shock 70 kDa protein 1A/1B; Heat shock 70 kDa protein 1A | 0.989 | 1.199 | 1.082 |
| LIM and SH3 domain protein 1; Metastatic lymph node gene 50 protein; Putative uncharacterized protein LASP1; cDNA FLJ51834, highly similar to LIM and SH3 domain protein 1; cDNA FLJ52195, highly similar to LIM and SH3 domain protein 1 | 0.981 | 0.977 | 0.872 |
| 60S ribosomal protein L26 | 0.981 | 0.765 | 0.972 |
| 20 kDa myosin light chain; MLC-2C; Myosin regulatory light chain 2, smooth muscle isoform; Myosin regulatory light chain 9; Myosin regulatory light chain MRLC1; Myosin regulatory light polypeptide 9; Myosin RLC | 0.981 | 1.027 | 0.924 |
| Guanine nucleotide-binding protein G(y) subunit alpha; Guanine nucleotide-binding protein subunit alpha-11 | 0.978 | 0.764 | 0.780 |
| Meg-3; Niban-like protein 1; Protein FAM129B | 0.972 | 0.829 | 0.789 |
| ADP-ribosylation factor-like protein 6-interacting protein 5; Cytoskeleton-related vitamin A-responsive protein; Dermal papilla-derived protein 11; Glutamate transporter EAAC1-interacting protein; GTRAP3-18; JM5; PRA1 family protein 3; Prenylated Rab acceptor protein 2; Protein JWa; Putative MAPK-activating protein PM27 | 0.969 | 1.128 | 1.069 |
| 60S ribosomal protein L27 | 0.968 | 0.799 | 0.741 |
| Beta-globin; Hemoglobin beta chain; Hemoglobin subunit beta; LVV-hemorphin-7 | 0.967 | 0.996 | 1.014 |
| GDP-4-keto-6-deoxy-D-mannose-3,5-epimerase-4-reductase; GDP-L-fucose synthase; Protein FX; Red cell NADP(H)-binding protein; Short-chain dehydrogenase/reductase family 4E member 1 | 0.964 | 0.927 | 0.848 |
| 26S protease regulatory subunit 6A; 26S proteasome AAA-ATPase subunit RPT5; Proteasome 26S subunit ATPase 3; Proteasome subunit P50; Tat-binding protein 1 | 0.963 | 1.125 | 1.059 |
| Apolipoprotein A-l-binding protein; YjeF N-terminal domain-containing protein 1 | 0.958 | 1.024 | 0.970 |
| APEX nuclease; Apurinic-apyrimidinic endonuclease 1; DNA-(apurinic or apyrimidinic site) lyase; Protein REF-1 | 0.954 | 1.016 | 0.900 |
| Signal recognition particle 54 kDa protein | 0.953 | 0.743 | 0.667 |
| 5F7; Basigin; Collagenase stimulatory factor; Extracellular matrix metalloproteinase inducer; Leukocyte activation antigen M6; OK blood group antigen; Tumor cell-derived collagenase stimulatory factor | 0.952 | 0.794 | 0.849 |
| AIR carboxylase; Multifunctional protein ADE2; Phosphoribosylaminoimidazole carboxylase; Phosphoribosylaminoimidazole-succinocarboxamide synthase; SAICAR synthetase | 0.952 | 0.740 | 0.673 |

TABLE 4-continued

| Variable | Comp 1 VIP | Comp 2 VIP | Comp 3 VIP |
|---|---|---|---|
| 70 kDa peroxisomal membrane protein; ATP-binding cassette sub-family D member 3 | 0.951 | 0.926 | 0.853 |
| Actin, aortic smooth muscle; Alpha-actin-2; Cell growth-inhibiting gene 46 protein; Actin, alpha 1, skeletal muscle | 0.951 | 0.935 | 0.971 |
| 3-hydroxybutyrate dehydrogenase type 2; Dehydrogenase/reductase SDR family member 6; Oxidoreductase UCPA; R-beta-hydroxybutyrate dehydrogenase | 0.946 | 0.753 | 0.896 |
| Kinesin light chain 4; Kinesin-like protein 8; cDNA FLJ58264, highly similar to Kinesin light chain 4 | 0.945 | 1.267 | 1.218 |
| Deubiquitinating enzyme 15; Ubiquitin carboxyl-terminal hydrolase 15; Ubiquitin thioesterase 15; Ubiquitin-specific-processing protease 15; Unph-2; Unph4 | 0.944 | 1.145 | 1.049 |
| Putative uncharacterized protein KIAA0664; Protein KIAA0664 | 0.933 | 0.738 | 0.830 |
| Protein SCO2 homolog, mitochondrial | 0.928 | 0.744 | 0.657 |
| 35-alpha calcimedin; Annexin A3; Annexin III; Annexin-3; Inositol 1,2-cyclic phosphate 2-phosphohydrolase; Lipocortin III; Placental anticoagulant protein III | 0.926 | 1.006 | 0.966 |
| Inosine phosphorylase; Purine nucleoside phosphorylase | 0.919 | 0.803 | 0.816 |
| Complex I-B8; NADH dehydrogenase [ubiquinone] 1 alpha subcomplex subunit 2; NADH-ubiquinone oxidoreductase B8 subunit | 0.916 | 0.719 | 0.780 |
| Lamin-B2 | 0.914 | 0.712 | 0.910 |
| Signal transducing adapter molecule 1; Putative uncharacterized protein STAM | 0.906 | 0.965 | 0.883 |
| Plasma membrane calcium ATPase isoform 1; Plasma membrane calcium pump isoform 1; Plasma membrane calcium-transporting ATPase 1 | 0.896 | 0.797 | 0.826 |
| Carbonyl reductase [NADPH] 3; NADPH-dependent carbonyl reductase 3 | 0.896 | 1.061 | 1.298 |
| DNA-directed RNA polymerase II subunit H; DNA-directed RNA polymerases I, II, and III 17.1 kDa polypeptide; DNA-directed RNA polymerases I, II, and III subunit RPABC3; RPB17; RPB8 homolog; Putative uncharacterized protein POLR2H | 0.892 | 1.439 | 1.271 |
| 70 kDa lamin; Lamin-A/C; Renal carcinoma antigen NY-REN-32; Lamin A/C; Progerin; Rhabdomyosarcoma antigen MU-RMS-40.12 | 0.888 | 0.914 | 0.853 |
| 22 kDa neuronal tissue-enriched acidic protein; Brain acid soluble protein 1; Neuronal axonal membrane protein NAP-22 | 0.888 | 0.915 | 0.984 |
| ADP-ribosylation factor-like protein 3 | 0.884 | 1.055 | 1.005 |
| Acetylglucosamine phosphomutase; N-acetylglucosamine-phosphate mutase; Phosphoacetylglucosamine mutase; Phosphoglucomutase-3 | 0.884 | 0.712 | 0.632 |
| Cytochrome c oxidase polypeptide VIIc; Cytochrome c oxidase subunit 7C, mitochondrial | 0.879 | 0.913 | 0.839 |
| Dolichyl-diphosphooligosaccharide--protein glycosyltransferase 67 kDa subunit; Dolichyl-diphosphooligosaccharide--protein glycosyltransferase subunit 1; Ribophorin I; Ribophorin-1; cDNA FLJ50809, highly similar to Dolichyl-diphosphooligosaccharide--protein glycosyltransferase 67 kDa subunit (EC 2.4.1.119); cDNA FLJ51908, highly similar to Dolichyl-diphosphooligosaccharide--proteinglycosyltransferase 67 kDa subunit (EC 2.4.1.119) | 0.878 | 0.715 | 0.974 |
| Cytochrome c oxidase subunit 7A2, mitochondrial; Cytochrome c oxidase subunit VIIa-liver/heart | 0.875 | 0.705 | 0.933 |
| 21 kDa transmembrane-trafficking protein; p24delta; S31III125; Tmp-21-I; Transmembrane emp24 domain-containing protein 10; Transmembrane protein Tmp21 | 0.875 | 0.690 | 0.754 |
| Cell cycle control protein 50A; Transmembrane protein 30A; cDNA FLJ55687, highly similar to Cell cycle control protein 50A | 0.868 | 2.133 | 1.883 |
| Oxidative stress-responsive 1 protein; Serine/threonine-protein kinase OSR1; Putative uncharacterized protein OXSR1 | 0.864 | 1.203 | 1.066 |
| Acyl-CoA-binding domain-containing protein 3; Golgi complex-associated protein 1; Golgi phosphoprotein 1; Golgi resident protein GCP60; PBR- and PKA-associated protein 7; Peripheral benzodiazepine receptor-associated protein PAP7 | 0.861 | 1.201 | 1.111 |
| Pyruvate carboxylase, mitochondrial; Pyruvic carboxylase; cDNA FLJ60715, highly similar to Pyruvate carboxylase, mitochondrial (EC 6.4.1.1) | 0.857 | 1.001 | 0.885 |
| Double-stranded RNA-binding protein Staufen homolog 1; Staufen, RNA binding protein, homolog 1 (*Drosophila*) | 0.855 | 1.316 | 1.229 |
| Q15149-6 | 0.851 | 0.704 | 1.087 |
| 40S ribosomal protein S19 | 0.848 | 0.732 | 0.944 |
| Intestine-specific plastin; Plastin-1 | 0.845 | 1.185 | 1.053 |
| Nidogen-2; Osteonidogen | 0.836 | 1.244 | 1.104 |
| Gastric cancer antigen Ga19; N-alpha-acetyltransferase 15, NatA auxiliary subunit; NMDA receptor-regulated protein 1; N-terminal acetyltransferase; Protein tubedown-1; Tbdn100 | 0.833 | 0.751 | 0.704 |
| 40S ribosomal protein S14 | 0.832 | 0.654 | 0.615 |
| Heterogeneous nuclear ribonucleoprotein L; cDNA FLJ75895, highly similar to *Homo sapiens* heterogeneous nuclear ribonucleoprotein L (HNRPL), transcript variant 2, mRNA; Putative uncharacterized protein HNRNPL | 0.829 | 0.747 | 0.663 |
| cDNA FLJ56102, highly similar to *Homo sapiens* calpastatin (CAST), transcript variant 8, mRNA; Calpain inhibitor; Calpastatin; Sperm BS-17 component; cDNA FLJ56123, highly similar to Calpastatin | 0.826 | 0.782 | 0.694 |
| Tropomyosin 3; Tropomyosin 3, isoform CRA_b; cDNA FLJ35393 fis, clone SKNSH2000971, highly similar to TROPOMYOSIN, CYTOSKELETAL TYPE | 0.826 | 0.829 | 0.732 |
| Macropain chain Z; Multicatalytic endopeptidase complex chain Z; Proteasome subunit beta type-7; Proteasome subunit Z; Proteasome (Prosome, macropain) subunit, beta type, 7; cDNA FLJ60039, highly similar to Proteasome subunit beta type 7 (EC 3.4.25.1); Proteasome (Prosome, macropain) subunit, beta type, 7, isoform CRA_b | 0.825 | 0.745 | 0.685 |
| DNA-directed RNA polymerase II 140 kDa polypeptide; DNA-directed RNA polymerase II subunit B; DNA-directed RNA polymerase II subunit RPB2; RNA polymerase II subunit 2; RNA polymerase II subunit B2; Putative uncharacterized protein POLR2B | 0.824 | 1.499 | 1.425 |

TABLE 4-continued

| Variable | Comp 1 VIP | Comp 2 VIP | Comp 3 VIP |
|---|---|---|---|
| 40S ribosomal protein S7; Putative uncharacterized protein RPS7 | 0.824 | 0.813 | 0.982 |
| Thyroid hormone receptor-associated protein 3; Thyroid hormone receptor-associated protein complex 150 kDa component | 0.823 | 1.280 | 1.131 |
| Large tumor suppressor homolog 1; Serine/threonine-protein kinase LATS1; WARTS protein kinase; LATS1 protein | 0.822 | 0.768 | 0.718 |
| 11S regulator complex subunit beta; Activator of multicatalytic protease subunit 2; Proteasome activator 28 subunit beta; Proteasome activator complex subunit 2 | 0.819 | 1.303 | 1.157 |
| Leukocyte common antigen; Receptor-type tyrosine-protein phosphatase C; T200 | 0.819 | 0.976 | 0.975 |
| Tight junction protein 2; Tight junction protein ZO-2; Zona occludens protein 2; Zonula occludens protein 2 | 0.811 | 0.919 | 0.836 |
| CDC42 GTPase-activating protein; GTPase-activating protein rhoOGAP; p50-RhoGAP; Rho GTPase-activating protein 1; Rho-related small GTPase protein activator; Rho-type GTPase-activating protein 1 | 0.805 | 0.963 | 1.011 |
| Calcium-activated neutral proteinase 2; Calpain large polypeptide L2; Calpain M-type; Calpain-2 catalytic subunit; Calpain-2 large subunit; Millimolar-calpain | 0.804 | 1.056 | 1.017 |
| ABP125; ABP130; Protein transport protein Sec31A; SEC31-like protein 1; SEC31-related protein A; Web1-like protein; SEC31A protein | 0.798 | 0.622 | 0.895 |
| Electron transfer flavoprotein subunit beta | 0.797 | 0.696 | 0.886 |
| Collapsin response mediator protein 2; Dihydropyrimidinase-related protein 2; N2A3; Unc-33-like phosphoprotein 2 | 0.796 | 0.874 | 1.048 |
| DEAD box protein 27; Probable ATP-dependent RNA helicase DDX27 | 0.781 | 1.299 | 1.171 |
| Copper amine oxidase; HPAO; Membrane primary amine oxidase; Semicarbazide-sensitive amine oxidase; Vascular adhesion protein 1 | 0.778 | 0.845 | 0.888 |
| Dolichyl-diphosphooligosaccharide--protein glycosyltransferase 63 kDa subunit; Dolichyl-diphosphooligosaccharide-protein glycosyltransferase subunit 2; RIBIIR; Ribophorin II; Ribophorin-2 | 0.777 | 0.766 | 1.033 |
| Argininosuccinate synthase; Citrulline--aspartate ligase | 0.776 | 0.987 | 0.880 |
| Glycoprotein 25L2; Transmembrane emp24 domain-containing protein 9 | 0.772 | 1.404 | 1.242 |
| NAP-1-related protein; Nucleosome assembly protein 1-like 1; cDNA FLJ30458 fis, clone BRACE2009421, highly similar to NUCLEOSOME ASSEMBLY PROTEIN 1-LIKE 1; cDNA FLJ58569, highly similar to Nucleosome assembly protein 1-like 1; cDNA FLJ16112 fis, clone 3NB692001853, highly similar to NUCLEOSOME ASSEMBLY PROTEIN 1-LIKE 1; Nucleosome assembly protein 1-like 1, isoform CRA_c | 0.763 | 1.080 | 0.954 |
| TESS; Testin | 0.761 | 1.013 | 0.896 |
| 14 kDa phosphohistidine phosphatase; Phosphohistidine phosphatase 1; Protein janus-A homolog | 0.761 | 0.888 | 0.888 |
| Guanine nucleotide-binding protein G(I)/G(S)/G(T) subunit beta-1; Transducin beta chain 1; Guanine nucleotide binding protein (G protein), beta polypeptide 1 | 0.758 | 1.071 | 1.024 |
| 130 kDa leucine-rich protein; GP130; Leucine-rich PPR motif-containing protein, mitochondrial | 0.756 | 0.741 | 0.954 |
| Cellugyrin; Synaptogyrin-2 | 0.754 | 0.685 | 0.839 |
| c-Ki-ras; c-K-ras; GTPase KRas; GTPase KRas, N-terminally processed; Ki-Ras; K-Ras 2 | 0.750 | 1.185 | 1.075 |
| 80K-H protein; Glucosidase 2 subunit beta; Glucosidase II subunit beta; Protein kinase C substrate 60.1 kDa protein heavy chain | 0.749 | 0.874 | 1.036 |
| Haptoglobin; Haptoglobin alpha chain; Haptoglobin beta chain; HP protein | 0.746 | 0.838 | 1.044 |
| 49 kDa TATA box-binding protein-interacting protein; 54 kDa erythrocyte cytosolic protein; INO80 complex subunit H; Nuclear matrix protein 238; Pontin 52; RuvB-like 1; TIP49a; TIP60-associated protein 54-alpha | 0.742 | 0.585 | 0.524 |
| Peptidyl-prolyl cis-trans isomerase NIMA-interacting 1; Peptidyl-prolyl cis-trans isomerase Pin1; Rotamase Pin1 | 0.741 | 0.769 | 0.689 |
| Acid ceramidase; Acid ceramidase subunit alpha; Acid ceramidase subunit beta; Acylsphingosine deacylase; N-acylsphingosine amidohydrolase; Putative 32 kDa heart protein | 0.740 | 1.345 | 1.559 |
| Annexin A2; Annexin II; Annexin-2; Calpactin I heavy chain; Calpactin-1 heavy chain; Chromobindin-8; Lipocortin II; p36; Placental anticoagulant protein IV; Protein I; Annexin A2 pseudogene 2; Lipocortin II pseudogene; Putative annexin A2-like protein; cDNA FLJ34687 fis, clone MESAN2000620, highly similar to Annexin A2 | 0.740 | 0.626 | 0.871 |
| Translocation protein 1; Translocation protein SEC62 | 0.735 | 1.515 | 1.341 |
| Smu-1 suppressor of mec-8 and unc-52 protein homolog; WD40 repeat-containing protein SMU1; cDNA FLJ54259, highly similar to Smu-1 suppressor of mec-8 and unc-52 protein homolog | 0.723 | 1.363 | 1.272 |
| UPF0568 protein C14orf166 | 0.722 | 0.730 | 0.998 |
| NADPH-cytochrome P450 reductase | 0.721 | 1.142 | 1.009 |
| 60S ribosomal protein L3; HIV-1 TAR RNA-binding protein B; Putative uncharacterized protein RPL3 | 0.715 | 0.561 | 0.512 |
| Actin-related protein 2/3 complex subunit 5; Arp2/3 complex 16 kDa subunit | 0.709 | 0.599 | 0.724 |
| Citrate synthase, mitochondrial; Citrate synthase | 0.706 | 0.689 | 0.932 |
| ATP-dependent 61 kDa nucleolar RNA helicase; DEAD box protein 21; DEAD box protein 56; Probable ATP-dependent RNA helicase DDX56; Putative uncharacterized protein DDX56 | 0.705 | 0.549 | 0.971 |
| Ribosome maturation protein SBDS; Shwachman-Bodian-Diamond syndrome protein | 0.705 | 0.681 | 0.704 |
| Selenide, water dikinase 1; Selenium donor protein 1; Selenophosphate synthase 1; cDNA FLJ60186, highly similar to Selenide, water dikinase 1 (EC 2.7.9.3); Selenophosphate synthetase 1; Selenophosphate synthetase 1, isoform CRA_a | 0.699 | 1.296 | 1.294 |
| eIF-2B GDP-GTP exchange factor subunit epsilon; Translation initiation factor eIF-2B subunit epsilon | 0.691 | 1.419 | 1.313 |

TABLE 4-continued

| Variable | Comp 1 VIP | Comp 2 VIP | Comp 3 VIP |
|---|---|---|---|
| C-terminal LIM domain protein 1; Elfin; LIM domain protein CLP-36; PDZ and LIM domain protein 1 | 0.673 | 0.568 | 0.950 |
| Calcyclin; Growth factor-inducible protein 2A9; MLN 4; Prolactin receptor-associated protein; Protein S100-A6; S100 calcium-binding protein A6 | 0.672 | 0.522 | 0.519 |
| Dolichyl-diphosphooligosaccharide--protein glycosyltransferase 48 kDa subunit | 0.670 | 0.522 | 0.898 |
| ICD-M; IDP; Isocitrate dehydrogenase [NADP], mitochondrial; NADP(+)-specific ICDH; Oxalosuccinate decarboxylase | 0.669 | 1.139 | 1.036 |
| 100 kDa coactivator; EBNA2 coactivator p100; p100 co-activator; Staphylococcal nuclease domain-containing protein 1; Tudor domain-containing protein 11 | 0.665 | 0.600 | 0.914 |
| Glutaredoxin-1; Thioltransferase-1 | 0.656 | 1.176 | 1.038 |
| Microsomal triglyceride transfer protein large subunit | 0.639 | 1.044 | 1.044 |
| Beta-coat protein; Coatomer subunit beta | 0.638 | 0.631 | 0.946 |
| 60S ribosomal protein L23a; Putative uncharacterized protein RPL23A; Ribosomal protein L23a, isoform CRA_a | 0.634 | 0.711 | 0.945 |
| 14-3-3 protein eta; Protein AS1; Tyrosine 3-monooxygenase/tryptophan 5-monooxygenase activation protein, eta polypeptide | 0.626 | 1.253 | 1.129 |
| Putative uncharacterized protein SUMO1; GAP-modifying protein 1; Sentrin; Small ubiquitin-related modifier 1; SMT3 homolog 3; Ubiquitin-homology domain protein PIC1; Ubiquitin-like protein SMT3C; Ubiquitin-like protein UBL1; SMT3 suppressor of mif two 3 homolog 1 (Yeast), isoform CRA_c; SMT3 suppressor of mif two 3 homolog 1 (Yeast), isoform CRA_b | 0.623 | 0.485 | 0.694 |
| Complex I-15 kDa; NADH dehydrogenase [ubiquinone] iron-sulfur protein 5; NADH-ubiquinone oxidoreductase 15 kDa subunit | 0.622 | 0.602 | 0.912 |
| Importin-7; Ran-binding protein 7 | 0.621 | 0.754 | 0.722 |
| Dnm1p/Vps1p-like protein; Dynamin family member proline-rich carboxyl-terminal domain less; Dynamin-1-like protein; Dynamin-like protein; Dynamin-like protein 4; Dynamin-like protein IV; Dynamin-related protein 1; cDNA FLJ59504, highly similar to Dynamin-1-like protein (EC 3.6.5.5) | 0.614 | 1.328 | 1.172 |
| Activated-platelet protein 1; Inducible poly(A)-binding protein; Polyadenylate-binding protein 4; Poly(A) binding protein, cytoplasmic 4 (Inducible form); Poly(A) binding protein, cytoplasmic 4 (Inducible form), isoform CRA_e | 0.611 | 0.710 | 0.994 |
| Succinyl-CoA ligase [GDP-forming] subunit alpha, mitochondrial; Succinyl-CoA synthetase subunit alpha | 0.604 | 0.498 | 0.906 |
| 27 kDa prosomal protein; Macropain iota chain; Multicatalytic endopeptidase complex iota chain; Proteasome iota chain; Proteasome subunit alpha type-6; cDNA FLJ51729, highly similar to Proteasome subunit alpha type 6 (EC 3.4.25.1); Proteasome (Prosome, macropain) subunit, alpha type, 6, isoform CRA_a; cDNA FLJ52022, highly similar to Proteasome subunit alpha type 6 (EC 3.4.25.1); cDNA, FLJ79122, highly similar to Proteasome subunit alpha type 6 (EC 3.4.25.1) | 0.603 | 1.148 | 1.138 |
| Cytosol aminopeptidase; Leucine aminopeptidase 3; Leucyl aminopeptidase; Peptidase S; Proline aminopeptidase; Prolyl aminopeptidase | 0.599 | 0.963 | 0.857 |
| 60S ribosomal protein L14; CAG-ISL 7; cDNA FLJ51325, highly similar to 60S ribosomal protein L14 | 0.589 | 0.522 | 0.744 |
| DNA topoisomerase 1; DNA topoisomerase I | 0.575 | 0.715 | 0.997 |
| 40S ribosomal protein S26; Putative 40S ribosomal protein S26-like 1 | 0.571 | 0.777 | 0.753 |
| Rho GDP-dissociation inhibitor 1; Rho-GDI alpha; cDNA FLJ50748, highly similar to Rho GDP-dissociation inhibitor 1; Putative uncharacterized protein ARHGDIA | 0.562 | 0.438 | 1.074 |
| Hsc70/Hsp90-organizing protein; Renal carcinoma antigen NY-REN-11; Stress-induced-phosphoprotein 1; Transformation-sensitive protein IEF SSP 3521 | 0.550 | 0.715 | 1.000 |
| Signal sequence receptor subunit delta; Translocon-associated protein subunit delta; Putative uncharacterized protein SSR4 | 0.548 | 0.602 | 0.556 |
| Putative uncharacterized protein MUTED | 0.547 | 0.734 | 0.906 |
| ATPase family AAA domain-containing protein 3A | 0.544 | 0.612 | 0.978 |
| Nuclear distribution protein C homolog; Nuclear migration protein nudC | 0.540 | 0.429 | 0.779 |
| Protein LSM12 homolog | 0.530 | 0.932 | 1.102 |
| Protein transport protein Sec61 subunit beta | 0.528 | 0.579 | 0.791 |
| Macropain subunit C5; Multicatalytic endopeptidase complex subunit C5; Proteasome component C5; Proteasome gamma chain; Proteasome subunit beta type-1 | 0.509 | 1.172 | 1.039 |
| Alcohol dehydrogenase 5; Alcohol dehydrogenase class chi chain; Alcohol dehydrogenase class-3; Alcohol dehydrogenase class-III; Glutathione-dependent formaldehyde dehydrogenase; S-(hydroxymethyl)glutathione dehydrogenase | 0.508 | 0.456 | 0.936 |
| DEAD box protein 47; Probable ATP-dependent RNA helicase DDX47 | 0.502 | 0.638 | 0.755 |
| Macropain delta chain; Multicatalytic endopeptidase complex delta chain; Proteasome delta chain; Proteasome subunit beta type-6; Proteasome subunit Y | 0.499 | 1.013 | 1.008 |
| Proteasome chain 13; Proteasome component C10-II; Proteasome subunit beta type-3; Proteasome theta chain | 0.499 | 1.147 | 1.422 |
| Guanine nucleotide-binding protein G(I)/G(S)/G(O) subunit gamma-5 | 0.493 | 0.673 | 1.014 |
| 60S ribosomal protein L35 | 0.480 | 0.523 | 0.899 |
| Putative uncharacterized protein DBN1; Developmentally-regulated brain protein; Drebrin | 0.468 | 0.770 | 0.774 |
| tRNA pseudouridine synthase A; tRNA pseudouridylate synthase I; tRNA-uridine isomerase I | 0.467 | 0.877 | 0.963 |
| Protein NDRG2; Protein Syld709613; cDNA FLJ55190, highly similar to Protein NDRG2 | 0.467 | 1.647 | 1.485 |
| AKAP 120-like protein; A-kinase anchor protein 350 kDa; A-kinase anchor protein 450 kDa; A-kinase anchor protein 9; Centrosome- and Golgi-localized PKN-associated protein; Protein hyperion; Protein kinase A-anchoring protein 9; Protein yotiao | 0.465 | 0.785 | 0.703 |
| Anandamide amidohydrolase 1; Fatty-acid amide hydrolase 1; Oleamide hydrolase 1 | 0.462 | 0.612 | 1.046 |
| Acyl-coenzyme A thioesterase 13; Thioesterase superfamily member 2 | 0.461 | 1.134 | 1.032 |

TABLE 4-continued

| Variable | Comp 1 VIP | Comp 2 VIP | Comp 3 VIP |
|---|---|---|---|
| 40S ribosomal protein S21; RPS21 protein; Ribosomal protein S21; Ribosomal protein S21, isoform CRA_e | 0.456 | 0.594 | 0.980 |
| NSFL1 cofactor p47; p97 cofactor p47; UBX domain-containing protein 2C | 0.448 | 0.600 | 1.023 |
| Glutaredoxin-3; PKC-interacting cousin of thioredoxin; PKC-theta-interacting protein; Thioredoxin-like protein 2 | 0.445 | 0.808 | 0.971 |
| Charcot-Leyden crystal protein; CLC; Eosinophil lysophospholipase; Galectin-10; Lysolecithin acylhydrolase | 0.445 | 1.579 | 1.477 |
| LanC-like protein 2; Testis-specific adriamycin sensitivity protein | 0.441 | 1.599 | 1.423 |
| Dimethylallyltranstransferase; Farnesyl diphosphate synthase; Farnesyl pyrophosphate synthase; Geranyltranstransferase | 0.441 | 0.469 | 0.821 |
| 26S protease regulatory subunit 7; 26S proteasome AAA-ATPase subunit RPT1; Proteasome 26S subunit ATPase 2; Protein MSS1; cDNA FLJ52353, highly similar to 26S protease regulatory subunit 7 | 0.436 | 0.409 | 0.774 |
| CCT-epsilon; T-complex protein 1 subunit epsilon | 0.432 | 0.768 | 0.859 |
| Glyceraldehyde-3-phosphate dehydrogenase | 0.428 | 0.605 | 0.994 |
| Ras-related protein Rab-6A | 0.427 | 0.874 | 1.046 |
| Nucleosome assembly protein 1-like 4b; Putative uncharacterized protein NAP1L4; Nucleosome assembly protein 1-like 4; Nucleosome assembly protein 2 | 0.426 | 0.331 | 0.996 |
| Myosin-VI; Unconventional myosin-6 | 0.422 | 0.789 | 0.865 |
| 26S proteasome non-ATPase regulatory subunit 3; 26S proteasome regulatory subunit RPN3; 26S proteasome regulatory subunit S3; Proteasome subunit p58; cDNA FLJ54148, highly similar to 26S proteasome non-ATPase regulatory subunit 3 | 0.420 | 0.562 | 0.992 |
| Placental ribonuclease inhibitor; Ribonuclease inhibitor; Ribonuclease/angiogenin inhibitor 1 | 0.419 | 0.470 | 0.883 |
| 30 kDa prosomal protein; Macropain subunit C2; Multicatalytic endopeptidase complex subunit C2; Proteasome component C2; Proteasome nu chain; Proteasome subunit alpha type-1; Proteasome subunit alpha type | 0.402 | 0.563 | 0.994 |
| IMPDH-II; Inosine-5-monophosphate dehydrogenase 2 | 0.401 | 0.356 | 0.652 |
| Bax antagonist selected in saccharomyces 1; Negative regulatory element-binding protein; Protein DBP-5; Protein SON; SON3 | 0.401 | 0.560 | 0.906 |
| AGX-1; AGX-2; Antigen X; Sperm-associated antigen 2; UDP-N-acetylgalactosamine pyrophosphorylase; UDP-N-acetylglucosamine pyrophosphorylase; UDP-N-acetylhexosamine pyrophosphorylase; UDP-N-acteylglucosamine pyrophosphorylase 1 | 0.400 | 1.176 | 1.039 |
| Heat shock 70 kDa protein 4; Heat shock 70-related protein APG-2; HSP70RY | 0.390 | 1.029 | 1.069 |
| Autocrine motility factor; Glucose-6-phosphate isomerase; Neuroleukin; Phosphoglucose isomerase; Phosphohexose isomerase; Sperm antigen 36 | 0.383 | 0.317 | 0.849 |
| ATP-dependent helicase SMARCA2; BRG1-associated factor 190B; Probable global transcription activator SNF2L2; Protein brahma homolog; SNF2-alpha; SWI/SNF-related matrix-associated actin-dependent regulator of chromatin subfamily A member 2 | 0.379 | 0.669 | 1.095 |
| PEP11 homolog; Vacuolar protein sorting-associated protein 29; Vesicle protein sorting 29 | 0.366 | 1.199 | 1.100 |
| Deubiquitinating enzyme 7; Herpesvirus-associated ubiquitin-specific protease; Ubiquitin carboxyl-terminal hydrolase 7; Ubiquitin thioesterase 7; Ubiquitin-specific-processing protease 7; Ubiquitin carboxyl-terminal hydrolase | 0.365 | 0.730 | 0.991 |
| Butyrate-induced protein 1; Protein tyrosine phosphatase-like protein PTPLAD1; Protein-tyrosine phosphatase-like A domain-containing protein 1; cDNA FLJ54138, highly similar to Homo sapiens butyrate-induced transcript 1 (HSPC121), mRNA | 0.365 | 0.301 | 0.736 |
| Amine oxidase [flavin-containing] B; Monoamine oxidase type B; cDNA FLJ51821, highly similar to Amine oxidase (flavin-containing) B (EC 1.4.3.4); cDNA FLJ52418, highly similar to Amine oxidase (flavin-containing) B (EC 1.4.3.4) | 0.364 | 1.217 | 1.126 |
| Cell proliferation-inducing gene 21 protein; Guanine nucleotide-binding protein subunit beta-2-like 1; Guanine nucleotide-binding protein subunit beta-like protein 12.3; Human lung cancer oncogene 7 protein; Receptor for activated C kinase; Receptor of activated protein kinase C 1 | 0.361 | 0.644 | 0.979 |
| CAAX farnesyltransferase subunit alpha; FTase-alpha; Protein farnesyltransferase/geranylgeranyltransferase type-1 subunit alpha; Ras proteins prenyltransferase subunit alpha; Type I protein geranyl-geranyltransferase subunit alpha | 0.356 | 1.417 | 1.499 |
| 1F5 antigen; 20 kDa homologous restriction factor; CD59 glycoprotein; MAC-inhibitory protein; MEM43 antigen; Membrane attack complex inhibition factor; Membrane inhibitor of reactive lysis; Protectin | 0.354 | 1.131 | 1.368 |
| Aldehyde dehydrogenase family 1 member A1; Aldehyde dehydrogenase, cytosolic; ALDH-E1; ALHDII; Retinal dehydrogenase 1 | 0.348 | 0.678 | 1.002 |
| Glycine hydroxymethyltransferase; Serine hydroxymethyltransferase, mitochondrial; Serine methylase; cDNA FLJ58585, highly similar to Serine hydroxymethyltransferase, mitochondrial (EC 2.1.2.1); Serine hydroxymethyltransferase 2 (Mitochondrial), isoform CRA_h | 0.345 | 0.677 | 0.978 |
| Macropain zeta chain; Multicatalytic endopeptidase complex zeta chain; Proteasome subunit alpha type-5; Proteasome zeta chain; cDNA FLJ52182, highly similar to Proteasome subunit alpha type 5 (EC 3.4.25.1); Proteasome (Prosome, macropain) subunit, alpha type, 5, isoform CRA_c | 0.339 | 0.954 | 0.900 |
| Methionine--tRNA ligase; Methionyl-tRNA synthetase, cytoplasmic; Putative uncharacterized protein MARS; cDNA FLJ16674 fis, clone THYMU3008136, highly similar to Methionyl-tRNA synthetase (EC 6.1.1.10) | 0.325 | 0.537 | 0.977 |
| Importin-9; Ran-binding protein 9 | 0.320 | 0.530 | 0.801 |
| Pre-mRNA-splicing factor SRP75; Splicing factor, arginine/serine-rich 4; SRP001LB | 0.310 | 1.096 | 1.336 |
| Anterior gradient protein 2 homolog; HPC8; Secreted cement gland protein XAG-2 homolog; Putative uncharacterized protein AGR2 | 0.310 | 1.524 | 1.365 |

TABLE 4-continued

| Variable | Comp 1 VIP | Comp 2 VIP | Comp 3 VIP |
|---|---|---|---|
| Coagulation factor XIII A chain; Protein-glutamine gamma-glutamyltransferase A chain; Transglutaminase A chain | 0.306 | 1.379 | 1.397 |
| DNA replication licensing factor MCM2; Minichromosome maintenance protein 2 homolog; Nuclear protein BM28 | 0.303 | 0.555 | 0.981 |
| Phosphate carrier protein, mitochondrial; Phosphate transport protein; Solute carrier family 25 member 3 | 0.299 | 0.569 | 0.911 |
| CCT-beta; T-complex protein 1 subunit beta | 0.291 | 0.540 | 0.980 |
| Protein ftsJ homolog 3; Putative rRNA methyltransferase 3; rRNA (uridine-2-O-)-methyltransferase 3 | 0.286 | 0.995 | 1.042 |
| High mobility group-like nuclear protein 2 homolog 1; NHP2-like protein 1; OTK27; SNU13 homolog; U4/U6.U5 tri-snRNP 15.5 kDa protein; NHP2 non-histone chromosome protein 2-like 1 (S. cerevisiae) | 0.280 | 0.676 | 0.992 |
| CCT-gamma; hTRiC5; T-complex protein 1 subunit gamma | 0.278 | 0.521 | 0.867 |
| Nuclear matrix protein 200; Pre-mRNA-processing factor 19; PRP19/PSO4 homolog; Senescence evasion factor | 0.276 | 0.291 | 0.352 |
| Protein mago nashi homolog; cDNA FLJ55283, moderately similar to Protein mago nashi homolog; Mago-nashi homolog, proliferation-associated (Drosophila); Mago-nashi homolog, proliferation-associated (Drosophila), isoform CRA_a | 0.272 | 1.125 | 1.047 |
| Mannose-6-phosphate isomerase; Phosphohexomutase; Phosphomannose isomerase; Mannose phosphate isomerase isoform | 0.261 | 0.847 | 0.931 |
| Carnitine/acylcarnitine translocase; Mitochondrial carnitine/acylcarnitine carrier protein; Solute carrier family 25 member 20; cDNA FLJ53016, highly similar to Mitochondrial carnitine/acylcarnitine carrier protein | 0.254 | 1.064 | 1.024 |
| Caspase-1; Caspase-1 subunit p10; Caspase-1 subunit p20; Interleukin-1 beta convertase; Interleukin-1 beta-converting enzyme; p45; cDNA FLJ59442, highly similar to Caspase-1 (EC 3.4.22.36) | 0.252 | 1.158 | 1.068 |
| 40S ribosomal protein S4, X isoform; SCR10; Single copy abundant mRNA protein | 0.252 | 0.522 | 0.958 |
| Dipeptidyl aminopeptidase II; Dipeptidyl peptidase 2; Dipeptidyl peptidase 7; Dipeptidyl peptidase II; Quiescent cell proline dipeptidase | 0.248 | 1.042 | 0.922 |
| Protein mago nashi homolog 2; Putative uncharacterized protein MAGOHB | 0.240 | 1.337 | 1.259 |
| Brain-type aldolase; Fructose-bisphosphate aldolase C; Fructose-bisphosphate aldolase; Putative uncharacterized protein ALDOC | 0.236 | 0.954 | 0.892 |
| Ras-related protein Rab-1A; YPT1-related protein; cDNA FLJ57768, highly similar to Ras-related protein Rab-1A | 0.230 | 0.572 | 0.900 |
| Brush border myosin I; Myosin I heavy chain; Myosin-Ia | 0.222 | 1.238 | 1.241 |
| CDC21 homolog; DNA replication licensing factor MCM4; P1-CDC21 | 0.220 | 0.172 | 0.646 |
| 28 kDa heat shock protein; Estrogen-regulated 24 kDa protein; Heat shock 27 kDa protein; Heat shock protein beta-1; Stress-responsive protein 27; cDNA FLJ52243, highly similar to Heat-shock protein beta-1 | 0.208 | 0.621 | 0.941 |
| ATP-dependent RNA helicase DDX19A; DDX19-like protein; DEAD box protein 19A; ATP-dependent RNA helicase DDX19B; DEAD box protein 19B; DEAD box RNA helicase DEAD5; cDNA FLJ52463, highly similar to ATP-dependent RNA helicase DDX19A (EC 3.6.1.—) | 0.207 | 0.443 | 0.447 |
| Double-stranded RNA-binding protein 76; Interleukin enhancer-binding factor 3; M-phase phosphoprotein 4; Nuclear factor associated with dsRNA; Nuclear factor of activated T-cells 90 kDa; Translational control protein 80; Putative uncharacterized protein ILF3; cDNA FLJ58801, highly similar to Interleukin enhancer-binding factor 3 | 0.202 | 0.696 | 0.934 |
| PHD finger protein 6; PHD-like zinc finger protein; cDNA FLJ60207, highly similar to PHD finger protein 6; PHD finger protein 6, isoform CRA_d | 0.201 | 1.197 | 1.485 |
| Glycosyltransferase 25 family member 1; Hydroxylysine galactosyltransferase 1; Procollagen galactosyltransferase 1 | 0.197 | 0.183 | 1.063 |
| D-fructose-6-phosphate amidotransferase 2; Glucosamine--fructose-6-phosphate aminotransferase [isomerizing] 2; Glutamine: fructose 6 phosphate amidotransferase 2; Hexosephosphate aminotransferase 2 | 0.197 | 1.720 | 1.634 |
| CCT-delta; Stimulator of TAR RNA-binding; T-complex protein 1 subunit delta | 0.189 | 0.562 | 0.972 |
| 5-3 exoribonuclease 2; DHM1-like protein; cDNA FLJ55645, highly similar to 5-3 exoribonuclease 2 (EC 3.1.11.—) | 0.187 | 0.495 | 0.838 |
| High mobility group protein 2a; High mobility group protein 4; High mobility group protein B3 | 0.182 | 0.609 | 1.217 |
| CCT-theta; Renal carcinoma antigen NY-REN-15; T-complex protein 1 subunit theta; cDNA FLJ53379, highly similar to T-complex protein 1 subunit theta; cDNA FLJ59382, highly similar to T-complex protein 1 subunit theta | 0.181 | 0.581 | 0.962 |
| CD63 antigen; Granulophysin; Lysosomal-associated membrane protein 3; Melanoma-associated antigen ME491; Ocular melanoma-associated antigen; OMA81H; Tetraspanin-30; Putative uncharacterized protein CD63; Lysosome-associated membrane protein-3 variant | 0.180 | 0.953 | 0.884 |
| Sideroflexin-1; Tricarboxylate carrier protein | 0.178 | 0.600 | 0.965 |
| Phosphopantothenate--cysteine ligase; Phosphopantothenoylcysteine synthetase | 0.178 | 0.853 | 1.016 |
| CCT-alpha; T-complex protein 1 subunit alpha | 0.175 | 0.864 | 0.990 |
| Aldehyde dehydrogenase family 18 member A1; Delta-1-pyrroline-5-carboxylate synthase; Gamma-glutamyl kinase; Gamma-glutamyl phosphate reductase; Glutamate 5-kinase; Glutamate-5-semialdehyde dehydrogenase; Glutamyl-gamma-semialdehyde dehydrogenase | 0.174 | 0.757 | 0.868 |
| Alpha-II spectrin; Fodrin alpha chain; Spectrin alpha chain, brain; Spectrin, non-erythroid alpha chain; Putative uncharacterized protein SPTAN1; cDNA FLJ59116, highly similar to Spectrin alpha chain, brain | 0.173 | 0.562 | 0.960 |

TABLE 4-continued

| Variable | Comp 1 VIP | Comp 2 VIP | Comp 3 VIP |
|---|---|---|---|
| Delta(3,5)-Delta(2,4)-dienoyl-CoA isomerase, mitochondrial | 0.167 | 0.512 | 0.972 |
| Farnesyl-diphosphate farnesyltransferase; FPP: FPP farnesyltransferase; Squalene synthase; cDNA FLJ50548, highly similar to Squalene synthetase (EC 2.5.1.21); cDNA FLJ50447, highly similar to Squalene synthetase (EC 2.5.1.21); cDNA, FLJ78892, highly similar to Squalene synthetase (EC 2.5.1.21); cDNA, FLJ79250, highly similar to Squalene synthetase (EC 2.5.1.21); cDNA, FLJ79430, highly similar to Squalene synthetase (EC 2.5.1.21); cDNA FLJ50660, highly similar to Squalene synthetase (EC 2.5.1.21); cDNA, FLJ79433, highly similar to Squalene synthetase (EC 2.5.1.21); cDNA FLJ33164 fis, clone UTERU2000542, highly similar to Squalene synthetase (EC 2.5.1.21) | 0.167 | 0.280 | 0.600 |
| DEAH box protein 30; Putative ATP-dependent RNA helicase DHX30 | 0.162 | 0.794 | 1.002 |
| Bifunctional coenzyme A synthase; Dephospho-CoA kinase; Dephospho-CoA pyrophosphorylase; Dephosphocoenzyme A kinase; NBP; Pantetheine-phosphate adenylyltransferase; Phosphopantetheine adenylyltransferase; POV-2 | 0.162 | 1.139 | 1.115 |
| DNA-dependent protein kinase catalytic subunit; DNPK1; p460 | 0.161 | 0.579 | 0.967 |
| CDC46 homolog; DNA replication licensing factor MCM5; P1-CDC46; MCM5 minichromosome maintenance deficient 5, cell division cycle 46 (*S. cerevisiae*), isoform CRA_c; Minichromosome maintenance complex component 5 | 0.159 | 0.349 | 0.925 |
| Protein A1S9; Ubiquitin-activating enzyme E1; Ubiquitin-like modifier-activating enzyme 1; cDNA FLJ54582, highly similar to Ubiquitin-activating enzyme E1 | 0.156 | 0.683 | 0.940 |
| CNDP dipeptidase 2; Cytosolic non-specific dipeptidase; Glutamate carboxypeptidase-like protein 1; Peptidase A | 0.155 | 1.122 | 0.999 |
| Ras-related protein Rab-5B; cDNA FLJ60627, highly similar to Ras-related protein Rab-5B; RAB5B, member RAS oncogene family, isoform CRA_b | 0.152 | 0.305 | 0.369 |
| 358 kDa nucleoporin; E3 SUMO-protein ligase RanBP2; Nuclear pore complex protein Nup358; Nucleoporin Nup358; p270; Ran-binding protein 2 | 0.152 | 0.806 | 0.988 |
| Paraspeckle protein 2; RNA-binding motif protein 14; RNA-binding protein 14; RRM-containing coactivator activator/modulator; Synaptotagmin-interacting protein | 0.142 | 0.762 | 0.779 |
| 11-zinc finger protein; CCCTC-binding factor; CTCFL paralog; Transcriptional repressor CTCF; Putative uncharacterized protein CTCF | 0.131 | 0.524 | 1.286 |
| 6-phosphofructokinase, muscle type; Phosphofructo-1-kinase isozyme A; Phosphofructokinase 1; Phosphohexokinase | 0.124 | 0.812 | 1.019 |
| Cyclin-A/CDK2-associated protein p19; Organ of Corti protein 2; Organ of Corti protein II; p19A; p19skp1; RNA polymerase II elongation factor-like protein; SIII; S-phase kinase-associated protein 1; Transcription elongation factor B | 0.123 | 0.644 | 0.779 |
| DRG family-regulatory protein 1; Likely ortholog of mouse immediate early response erythropoietin 4; Zinc finger CCCH domain-containing protein 15 | 0.121 | 0.869 | 0.890 |
| 39S ribosomal protein L53, mitochondrial | 0.119 | 0.960 | 0.919 |
| Met-induced mitochondrial protein; Mitochondrial carrier homolog 2 | 0.116 | 0.476 | 0.951 |
| Protein H105e3; Sterol-4-alpha-carboxylate 3-dehydrogenase, decarboxylating; Putative uncharacterized protein NSDHL | 0.105 | 1.222 | 1.087 |
| Bw-45; HLA class I histocompatibility antigen, B-45 alpha chain; MHC class I antigen B*45 | 0.095 | 0.796 | 0.733 |
| Hsc70-interacting protein; Progesterone receptor-associated p48 protein; Protein FAM10A1; Putative tumor suppressor ST13; Renal carcinoma antigen NY-REN-33; Suppression of tumorigenicity 13 protein; ST13 protein; Putative protein FAM10A5; Putative protein FAM10A4 | 0.095 | 0.714 | 0.961 |
| BRCA1-A complex subunit MERIT40; Mediator of RAP80 interactions and targeting subunit of 40 kDa; New component of the BRCA1-A complex | 0.091 | 0.275 | 0.504 |
| Ezrin-radixin-moesin-binding phosphoprotein 50; Na(+)/H(+) exchange regulatory cofactor NHE-RF1; Regulatory cofactor of Na(+)/H(+) exchanger; Sodium-hydrogen exchanger regulatory factor 1; Solute carrier family 9 isoform A3 regulatory factor 1 | 0.088 | 0.557 | 0.968 |
| Valyl-tRNA synthetase; Protein G7a; Valine--tRNA ligase | 0.084 | 0.710 | 0.910 |
| HCV F-transactivated protein 2; Up-regulated during skeletal muscle growth protein 5 | 0.083 | 0.468 | 0.994 |
| Adenylate cyclase-stimulating G alpha protein; Extra large alphas protein; Guanine nucleotide-binding protein G(s) subunit alpha isoforms XLas; Putative uncharacterized protein GNAS; Guanine nucleotide-binding protein G(s) subunit alpha isoforms short | 0.073 | 1.209 | 1.091 |
| CCT-eta; HIV-1 Nef-interacting protein; T-complex protein 1 subunit eta; Putative uncharacterized protein CCT7; cDNA FLJ59454, highly similar to T-complex protein 1 subunit eta; Chaperonin containing TCP1, subunit 7 (Eta), isoform CRA_a | 0.071 | 0.574 | 0.934 |
| Collagen alpha-1(VI) chain; cDNA FLJ61362, highly similar to Collagen alpha-1(VI) chain | 0.068 | 1.608 | 1.496 |
| ARF-binding protein 1; E3 ubiquitin-protein ligase HUWE1; HECT, UBA and WWE domain-containing protein 1; Homologous to E6AP carboxyl terminus homologous protein 9; Large structure of UREB1; Mcl-1 ubiquitin ligase E3; Upstream regulatory element-binding protein 1 | 0.066 | 0.661 | 0.963 |
| Alpha-1-acid glycoprotein 2; Orosomucoid-2 | 0.060 | 1.836 | 1.804 |
| Protein NipSnap homolog 3A; Protein NipSnap homolog 4; Target for *Salmonella* secreted protein C | 0.060 | 0.931 | 1.090 |
| Antioxidant protein 1; HBC189; Peroxiredoxin III; Peroxiredoxin-3; Protein MER5 homolog; Thioredoxin-dependent peroxide reductase, mitochondrial | 0.058 | 0.578 | 0.972 |
| Aspartate carbamoyltransferase; CAD protein; Dihydroorotase; Glutamine-dependent carbamoyl-phosphate synthase | 0.049 | 0.820 | 0.923 |
| Nuclear mitotic apparatus protein 1; SP-H antigen | 0.045 | 0.486 | 0.961 |
| 50 kDa nucleoporin; Nuclear pore complex protein Nup50; Nuclear pore-associated protein 60 kDa-like; Nucleoporin Nup50 | 0.043 | 0.036 | 0.745 |
| [Acyl-carrier-protein] S-acetyltransferase; [Acyl-carrier-protein] S-malonyltransferase; 3-hydroxypalmitoyl-[acyl-carrier-protein] dehydratase; 3-oxoacyl-[acyl-carrier-protein] reductase; 3-oxoacyl-[acyl-carrier-protein] synthase; Enoyl-[acyl-carrier-protein] reductase; Fatty acid synthase; Oleoyl-[acyl-carrier-protein] hydrolase | 0.035 | 0.582 | 0.581 |

TABLE 4-continued

| Variable | Comp 1 VIP | Comp 2 VIP | Comp 3 VIP |
|---|---|---|---|
| DNA mismatch repair protein Msh6; G/T mismatch-binding protein; MutS-alpha 160 kDa subunit; cDNA FLJ55677, highly similar to DNA mismatch repair protein MSH6 | 0.029 | 0.674 | 0.714 |
| Heterogeneous nuclear ribonucleoprotein H; Heterogeneous nuclear ribonucleoprotein H, N-terminally processed | 0.025 | 0.583 | 0.972 |
| Protein-tyrosine phosphatase 1D; Protein-tyrosine phosphatase 2C; SH-PTP2; SH-PTP3; Tyrosine-protein phosphatase non-receptor type 11 | 0.018 | 0.430 | 0.913 |
| ATP-dependent RNA helicase A; DEAH box protein 9; Nuclear DNA helicase II | 0.006 | 0.562 | 0.967 |
| Cysteine dioxygenase type 1; Cysteine dioxygenase type I | 0.005 | 1.364 | 1.209 |

It has been observed that certain mitochondrial proteins are differentially expressed and their levels can be associated with the presence or absence of UC or CD disease. For example, sulfur dioxygenase (ETHE1), thiosulfate sulfur transferase (TST), cytochrome c oxidase subunit IV, sulfide dehydrogenase genes (SQR) and complexes III and IV of mithochondrial respiratory chain obtained from a gut mucus sample of a human subject can be indicative of the presence of UC or CD or IBD in the subject. However it will be appreciated that any other protein(s) listed in table 4 or 5 alone or in combination that is or are differentially expressed can also be used to assess the presence/absence/severity of UC or CD disease.

Expression of certain cytokines above normal levels can also be used to detect the presence of *A. parvulum*. For example the presence of *A. parvulum* is correlated with expression (or overexpression) of Cxcl1, Il17a, Il12 and Il1β. Therefore there is provided an assay for identifying the likelihood of an individual of having UC or CD or IBD by measuring a relative abundance of *A. parvulum* by measuring the expression of Cxcl1, Il17a, Il12 or Il1β. This correlation can also be used to provide a method of diagnostic that comprises collecting samples to measure one or more cytokines, determining the presence of *A. parvulum* based on the cytokine(s) measurement and establishing a diagnosis.

Table 5 List of all differentially expressed mitochondrial proteins and their variable importance in projection scores (VIP) derived from the calculated PLS-DA model.

TABLE 5

| Variable | Comp. 1 VIP | Comp. 2 VIP | Comp. 3 VIP |
|---|---|---|---|
| Complex I-PDSW; NADH dehydrogenase [ubiquinone] 1 beta subcomplex subunit 10; NADH-ubiquinone oxidoreductase PDSW subunit; NADH dehydrogenase (Ubiquinone) 1 beta subcomplex, 10, 22 kDa, isoform CRA_a; NDUFB10 protein | 1.834 | 1.448 | 1.178 |
| Complex I-75 kD; NADH-ubiquinone oxidoreductase 75 kDa subunit, mitochondrial; cDNA FLJ60586, highly similar to NADH-ubiquinone oxidoreductase 75 kDa subunit, mitochondrial (EC 1.6.5.3) | 1.788 | 1.323 | 1.100 |
| Isovaleryl-CoA dehydrogenase, mitochondrial; cDNA FLJ16602 fis, clone TESTI4007816, highly similar to Isovaleryl-CoA dehydrogenase, mitochondrial (EC 1.3.99.10); Isovaleryl Coenzyme A dehydrogenase, isoform CRA_b | 1.748 | 1.559 | 1.324 |
| Complex I-39 kD; NADH dehydrogenase [ubiquinone] 1 alpha subcomplex subunit 9, mitochondrial; NADH-ubiquinone oxidoreductase 39 kDa subunit | 1.706 | 1.331 | 1.100 |
| Cytochrome c oxidase polypeptide Vb; Cytochrome c oxidase subunit 5B, mitochondrial | 1.666 | 1.237 | 1.006 |
| Complex III subunit 5; Complex III subunit IX; Cytochrome b-c1 complex subunit 11; Cytochrome b-c1 complex subunit 5; Cytochrome b-c1 complex subunit Rieske, mitochondrial; Rieske iron-sulfur protein; Ubiquinol-cytochrome c reductase 8 kDa protein; Ubiquinol-cytochrome c reductase iron-sulfur subunit; Putative cytochrome b-c1 complex subunit Rieske-like protein 1 | 1.658 | 1.249 | 1.038 |
| Complex III subunit 7; Complex III subunit VII; Cytochrome b-c1 complex subunit 7; QP-C; Ubiquinol-cytochrome c reductase complex 14 kDa protein; cDNA FLJ52271, moderately similar to Ubiquinol-cytochrome c reductase complex 14 kDa protein (EC 1.10.2.2) | 1.625 | 1.220 | 1.007 |
| Complex III subunit 2; Core protein II; Cytochrome b-c1 complex subunit 2, mitochondrial; Ubiquinol-cytochrome-c reductase complex core protein 2 | 1.551 | 1.167 | 1.207 |
| Angiotensin-binding protein; Microsomal endopeptidase; Mitochondrial oligopeptidase M; Neurolysin, mitochondrial; Neurotensin endopeptidase | 1.547 | 1.997 | 1.627 |
| Rhodanese; Thiosulfate sulfurtransferase | 1.504 | 1.169 | 0.954 |
| Complex I-ASHI; NADH dehydrogenase [ubiquinone] 1 beta subcomplex subunit 8, mitochondrial; NADH-ubiquinone oxidoreductase ASHI subunit; NADH dehydrogenase (Ubiquinone) 1 beta subcomplex, 8, 19 kDa; NADH dehydrogenase (Ubiquinone) 1 beta subcomplex, 8, 19 kDa, isoform CRA_a; cDNA FLJ52503, highly similar to NADH dehydrogenase (ubiquinone) 1 beta subcomplex subunit 8, mitochondrial (EC 1.6.5.3) (EC 1.6.99.3) (NADH-ubiquinone oxidoreductase ASHI subunit) (Complex I-ASHI) (CI-ASHI) | 1.489 | 1.117 | 1.207 |
| Iron-sulfur subunit of complex II; Succinate dehydrogenase [ubiquinone] iron-sulfur subunit, mitochondrial | 1.486 | 1.167 | 1.040 |
| Complex III subunit 1; Core protein I; Cytochrome b-c1 complex subunit 1, mitochondrial; Ubiquinol-cytochrome-c reductase complex core protein 1 | 1.474 | 1.124 | 0.922 |
| Complex I-B14.5a; NADH dehydrogenase [ubiquinone] 1 alpha subcomplex subunit 7; NADH-ubiquinone oxidoreductase subunit B14.5a | 1.470 | 1.088 | 1.194 |
| Complex I-23 kD; NADH dehydrogenase [ubiquinone] iron-sulfur protein 8, mitochondrial; NADH-ubiquinone oxidoreductase 23 kDa subunit; TYKY subunit | 1.443 | 1.178 | 0.982 |
| Cytochrome c oxidase polypeptide IV; Cytochrome c oxidase subunit 4 isoform 1, mitochondrial; Cytochrome c oxidase subunit IV isoform 1; COX4I1 protein | 1.432 | 1.063 | 0.934 |

TABLE 5-continued

| Variable | Comp. 1 VIP | Comp. 2 VIP | Comp. 3 VIP |
|---|---|---|---|
| Cytochrome c oxidase polypeptide VIc; Cytochrome c oxidase subunit 6C | 1.416 | 1.074 | 0.929 |
| Glutathione S-transferase kappa 1; Glutathione S-transferase subunit 13; GST 13-13; GST class-kappa; GSTK1-1 | 1.404 | 1.172 | 0.975 |
| Cytochrome c oxidase polypeptide II; Cytochrome c oxidase subunit 2 | 1.375 | 1.120 | 0.943 |
| GTP-specific succinyl-CoA synthetase subunit beta; Succinyl-CoA ligase [GDP-forming] subunit beta, mitochondrial; Succinyl-CoA synthetase beta-G chain | 1.363 | 1.127 | 0.961 |
| 250/210 kDa paraneoplastic pemphigus antigen; Desmoplakin | 1.354 | 1.040 | 0.867 |
| Complex I-51 kD; NADH dehydrogenase [ubiquinone] flavoprotein 1, mitochondrial; NADH dehydrogenase flavoprotein 1; NADH-ubiquinone oxidoreductase 51 kDa subunit; cDNA FLJ57949, highly similar to NADH-ubiquinone oxidoreductase 51 kDa subunit, mitochondrial (EC 1.6.5.3); cDNA, FLJ79021, highly similar to NADH-ubiquinone oxidoreductase 51 kDa subunit, mitochondrial (EC 1.6.5.3) | 1.353 | 1.034 | 1.066 |
| Alu corepressor 1; Antioxidant enzyme B166; Liver tissue 2D-page spot 71B; Peroxiredoxin V; Peroxiredoxin-5, mitochondrial; Peroxisomal antioxidant enzyme; PLP; Thioredoxin peroxidase PMP20; Thioredoxin reductase; TPx type VI; Putative uncharacterized protein PRDX5 | 1.336 | 0.994 | 0.821 |
| ICD-M; IDP; Isocitrate dehydrogenase [NADP], mitochondrial; NADP(+)-specific ICDH; Oxalosuccinate decarboxylase | 1.320 | 1.210 | 1.078 |
| Flavoprotein subunit of complex II; Succinate dehydrogenase [ubiquinone] flavoprotein subunit, mitochondrial | 1.292 | 1.057 | 1.032 |
| Brain-type aldolase; Fructose-bisphosphate aldolase C; Fructose-bisphosphate aldolase; Putative uncharacterized protein ALDOC | 1.289 | 1.115 | 0.906 |
| Complex I-13 kD-A; NADH dehydrogenase [ubiquinone] iron-sulfur protein 6, mitochondrial; NADH-ubiquinone oxidoreductase 13 kDa-A subunit | 1.261 | 0.935 | 0.781 |
| Ethylmalonic encephalopathy protein 1; Hepatoma subtracted clone one protein; Protein ETHE1, mitochondrial | 1.252 | 0.951 | 0.851 |
| Complex I-B15; NADH dehydrogenase [ubiquinone] 1 beta subcomplex subunit 4; NADH-ubiquinone oxidoreductase B15 subunit; Putative uncharacterized protein NDUFB4 | 1.241 | 0.922 | 0.749 |
| DEAH box protein 30; Putative ATP-dependent RNA helicase DHX30 | 1.213 | 1.450 | 1.220 |
| Cytochrome c oxidase polypeptide VIIc; Cytochrome c oxidase subunit 7C, mitochondrial | 1.211 | 0.897 | 0.751 |
| Amine oxidase [flavin-containing] A; Monoamine oxidase type A; cDNA FLJ61220, highly similar to Amine oxidase (flavin-containing) A (EC 1.4.3.4) | 1.204 | 0.970 | 0.866 |
| Carnitine O-palmitoyltransferase 2, mitochondrial; Carnitine palmitoyltransferase II | 1.141 | 0.869 | 0.871 |
| Amine oxidase [flavin-containing] B; Monoamine oxidase type B; cDNA FLJ51821, highly similar to Amine oxidase (flavin-containing) B (EC 1.4.3.4); cDNA FLJ52418, highly similar to Amine oxidase (flavin-containing) B (EC 1.4.3.4) | 1.066 | 1.289 | 1.107 |
| Glutaminase kidney isoform, mitochondrial; K-glutaminase; L-glutamine amidohydrolase | 1.033 | 1.317 | 1.087 |
| Acyl-coenzyme A thioesterase 13; Thioesterase superfamily member 2 | 1.006 | 1.393 | 1.190 |
| Cathepsin D; Cathepsin D heavy chain; Cathepsin D light chain | 1.004 | 0.784 | 0.652 |
| 78 kDa gastrin-binding protein; Long chain 3-hydroxyacyl-CoA dehydrogenase; Long-chain enoyl-CoA hydratase; TP-alpha; Trifunctional enzyme subunit alpha, mitochondrial | 0.999 | 0.742 | 0.836 |
| Elongation factor Tu, mitochondrial; P43 | 0.991 | 0.754 | 0.929 |
| Enoyl-CoA hydratase 1; Enoyl-CoA hydratase, mitochondrial; Short-chain enoyl-CoA hydratase | 0.968 | 0.842 | 0.714 |
| Dihydrolipoamide dehydrogenase; Dihydrolipoyl dehydrogenase, mitochondrial; Glycine cleavage system L protein; cDNA FLJ50515, highly similar to Dihydrolipoyl dehydrogenase, mitochondrial (EC 1.8.1.4); Dihydrolipoyl dehydrogenase | 0.956 | 0.716 | 0.728 |
| Delta(3),delta(2)-enoyl-CoA isomerase; Diazepam-binding inhibitor-related protein 1; Dodecenoyl-CoA isomerase; DRS-1; Hepatocellular carcinoma-associated antigen 88; Peroxisomal 3,2-trans-enoyl-CoA isomerase; Renal carcinoma antigen NY-REN-1; Putative uncharacterized protein PECI | 0.945 | 0.706 | 0.578 |
| Catalase | 0.924 | 0.881 | 0.801 |
| 3-ketoacyl-CoA thiolase; Acetyl-CoA acyltransferase; Beta-ketothiolase; TP-beta; Trifunctional enzyme subunit beta, mitochondrial; cDNA FLJ56214, highly similar to Trifunctional enzyme subunit beta, mitochondrial; Putative uncharacterized protein HADHB | 0.892 | 0.696 | 0.981 |
| Aldehyde dehydrogenase family 6 member A1; Methylmalonate-semialdehyde dehydrogenase [acylating], mitochondrial | 0.882 | 0.756 | 0.616 |
| Malic enzyme 2; NAD-dependent malic enzyme, mitochondrial | 0.872 | 1.419 | 1.325 |
| Outer mitochondrial membrane protein porin 2; Voltage-dependent anion-selective channel protein 2; Voltage-dependent anion channel 2; cDNA FLJ60120, highly similar to Voltage-dependent anion-selective channel protein 2; cDNA, FLJ78818, highly similar to Voltage-dependent anion-selective channel protein 2 | 0.871 | 0.649 | 0.538 |
| Aspartate aminotransferase, mitochondrial; Fatty acid-binding protein; Glutamate oxaloacetate transaminase 2; Plasma membrane-associated fatty acid-binding protein; Transaminase A | 0.869 | 0.668 | 0.605 |
| Aldehyde dehydrogenase 5; Aldehyde dehydrogenase family 1 member B1; Aldehyde dehydrogenase X, mitochondrial; cDNA FLJ51238, highly similar to Aldehyde dehydrogenase X, mitochondrial (EC 1.2.1.3) | 0.861 | 0.893 | 0.729 |
| Protein NipSnap homolog 1 | 0.849 | 0.635 | 0.541 |
| Calcium-binding mitochondrial carrier protein Aralar2; Citrin; Mitochondrial aspartate glutamate carrier 2; Solute carrier family 25 member 13 | 0.840 | 0.650 | 0.691 |
| Elongation factor Ts, mitochondrial; Elongation factor Ts | 0.822 | 0.893 | 0.726 |
| Cytosol aminopeptidase; Leucine aminopeptidase 3; Leucyl aminopeptidase; Peptidase S; Proline aminopeptidase; Prolyl aminopeptidase | 0.797 | 0.590 | 0.848 |
| Outer mitochondrial membrane protein porin 1; Plasmalemmal porin; Porin 31HL; Porin 31HM; Voltage-dependent anion-selective channel protein 1 | 0.766 | 0.602 | 0.533 |

TABLE 5-continued

| Variable | Comp. 1 VIP | Comp. 2 VIP | Comp. 3 VIP |
|---|---|---|---|
| Superoxide dismutase [Mn], mitochondrial; Superoxide dismutase | 0.723 | 0.581 | 0.916 |
| Sideroflexin-1; Tricarboxylate carrier protein | 0.721 | 0.705 | 1.238 |
| Aldehyde dehydrogenase family 18 member A1; Delta-1-pyrroline-5-carboxylate synthase; Gamma-glutamyl kinase; Gamma-glutamyl phosphate reductase; Glutamate 5-kinase; Glutamate-5-semialdehyde dehydrogenase; Glutamyl-gamma-semialdehyde dehydrogenase | 0.716 | 0.559 | 1.164 |
| 39S ribosomal protein L53, mitochondrial | 0.705 | 0.812 | 0.703 |
| Glycine hydroxymethyltransferase; Serine hydroxymethyltransferase, mitochondrial; Serine methylase; cDNA FLJ58585, highly similar to Serine hydroxymethyltransferase, mitochondrial (EC 2.1.2.1); Serine hydroxymethyltransferase 2 (Mitochondrial), isoform CRA_h | 0.687 | 0.690 | 1.139 |
| Antioxidant enzyme AOE372; Peroxiredoxin IV; Peroxiredoxin-4; Thioredoxin peroxidase AO372; Thioredoxin-dependent peroxide reductase A0372 | 0.651 | 1.017 | 1.015 |
| Hematopoietic cell-specific LYN substrate 1; Hematopoietic lineage cell-specific protein; LckBP1; p75 | 0.635 | 0.872 | 0.708 |
| Acetoacetyl-CoA thiolase; Acetyl-CoA acetyltransferase, mitochondrial; T2 | 0.592 | 0.646 | 0.573 |
| Complex I-B8; NADH dehydrogenase [ubiquinone] 1 alpha subcomplex subunit 2; NADH-ubiquinone oxidoreductase B8 subunit | 0.570 | 1.106 | 0.937 |
| Heat shock-related 70 kDa protein 2; cDNA FLJ40505 fis, clone TESTI2045562, highly similar to HEAT SHOCK-RELATED 70 kDa PROTEIN 2 | 0.551 | 1.027 | 0.850 |
| Pyruvate carboxylase, mitochondrial; Pyruvic carboxylase; cDNA FLJ60715, highly similar to Pyruvate carboxylase, mitochondrial (EC 6.4.1.1) | 0.542 | 0.477 | 0.394 |
| Hydroxysteroid dehydrogenase-like protein 2; cDNA FLJ61200, highly similar to *Homo sapiens* hydroxysteroid dehydrogenase like 2 (HSDL2), mRNA | 0.509 | 0.403 | 0.419 |
| PDHE1-A type I; Pyruvate dehydrogenase E1 component subunit alpha, somatic form, mitochondrial | 0.498 | 0.372 | 0.801 |
| Antioxidant protein 1; HBC189; Peroxiredoxin III; Peroxiredoxin-3; Protein MER5 homolog; Thioredoxin-dependent peroxide reductase, mitochondrial | 0.490 | 0.707 | 1.120 |
| 3-hydroxybutyrate dehydrogenase type 2; Dehydrogenase/reductase SDR family member 6; Oxidoreductase UCPA; R-beta-hydroxybutyrate dehydrogenase | 0.476 | 0.807 | 0.883 |
| 3-5 RNA exonuclease OLD35; PNPase old-35; Polynucleotide phosphorylase 1; Polynucleotide phosphorylase-like protein; Polyribonucleotide nucleotidyltransferase 1, mitochondrial | 0.470 | 1.236 | 1.035 |
| 3-ketoacyl-CoA thiolase, mitochondrial; Acetyl-CoA acyltransferase; Beta-ketothiolase; Mitochondrial 3-oxoacyl-CoA thiolase; T1 | 0.461 | 0.677 | 1.061 |
| Delta(3,5)-Delta(2,4)-dienoyl-CoA isomerase, mitochondrial | 0.458 | 0.638 | 1.143 |
| Carnitine/acylcarnitine translocase; Mitochondrial carnitine/acylcarnitine carrier protein; Solute carrier family 25 member 20; cDNA FLJ53016, highly similar to Mitochondrial carnitine/acylcarnitine carrier protein | 0.453 | 2.048 | 1.697 |
| Protein SCO2 homolog, mitochondrial | 0.439 | 1.323 | 1.107 |
| HCNPpp; Hippocampal cholinergic neurostimulating peptide; Neuropolypeptide h3; Phosphatidylethanolamine-binding protein 1; Prostatic-binding protein; Raf kinase inhibitor protein; cDNA FLJ51535, highly similar to Phosphatidylethanolamine-binding protein 1 | 0.411 | 0.517 | 0.981 |
| Collapsin response mediator protein 2; Dihydropyrimidinase-related protein 2; N2A3; Unc-33-like phosphoprotein 2 | 0.403 | 0.309 | 1.150 |
| 28S ribosomal protein S9, mitochondrial | 0.356 | 2.072 | 1.692 |
| Met-induced mitochondrial protein; Mitochondrial carrier homolog 2 | 0.353 | 0.461 | 1.075 |
| Phosphate carrier protein, mitochondrial; Phosphate transport protein; Solute carrier family 25 member 3 | 0.353 | 0.514 | 1.140 |
| Acyl-CoA-binding domain-containing protein 3; Golgi complex-associated protein 1; Golgi phosphoprotein 1; Golgi resident protein GCP60; PBR- and PKA-associated protein 7; Peripheral benzodiazepine receptor-associated protein PAP7 | 0.351 | 1.694 | 1.801 |
| HCV F-transactivated protein 2; Up-regulated during skeletal muscle growth protein 5 | 0.344 | 0.707 | 1.117 |
| Protein-tyrosine phosphatase 1D; Protein-tyrosine phosphatase 2C; SH-PTP2; SH-PTP3; Tyrosine-protein phosphatase non-receptor type 11 | 0.303 | 0.699 | 1.024 |
| ATP synthase subunit a; F-ATPase protein 6 | 0.260 | 0.193 | 0.279 |
| Complex III subunit 3; Complex III subunit III; Cytochrome b; Cytochrome b-c1 complex subunit 3; Ubiquinol-cytochrome-c reductase complex cytochrome b subunit | 0.235 | 0.489 | 0.692 |
| Clathrin heavy chain 1; Clathrin heavy chain on chromosome 17 | 0.226 | 0.477 | 0.730 |
| Glutamate dehydrogenase 1, mitochondrial; cDNA FLJ55203, highly similar to Glutamate dehydrogenase 1, mitochondrial (EC 1.4.1.3); cDNA FLJ16138 fis, clone BRALZ2017531, highly similar to Glutamate dehydrogenase 1, mitochondrial (EC 1.4.1.3); Glutamate dehydrogenase 1, isoform CRA_a; Glutamate dehydrogenase 2, mitochondrial | 0.216 | 0.315 | 0.598 |
| Succinyl-CoA ligase [GDP-forming] subunit alpha, mitochondrial; Succinyl-CoA synthetase subunit alpha | 0.189 | 0.452 | 1.125 |
| Complex I-15 kDa; NADH dehydrogenase [ubiquinone] iron-sulfur protein 5; NADH-ubiquinone oxidoreductase 15 kDa subunit | 0.163 | 1.344 | 1.142 |
| Complex I-49 kD; NADH dehydrogenase [ubiquinone] iron-sulfur protein 2, mitochondrial; NADH-ubiquinone oxidoreductase 49 kDa subunit; cDNA, FLJ78876, highly similar to NADH-ubiquinone oxidoreductase 49 kDa subunit, mitochondrial (EC 1.6.5.3) | 0.137 | 0.301 | 1.161 |
| 3-hydroxyisobutyryl-CoA hydrolase, mitochondrial; 3-hydroxyisobutyryl-coenzyme A hydrolase | 0.106 | 1.378 | 1.513 |
| Alcohol dehydrogenase 5; Alcohol dehydrogenase class chi chain; Alcohol dehydrogenase class-3; Alcohol dehydrogenase class-III; Glutathione-dependent formaldehyde dehydrogenase; S-(hydroxymethyl)glutathione dehydrogenase | 0.093 | 0.471 | 1.107 |

TABLE 5-continued

| Variable | Comp. 1 VIP | Comp. 2 VIP | Comp. 3 VIP |
|---|---|---|---|
| Electron transfer flavoprotein subunit beta | 0.091 | 0.479 | 1.047 |
| 130 kDa leucine-rich protein; GP130; Leucine-rich PPR motif-containing protein, mitochondrial | 0.057 | 0.480 | 1.135 |
| ATP-specific succinyl-CoA synthetase subunit beta; Renal carcinoma antigen NY-REN-39; Succinyl-CoA ligase [ADP-forming] subunit beta, mitochondrial; Succinyl-CoA synthetase beta-A chain; Succinate-CoA ligase, ADP-forming, beta subunit | 0.024 | 0.865 | 0.725 |
| Citrate synthase, mitochondrial; Citrate synthase | 0.014 | 0.627 | 1.020 |

In yet another embodiment of the invention there is provided an assay that allows the measurement of the gut microbiota composition and the meta-proteome from a same sample. More specifically the assay comprises the collection of mucus at the luminal interface of the gut during endoscopy by flushing a physiological solution, such as sterile saline, onto the mucosa to remove the strongly adherent mucus layer overlaying the intestinal mucosal epithelial cells thereby sampling the microbial community and host and bacterial proteins embedded within the mucus layer. Aspirates are then collected directly through the colonoscope and the samples are preferably immediately put on ice right in the endoscopy suite. The sample can then be analyzed at the point of care or transferred to a laboratory. Bacteria and proteins can then be identified and/or measured as described above. This method advantageously permits the establishment of a protein and bacterial profile in the same patient at a pre-determined time point.

The establishment of the presence of disease using bacterial taxa can be used to determine a course of treatment in a patient. Treatment is normally based on accepted diseases indexes. The methods and assays provided by the invention can complement or replace such disease indexes to provide more accurate diagnosis and thereby permit more efficacious treatments.

It will be appreciated that the above described assays for identifying and measuring gut proteins and bacteria can be performed as a function of time thereby allowing an assessment of the progression of the disease as well as of the efficacy of a treatment. Staging of IBD (and CD and UC) is particularly useful for choosing the appropriate treatment to be delivered. For example, treatment regimen may advantageously be adjusted taking in consideration the levels of $H_2S$ producing bacteria, which as described above, are more elevated as the severity of the disease increases. Thus regimens that are more aggressive towards mitigating the effects of the $H_2S$ producing bacteria can be timely administered to optimize the therapeutic dose. Treatment optimization using the information on the presence/stage of IBD, UC and CD provided by the measuring of bacteria and protein as described above, can be applied to known therapeutic agents such as but not limited to aminosalycilates, immunomodulators, anti-integrins, anti-cytokines, enteral feed programs, steroids, corticosteroids, antibiotics, anti-TNFα, bismuth and the like. In particular, as further described below, bismuth can be used effectively as treatment when *A. parvulum* is detected in a patient and or assessed to be above certain critical abundance levels.

In table 6 taxa that vary significantly in abundance in Il10−/− mice in response to *A. parvulum* colonization and/or bismuth administration are listed. As can be seen from the table bismuth treatment may be indicated or beneficial when the relative abundance of taxa other than *A. parvulum* are within levels indicative of disease.

TABLE 6

| Variable | Minimum | Maximum | Mean | Std. dev. | p\|Atopo | p\|AtopoBis | p\|Bis | p\|SPF |
|---|---|---|---|---|---|---|---|---|
| PHYLUM | | | | | | | | |
| Basidiomycota\|Atopo | 0.000 | 0.000 | 0.000 | 0.000 | 1 | 1.000 | 1.000 | 0.000 |
| Basidiomycota\|AtopoBis | 0.000 | 0.000 | 0.000 | 0.000 | 1.000 | 1 | 1.000 | 0.000 |
| Basidiomycota\|Bis | 0.000 | 0.000 | 0.000 | 0.000 | 1.000 | 1.000 | 1 | 0.000 |
| Basidiomycota\|SPF | 0.000 | 80.000 | 25.429 | 32.103 | 0.000 | 0.000 | 0.000 | 1 |
| Firmicutes\|Atopo | 57699.000 | 101958.000 | 79769.875 | 13542.546 | 1 | 0.869 | 0.002 | 0.194 |
| Firmicutes\|AtopoBis | 49410.000 | 184098.000 | 104984.625 | 60115.166 | 0.869 | 1 | 0.003 | 0.255 |
| Firmicutes\|Bis | 105913.000 | 199488.000 | 175443.625 | 40788.918 | 0.002 | 0.003 | 1 | 0.084 |
| Firmicutes\|SPF | 64133.000 | 198934.000 | 121645.143 | 57520.397 | 0.194 | 0.255 | 0.084 | 1 |
| Cyanobacteria\|Atopo | 1.000 | 136.000 | 56.125 | 53.731 | 1 | 0.023 | 0.007 | 0.006 |
| Cyanobacteria\|AtopoBis | 63.000 | 553.000 | 216.125 | 157.070 | 0.023 | 1 | 0.680 | 0.563 |
| Cyanobacteria\|Bis | 52.000 | 669.000 | 261.000 | 194.269 | 0.007 | 0.680 | 1 | 0.857 |
| Cyanobacteria\|SPF | 30.000 | 872.000 | 370.000 | 326.109 | 0.006 | 0.563 | 0.857 | 1 |
| Fusobacteria\|Atopo | 0.000 | 20.000 | 3.500 | 6.845 | 1 | 0.008 | 0.089 | 0.007 |
| Fusobacteria\|AtopoBis | 1.000 | 34434.000 | 6670.125 | 12103.868 | 0.008 | 1 | 0.341 | 0.889 |
| Fusobacteria\|Bis | 0.000 | 3175.000 | 445.125 | 1109.012 | 0.089 | 0.341 | 1 | 0.289 |
| Fusobacteria\|SPF | 5.000 | 96.000 | 38.571 | 31.921 | 0.007 | 0.889 | 0.289 | 1 |
| Bacteroidetes\|Atopo | 86976.000 | 133781.000 | 108741.375 | 14150.040 | 1 | 0.216 | <0.0001 | 0.011 |
| Bacteroidetes\|AtopoBis | 232.000 | 117882.000 | 64729.375 | 53917.801 | 0.216 | 1 | 0.004 | 0.175 |
| Bacteroidetes\|Bis | 98.000 | 519.000 | 209.500 | 134.340 | <0.0001 | 0.004 | 1 | 0.151 |
| Bacteroidetes\|SPF | 71.000 | 107705.000 | 28633.857 | 48179.254 | 0.011 | 0.175 | 0.151 | 1 |
| CLASS | | | | | | | | |
| Fusobacteria (class)\|Atopo | 0.000 | 20.000 | 3.500 | 6.845 | 1 | 0.008 | 0.089 | 0.007 |
| Fusobacteria (class)\|AtopoBis | 1.000 | 34434.000 | 6670.125 | 12103.868 | 0.008 | 1 | 0.341 | 0.889 |

TABLE 6-continued

| Variable | Minimum | Maximum | Mean | Std. dev. | p\|Atopo | p\|AtopoBis | p\|Bis | p\|SPF |
|---|---|---|---|---|---|---|---|---|
| Fusobacteria (class)\|Bis | 0.000 | 3175.000 | 445.125 | 1109.012 | 0.089 | 0.341 | 1 | 0.289 |
| Fusobacteria (class)\|SPF | 5.000 | 96.000 | 38.571 | 31.921 | 0.007 | 0.889 | 0.289 | 1 |
| Erysipelotrichi\|Atopo | 998.000 | 7663.000 | 4385.500 | 2215.367 | 1 | 0.409 | 0.011 | 0.004 |
| Erysipelotrichi\|AtopoBis | 928.000 | 8147.000 | 3320.375 | 2780.457 | 0.409 | 1 | 0.088 | 0.037 |
| Erysipelotrichi\|Bis | 2.000 | 10136.000 | 1779.000 | 3443.700 | 0.011 | 0.088 | 1 | 0.660 |
| Erysipelotrichi\|SPF | 6.000 | 3618.000 | 861.857 | 1483.609 | 0.004 | 0.037 | 0.660 | 1 |
| Negativicutes\|Atopo | 1.000 | 2446.000 | 783.625 | 939.756 | 1 | 0.741 | 0.078 | 0.198 |
| Negativicutes\|AtopoBis | 5.000 | 32.000 | 16.375 | 8.568 | 0.741 | 1 | 0.036 | 0.333 |
| Negativicutes\|Bis | 0.000 | 10.000 | 3.625 | 3.335 | 0.078 | 0.036 | 1 | 0.003 |
| Negativicutes\|SPF | 1.000 | 7076.000 | 2222.286 | 2915.263 | 0.198 | 0.333 | 0.003 | 1 |
| Clostridia\|Atopo | 49447.000 | 95800.000 | 72002.750 | 15417.245 | 1 | 0.826 | 0.002 | 0.111 |
| Clostridia\|AtopoBis | 41041.000 | 155491.000 | 88416.125 | 47521.587 | 0.826 | 1 | 0.005 | 0.167 |
| Clostridia\|Bis | 95673.000 | 193932.000 | 161745.625 | 37810.173 | 0.002 | 0.005 | 1 | 0.184 |
| Clostridia\|SPF | 54427.000 | 194395.000 | 116338.286 | 57644.557 | 0.111 | 0.167 | 0.184 | 1 |
| Agaricomycetes\|Atopo | 0.000 | 0.000 | 0.000 | 0.000 | 1 | 1.000 | 1.000 | 0.000 |
| Agaricomycetes\|AtopoBis | 0.000 | 0.000 | 0.000 | 0.000 | 1.000 | 1 | 1.000 | 0.000 |
| Agaricomycetes\|Bis | 0.000 | 0.000 | 0.000 | 0.000 | 1.000 | 1.000 | 1 | 0.000 |
| Agaricomycetes\|SPF | 0.000 | 80.000 | 25.429 | 32.103 | 0.000 | 0.000 | 0.000 | 1 |
| Bacteroidia\|Atopo | 86976.000 | 133781.000 | 108741.375 | 14150.040 | 1 | 0.216 | <0.0001 | 0.011 |
| Bacteroidia\|AtopoBis | 232.000 | 117882.000 | 64729.375 | 53917.801 | 0.216 | 1 | 0.004 | 0.175 |
| Bacteroidia\|Bis | 96.000 | 519.000 | 209.250 | 134.578 | <0.0001 | 0.004 | 1 | 0.151 |
| Bacteroidia\|SPF | 71.000 | 107705.000 | 28633.857 | 48179.254 | 0.011 | 0.175 | 0.151 | 1 |
| Betaproteobacteria\|Atopo | 0.000 | 295.000 | 44.375 | 101.677 | 1 | 0.067 | 0.837 | 0.001 |
| Betaproteobacteria\|AtopoBis | 11.000 | 61.000 | 30.375 | 15.638 | 0.067 | 1 | 0.105 | 0.102 |
| Betaproteobacteria\|Bis | 5.000 | 27.000 | 13.625 | 8.297 | 0.837 | 0.105 | 1 | 0.001 |
| Betaproteobacteria\|SPF | 38.000 | 133.000 | 62.143 | 33.810 | 0.001 | 0.102 | 0.001 | 1 |
| ORDER | | | | | | | | |
| Clostridiales\|Atopo | 49447.000 | 95800.000 | 72002.750 | 15417.245 | 1 | 0.826 | 0.002 | 0.111 |
| Clostridiales\|AtopoBis | 41041.000 | 155488.000 | 88397.875 | 47505.759 | 0.826 | 1 | 0.005 | 0.167 |
| Clostridiales\|Bis | 95673.000 | 193932.000 | 161745.500 | 37810.379 | 0.002 | 0.005 | 1 | 0.84 |
| Clostridiales\|SPF | 54427.000 | 194394.000 | 116338.000 | 57644.323 | 0.111 | 0.167 | 0.184 | 1 |
| Alteromonadales\|Atopo | 0.000 | 1.000 | 0.125 | 0.354 | 1 | 0.724 | 0.282 | 0.000 |
| Alteromonadales\|AtopoBis | 0.000 | 1.000 | 0.250 | 0.463 | 0.724 | 1 | 0.470 | 0.001 |
| Alteromonadales\|Bis | 0.000 | 126.000 | 24.875 | 47.975 | 0.282 | 0.470 | 1 | 0.007 |
| Alteromonadales\|SPF | 1.000 | 915.000 | 264.143 | 345.489 | 0.000 | 0.001 | 0.007 | 1 |
| Bacteroidales\|Atopo | 86976.000 | 133781.000 | 108741.375 | 14150.040 | 1 | 0.216 | <0.0001 | 0.011 |
| Bacteroidales\|AtopoBis | 232.000 | 117882.000 | 64729.375 | 53917.801 | 0.216 | 1 | 0.004 | 0.175 |
| Bacteroidales\|Bis | 96.000 | 519.000 | 209.250 | 134.578 | <0.0001 | 0.004 | 1 | 0.151 |
| Bacteroidales\|SPF | 71.000 | 107705.000 | 28633.857 | 48179.254 | 0.011 | 0.175 | 0.151 | 1 |
| Oceanospirillales\|Atopo | 0.000 | 5.000 | 2.000 | 1.852 | 1 | 0.393 | 0.576 | 0.004 |
| Oceanospirillales\|AtopoBis | 0.000 | 74.000 | 23.125 | 27.910 | 0.393 | 1 | 0.158 | 0.037 |
| Oceanospirillales\|Bis | 0.000 | 56.000 | 11.250 | 21.645 | 0.576 | 0.158 | 1 | 0.001 |
| Oceanospirillales\|SPF | 3.000 | 4829.000 | 1391.571 | 1770.378 | 0.004 | 0.037 | 0.001 | 1 |
| Agaricales\|Atopo | 0.000 | 0.000 | 0.000 | 0.000 | 1 | 1.000 | 1.000 | 0.000 |
| Agaricales\|AtopoBis | 0.000 | 0.000 | 0.000 | 0.000 | 1.000 | 1 | 1.000 | 0.000 |
| Agaricales\|Bis | 0.000 | 0.000 | 0.000 | 0.000 | 1.000 | 1.000 | 1 | 0.000 |
| Agaricales\|SPF | 0.000 | 80.000 | 25.429 | 32.103 | 0.000 | 0.000 | 0.000 | 1 |
| Actinomycetales\|Atopo | 0.000 | 1.000 | 0.500 | 0.535 | 1 | 0.446 | 0.796 | 0.002 |
| Actinomycetales\|AtopoBis | 0.000 | 4.000 | 1.250 | 1.488 | 0.446 | 1 | 0.615 | 0.020 |
| Actinomycetales\|Bis | 0.000 | 11.000 | 1.875 | 3.834 | 0.796 | 0.615 | 1 | 0.005 |
| Actinomycetales\|SPF | 1.000 | 61.000 | 12.286 | 21.593 | 0.002 | 0.020 | 0.005 | 1 |
| Erysipelotrichales\|Atopo | 998.000 | 7663.000 | 4385.500 | 2215.367 | 1 | 0.409 | 0.011 | 0.004 |
| Erysipelotrichales\|AtopoBis | 928.000 | 8147.000 | 3320.375 | 2780.457 | 0.409 | 1 | 0.088 | 0.037 |
| Erysipelotrichales\|Bis | 2.000 | 10136.000 | 1779.000 | 3443.700 | 0.011 | 0.088 | 1 | 0.660 |
| Erysipelotrichales\|SPF | 6.000 | 3618.000 | 861.857 | 1483.609 | 0.004 | 0.037 | 0.660 | 1 |
| Neisseriales\|Atopo | 0.000 | 0.000 | 0.000 | 0.000 | 1 | 0.004 | 0.585 | 0.441 |
| Neisseriales\|AtopoBis | 0.000 | 2.000 | 0.750 | 0.707 | 0.004 | 1 | 0.022 | 0.048 |
| Neisseriales\|Bis | 0.000 | 1.000 | 0.125 | 0.354 | 0.585 | 0.022 | 1 | 0.809 |
| Neisseriales\|SPF | 0.000 | 8.000 | 1.143 | 3.024 | 0.441 | 0.048 | 0.809 | 1 |
| Pasteurellales\|Atopo | 0.000 | 1.000 | 0.125 | 0.354 | 1 | 0.594 | 0.530 | 0.000 |
| Pasteurellales\|AtopoBis | 0.000 | 4.000 | 0.750 | 1.488 | 0.594 | 1 | 0.925 | 0.001 |
| Pasteurellales\|Bis | 0.000 | 14.000 | 2.000 | 4.899 | 0.530 | 0.925 | 1 | 0.001 |
| Pasteurellales\|SPF | 2.000 | 56.000 | 20.143 | 21.836 | 0.000 | 0.001 | 0.001 | 1 |
| Chromatiales\|Atopo | 0.000 | 0.000 | 0.000 | 0.000 | 1 | 1.000 | 0.560 | 0.000 |
| Chromatiales\|AtopoBis | 0.000 | 0.000 | 0.000 | 0.000 | 1.000 | 1 | 0.560 | 0.000 |
| Chromatiales\|Bis | 0.000 | 2.000 | 0.250 | 0.707 | 0.560 | 0.560 | 1 | 0.001 |
| Chromatiales\|SPF | 0.000 | 14.000 | 4.571 | 5.255 | 0.000 | 0.000 | 0.001 | 1 |
| Vibrionales\|Atopo | 0.000 | 13.000 | 2.375 | 4.534 | 1 | 0.191 | 0.374 | <0.0001 |
| Vibrionales\|AtopoBis | 1.000 | 14.000 | 5.000 | 5.155 | 0.191 | 1 | 0.677 | 0.006 |
| Vibrionales\|Bis | 0.000 | 23.000 | 6.250 | 8.097 | 0.374 | 0.677 | 1 | 0.002 |
| Vibrionales\|SPF | 20.000 | 48532.000 | 15351.143 | 18959.865 | <0.0001 | 0.006 | 0.002 | 1 |
| Burkholderiales\|Atopo | 0.000 | 294.000 | 43.875 | 101.490 | 1 | 0.052 | 0.978 | 0.001 |
| Burkholderiales\|AtopoBis | 10.000 | 58.000 | 27.750 | 15.351 | 0.052 | 1 | 0.056 | 0.137 |
| Burkholderiales\|Bis | 5.000 | 19.000 | 11.125 | 5.357 | 0.978 | 0.056 | 1 | 0.001 |
| Burkholderiales\|SPF | 32.000 | 133.000 | 58.571 | 35.156 | 0.001 | 0.137 | 0.001 | 1 |

TABLE 6-continued

| Variable | Minimum | Maximum | Mean | Std. dev. | p\|Atopo | p\|AtopoBis | p\|Bis | p\|SPF |
|---|---|---|---|---|---|---|---|---|
| Fusobacteriales\|Atopo | 0.000 | 20.000 | 3.500 | 6.845 | 1 | 0.008 | 0.089 | 0.007 |
| Fusobacteriales\|AtopoBis | 1.000 | 34434.000 | 6670.125 | 12103.868 | 0.008 | 1 | 0.341 | 0.889 |
| Fusobacteriales\|Bis | 0.000 | 3175.000 | 445.125 | 1109.012 | 0.089 | 0.341 | 1 | 0.289 |
| Fusobacteriales\|SPF | 5.000 | 96.000 | 38.571 | 31.921 | 0.007 | 0.889 | 0.289 | 1 |
| Bacillales\|Atopo | 73.000 | 348.000 | 155.000 | 97.999 | 1 | 0.000 | 0.007 | 0.115 |
| Bacillales\|AtopoBis | 1326.000 | 30228.000 | 8866.125 | 9642.601 | 0.000 | 1 | 0.336 | 0.050 |
| Bacillales\|Bis | 46.000 | 13607.000 | 5683.500 | 4962.745 | 0.007 | 0.336 | 1 | 0.304 |
| Bacillales\|SPF | 163.000 | 7884.000 | 1604.857 | 2795.624 | 0.115 | 0.050 | 0.304 | 1 |
| Selenomonadales\|Atopo | 1.000 | 2446.000 | 783.625 | 939.756 | 1 | 0.741 | 0.078 | 0.198 |
| Selenomonadales\|AtopoBis | 5.000 | 32.000 | 16.375 | 8.568 | 0.741 | 1 | 0.036 | 0.333 |
| Selenomonadales\|Bis | 0.000 | 10.000 | 3.625 | 3.335 | 0.078 | 0.036 | 1 | 0.003 |
| Selenomonadales\|SPF | 1.000 | 7076.000 | 2222.286 | 2915.263 | 0.198 | 0.333 | 0.003 | 1 |
| Lactobacillales\|Atopo | 295.000 | 7198.000 | 2442.750 | 2396.791 | 1 | 0.783 | 0.296 | 0.032 |
| Lactobacillales\|AtopoBis | 187.000 | 18776.000 | 4365.625 | 6472.746 | 0.783 | 1 | 0.187 | 0.060 |
| Lactobacillales\|Bis | 848.000 | 22750.000 | 6231.875 | 7499.344 | 0.296 | 0.187 | 1 | 0.002 |
| Lactobacillales\|SPF | 66.000 | 1769.000 | 444.000 | 610.249 | 0.032 | 0.060 | 0.002 | 1 |
| FAMILY | | | | | | | | |
| Staphylococcaceae\|Atopo | 0.000 | 9.000 | 1.375 | 3.114 | 1 | 0.002 | 0.004 | 0.010 |
| Staphylococcaceae\|AtopoBis | 6.000 | 82.000 | 32.625 | 28.213 | 0.002 | 1 | 0.793 | 0.637 |
| Staphylococcaceae\|Bis | 0.000 | 132.000 | 40.000 | 45.854 | 0.004 | 0.793 | 1 | 0.827 |
| Staphylococcaceae\|SPF | 2.000 | 838.000 | 191.000 | 333.003 | 0.010 | 0.637 | 0.827 | 1 |
| Enterococcaceae\|Atopo | 11.000 | 38.000 | 20.750 | 9.588 | 1 | 0.000 | 0.014 | 0.040 |
| Enterococcaceae\|AtopoBis | 122.000 | 1580.000 | 725.125 | 549.030 | 0.000 | 1 | 0.178 | 0.106 |
| Enterococcaceae\|Bis | 0.000 | 1440.000 | 567.125 | 531.694 | 0.014 | 0.178 | 1 | 0.753 |
| Enterococcaceae\|SPF | 39.000 | 1383.000 | 261.286 | 495.744 | 0.040 | 0.106 | 0.753 | 1 |
| Eubacteriaceae\|Atopo | 3.000 | 43.000 | 8.875 | 13.861 | 1 | 0.061 | 0.518 | 0.001 |
| Eubacteriaceae\|AtopoBis | 10.000 | 32.000 | 18.500 | 8.783 | 0.061 | 1 | 0.220 | 0.111 |
| Eubacteriaceae\|Bis | 1.000 | 2387.000 | 313.625 | 838.348 | 0.518 | 0.220 | 1 | 0.005 |
| Eubacteriaceae\|SPF | 13.000 | 1107.000 | 485.143 | 399.257 | 0.001 | 0.111 | 0.005 | 1 |
| Ferrimonadaceae\|Atopo | 0.000 | 0.000 | 0.000 | 0.000 | 1 | 0.625 | 1.000 | <0.0001 |
| Ferrimonadaceae\|AtopoBis | 0.000 | 1.000 | 0.125 | 0.354 | 0.625 | 1 | 0.625 | 0.000 |
| Ferrimonadaceae\|Bis | 0.000 | 0.000 | 0.000 | 0.000 | 1.000 | 0.625 | 1 | <0.0001 |
| Ferrimonadaceae\|SPF | 0.000 | 623.000 | 140.714 | 227.571 | <0.0001 | 0.000 | <0.0001 | 1 |
| Alcanivoracaceae\|Atopo | 0.000 | 4.000 | 1.500 | 1.773 | 1 | 0.477 | 0.314 | 0.064 |
| Alcanivoracaceae\|AtopoBis | 0.000 | 73.000 | 22.125 | 28.119 | 0.477 | 1 | 0.086 | 0.245 |
| Alcanivoracaceae\|Bis | 0.000 | 4.000 | 0.500 | 1.414 | 0.314 | 0.086 | 1 | 0.005 |
| Alcanivoracaceae\|SPF | 0.000 | 554.000 | 143.286 | 208.723 | 0.064 | 0.245 | 0.005 | 1 |
| Bacteroidaceae\|Atopo | 86967.000 | 133771.000 | 108707.250 | 14136.218 | 1 | 0.226 | <0.0001 | 0.007 |
| Bacteroidaceae\|AtopoBis | 211.000 | 117745.000 | 64625.875 | 53942.157 | 0.226 | 1 | 0.005 | 0.125 |
| Bacteroidaceae\|Bis | 74.000 | 515.000 | 171.750 | 143.702 | <0.0001 | 0.005 | 1 | 0.239 |
| Bacteroidaceae\|SPF | 57.000 | 107600.000 | 28388.714 | 48274.613 | 0.007 | 0.125 | 0.239 | 1 |
| Oceanospirillaceae\|Atopo | 0.000 | 1.000 | 0.250 | 0.463 | 1 | 0.424 | 0.722 | 0.000 |
| Oceanospirillaceae\|AtopoBis | 0.000 | 4.000 | 1.000 | 1.414 | 0.424 | 1 | 0.657 | 0.003 |
| Oceanospirillaceae\|Bis | 0.000 | 16.000 | 3.250 | 6.228 | 0.722 | 0.657 | 1 | 0.001 |
| Oceanospirillaceae\|SPF | 3.000 | 3579.000 | 1056.714 | 1313.005 | 0.000 | 0.003 | 0.001 | 1 |
| Halomonadaceae\|Atopo | 0.000 | 0.000 | 0.000 | 0.000 | 1 | 1.000 | 1.000 | 0.000 |
| Halomonadaceae\|AtopoBis | 0.000 | 0.000 | 0.000 | 0.000 | 1.000 | 1 | 1.000 | 0.000 |
| Halomonadaceae\|Bis | 0.000 | 0.000 | 0.000 | 0.000 | 1.000 | 1.000 | 1 | 0.000 |
| Halomonadaceae\|SPF | 0.000 | 18.000 | 5.857 | 7.010 | 0.000 | 0.000 | 0.000 | 1 |
| Lactobacillaceae\|Atopo | 263.000 | 7137.000 | 2406.750 | 2385.720 | 1 | 0.004 | 0.000 | 0.001 |
| Lactobacillaceae\|AtopoBis | 3.000 | 27.000 | 12.375 | 9.226 | 0.004 | 1 | 0.440 | 0.586 |
| Lactobacillaceae\|Bis | 0.000 | 1026.000 | 133.000 | 360.889 | 0.000 | 0.440 | 1 | 0.840 |
| Lactobacillaceae\|SPF | 0.000 | 81.000 | 19.571 | 30.127 | 0.001 | 0.586 | 0.840 | 1 |
| Neisseriaceae\|Atopo | 0.000 | 0.000 | 0.000 | 0.000 | 1 | 0.004 | 0.585 | 0.441 |
| Neisseriaceae\|AtopoBis | 0.000 | 2.000 | 0.750 | 0.707 | 0.004 | 1 | 0.022 | 0.048 |
| Neisseriaceae\|Bis | 0.000 | 1.000 | 0.125 | 0.354 | 0.585 | 0.022 | 1 | 0.809 |
| Neisseriaceae\|SPF | 0.000 | 8.000 | 1.143 | 3.024 | 0.441 | 0.048 | 0.809 | 1 |
| Halothiobacillaceae\|Atopo | 0.000 | 0.000 | 0.000 | 0.000 | 1 | 1.000 | 1.000 | <0.0001 |
| Halothiobacillaceae\|AtopoBis | 0.000 | 0.000 | 0.000 | 0.000 | 1.000 | 1 | 1.000 | <0.0001 |
| Halothiobacillaceae\|Bis | 0.000 | 0.000 | 0.000 | 0.000 | 1.000 | 1.000 | 1 | <0.0001 |
| Halothiobacillaceae\|SPF | 0.000 | 14.000 | 4.571 | 5.255 | <0.0001 | <0.0001 | <0.0001 | 1 |
| Pasteurellaceae\|Atopo | 0.000 | 1.000 | 0.125 | 0.354 | 1 | 0.594 | 0.530 | 0.000 |
| Pasteurellaceae\|AtopoBis | 0.000 | 4.000 | 0.750 | 1.488 | 0.594 | 1 | 0.925 | 0.001 |
| Pasteurellaceae\|Bis | 0.000 | 14.000 | 2.000 | 4.899 | 0.530 | 0.925 | 1 | 0.001 |
| Pasteurellaceae\|SPF | 2.000 | 56.000 | 20.143 | 21.836 | 0.000 | 0.001 | 0.001 | 1 |
| Erysipelotrichaceae\|Atopo | 998.000 | 7663.000 | 4385.500 | 2215.367 | 1 | 0.409 | 0.011 | 0.004 |
| Erysipelotrichaceae\|AtopoBis | 928.000 | 8147.000 | 3320.375 | 2780.457 | 0.409 | 1 | 0.088 | 0.037 |
| Erysipelotrichaceae\|Bis | 2.000 | 10136.000 | 1779.000 | 3443.700 | 0.011 | 0.088 | 1 | 0.660 |
| Erysipelotrichaceae\|SPF | 6.000 | 3618.000 | 861.857 | 1483.609 | 0.004 | 0.037 | 0.660 | 1 |
| Fusobacteriaceae\|Atopo | 0.000 | 20.000 | 3.500 | 6.845 | 1 | 0.008 | 0.089 | 0.007 |
| Fusobacteriaceae\|AtopoBis | 1.000 | 34434.000 | 6670.125 | 12103.868 | 0.008 | 1 | 0.341 | 0.889 |
| Fusobacteriaceae\|Bis | 0.000 | 3175.000 | 445.125 | 1109.012 | 0.089 | 0.341 | 1 | 0.289 |

TABLE 6-continued

| Variable | Minimum | Maximum | Mean | Std. dev. | p\|Atopo | p\|AtopoBis | p\|Bis | p\|SPF |
|---|---|---|---|---|---|---|---|---|
| Fusobacteriaceae\|SPF | 5.000 | 96.000 | 38.571 | 31.921 | 0.007 | 0.889 | 0.289 | 1 |
| Bacillaceae\|Atopo | 71.000 | 336.000 | 147.875 | 94.253 | 1 | 0.001 | 0.024 | 0.311 |
| Bacillaceae\|AtopoBis | 1182.000 | 28393.000 | 8495.875 | 9032.956 | 0.001 | 1 | 0.284 | 0.028 |
| Bacillaceae\|Bis | 6.000 | 13296.000 | 5596.125 | 4907.619 | 0.024 | 0.284 | 1 | 0.244 |
| Bacillaceae\|SPF | 65.000 | 7836.000 | 1401.571 | 2847.097 | 0.311 | 0.028 | 0.244 | 1 |
| Listeriaceae\|Atopo | 0.000 | 1.000 | 0.375 | 0.518 | 1 | 0.006 | 0.029 | 0.477 |
| Listeriaceae\|AtopoBis | 0.000 | 17.000 | 7.250 | 6.497 | 0.006 | 1 | 0.590 | 0.055 |
| Listeriaceae\|Bis | 0.000 | 14.000 | 5.000 | 4.751 | 0.029 | 0.590 | 1 | 0.161 |
| Listeriaceae\|SPF | 0.000 | 29.000 | 4.571 | 10.799 | 0.477 | 0.055 | 0.161 | 1 |
| Streptococcaceae\|Atopo | 0.000 | 21.000 | 7.500 | 7.521 | 1 | 0.182 | 0.001 | 0.056 |
| Streptococcaceae\|AtopoBis | 0.000 | 17141.000 | 3433.000 | 6026.709 | 0.182 | 1 | 0.046 | 0.532 |
| Streptococcaceae\|Bis | 9.000 | 22660.000 | 5396.500 | 7790.156 | 0.001 | 0.046 | 1 | 0.193 |
| Streptococcaceae\|SPF | 8.000 | 237.000 | 84.714 | 100.521 | 0.056 | 0.532 | 0.193 | 1 |
| Vibrionaceae\|Atopo | 0.000 | 13.000 | 2.375 | 4.534 | 1 | 0.191 | 0.374 | <0.0001 |
| Vibrionaceae\|AtopoBis | 1.000 | 14.000 | 5.000 | 5.155 | 0.191 | 1 | 0.677 | 0.006 |
| Vibrionaceae\|Bis | 0.000 | 23.000 | 6.125 | 8.097 | 0.374 | 0.677 | 1 | 0.002 |
| Vibrionaceae\|SPF | 20.000 | 48532.000 | 15351.143 | 18959.865 | <0.0001 | 0.006 | 0.002 | 1 |
| Methylococcaceae\|Atopo | 0.000 | 0.000 | 0.000 | 0.000 | 1 | 1.000 | 1.000 | 0.027 |
| Methylococcaceae\|AtopoBis | 0.000 | 0.000 | 0.000 | 0.000 | 1.000 | 1 | 1.000 | 0.027 |
| Methylococcaceae\|Bis | 0.000 | 0.000 | 0.000 | 0.000 | 1.000 | 1.000 | 1 | 0.027 |
| Methylococcaceae\|SPF | 0.000 | 2.000 | 0.429 | 0.787 | 0.027 | 0.027 | 0.027 | 1 |
| Sutterellaceae\|Atopo | 0.000 | 14.000 | 3.125 | 5.592 | 1 | 0.020 | 0.708 | 0.007 |
| Sutterellaceae\|AtopoBis | 1.000 | 37.000 | 12.125 | 12.253 | 0.020 | 1 | 0.050 | 0.645 |
| Sutterellaceae\|Bis | 0.000 | 10.000 | 2.500 | 3.381 | 0.708 | 0.050 | 1 | 0.019 |
| Sutterellaceae\|SPF | 1.000 | 125.000 | 33.571 | 44.071 | 0.007 | 0.645 | 0.019 | 1 |
| Veillonellaceae\|Atopo | 1.000 | 2444.000 | 780.750 | 938.048 | 1 | 0.815 | 0.085 | 0.197 |
| Veillonellaceae\|AtopoBis | 5.000 | 26.000 | 12.625 | 7.689 | 0.815 | 1 | 0.050 | 0.287 |
| Veillonellaceae\|Bis | 0.000 | 10.000 | 3.375 | 3.378 | 0.085 | 0.050 | 1 | 0.003 |
| Veillonellaceae\|SPF | 1.000 | 7076.000 | 2221.857 | 2915.640 | 0.197 | 0.287 | 0.003 | 1 |
| Catabacteriaceae\|Atopo | 0.000 | 2.000 | 0.250 | 0.707 | 1 | 0.643 | 0.220 | 0.004 |
| Catabacteriaceae\|AtopoBis | 0.000 | 0.000 | 0.000 | 0.000 | 0.643 | 1 | 0.091 | 0.001 |
| Catabacteriaceae\|Bis | 0.000 | 1472.000 | 314.000 | 592.517 | 0.220 | 0.091 | 1 | 0.097 |
| Catabacteriaceae\|SPF | 0.000 | 525.000 | 113.857 | 201.222 | 0.004 | 0.001 | 0.097 | 1 |
| Shewanellaceae\|Atopo | 0.000 | 0.000 | 0.000 | 0.000 | 1 | 1.000 | 0.352 | 0.000 |
| Shewanellaceae\|AtopoBis | 0.000 | 0.000 | 0.000 | 0.000 | 1.000 | 1 | 0.352 | 0.000 |
| Shewanellaceae\|Bis | 0.000 | 1.000 | 0.250 | 0.463 | 0.352 | 0.352 | 1 | 0.003 |
| Shewanellaceae\|SPF | 0.000 | 118.000 | 24.429 | 42.637 | 0.000 | 0.000 | 0.003 | 1 |
| Hahellaceae\|Atopo | 0.000 | 1.000 | 0.250 | 0.463 | 1 | 0.427 | 0.947 | 0.002 |
| Hahellaceae\|AtopoBis | 0.000 | 0.000 | 0.000 | 0.000 | 0.427 | 1 | 0.389 | 0.000 |
| Hahellaceae\|Bis | 0.000 | 4.000 | 0.625 | 1.408 | 0.947 | 0.389 | 1 | 0.003 |
| Hahellaceae\|SPF | 0.000 | 200.000 | 56.143 | 70.099 | 0.002 | 0.000 | 0.003 | 1 |
| Actinomycetaceae\|Atopo | 0.000 | 1.000 | 0.125 | 0.354 | 1 | 0.190 | 0.325 | 0.000 |
| Actinomycetaceae\|AtopoBis | 0.000 | 3.000 | 0.875 | 1.126 | 0.190 | 1 | 0.743 | 0.017 |
| Actinomycetaceae\|Bis | 0.000 | 9.000 | 1.375 | 3.114 | 0.325 | 0.743 | 1 | 0.007 |
| Actinomycetaceae\|SPF | 1.000 | 60.000 | 11.571 | 21.454 | 0.000 | 0.017 | 0.007 | 1 |
| Alteromonadaceae\|Atopo | 0.000 | 1.000 | 0.125 | 0.354 | 1 | 1.000 | 0.274 | 0.001 |
| Alteromonadaceae\|AtopoBis | 0.000 | 1.000 | 0.125 | 0.354 | 1.000 | 1 | 0.274 | 0.001 |
| Alteromonadaceae\|Bis | 0.000 | 125.000 | 24.625 | 47.533 | 0.274 | 0.274 | 1 | 0.027 |
| Alteromonadaceae\|SPF | 0.000 | 280.000 | 99.000 | 107.201 | 0.001 | 0.001 | 0.027 | 1 |
| Lycoperdaceae\|Atopo | 0.000 | 0.000 | 0.000 | 0.000 | 1 | 1.000 | 1.000 | 0.000 |
| Lycoperdaceae\|AtopoBis | 0.000 | 0.000 | 0.000 | 0.000 | 1.000 | 1 | 1.000 | 0.000 |
| Lycoperdaceae\|Bis | 0.000 | 0.000 | 0.000 | 0.000 | 1.000 | 1.000 | 1 | 0.000 |
| Lycoperdaceae\|SPF | 0.000 | 80.000 | 25.429 | 32.103 | 0.000 | 0.000 | 0.000 | 1 |
| Peptostreptococcaceae\|Atopo | 0.000 | 0.000 | 0.000 | 0.000 | 1 | 0.308 | 0.352 | 0.006 |
| Peptostreptococcaceae\|AtopoBis | 0.000 | 3.000 | 0.625 | 1.188 | 0.308 | 1 | 0.929 | 0.078 |
| Peptostreptococcaceae\|Bis | 0.000 | 2.000 | 0.500 | 0.926 | 0.352 | 0.929 | 1 | 0.065 |
| Peptostreptococcaceae\|SPF | 0.000 | 11.000 | 3.714 | 4.348 | 0.006 | 0.078 | 0.065 | 1 |
| GENUS | | | | | | | | |
| *Morganella*\|Atopo | 0.000 | 0.000 | 0.000 | 0.000 | 1 | 1.000 | 1.000 | 0.000 |
| *Morganella*\|AtopoBis | 0.000 | 0.000 | 0.000 | 0.000 | 1.000 | 1 | 1.000 | 0.000 |
| *Morganella*\|Bis | 0.000 | 0.000 | 0.000 | 0.000 | 1.000 | 1.000 | 1 | 0.000 |
| *Morganella*\|SPF | 0.000 | 80.000 | 25.429 | 32.103 | 0.000 | 0.000 | 0.000 | 1 |
| *Erwinia*\|Atopo | 0.000 | 24.000 | 12.750 | 8.714 | 1 | 0.826 | 0.710 | 0.003 |
| *Erwinia*\|AtopoBis | 0.000 | 145.000 | 49.625 | 60.985 | 0.826 | 1 | 0.880 | 0.006 |
| *Erwinia*\|Bis | 0.000 | 50896.000 | 10198.375 | 19632.394 | 0.710 | 0.880 | 1 | 0.010 |
| *Erwinia*\|SPF | 146.000 | 2984.000 | 919.857 | 992.120 | 0.003 | 0.006 | 0.010 | 1 |
| *Peptostreptococcus*\|Atopo | 0.000 | 0.000 | 0.000 | 0.000 | 1 | 0.308 | 0.352 | 0.006 |
| *Peptostreptococcus*\|AtopoBis | 0.000 | 3.000 | 0.625 | 1.188 | 0.308 | 1 | 0.929 | 0.078 |

TABLE 6-continued

| Variable | Minimum | Maximum | Mean | Std. dev. | p\|Atopo | p\|AtopoBis | p\|Bis | p\|SPF |
|---|---|---|---|---|---|---|---|---|
| *Peptostreptococcus*\|Bis | 0.000 | 2.000 | 0.500 | 0.926 | 0.352 | 0.929 | 1 | 0.065 |
| *Peptostreptococcus*\|SPF | 0.000 | 11.000 | 3.714 | 4.348 | 0.006 | 0.078 | 0.065 | 1 |
| *Dorea*\|Atopo | 0.000 | 9.000 | 2.625 | 2.973 | 1 | 0.757 | 0.527 | 0.041 |
| *Dorea*\|AtopoBis | 0.000 | 20.000 | 5.750 | 7.888 | 0.757 | 1 | 0.346 | 0.081 |
| *Dorea*\|Bis | 0.000 | 10.000 | 2.375 | 3.926 | 0.527 | 0.346 | 1 | 0.008 |
| *Dorea*\|SPF | 0.000 | 30.000 | 13.429 | 10.114 | 0.041 | 0.081 | 0.008 | 1 |
| *Ruminococcus*\|Atopo | 13.000 | 281.000 | 62.375 | 89.427 | 1 | 0.030 | 0.021 | 0.002 |
| *Ruminococcus*\|AtopoBis | 29.000 | 1586.000 | 441.500 | 610.453 | 0.030 | 1 | 0.891 | 0.341 |
| *Ruminococcus*\|Bis | 33.000 | 1006.000 | 398.250 | 401.712 | 0.021 | 0.891 | 1 | 0.412 |
| *Ruminococcus*\|SPF | 69.000 | 20346.000 | 4684.143 | 8151.122 | 0.002 | 0.341 | 0.412 | 1 |
| *Kangiella*\|Atopo | 0.000 | 0.000 | 0.000 | 0.000 | 1 | 1.000 | 0.548 | 0.003 |
| *Kangiella*\|AtopoBis | 0.000 | 0.000 | 0.000 | 0.000 | 1.000 | 1 | 0.548 | 0.003 |
| *Kangiella*\|Bis | 0.000 | 1.000 | 0.125 | 0.354 | 0.548 | 0.548 | 1 | 0.015 |
| *Kangiella*\|SPF | 0.000 | 23.000 | 4.429 | 8.344 | 0.003 | 0.003 | 0.015 | 1 |
| *Enterovibrio*\|Atopo | 0.000 | 0.000 | 0.000 | 0.000 | 1 | 1.000 | 1.000 | <0.0001 |
| *Enterovibrio*\|AtopoBis | 0.000 | 0.000 | 0.000 | 0.000 | 1.000 | 1 | 1.000 | <0.0001 |
| *Enterovibrio*\|Bis | 0.000 | 0.000 | 0.000 | 0.000 | 1.000 | 1.000 | 1 | <0.0001 |
| *Enterovibrio*\|SPF | 0.000 | 239.000 | 88.000 | 92.454 | <0.0001 | <0.0001 | <0.0001 | 1 |
| *Coprobacillus*\|Atopo | 331.000 | 2302.000 | 1152.125 | 678.666 | 1 | 0.003 | 0.008 | 0.004 |
| *Coprobacillus*\|AtopoBis | 0.000 | 1735.000 | 257.375 | 605.539 | 0.003 | 1 | 0.772 | 0.970 |
| *Coprobacillus*\|Bis | 0.000 | 1309.000 | 200.625 | 452.797 | 0.008 | 0.772 | 1 | 0.750 |
| *Coprobacillus*\|SPF | 0.000 | 924.000 | 177.571 | 348.761 | 0.004 | 0.970 | 0.750 | 1 |
| *Actinomyces*\|Atopo | 0.000 | 1.000 | 0.125 | 0.354 | 1 | 0.190 | 0.325 | 0.000 |
| *Actinomyces*\|AtopoBis | 0.000 | 3.000 | 0.875 | 1.126 | 0.190 | 1 | 0.743 | 0.017 |
| *Actinomyces*\|Bis | 0.000 | 9.000 | 1.375 | 3.114 | 0.325 | 0.743 | 1 | 0.007 |
| *Actinomyces*\|SPF | 1.000 | 60.000 | 11.571 | 21.454 | 0.000 | 0.017 | 0.007 | 1 |
| *Marinomonas*\|Atopo | 0.000 | 1.000 | 0.250 | 0.463 | 1 | 0.694 | 0.694 | 0.002 |
| *Marinomonas*\|AtopoBis | 0.000 | 1.000 | 0.375 | 0.518 | 0.694 | 1 | 0.431 | 0.007 |
| *Marinomonas*\|Bis | 0.000 | 1.000 | 0.125 | 0.354 | 0.694 | 0.431 | 1 | 0.001 |
| *Marinomonas*\|SPF | 0.000 | 494.000 | 144.857 | 185.634 | 0.002 | 0.007 | 0.001 | 1 |
| *Vibrio*\|Atopo | 0.000 | 13.000 | 2.375 | 4.534 | 1 | 0.216 | 0.381 | <0.0001 |
| *Vibrio*\|AtopoBis | 1.000 | 12.000 | 4.750 | 4.683 | 0.216 | 1 | 0.718 | 0.006 |
| *Vibrio*\|Bis | 0.000 | 23.000 | 6.125 | 8.097 | 0.381 | 0.718 | 1 | 0.002 |
| *Vibrio*\|SPF | 19.000 | 48256.000 | 15217.857 | 18829.126 | <0.0001 | 0.006 | 0.002 | 1 |
| *Dialister*\|Atopo | 0.000 | 9.000 | 1.375 | 3.114 | 1 | 0.020 | 0.534 | 0.129 |
| *Dialister*\|AtopoBis | 0.000 | 18.000 | 6.625 | 6.675 | 0.020 | 1 | 0.003 | 0.465 |
| *Dialister*\|Bis | 0.000 | 1.000 | 0.250 | 0.463 | 0.534 | 0.003 | 1 | 0.034 |
| *Dialister*\|SPF | 0.000 | 7.000 | 3.571 | 3.101 | 0.129 | 0.465 | 0.034 | 1 |
| *Halothiobacillus*\|Atopo | 0.000 | 0.000 | 0.000 | 0.000 | 1 | 1.000 | 1.000 | <0.0001 |
| *Halothiobacillus*\|AtopoBis | 0.000 | 0.000 | 0.000 | 0.000 | 1.000 | 1 | 1.000 | <0.0001 |
| *Halothiobacillus*\|Bis | 0.000 | 0.000 | 0.000 | 0.000 | 1.000 | 1.000 | 1 | <0.0001 |
| *Halothiobacillus*\|SPF | 0.000 | 14.000 | 4.571 | 5.255 | <0.0001 | <0.0001 | <0.0001 | 1 |
| *Trichococcus*\|Atopo | 0.000 | 6.000 | 1.125 | 2.031 | 1 | 0.007 | 0.041 | 0.009 |
| *Trichococcus*\|AtopoBis | 0.000 | 0.000 | 0.000 | 0.000 | 0.007 | 1 | 0.519 | 1.000 |
| *Trichococcus*\|Bis | 0.000 | 1.000 | 0.125 | 0.354 | 0.041 | 0.519 | 1 | 0.533 |
| *Trichococcus*\|SPF | 0.000 | 0.000 | 0.000 | 0.000 | 0.009 | 1.000 | 0.533 | 1 |
| *Nitrincola*\|Atopo | 0.000 | 0.000 | 0.000 | 0.000 | 1 | 0.577 | 1.000 | 0.001 |
| *Nitrincola*\|AtopoBis | 0.000 | 3.000 | 0.375 | 1.061 | 0.577 | 1 | 0.577 | 0.003 |
| *Nitrincola*\|Bis | 0.000 | 0.000 | 0.000 | 0.000 | 1.000 | 0.577 | 1 | 0.001 |
| *Nitrincola*\|SPF | 0.000 | 226.000 | 55.143 | 83.762 | 0.001 | 0.003 | 0.001 | 1 |
| *Serratia*\|Atopo | 0.000 | 0.000 | 0.000 | 0.000 | 1 | 0.198 | 1.000 | 0.000 |
| *Serratia*\|AtopoBis | 0.000 | 3.000 | 0.750 | 1.165 | 0.198 | 1 | 0.198 | 0.009 |
| *Serratia*\|Bis | 0.000 | 0.000 | 0.000 | 0.000 | 1.000 | 0.198 | 1 | 0.000 |
| *Serratia*\|SPF | 0.000 | 621.000 | 192.286 | 237.182 | 0.000 | 0.009 | 0.000 | 1 |
| *Ferrimonas*\|Atopo | 0.000 | 0.000 | 0.000 | 0.000 | 1 | 0.625 | 1.000 | <0.0001 |
| *Ferrimonas*\|AtopoBis | 0.000 | 1.000 | 0.125 | 0.354 | 0.625 | 1 | 0.625 | 0.000 |
| *Ferrimonas*\|Bis | 0.000 | 0.000 | 0.000 | 0.000 | 1.000 | 0.625 | 1 | <0.0001 |
| *Ferrimonas*\|SPF | 0.000 | 623.000 | 140.714 | 227.571 | <0.0001 | 0.000 | <0.0001 | 1 |
| *Butyrivibrio*\|Atopo | 0.000 | 1.000 | 0.125 | 0.354 | 1 | 1.000 | 0.534 | 0.032 |
| *Butyrivibrio*\|AtopoBis | 0.000 | 1.000 | 0.125 | 0.354 | 1.000 | 1 | 0.534 | 0.032 |
| *Butyrivibrio*\|Bis | 0.000 | 0.000 | 0.000 | 0.000 | 0.534 | 0.534 | 1 | 0.006 |
| *Butyrivibrio*\|SPF | 0.000 | 1.000 | 0.571 | 0.535 | 0.032 | 0.032 | 0.006 | 1 |
| *Oscillospira*\|Atopo | 0.000 | 3.000 | 0.750 | 1.165 | 1 | 0.055 | 0.144 | 0.000 |
| *Oscillospira*\|AtopoBis | 1.000 | 7.000 | 3.125 | 2.167 | 0.055 | 1 | 0.646 | 0.083 |
| *Oscillospira*\|Bis | 0.000 | 3538.000 | 715.625 | 1371.803 | 0.144 | 0.646 | 1 | 0.030 |
| *Oscillospira*\|SPF | 2.000 | 3855.000 | 713.000 | 1439.678 | 0.000 | 0.083 | 0.030 | 1 |
| *Epulopiscium*\|Atopo | 0.000 | 9.000 | 1.625 | 3.068 | 1 | 0.434 | 0.099 | 0.014 |
| *Epulopiscium*\|AtopoBis | 0.000 | 2.000 | 0.375 | 0.744 | 0.434 | 1 | 0.015 | 0.001 |
| *Epulopiscium*\|Bis | 0.000 | 8385.000 | 1199.875 | 2932.011 | 0.099 | 0.015 | 1 | 0.393 |
| *Epulopiscium*\|SPF | 2.000 | 60.000 | 17.429 | 24.110 | 0.014 | 0.001 | 0.393 | 1 |
| *Escherichia*\|Atopo | 0.000 | 7.000 | 2.000 | 2.507 | 1 | 0.029 | 0.557 | 0.351 |
| *Escherichia*\|AtopoBis | 0.000 | 0.000 | 0.000 | 0.000 | 0.029 | 1 | 0.110 | 0.002 |
| *Escherichia*\|Bis | 0.000 | 52.000 | 10.375 | 19.799 | 0.557 | 0.110 | 1 | 0.133 |
| *Escherichia*\|SPF | 0.000 | 5.000 | 2.714 | 1.799 | 0.351 | 0.002 | 0.133 | 1 |
| *Alkalimonas*\|Atopo | 0.000 | 0.000 | 0.000 | 0.000 | 1 | 1.000 | 1.000 | 0.006 |
| *Alkalimonas*\|AtopoBis | 0.000 | 0.000 | 0.000 | 0.000 | 1.000 | 1 | 1.000 | 0.006 |
| *Alkalimonas*\|Bis | 0.000 | 0.000 | 0.000 | 0.000 | 1.000 | 1.000 | 1 | 0.006 |

TABLE 6-continued

| Variable | Minimum | Maximum | Mean | Std. dev. | p\|Atopo | p\|AtopoBis | p\|Bis | p\|SPF |
|---|---|---|---|---|---|---|---|---|
| *Alkalimonas*\|SPF | 0.000 | 30.000 | 7.714 | 11.339 | 0.006 | 0.006 | 0.006 | 1 |
| *Listeria*\|Atopo | 0.000 | 1.000 | 0.375 | 0.518 | 1 | 0.006 | 0.029 | 0.477 |
| *Listeria*\|AtopoBis | 0.000 | 17.000 | 7.250 | 6.497 | 0.006 | 1 | 0.590 | 0.055 |
| *Listeria*\|Bis | 0.000 | 14.000 | 5.000 | 4.751 | 0.029 | 0.590 | 1 | 0.161 |
| *Listeria*\|SPF | 0.000 | 29.000 | 4.571 | 10.799 | 0.477 | 0.055 | 0.161 | 1 |
| *Streptococcus*\|Atopo | 0.000 | 21.000 | 7.500 | 7.521 | 1 | 0.182 | 0.001 | 0.056 |
| *Streptococcus*\|AtopoBis | 0.000 | 17141.000 | 3433.000 | 6026.709 | 0.182 | 1 | 0.046 | 0.532 |
| *Streptococcus*\|Bis | 9.000 | 22660.000 | 5396.500 | 7790.156 | 0.001 | 0.046 | 1 | 0.193 |
| *Streptococcus*\|SPF | 8.000 | 237.000 | 84.714 | 100.521 | 0.056 | 0.532 | 0.193 | 1 |
| *Actinobacillus*\|Atopo | 0.000 | 0.000 | 0.000 | 0.000 | 1 | 0.681 | 0.328 | 0.000 |
| *Actinobacillus*\|AtopoBis | 0.000 | 1.000 | 0.125 | 0.354 | 0.681 | 1 | 0.571 | 0.001 |
| *Actinobacillus*\|Bis | 0.000 | 8.000 | 1.125 | 2.800 | 0.328 | 0.571 | 1 | 0.005 |
| *Actinobacillus*\|SPF | 0.000 | 39.000 | 12.000 | 15.011 | 0.000 | 0.001 | 0.005 | 1 |
| *Roseburia*\|Atopo | 10.000 | 46.000 | 23.125 | 12.722 | 1 | 0.773 | 0.040 | 0.321 |
| *Roseburia*\|AtopoBis | 1.000 | 56.000 | 22.875 | 17.836 | 0.773 | 1 | 0.078 | 0.203 |
| *Roseburia*\|Bis | 1.000 | 22.000 | 7.875 | 7.453 | 0.040 | 0.078 | 1 | 0.003 |
| *Roseburia*\|SPF | 8.000 | 192.000 | 65.429 | 64.714 | 0.321 | 0.203 | 0.003 | 1 |
| *Bacillus*\|Atopo | 70.000 | 331.000 | 145.500 | 92.705 | 1 | 0.001 | 0.023 | 0.298 |
| *Bacillus*\|AtopoBis | 1162.000 | 24417.000 | 7572.750 | 7652.213 | 0.001 | 1 | 0.284 | 0.029 |
| *Bacillus*\|Bis | 5.000 | 11338.000 | 4861.250 | 4100.801 | 0.023 | 0.284 | 1 | 0.250 |
| *Bacillus*\|SPF | 57.000 | 7717.000 | 1376.429 | 2805.259 | 0.298 | 0.029 | 0.250 | 1 |
| *Parabacteroides*\|Atopo | 0.000 | 40.000 | 8.875 | 13.559 | 1 | 0.195 | 0.562 | 0.036 |
| *Parabacteroides*\|AtopoBis | 1.000 | 35.000 | 12.750 | 10.820 | 0.195 | 1 | 0.061 | 0.397 |
| *Parabacteroides*\|Bis | 0.000 | 9.000 | 3.750 | 3.284 | 0.562 | 0.061 | 1 | 0.008 |
| *Parabacteroides*\|SPF | 0.000 | 43.000 | 23.571 | 16.662 | 0.036 | 0.397 | 0.008 | 1 |
| *Sarcina*\|Atopo | 0.000 | 1.000 | 0.125 | 0.354 | 1 | 0.005 | 0.009 | 0.317 |
| *Sarcina*\|AtopoBis | 0.000 | 1929.000 | 424.250 | 698.617 | 0.005 | 1 | 0.815 | 0.082 |
| *Sarcina*\|Bis | 0.000 | 2282.000 | 700.125 | 966.646 | 0.009 | 0.815 | 1 | 0.131 |
| *Sarcina*\|SPF | 0.000 | 8.000 | 2.286 | 3.147 | 0.317 | 0.082 | 0.131 | 1 |
| *Enterococcus*\|Atopo | 11.000 | 38.000 | 20.750 | 9.588 | 1 | 0.000 | 0.016 | 0.040 |
| *Enterococcus*\|AtopoBis | 121.000 | 1543.000 | 718.125 | 539.764 | 0.000 | 1 | 0.161 | 0.100 |
| *Enterococcus*\|Bis | 0.000 | 1425.000 | 558.625 | 527.899 | 0.016 | 0.161 | 1 | 0.773 |
| *Enterococcus*\|SPF | 39.000 | 1382.000 | 260.429 | 495.621 | 0.040 | 0.100 | 0.773 | 1 |
| *Carnobacterium*\|Atopo | 0.000 | 1.000 | 0.125 | 0.354 | 1 | 0.006 | 0.045 | 0.543 |
| *Carnobacterium*\|AtopoBis | 0.000 | 42.000 | 17.500 | 18.769 | 0.006 | 1 | 0.451 | 0.040 |
| *Carnobacterium*\|Bis | 0.000 | 29.000 | 6.500 | 10.100 | 0.045 | 0.451 | 1 | 0.185 |
| *Carnobacterium*\|SPF | 0.000 | 4.000 | 1.000 | 1.732 | 0.543 | 0.040 | 0.185 | 1 |
| *Coprococcus*\|Atopo | 244.000 | 35300.000 | 7793.625 | 11731.118 | 1 | 0.001 | 0.012 | 0.220 |
| *Coprococcus*\|AtopoBis | 10.000 | 79.000 | 40.625 | 22.671 | 0.001 | 1 | 0.433 | 0.050 |
| *Coprococcus*\|Bis | 6.000 | 5234.000 | 893.750 | 1803.125 | 0.012 | 0.433 | 1 | 0.228 |
| *Coprococcus*\|SPF | 20.000 | 31009.000 | 6867.571 | 12275.631 | 0.220 | 0.050 | 0.228 | 1 |
| *Enterobacter*\|Atopo | 0.000 | 3.000 | 0.500 | 1.069 | 1 | 0.849 | 0.333 | 0.000 |
| *Enterobacter*\|AtopoBis | 0.000 | 1.000 | 0.375 | 0.518 | 0.849 | 1 | 0.437 | 0.001 |
| *Enterobacter*\|Bis | 0.000 | 12.000 | 2.875 | 4.794 | 0.333 | 0.437 | 1 | 0.007 |
| *Enterobacter*\|SPF | 3.000 | 2140.000 | 682.571 | 877.138 | 0.000 | 0.001 | 0.007 | 1 |
| *Neisseria*\|Atopo | 0.000 | 0.000 | 0.000 | 0.000 | 1 | 0.003 | 0.538 | 0.387 |
| *Neisseria*\|AtopoBis | 0.000 | 2.000 | 0.750 | 0.707 | 0.003 | 1 | 0.014 | 0.032 |
| *Neisseria*\|Bis | 0.000 | 1.000 | 0.125 | 0.354 | 0.538 | 0.014 | 1 | 0.785 |
| *Neisseria*\|SPF | 0.000 | 5.000 | 0.714 | 1.890 | 0.387 | 0.032 | 0.785 | 1 |
| *Photobacterium*\|Atopo | 0.000 | 0.000 | 0.000 | 0.000 | 1 | 0.222 | 1.000 | <0.0001 |
| *Photobacterium*\|AtopoBis | 0.000 | 2.000 | 0.250 | 0.707 | 0.222 | 1 | 0.222 | <0.0001 |
| *Photobacterium*\|Bis | 0.000 | 0.000 | 0.000 | 0.000 | 1.000 | 0.222 | 1 | <0.0001 |
| *Photobacterium*\|SPF | 1.000 | 121.000 | 42.286 | 49.671 | <0.0001 | <0.0001 | <0.0001 | 1 |
| *Brenneria*\|Atopo | 0.000 | 0.000 | 0.000 | 0.000 | 1 | 1.000 | 1.000 | 0.000 |
| *Brenneria*\|AtopoBis | 0.000 | 0.000 | 0.000 | 0.000 | 1.000 | 1 | 1.000 | 0.000 |
| *Brenneria*\|Bis | 0.000 | 0.000 | 0.000 | 0.000 | 1.000 | 1.000 | 1 | 0.000 |
| *Brenneria*\|SPF | 0.000 | 595.000 | 156.429 | 226.566 | 0.000 | 0.000 | 0.000 | 1 |
| *Oceanobacillus*\|Atopo | 0.000 | 0.000 | 0.000 | 0.000 | 1 | 0.465 | 0.005 | 1.000 |
| *Oceanobacillus*\|AtopoBis | 0.000 | 1.000 | 0.125 | 0.354 | 0.465 | 1 | 0.026 | 0.480 |
| *Oceanobacillus*\|Bis | 0.000 | 2.000 | 0.625 | 0.744 | 0.005 | 0.026 | 1 | 0.006 |
| *Oceanobacillus*\|SPF | 0.000 | 0.000 | 0.000 | 0.000 | 1.000 | 0.480 | 0.006 | 1 |
| *Lactobacillus*\|Atopo | 263.000 | 7137.000 | 2406.750 | 2385.720 | 1 | 0.000 | <0.0001 | <0.0001 |
| *Lactobacillus*\|AtopoBis | 3.000 | 27.000 | 12.375 | 9.226 | 0.000 | 1 | 0.277 | 0.441 |
| *Lactobacillus*\|Bis | 0.000 | 1026.000 | 133.000 | 360.889 | <0.0001 | 0.277 | 1 | 0.774 |
| *Lactobacillus*\|SPF | 0.000 | 81.000 | 19.571 | 30.127 | <0.0001 | 0.441 | 0.774 | 1 |
| *Xanthomonas*\|Atopo | 0.000 | 1.000 | 0.125 | 0.354 | 1 | 0.620 | 0.138 | 0.007 |
| *Xanthomonas*\|AtopoBis | 0.000 | 0.000 | 0.000 | 0.000 | 0.620 | 1 | 0.052 | 0.002 |
| *Xanthomonas*\|Bis | 0.000 | 1005.000 | 207.500 | 395.202 | 0.138 | 0.052 | 1 | 0.163 |
| *Xanthomonas*\|SPF | 0.000 | 29.000 | 6.000 | 10.360 | 0.007 | 0.002 | 0.163 | 1 |
| *Sutterella*\|Atopo | 0.000 | 14.000 | 3.125 | 5.592 | 1 | 0.009 | 0.657 | 0.003 |
| *Sutterella*\|AtopoBis | 1.000 | 37.000 | 12.125 | 12.253 | 0.009 | 1 | 0.026 | 0.586 |
| *Sutterella*\|Bis | 0.000 | 10.000 | 2.500 | 3.381 | 0.657 | 0.026 | 1 | 0.009 |
| *Sutterella*\|SPF | 1.000 | 125.000 | 33.571 | 44.071 | 0.003 | 0.586 | 0.009 | 1 |
| *Staphylococcus*\|Atopo | 0.000 | 8.000 | 1.250 | 2.765 | 1 | 0.000 | 0.001 | 0.003 |
| *Staphylococcus*\|AtopoBis | 6.000 | 82.000 | 32.625 | 28.213 | 0.000 | 1 | 0.744 | 0.558 |
| *Staphylococcus*\|Bis | 0.000 | 132.000 | 40.000 | 45.854 | 0.001 | 0.744 | 1 | 0.785 |
| *Staphylococcus*\|SPF | 2.000 | 838.000 | 191.000 | 333.003 | 0.003 | 0.558 | 0.785 | 1 |
| *Lachnobacterium*\|Atopo | 0.000 | 22.000 | 4.125 | 7.605 | 1 | 0.072 | 0.275 | 0.068 |

TABLE 6-continued

| Variable | Minimum | Maximum | Mean | Std. dev. | p\|Atopo | p\|AtopoBis | p\|Bis | p\|SPF |
|---|---|---|---|---|---|---|---|---|
| Lachnobacterium\|AtopoBis | 0.000 | 0.000 | 0.000 | 0.000 | 0.072 | 1 | 0.006 | 0.001 |
| Lachnobacterium\|Bis | 0.000 | 11871.000 | 2128.000 | 4324.494 | 0.275 | 0.006 | 1 | 0.418 |
| Lachnobacterium\|SPF | 0.000 | 809.000 | 230.857 | 372.166 | 0.068 | 0.001 | 0.418 | 1 |
| Vagococcus\|Atopo | 0.000 | 0.000 | 0.000 | 0.000 | 1 | 0.001 | 0.004 | 0.129 |
| Vagococcus\|AtopoBis | 0.000 | 37.000 | 7.000 | 12.387 | 0.001 | 1 | 0.570 | 0.049 |
| Vagococcus\|Bis | 0.000 | 34.000 | 8.500 | 12.166 | 0.004 | 0.570 | 1 | 0.144 |
| Vagococcus\|SPF | 0.000 | 3.000 | 0.857 | 1.215 | 0.129 | 0.049 | 0.144 | 1 |
| Leclercia\|Atopo | 0.000 | 2.000 | 0.500 | 0.756 | 1 | 0.298 | 0.501 | <0.0001 |
| Leclercia\|AtopoBis | 0.000 | 4.000 | 0.500 | 1.414 | 0.298 | 1 | 0.707 | <0.0001 |
| Leclercia\|Bis | 0.000 | 1.000 | 0.250 | 0.463 | 0.501 | 0.707 | 1 | <0.0001 |
| Leclercia\|SPF | 12.000 | 4650.000 | 1419.143 | 1875.855 | <0.0001 | <0.0001 | <0.0001 | 1 |
| Fusobacterium\|Atopo | 0.000 | 20.000 | 3.500 | 6.845 | 1 | 0.006 | 0.065 | 0.005 |
| Fusobacterium\|AtopoBis | 1.000 | 34434.000 | 6670.000 | 12103.946 | 0.006 | 1 | 0.307 | 0.865 |
| Fusobacterium\|Bis | 0.000 | 3175.000 | 445.125 | 1109.012 | 0.065 | 0.307 | 1 | 0.249 |
| Fusobacterium\|SPF | 4.000 | 94.000 | 38.000 | 31.559 | 0.005 | 0.865 | 0.249 | 1 |
| Citrobacter\|Atopo | 0.000 | 0.000 | 0.000 | 0.000 | 1 | 1.000 | 1.000 | 0.000 |
| Citrobacter\|AtopoBis | 0.000 | 0.000 | 0.000 | 0.000 | 1.000 | 1 | 1.000 | 0.000 |
| Citrobacter\|Bis | 0.000 | 0.000 | 0.000 | 0.000 | 1.000 | 1.000 | 1 | 0.000 |
| Citrobacter\|SPF | 0.000 | 41.000 | 11.857 | 16.477 | 0.000 | 0.000 | 0.000 | 1 |
| Hahella\|Atopo | 0.000 | 1.000 | 0.250 | 0.463 | 1 | 0.265 | 0.925 | 0.000 |
| Hahella\|AtopoBis | 0.000 | 0.000 | 0.000 | 0.000 | 0.265 | 1 | 0.229 | <0.0001 |
| Hahella\|Bis | 0.000 | 4.000 | 0.625 | 1.408 | 0.925 | 0.229 | 1 | 0.000 |
| Hahella\|SPF | 0.000 | 200.000 | 56.143 | 70.099 | 0.000 | <0.0001 | 0.000 | 1 |
| Alcanivorax\|Atopo | 0.000 | 4.000 | 1.500 | 1.773 | 1 | 0.481 | 0.085 | 0.045 |
| Alcanivorax\|AtopoBis | 0.000 | 73.000 | 22.125 | 28.119 | 0.481 | 1 | 0.019 | 0.170 |
| Alcanivorax\|Bis | 0.000 | 0.000 | 0.000 | 0.000 | 0.085 | 0.019 | 1 | 0.001 |
| Alcanivorax\|SPF | 0.000 | 531.000 | 138.857 | 200.897 | 0.045 | 0.170 | 0.001 | 1 |
| Facklamia\|Atopo | 0.000 | 0.000 | 0.000 | 0.000 | 1 | 1.000 | 1.000 | 0.003 |
| Facklamia\|AtopoBis | 0.000 | 0.000 | 0.000 | 0.000 | 1.000 | 1 | 1.000 | 0.003 |
| Facklamia\|Bis | 0.000 | 0.000 | 0.000 | 0.000 | 1.000 | 1.000 | 1 | 0.003 |
| Facklamia\|SPF | 0.000 | 56.000 | 11.571 | 21.509 | 0.003 | 0.003 | 0.003 | 1 |
| Faecalibacterium\|Atopo | 0.000 | 252.000 | 39.625 | 86.169 | 1 | 0.010 | 0.687 | 0.007 |
| Faecalibacterium\|AtopoBis | 8.000 | 120.000 | 57.000 | 37.413 | 0.010 | 1 | 0.004 | 0.811 |
| Faecalibacterium\|Bis | 1.000 | 31.000 | 13.375 | 11.476 | 0.687 | 0.004 | 1 | 0.003 |
| Faecalibacterium\|SPF | 8.000 | 212.000 | 88.571 | 76.868 | 0.007 | 0.811 | 0.003 | 1 |
| Eubacterium\|Atopo | 3.000 | 43.000 | 8.875 | 13.861 | 1 | 0.024 | 0.417 | 0.000 |
| Eubacterium\|AtopoBis | 10.000 | 32.000 | 18.500 | 8.783 | 0.024 | 1 | 0.130 | 0.052 |
| Eubacterium\|Bis | 1.000 | 2387.000 | 313.625 | 838.348 | 0.417 | 0.130 | 1 | 0.001 |
| Eubacterium\|SPF | 13.000 | 1107.000 | 485.143 | 399.257 | 0.000 | 0.052 | 0.001 | 1 |
| Shewanella\|Atopo | 0.000 | 0.000 | 0.000 | 0.000 | 1 | 1.000 | 0.144 | <0.0001 |
| Shewanella\|AtopoBis | 0.000 | 0.000 | 0.000 | 0.000 | 1.000 | 1 | 0.144 | <0.0001 |
| Shewanella\|Bis | 0.000 | 1.000 | 0.250 | 0.463 | 0.144 | 0.144 | 1 | <0.0001 |
| Shewanella\|SPF | 0.000 | 118.000 | 24.429 | 42.637 | <0.0001 | <0.0001 | <0.0001 | 1 |
| Tatumella\|Atopo | 0.000 | 0.000 | 0.000 | 0.000 | 1 | 0.454 | 1.000 | <0.0001 |
| Tatumella\|AtopoBis | 0.000 | 1.000 | 0.125 | 0.354 | 0.454 | 1 | 0.454 | 0.000 |
| Tatumella\|Bis | 0.000 | 0.000 | 0.000 | 0.000 | 1.000 | 0.454 | 1 | <0.0001 |
| Tatumella\|SPF | 0.000 | 76.000 | 26.714 | 33.674 | <0.0001 | 0.000 | <0.0001 | 1 |
| Bacteroides\|Atopo | 86967.000 | 133771.000 | 108707.250 | 14136.218 | 1 | 0.075 | <0.0001 | 0.000 |
| Bacteroides\|AtopoBis | 211.000 | 117745.000 | 64625.875 | 53942.157 | 0.075 | 1 | 0.000 | 0.027 |
| Bacteroides\|Bis | 74.000 | 515.000 | 171.750 | 143.702 | <0.0001 | 0.000 | 1 | 0.083 |
| Bacteroides\|SPF | 57.000 | 107600.000 | 28388.714 | 48274.613 | 0.000 | 0.027 | 0.083 | 1 |

It has also been found that *A. parvulum* is correlated with the presence/abundance of GALT foci. Therefore there is provided an assay for identifying the likelihood of an individual of having UC or CD or IBD by measuring a relative abundance of *A. parvulum* by measuring the abundance of GALT foci. This correlation can also be used to provide a method of diagnostic that comprises collecting samples to measure the abundance of GAT foci, determining the presence of *A. parvulum* based on the cytokine(s) measurement and establishing a diagnosis.

In other aspect of the invention it has been shown that certain OTU's and/or taxa are indicative of improve therapeutic response. Table 7 exemplifies OTU's and/or taxa that exhibit a significant difference between the levels of bacteria between patients that responded to treatment. The patients in the two groups (responded to treatment/failed to respond to treatment) received a systemic corticosteroid medication (prednisone) as their acute anti-inflammatory therapy. Two patients (in the group that responded) received the mucosally active corticosteroid medication Entocort instead. Azathioprine (n=11) or methotrexate (n=4) immunomodulator medication was initiated in the patients for maintenance therapy. The clinical failure of response was determined by Physician Global Assessment and Pediatric Crohn's Disease Activity Index scoring determinations.

Clearly from the data of table 7 there is link between the level of bacteria and the efficacy of treatment. Thus when a patient exhibits bacterial levels in one or more taxa or OTU's from table 7 that are more elevated than a predetermined level or average corresponding to responders level the patient is likely not to respond to treatment. Alternatively patients exhibiting levels of bacteria lower that a predetermined level or average corresponding to non responders will profit the most from the treatment. The patient that did not respond have a different physiological or pathological status as assessed by standard diagnostic tests. For example patients with levels of *Erwinia* greater than about 3431 or preferably greater than about 13482 (one std dev) are likely not to respond and patient with lower levels than these likely to benefit most.

TABLE 7

|  | Observations | Minimum | Maximum | Mean | Std. deviation | p\| responded | p\| Failed |
|---|---|---|---|---|---|---|---|
| Analysis at OTU level Variable |  |  |  |  |  |  |  |
| *Eubacterium* (OTU589746)\|responded | 9 | 0.000 | 4.000 | 1.333 | 1.732 | 1 | 0.011 |
| *Eubacterium* (OTU589746)\|Failed | 6 | 2.000 | 20.000 | 9.667 | 7.174 | 0.011 | 1 |
| *Oribacteriumsinus* (OTU470747)\|responded | 9 | 0.000 | 11.000 | 2.778 | 3.598 | 1 | 0.005 |
| *Oribacteriumsinus* (OTU470747)\|Failed | 6 | 2.000 | 77.000 | 28.000 | 25.954 | 0.005 | 1 |
| *Veillonellaceae* (OTU535825)\|responded | 9 | 0.000 | 40.000 | 9.000 | 14.186 | 1 | 0.024 |
| *Veillonellaceae* (OTU535825)\|Failed | 6 | 2.000 | 93.000 | 49.500 | 38.667 | 0.024 | 1 |
| *Enterobacteriaceae* (OTU323418)\|responded | 9 | 0.000 | 180.000 | 23.889 | 59.675 | 1 | 0.035 |
| *Enterobacteriaceae* (OTU323418)\|Failed | 6 | 1.000 | 140.000 | 34.000 | 55.714 | 0.035 | 1 |
| *Lachnospiraceae* (OTU71387)\|responded | 9 | 0.000 | 137.000 | 16.000 | 45.418 | 1 | 0.015 |
| *Lachnospiraceae* (OTU71387)\|Failed | 6 | 2.000 | 259.000 | 73.500 | 95.663 | 0.015 | 1 |
| *Atopobium* (OTU529659)\|responded | 9 | 0.000 | 101.000 | 17.889 | 32.259 | 1 | 0.018 |
| *Atopobium* (OTU529659)\|Failed | 6 | 19.000 | 187.000 | 78.667 | 62.516 | 0.018 | 1 |
| *Mogibacterium* (OTU46159)\|responded | 9 | 0.000 | 163.000 | 21.556 | 53.346 | 1 | 0.043 |
| *Mogibacterium* (OTU46159)\|Failed | 6 | 3.000 | 376.000 | 79.167 | 146.389 | 0.043 | 1 |
| *Propionibacteriumacnes* (OTU368907)\|responded | 9 | 0.000 | 192.000 | 32.667 | 68.431 | 1 | 0.044 |
| *Propionibacteriumacnes* (OTU368907)\|Failed | 6 | 1.000 | 363.000 | 63.500 | 146.761 | 0.044 | 1 |
| *Alteromonadaceae*; BD2-13 (OTU110075)\|responded | 9 | 0.000 | 44.000 | 8.444 | 15.001 | 1 | 0.022 |
| *Alteromonadaceae*; BD2-13 (OTU110075)\|Failed | 6 | 1.000 | 715.000 | 142.000 | 281.637 | 0.022 | 1 |
| *Coprococcus* (OTU182512)\|responded | 9 | 0.000 | 133.000 | 23.778 | 43.249 | 1 | 0.045 |
| *Coprococcus* (OTU182512)\|Failed | 6 | 3.000 | 282.000 | 129.167 | 128.205 | 0.045 | 1 |
| *Lachnospiraceae* (OTU303772)\|responded | 9 | 1.000 | 78.000 | 14.778 | 25.806 | 1 | 0.043 |
| *Lachnospiraceae* (OTU303772)\|Failed | 6 | 2.000 | 509.000 | 167.667 | 205.745 | 0.043 | 1 |
| *Clostridiales* (OTU204932)\|responded | 9 | 0.000 | 2054.000 | 237.222 | 681.670 | 1 | 0.024 |
| *Clostridiales* (OTU204932)\|Failed | 6 | 11.000 | 5639.000 | 1037.833 | 2257.516 | 0.024 | 1 |
| *Bacteroidales* (OTU183618)\|responded | 9 | 0.000 | 2059.000 | 246.667 | 681.482 | 1 | 0.023 |
| *Bacteroidales* (OTU183618)\|Failed | 6 | 9.000 | 6706.000 | 1295.167 | 2666.325 | 0.023 | 1 |
| *Ruminococcaceae* (OTU195252)\|responded | 9 | 0.000 | 120.000 | 21.889 | 40.946 | 1 | 0.044 |
| *Ruminococcaceae* (OTU195252)\|Failed | 6 | 2.000 | 9494.000 | 1716.333 | 3814.455 | 0.044 | 1 |
| *Sutterella* (OTU295422)\|responded | 9 | 2.000 | 1132.000 | 145.556 | 371.004 | 1 | 0.018 |
| *Sutterella* (OTU295422)\|Failed | 6 | 17.000 | 20759.000 | 6729.833 | 8755.580 | 0.018 | 1 |
| *Enterobacteriaceae* (OTU307080)\|responded | 9 | 6.000 | 13849.000 | 1846.333 | 4559.821 | 1 | 0.025 |
| *Enterobacteriaceae* (OTU307080)\|Failed | 6 | 165.000 | 15872.000 | 4616.833 | 5840.027 | 0.025 | 1 |
| *Ruminococcus* (OTU174136)\|responded | 9 | 0.000 | 24.000 | 6.667 | 9.000 | 1 | 0.033 |
| *Ruminococcus* (OTU174136)\|Failed | 6 | 1.000 | 48877.000 | 8170.833 | 19941.884 | 0.033 | 1 |
| *Clostridiumramosum* (OTU470139)\|responded | 9 | 5.000 | 10411.000 | 1186.444 | 3459.360 | 1 | 0.045 |
| *Clostridiumramosum* (OTU470139)\|Failed | 6 | 10.000 | 139273.000 | 36964.333 | 53876.950 | 0.045 | 1 |
| *Erwinia* (OTU289103)\|responded | 9 | 3.000 | 30231.000 | 3425.667 | 10052.419 | 1 | 0.010 |
| *Erwinia* (OTU289103)\|Failed | 6 | 78.000 | 164661.000 | 42988.167 | 62253.786 | 0.010 | 1 |
| Analysis at genus level Variable |  |  |  |  |  |  |  |
| *Erwinia*\|responded | 9 | 3.000 | 30231.000 | 3430.778 | 10050.512 | 1 | 0.013 |
| *Erwinia*\|Failed | 6 | 78.000 | 164661.000 | 42989.333 | 62253.169 | 0.013 | 1 |
| *Atopobium*\|responded | 9 | 0.000 | 307.000 | 51.556 | 101.187 | 1 | 0.045 |
| *Atopobium*\|Failed | 6 | 23.000 | 231.000 | 90.167 | 76.434 | 0.045 | 1 |
| *Propionibacterium*\|responded | 9 | 0.000 | 196.000 | 40.444 | 79.783 | 1 | 0.042 |
| *Propionibacterium*\|Failed | 6 | 2.000 | 363.000 | 63.833 | 146.593 | 0.042 | 1 |

It will be appreciated that more than one taxa and/or OTU can be combined to identify patients that are more likely to respond to treatment. For example one could combine the measurement of OTU295422 and of taxa *Erwinia* in a patient and if the levels are below about 145 and about 3430 respectively then the patient is considered likely to respond. It should be noted that OTU's are most of the time closely related to a taxa therefore the above described approach would also be applicable using taxa associated with an OTU.

Thus in one aspect the present invention provides a method to test or assay or measure the levels of gut bacteria obtained directly from the gut or from stools and in which the actual measurement of bacterial levels is done in vitro. The measured levels can be used to assess the nature, severity or stage of IBD, CD or UC disease and determine treatment course such as the administration of certain drugs.

Furthermore there is also provided a method in which a test to measure the level(s) of bacteria as described above is requested to provide the results of an analysis to determine whether a patient has IBD, CD or UC or to determine the severity or stage of such disease by assessing bacterial levels as described above and administering a treatment if the patient exhibit the type and levels of bacteria associated with disease or the severity or stage of the disease.

Thus the present invention provides to the identification of pathological states or characteristics of patients by identifying bacteria associated with disease and of physiological states by providing levels of bacteria present in disease or at different stages or severity of disease.

The bacterial taxa and proteins described above can be referred to as diagnostic markers. These diagnostic markers can be used in a method for classifying a sample as being associated with IBD, UC or CD. The method comprises the steps of determining a presence or level of one or more of the diagnostic markers and comparing the presence or level to samples from IBD, UC or CD patients and/or normal patients. A combination of diagnostic markers may be combined together and may also further be combined with a standard diagnostic results derived from a disease activity index.

The algorithm can be a statistical algorithm which may comprise a learning statistical classifier system (or combination of such systems) such as neural network, random forest, interactive tree and the like, as would be known to a person skilled in the art. The predictive value of the classifying system maybe predetermined and may for example be at least 60%, 70%, 80%, 90% or 95%. The classification result may be provided to a clinician such as a gastroenterologist or general practitioner.

In yet a further aspect of the invention there is provided a method of classifying a gut sample to determine an association with IBD, UC or CD that comprises determining a diagnostic marker profile by detecting a presence or level of at least one gut diagnostic marker and classifying the sample as IBD, UC or CD by comparing the diagnostic marker profile to samples from IBD, UC or CD patients or normal subjects or combination thereof. The profile can be combined with a diagnostic based on a disease activity index specific for IBD, UC or CD.

The diagnostic marker can be selected from $H_2S$ producing bacteria, Proteobacteria, butyrate producing bacteria, *Fusobacterium nucleatum*, *Veillonella parvula*, *Atopobium parvulum*, Firmicutes, Clostridia, Clostridiales, Lachnopiraceae, Eubacterium, Roseburia, Coprococcus, Clostridium, *Eubacterium rectale*, *Clostridium coccoides*, *Roseburia inulivorans*, Verrucomicrobiae, Clostridiales, Verrucomicrobiales, Verrucomicrobiaceae, Lachnospiraceae, Paenibacillaceae, Akkermansia, Turicibacter, Paenibacillus, Pasteurellales, Chromatialles, Hydrogenophilales, Oceanospirillales, Rhizobiales, Halomonadaceae, Pasteurellaceae, Bradyrhizobiaceae, Methylococcaceae, Hydrogenophilaceae, Porphyromonas, Lautropia, Methylobacterium, Haemophilus, Finegoldia, Nitrincola, Hydrogenophilu, Actinobacillus, Anaerococcus, Mobiluncus, Enterobacter, Vitreoscilla, Alcanivorax, Veillonella, Tatumella, Staphylococcaceae, Paenibacillaceae, Listeriaceae, Listeria, Paenibacillus, Staphylococcus, Negativicutes, Betaproteobacteria, Pasteurellales, Chromatialles, Burkholderiales, Selenomonadales, Pasteurellaceae, Haemophilus, Pantoea, Carnobacteriaceae, Granulicatella, Mogibacterium, Proprionibacterium, Bacillaceae, Atopobium, Hydrogenophilales, Rhizobiales, Bradyrhyzobiaceae, Hydrogenophylaceae, Porphyromonas, Lautropia, Tannarella, Finegoldia, Hydrogenophilus, Catonella, Mobilumcus, Alcanivorax, Afipia, sulfur dioxygenase (ETHE1), thiosulfate sulfur transferase (TST), cytochrome c oxidase subunit IV, sulfide dehydrogenase (SQR), complexes III and IV of mithochondrial respiratory chain, Cxcl1, IL17a, Il12, Il1β and combination thereof.

The profile may consist of level(s) of a marker or the combination of levels from different markers or the relative levels (ratios) of markers combined or not with a diagnosis based on a disease activity index. The profile may also comprise levels of markers over time or stages of the disease(s) or severity of the disease(s). The profile may also be weighted with respect to the markers or the diagnosis.

There is also provided an apparatus comprising a diagnostic marker detector capable of detecting one or more of the markers described above for example by methods described in this application, a processor configured to classify the sample as an IBD, UC or CD sample by comparing the diagnostic marker profile to samples from IBD, CD, UC or normal subjects or combination thereof and a result display unit to display to a user a classification obtained from the processor. The processor may also receive from an input a diagnostic result based on a disease activity index specific for IBD, UC or CD and combine this diagnostic result with the diagnostic marker profile to generate the classification. Thus the processor may use training data or a training cohort to identify the characterisitics of the diagnostic marker that provides a reliable classification. The data provided here (levels of bacteria and proteins for example) with their correlation to presence of disease or disease severity or progression can be used as a training cohort. However it will be appreciated that additional data could be generated to improve the training data based on the guidance of the results presented in this application.

It will be understood that the processor may use algorithms as described above.

EXAMPLES

Example 1

An inception cohort of 157 patients (84 Crohn's disease (CD), 20 ulcerative colitis (UC) and 53 controls; Table 8) was recruited.

TABLE 8

| #SampleID | Description | M/F | age | Site Sampled | Visual Appearance | Paris Classification | PCDAI/ PUCAI | Experiment |
|---|---|---|---|---|---|---|---|---|
| HMC002RC | UC | F | 16 | RC | normal | E1, S0 | 20 (Mild) | Illumina |
| HMC003RC | Control | F | 9 | RC | normal | n/a | n/a | Illumina |
| HMC004RC | Control | M | 12 | RC | normal | n/a | n/a | 454Pyro |
| HMC005RC | Control | F | 10 | RC | normal | n/a | n/a | Illumina |
| HMC006RC | Control | M | 15 | RC | normal | n/a | n/a | Illumina |
| HMC012RC | CD | M | 13 | RC | normal | A1b, L1, B1, G0 | 12.5 (Mild) | Illumina |
| HMC013RC | UC | M | 12 | RC | inflammed | E4, S1 | 65 (Severe) | Illumina |
| HMC014RC | CD | F | 14 | RC | normal | A1b, L3, L4a, B1, G1 | 37.5 (Moderate | 454pyro |
| HMC015RC | CD | F | 14 | RC | normal | A1b, L1, B2, G0 | 10 (Mild) | Illumina |
| HMC016RC | CD | M | 13 | RC | normal | A1b, L3, B1, G0 | 20 (Mild) | Illumina |
| HMC017RC | CD | M | 13 | RC | inflammed | A1b, L2, L4a, B1, G1 | 57.5 (Severe) | Illumina |
| HMC018RC | Control | M | 13 | RC | normal | n/a | n/a | Illumina |
| HMC019RC | UC | M | 14 | RC | inflammed | E4, S1 | 80 (Severe) | Illumina/454pyro |
| HMC020RC | Control | F | 12 | RC | normal | n/a | n/a | 454Pyro |
| HMC022RC | CD | M | 14 | RC | normal | A1b, L1, B1, G1 | 37.5 (Moderate | Illumina |
| HMC023RC | UC | M | 14 | RC | normal | E4, S1 | 50 (Moderate | Illumina/454pyro |
| HMC024RC | UC | M | 16 | RC | normal | E3, S1 | 40 (Moderate | 454pyro |
| HMC025RC | CD | F | 15 | RC | normal | A1b, L4b, B1, G0 | 20 (Mild) | Illumina |
| HMC026RC | Control | F | 16 | RC | normal | n/a | n/a | 454Pyro |
| HMC027RC | Control | F | 16 | RC | normal | n/a | n/a | Illumina |
| HMC028RC | Control | M | 13 | RC | normal | n/a | n/a | Illumina/454pyro |
| HMC029RC | CD | M | 14 | RC | inflammed | A1b, L3, L4a, B1, G0 | 32.5 (Moderate | Illumina |
| HMC030RC | CD | F | 17 | RC | inflammed | A1b, L3, L4a, B1, G0 | 45 (Severe) | Illumina |
| HMC038RC | CD | F | 16 | RC | inflammed | A1b, L2, B1p, G0 | 20 (Mild) | Illumina |
| HMC039RC | CD | F | 13 | RC | normal | A1b, L1, L4a, B1, G1 | 60 (Severe) | Illumina |
| HMC041RC | CD | F | 15 | RC | normal | A1b, L3, B1, G0 | 57.5 (Severe) | Illumina |
| HMC042RC | Control | M | 17 | RC | normal | n/a | n/a | Illumina |
| HMC043RC | Control | F | 16 | RC | normal | n/a | n/a | Illumina |
| HMC044RC | CD | F | 15 | RC | normal | A1b, L1, B3, G1 | 52.5 (Severe) | Illumina |
| HMC045RC | UC | M | 17 | RC | normal | E3 | 45 (Moderate | Illumina |
| HMC046RC | UC | F | 4 | RC | inflammed | E4, S1 | 65 (Severe) | Illumina/454pyro |
| HMC047RC | CD | M | 16 | RC | inflammed | A1b, L3, L4a, B1, G1 | 65 (Severe) | Illumina |
| HMC049RC | CD | M | 12 | RC | normal | A1b, L1, B1, G1 | 40 (Severe) | Illumina/454pyro |
| HMC050RC | CD | F | 16 | RC | normal | A1b, L1, B1, G0 | 12.5 (Mild) | Illumina |
| HMC051RC | CD | F | 16 | RC | inflammed | A1b, L3, L4a, B1, G0 | 65 (Severe) | Illumina |
| HMC052RC | Control | F | 8 | RC | normal | n/a | n/a | 454Pyro |
| HMC055RC | Control | M | 6 | RC | normal | n/a | n/a | Illumina/454pyro |
| HMC056RC | Control | F | 8 | RC | normal | n/a | n/a | Illumina |
| HMC059RC | Control | M | 14 | RC | normal | n/a | n/a | Illumina |
| HMC061RC | CD | M | 9 | RC | inflammed | A1a, L2, B1, G0 | 32.5 (Moderate | Illumina/454pyro |
| HMC062RC | CD | F | 15 | RC | inflammed | A1b, L3, L4a, B3, G0 | 57.5 (Severe) | Illumina |
| HMC063RC | CD | M | 13 | RC | normal | A1b, L1, L4a, B1, G1 | 65 (Severe) | Illumina/454pyro |
| HMC064RC | UC | M | 18 | RC | inflammed | E4, S1 | 0 (Inactive) | Illumina |
| HMC065RC | CD | M | 16 | RC | normal | A1b, L1, B2, B3, G0 | 50 (Severe) | Illumina |
| HMC066RC | UC | F | 18 | RC | inflammed | E4, S0 | 35 (Moderate | Illumina/454pyro |
| HMC067RC | Control | F | 17 | RC | normal | n/a | n/a | Illumina |
| HMC068RC | CD | M | 17 | RC | inflammed | A1b, L2, B1, G0 | 32.5 (Moderate | 454Pyro |
| HMC069RC | Control | F | 17 | RC | normal | n/a | n/a | Illumina |
| HMC070RC | Control | F | 8 | RC | normal | n/a | n/a | 454Pyro |
| HMC071RC | Control | M | 11 | RC | normal | n/a | n/a | Illumina |
| HMC072RC | CD | M | 12 | RC | inflammed | A1b, L3, L4a, B1, G1 | 55 (Severe) | Illumina |

TABLE 8-continued

| #SampleID | Description | M/F | age | Site Sampled | Visual Appearance | Paris Classification | PCDAI/ PUCAI | Experiment |
|---|---|---|---|---|---|---|---|---|
| HMC073RC | Control | F | 16 | RC | normal | n/a | n/a | Illumina |
| HMC074RC | Control | F | 16 | RC | normal | n/a | n/a | 454Pyro |
| HMC075RC | CD | M | 14 | RC | inflamed | A1b, L2, B1, G1 | 50 (Severe) | Illumina |
| HMC076RC | UC | F | 17 | RC | inflamed | E4, S0 | 55 (Moderate | Illumina/454pyro |
| HMC077RC | UC | M | 17 | RC | normal | E3, S0 | 50 (Moderate | Illumina/454pyro |
| HMC078RC | CD | F | 15 | RC | normal | A1b, L1, B1, G0 | 45 (Severe) | Illumina |
| HMC079RC | CD | M | 16 | RC | inflamed | A1b, L3, B1, G0 | 45 (Severe) | Illumina |
| HMC081RC | CD | M | 11 | RC | normal | A1b, L1, B1, G1 | 67.5 (Severe) | Illumina |
| HMC082RC | CD | F | 15 | RC | inflamed | A1a, L3, B1, G0 | 27.5 (Mild) | Illumina |
| HMC085RC | CD | M | 16 | RC | normal | A1b, L2, B1, G1 | 62.5 (Severe) | Illumina/454pyro |
| HMC086RC | CD | M | 8 | RC | normal | A1a, L1, L4a, L4b, B1, G0 | 22.5 (Mild) | Illumina |
| HMC087RC | Control | F | 18 | RC | normal | n/a | n/a | Illumina/454pyro |
| HMC088RC | UC | M | 16 | RC | inflamed | E1, S0 | 20 (Mild) | Illumina |
| HMC090RC | CD | M | 16 | RC | inflamed | A1b, L3, L4, B1, G0 | 52.5 (Severe) | Illumina/454pyro |
| HMC091RC | Control | M | 12 | RC | normal | n/a | n/a | Illumina |
| HMC092RC | UC | M | 12 | RC | normal | E3, S1 | 80 (Severe) | Illumina/454pyro |
| HMC093RC | CD | M | 12 | RC | normal | A1b, L1, B1p, G0 | 27.5 (Mild) | Illumina/454pyro |
| HMC094RC | CD | M | 11 | RC | normal | A1b, L1, B1p, G0 | 45 (Severe) | Illumina |
| HMC095RC | CD | M | 11 | RC | normal | A1b, L3, B1p, G1 | 65 (Severe) | Illumina |
| HMC097RC | CD | M | 12 | RC | inflamed | A1b, L3, L4a, B1, G0 | 40 (Severe) | 454Pyro |
| HMC098RC | Control | F | 16 | RC | normal | n/a | n/a | Illumina |
| HMC100RC | Control | M | 15 | RC | normal | n/a | n/a | Illumina |
| HMC102RC | Control | F | 17 | RC | normal | n/a | n/a | Illumina |
| HMC103RC | UC | F | 17 | RC | inflamed | E4, S0 | 50 (Moderate | Illumina |
| HMC106DC | Control | F | 16 | DC | normal | n/a | n/a | qPCR/qRTPCR |
| HMC109DC | Control | F | 3 | DC | normal | n/a | n/a | qPCR/qRTPCR |
| HMC112DC | Control | M | 9 | DC | normal | n/a | n/a | qPCR/qRTPCR |
| HMC113DC | UC | M | 15 | DC | inflamed | E2, S1 | 0 ((Inactive)) | qRTPCR |
| HMC117DC | Control | F | 15 | DC | normal | n/a | n/a | qRTPCR |
| HMC201RC | CD | F | 11 | RC | inflamed | A1b, L2, B1, G1 | 37.5 (Moderate | Illumina/Massspec/ qPCR/qRTP |
| HMC202RC | CD | M | 17 | RC | inflamed | A1b, L3, B1, G0 | 37.5 (Moderate | Illumina/Massspec/ qPCR/qRTP |
| HMC203RC | CD | M | 11 | RC | inflamed | A1b, L3, B1, G0 | 45 (Severe) | Illumina/Massspec/ qPCR/qRTP |
| HMC204RC | CD | M | 13 | RC | normal | A1b, L1, L4b, B1, G1 | 45 (Severe) | Illumina/qRTPCR |
| HMC205RC | CD | M | 13 | RC | normal | A1b, L1, L4a, B1, P, G1 | 45 (Severe) | Illumina/qPCR/qRTPCR |
| HMC206RC | CD | M | 14 | RC | inflamed | A1b, L3, B1, G1 | 45 (Severe) | qRTPCR |
| HMC207RC | UC | F | 13 | RC | inflamed | E4, S1 | 70 (Severe) | Illumina |
| HMC208RC | Control | F | 16 | RC | normal | n/a | n/a | Illumina/qPCR/qRTPCR |
| HMC210RC | CD | F | 17 | RC | normal | A1b, L1, B1, G0 | 37.5 (Moderate | qRTPCR |
| HMC211RC | control | M | 13 | RC | normal | n/a | n/a | qRTPCR |
| HMC212RC | control | F | 15 | RC | normal | n/a | n/a | qRTPCR |
| HMC213RC | CD | M | 10 | RC | inflamed | A1b, L3, B1, G1 | 60 (Severe) | qPCR/MassSpec |
| HMC214RC | UC | F | 17 | RC | inflamed | E3, S0 | 35 (Moderate | qRTPCR |
| HMC215RC | UC | F | 12 | RC | inflamed | E4, S1 | 65 (Severe) | qRTPCR |
| HMC217RC | CD | F | 14 | RC | normal | A1b, L1, L4a, B1, G0 | 55 (Severe) | qPCR/qRTPCR |
| HMC219RC | CD | M | 14 | RC | inflamed | A1b, L3, B1, G1 | 37.5 (Moderate | MassSpec/qRTPCR |
| HMC220RC | CD | M | 13 | RC | inflamed | A1b, L3, B1, G0 | 60 (Severe) | MassSpec/qRTPCR |
| HMC221RC | control | F | 9 | RC | normal | n/a | n/a | qPCR/qRTPCR |
| HMC222RC | control | M | 10 | RC | normal | n/a | n/a | qPCR/qRTPCR |

TABLE 8-continued

| #SampleID | Description | M/F | age | Site Sampled | Visual Appearance | Paris Classification | PCDAI/ PUCAI | Experiment |
|---|---|---|---|---|---|---|---|---|
| HMC223RC | CD | F | 9 | RC | inflammed | A1a, L2, B1, G1 | 45 (Severe) | MassSpec/qRTPCR |
| HMC224RC | control | M | 15 | RC | normal | n/a | n/a | qPCR/qRTPCR/ MassSpec |
| HMC225RC | control | F | 15 | RC | normal | n/a | n/a | qRTPCR |
| HMC227RC | CD | F | 13 | RC | inflammed | A1b, L3, B1, G0 | 32.5 (Moderate | qPCR/qRTPCR/ MassSpec |
| HMC228RC | CD | M | 13 | RC | inflammed | A1b, L3, B1, P, G0 | 62.5 (Severe) | MassSpec/qRTPCR |
| HMC229RC | CD | M | 10 | RC | inflammed | A1b, L2, L4a, B1, G0 | 57.5 (Severe) | qPCR/qRTPCR |
| HMC230RC | CD | M | 14 | RC | inflammed | A1b, L3, L4a, B1, P, G0 | 52.5 (Severe) | qPCR/qRTPCR |
| HMC231RC | CD | F | 15 | RC | normal | A1b, L1, B1, G0 | 37.5 (Moderate | qPCR/qRTPCR |
| HMC232RC | control | F | 15 | RC | normal | n/a | n/a | qPCR/qRTPCR/ MassSpec |
| HMC234RC | CD | F | 13 | RC | inflammed | A1b, L3, B1, G0 | 52.5 (Severe) | qRTPCR |
| HMC235RC | control | M | 11 | RC | normal | n/a | n/a | qRTPCR |
| HMC237RC | control | M | 14 | RC | normal | n/a | n/a | MassSpec/qRTPCR |
| HMC238RC | Control | M | 14 | RC | normal | n/a | n/a | qPCR/qRTPCR |
| HMC239RC | CD | M | 3 | RC | infamed | A1a, L3, B1p, G0 | 22.5 (Mild) | MassSpec/qRTPCR |
| HMC240RC | CD | M | 10 | RC | normal | A1b, L1, B1, G0 | 55 (Severe) | qRTPCR |
| HMC241RC | Control | F | 12 | RC | normal | n/a | n/a | qRTPCR |
| HMC243RC | UC | M | 8 | RC | inflammed | E1, S0 | 45 (Moderate | qRTPCR |
| HMC245RC | Control | M | 16 | RC | normal | n/a | n/a | qRTPCR |
| HMC246RC | Control | M | 13 | RC | normal | n/a | n/a | qRTPCR |
| HMC247RC | UC | F | 13 | RC | inflammed | E4, S1 | 80 (Severe) | qRTPCR |
| HMC249RC | UC | M | 14 | RC | inflammed | E4, S0 | 45 (Moderate | qRTPCR |
| HMC252RC | CD | M | 9 | RC | inflammed | A1a, L3, B1, G0 | 37.5 (Moderate | MassSpec |
| HMC253RC | CD | F | 11 | RC | inflammed | A1b, L2, L4a, B1 | 40 (Severe) | qPCR |
| HMC254RC | CD | M | 12 | RC | normal | A1a, L1, L4a, B2B3 | 27.5 (Mild) | MassSpec |
| HMC256RC | CD | F | 10 | RC | inflammed | A1b, L2, B1 | 30 (Moderate | MassSpec |
| HMC258RC | Control | M | 15 | RC | normal | n/a | n/a | MassSpec |
| HMC260RC | CD | M | 13 | RC | inflammed | A1b, L2, B1p | 47.5 (Severe) | qPCR |
| HMC261RC | CD | F | 13 | RC | normal | A1b, L3, L4, B1p | 32.5 (Moderate | qPCR |
| HMC264RC | CD | F | 15 | RC | normal | A1bL3L4aB1G0 | 30 (Moderate | qPCR |
| HMC266RC | CD | F | 10 | RC | inflammed | A1a, L2, B1 | 27.5 (Mild) | qPCR |
| HMC269RC | CD | M | 8 | RC | normal | A1a, L3, L4a, B1 | 2.5 (Inactive) | qPCR |
| HMC270RC | Control | F | 17 | RC | normal | n/a | n/a | qPCR |
| HMC271RC | CD | M | 15 | RC | inflammed | A1a, L3, B1p, G0 | 62.5 (Severe) | qPCR/MassSpec |
| HMC272RC | CD | M | 12 | RC | inflammed | A1a, L3, B1p, G1 | 50 (Severe) | MassSpec |
| HMC280RC | CD | M | 15 | RC | inflammed | A1b, L3, B1 | 35 (Moderate | MassSpec |
| HMC281RC | Control | F | 15 | RC | normal | n/a | n/a | MassSpec |
| HMC285RC | CD | F | 9 | RC | inflammed | A1a, L3, B1, G0 | 17.5 (Mild) | qPCR |
| HMC286RC | CD | M | 15 | RC | inflammed | A1b, L3, L4a, B1 | 5 (Inactive) | qPCR |
| HMC288RC | CD | M | 14 | RC | inflammed | A1b, L3, B1p | 62.5 (Severe) | qPCR/MassSpec |
| HMC289RC | CD | M | 12 | RC | inflammed | A1b, L3, B1p | 67.5 (Severe) | qPCR |
| HMC293RC | CD | F | 12 | RC | inflammed | A1b, L2, B1, G1 | 22.5 (Mild) | qPCR |
| HMC295RC | CD | F | 14 | RC | inflammed | L2, B1, G0 | 20 (Mild) | qPCR |
| HMC297RC | Control | F | 17 | RC | normal | n/a | n/a | qPCR |
| HMC298RC | CD | M | 12 | RC | normal | A1b, L1, B1 | 52.5 (Severe) | qPCR |
| HMC300RC | CD | M | 10 | RC | inflammed | A1a, L3, L4a, B1, G1 | 27.5 (Mild) | MassSpec |
| HMC301RC | CD | F | 14 | RC | inflammed | A1b, L3, L4a, B1, G0 | 60 (Severe) | MassSpec |

TABLE 8-continued

| #SampleID | Description | M/F | age | Site Sampled | Visual Appearance | Paris Classification | PCDAI/PUCAI | Experiment |
|---|---|---|---|---|---|---|---|---|
| HMC305RC | CD | M | 4 | RC | normal | A1a, L3, L4a, B2p, G0 | 12.5 (Mild) | qPCR |
| HMC307RC | Control | F | 16 | RC | normal | n/a | n/a | qPCR/MassSpec |
| HMC309RC | Control | M | 10 | RC | normal | n/a | n/a | qPCR/MassSpec |
| HMC313RC | Control | M | 16 | RC | normal | n/a | n/a | qPCR |
| HMC315RC | Control | M | 16 | RC | normal | n/a | n/a | MassSpec |
| HMC316RC | CD | M | 14 | RC | inflammed | A1b, L3, L4a, B1 | 17.5 (Mild) | qPCR/MassSpec |
| HMC317RC | CD | M | 15 | RC | normal | A1b, L1, L4a, B1p | 0 (Inactive) | qPCR |
| HMC319RC | CD | M | 12 | RC | normal | L1, B1, G1 | 40 (Severe) | qPCR |
| HMC321RC | Control | F | 16 | RC | normal | n/a | n/a | qPCR |
| HMC322RC | CD | M | 12 | RC | inflammed | A1bL3B1P | 27.5 (Mild) | qPCR |
| HMC323RC | CD | F | 16 | RC | inflammed | A1bL3B1G0 | 35 (Moderate) | qPCR |
| HMC327RC | CD | F | 10 | RC | inflammed | A1aL2B1 | 25 (Mild) | MassSpec |

The microbiota at the intestinal mucosal interface embedded within the mucus layer and in direct contact with the site of disease was collected, and the microbial composition was characterized. The IBD microbiota was characterized by a smaller core as compared to controls (FIG. 5A, 5B and Table 1), indicating a loss of microbiota homeostasis. In addition, two taxa from the core microbiota that are potent $H_2S$ producers, *Fusobacterium nucleatum* and *Veillonella parvula* were found to be more abundant in CD and UC patients, respectively, as compared to controls (P<0.013; Table 1). Notably, *F. nucleatum* has been previously associated with adult IBD and shown to promote tumorigenesis in Apc$^{min/+}$ mice[4-6]. To identify microbes associated with IBD, the microbial taxa composition of CD, UC and control communities were compared using a nonparametric Kruskal-Wallis test, which indicated significant discriminating factors in 48 taxa (P<0.015; Supplementary Table 5). The relative abundances of Firmicutes, Clostridia, Clostridiales, and Lachnospiraceae, which are the major producers of butyrate, were decreased in CD and UC as compared to control microbiota while the relative abundances of Negativicutes, Selenomonadales, *Veillonella* and Betaproteobacteria were increased (Table 2). Taxa associated with disease activity were identified to identify the microbes modulating IBD severity. A Kruskal-Wallis test identified 11 unique taxa exhibiting differential abundance between CD patients with mild, moderate or severe inflammation (Table 3). Partial least square discriminant analysis (PLS-DA) clustered CD patients with severe inflammation separately from those with mild inflammation (FIG. 1a; p=0.001). Taxa biplot analysis indicated that certain taxa namely, *Carnobacteriaceae, Granulicatella, Mogibacterium, Proprionibacterium, Bacillaceae* and *Atopobium* were more abundant in patients with severe as compared to mild inflammation (FIG. 1b). In contrast, *Clostridia*, which are major butyrate-producers, were drivers of mild inflammation and exhibited a significant decline in relative abundance with increased disease severity. *Atopobium* was further classified as *Atopobium parvulum* (OTU#529659), a potent $H_2S$ producer implicated in halitosis[7,8]. $H_2S$ is now recognized as an important mediator of many physiological and pathological processes and has been associated with IBD and colorectal cancer[9,10]. Sulfide inhibits butyrate metabolism, the major energy source for colonocytes, and cytochrome c oxidase activity, the site of ATP production[9]. Therefore, a higher concentration of $H_2S$ might severely impair cellular bioenergetics. This would induce colonocyte starvation and death, disrupt the epithelial barrier and potentially lead to inflammation.

The relative abundance of *A. parvulum* was validated by quantitative polymerase chain reaction (qPCR) and found to be positively correlated with disease severity (FIG. 1c). The correlation between *A. parvulum* and CD was also confirmed by 454 pyrosequencing of a subset of samples followed by linear discriminant analysis effect size[11] (LEfSe; Supplementary FIG. 2-3). Importantly, the increased abundance of *A. parvulum* was not observed in UC and therefore is not simply a consequence of inflammation, suggesting a causal effect in CD.

Figure 2A:
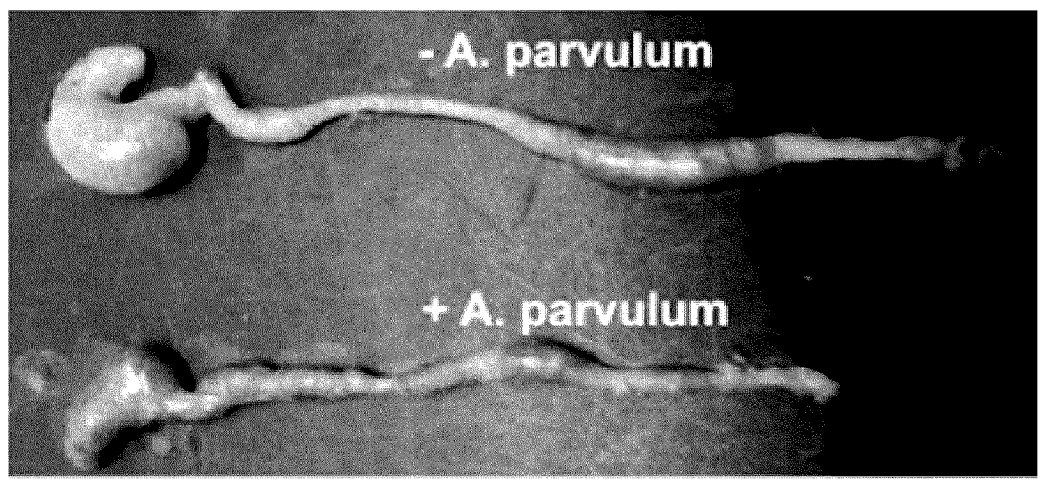
FIG. 2 A is a photomicrograph showing the cecum and colon from gnotobiotic $1110^{-/-}$ mice that were either associated or not with *A. parvulum*.
Figure 2B:
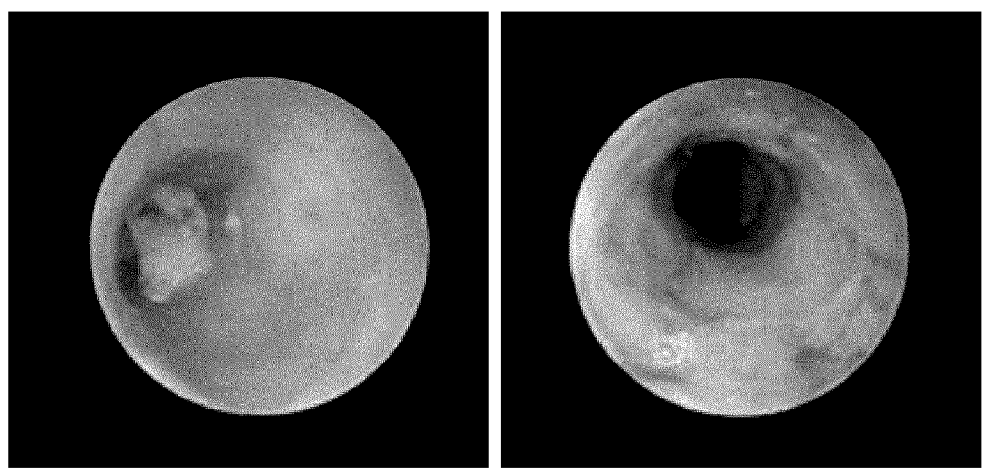
Figure 2C:
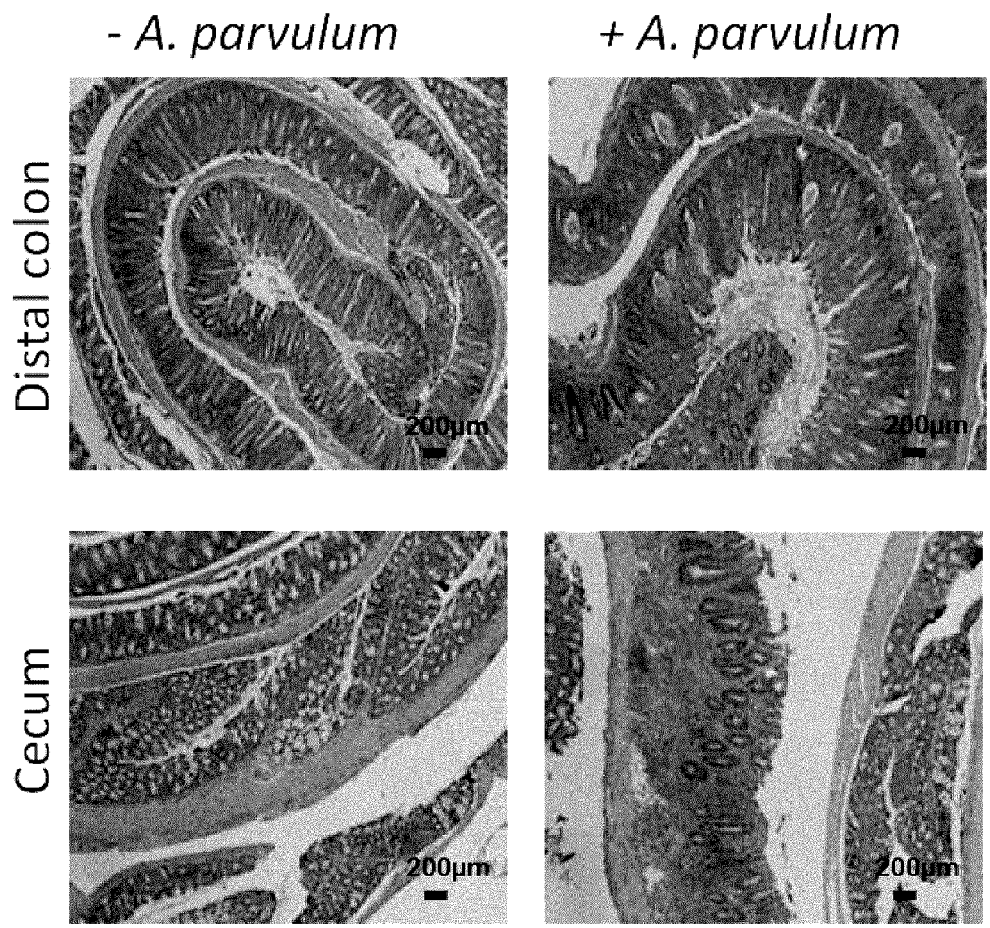
Figure 2D:
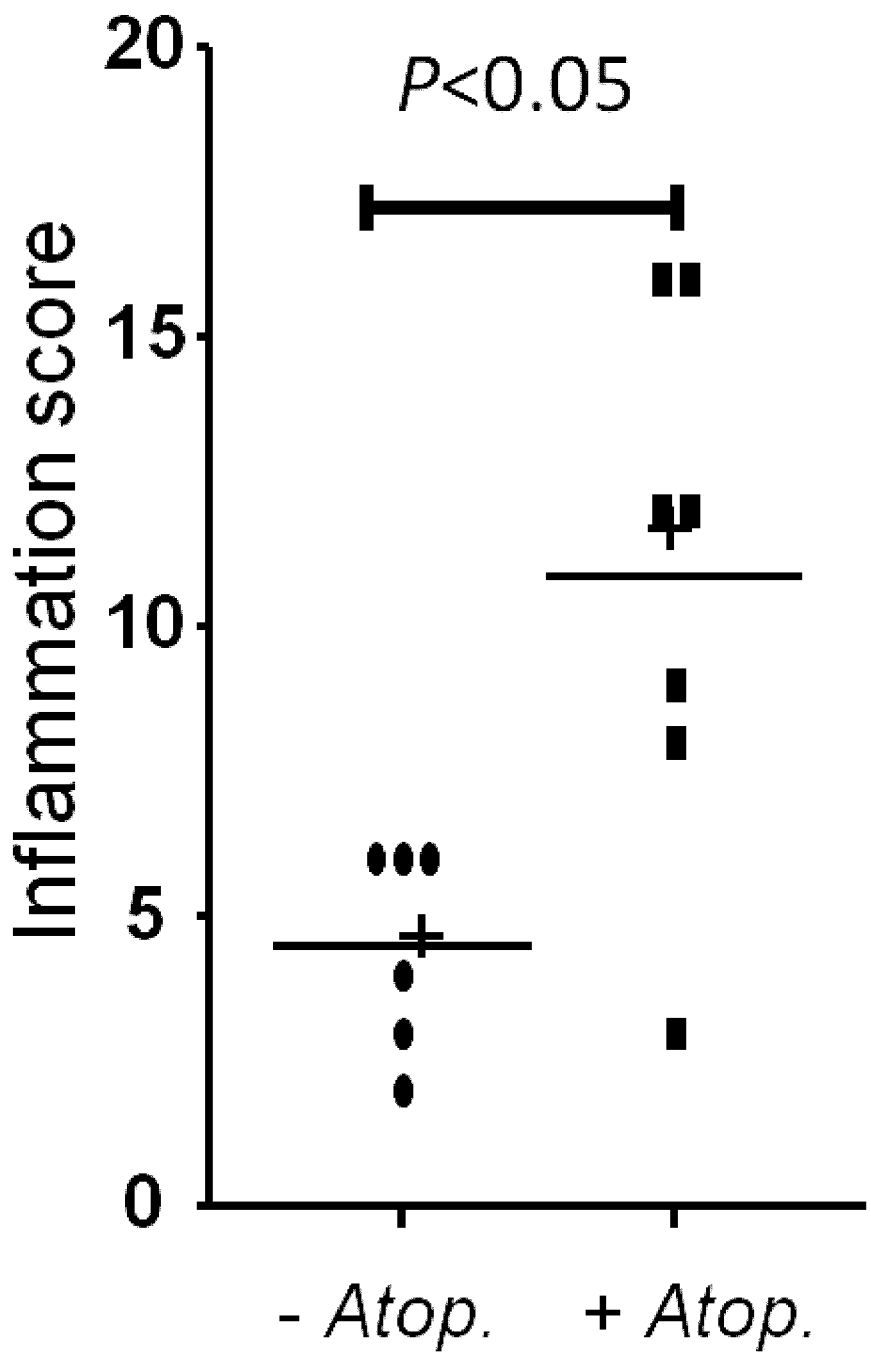

To evaluate the colitogenic potential of *A. parvulum*, we utilized colitic-susceptible Il10$^{-/-}$ mice[12,13]. Germ-free Il10$^{-/-}$ mice were transferred to specific pathogen free (SPF) housing and gavaged with *A. parvulum* (10$^8$ CFU/mouse/week) for 6 weeks. Compared to control uninfected Il10$^{-/-}$ mice, *A. parvulum*-colonized Il10$^{-/-}$ mice showed macroscopic evidence of cecal atrophy and colon length reduction (FIG. 2a). Colonoscopy imaging revealed mucosal erythema, friability and mucosal ulceration in *A. parvulum*-colonized Il10$^{-/-}$ mice compared to the healthy mucosa observed in controlled mice (FIG. 2b). Histological assessment of the intestinal tract showed evidence of inflammation with crypt hyperplasia, ulcers, goblet cell depletion and immune cell infiltration observed in the cecum and the distal part of the colon of *A. parvulum*-associated Il10$^{-/-}$ mice compared to uninfected control Il10$^{-/-}$ mice (FIG. 2c). Accordingly, histologic inflammation scores were significantly higher in *A. parvulum* associated Il10$^{-/-}$ mice compared to uninfected mice (P<0.05; FIG. 2d). At the molecular level, the colon of *A. parvulum*-infected Il10$^{-/-}$ mice showed increased Cxcl1 and Il17 mRNA accumulation compared to uninfected Il10$^{-/-}$ mice (fold increases of 8 and 5 respectively; P<0.01). These results indicate that the $H_2S$-producing bacterium *A. parvulum* induces pancolitis in a genetically susceptible mouse model of IBD.

To gain mechanistic insights into the role of $H_2S$-producing microbes in IBD severity, an unbiased, quantitative proteomic analysis of mucosal biopsies of IBD subjects of various disease severity (n=21) and controls (n=8) was conducted. Measurements for 3880 proteins were obtained of which 490 were identified as differentially expressed by comparing the 3 major groups, severe vs. moderate vs. control (one-way ANOVA with P<0.05). Mitochondrial proteins were identified as a major discriminant feature representing 21.7% of all differentially expressed proteins (FIG.

Figure 3A:
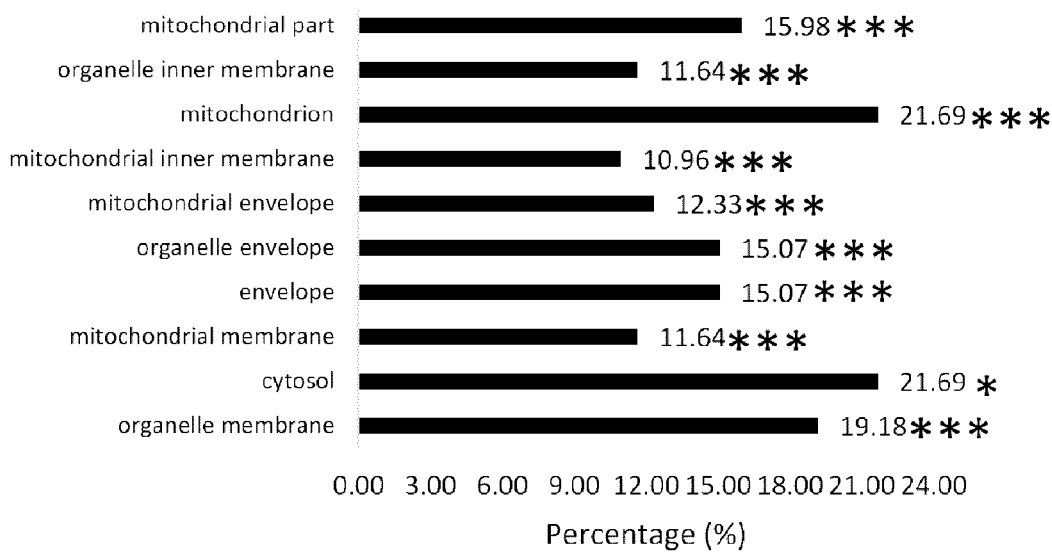
FIG. 3 A is a functional annotation ("cellular component') analysis of the differentially expressed proteins; the 10 most significantly enriched functional groups (GO terms) are shown ($P<10^{-13}$); asterisks denote classifications that were significantly enriched compared to the whole proteomic dataset, *$P<0.05$ and ***$P<0.001$ (Fisher's exact test).
Figure 3B:
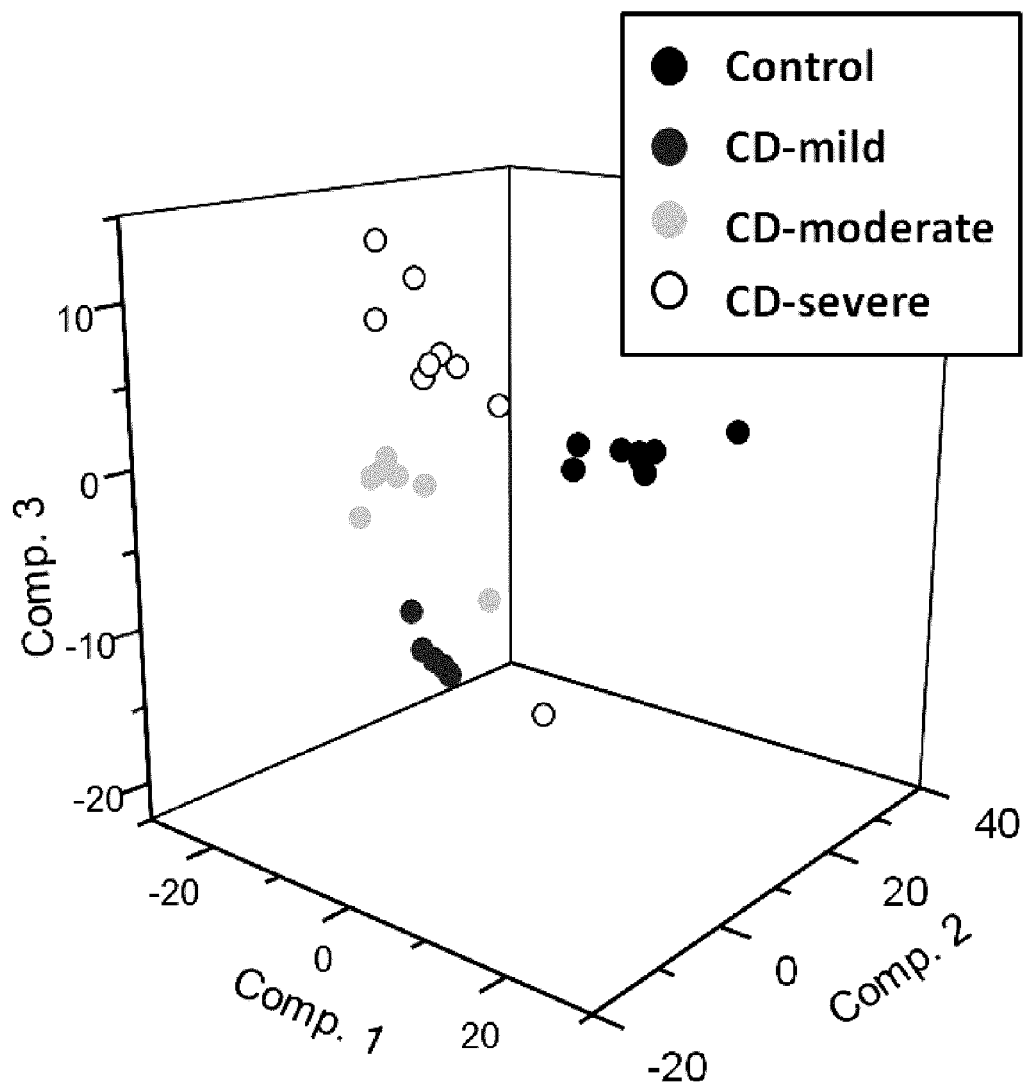
Figure 3C:
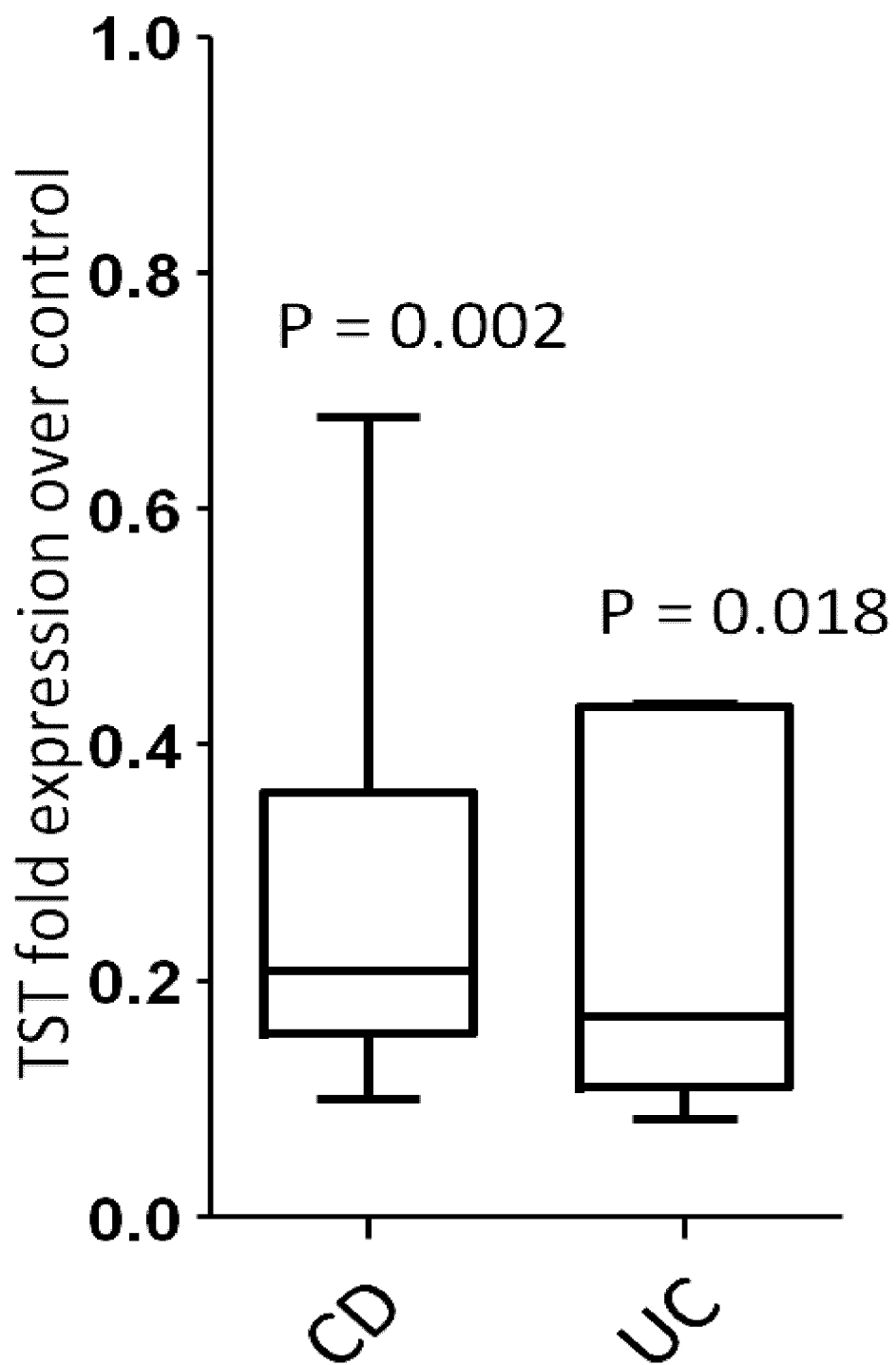
Figure 3D:
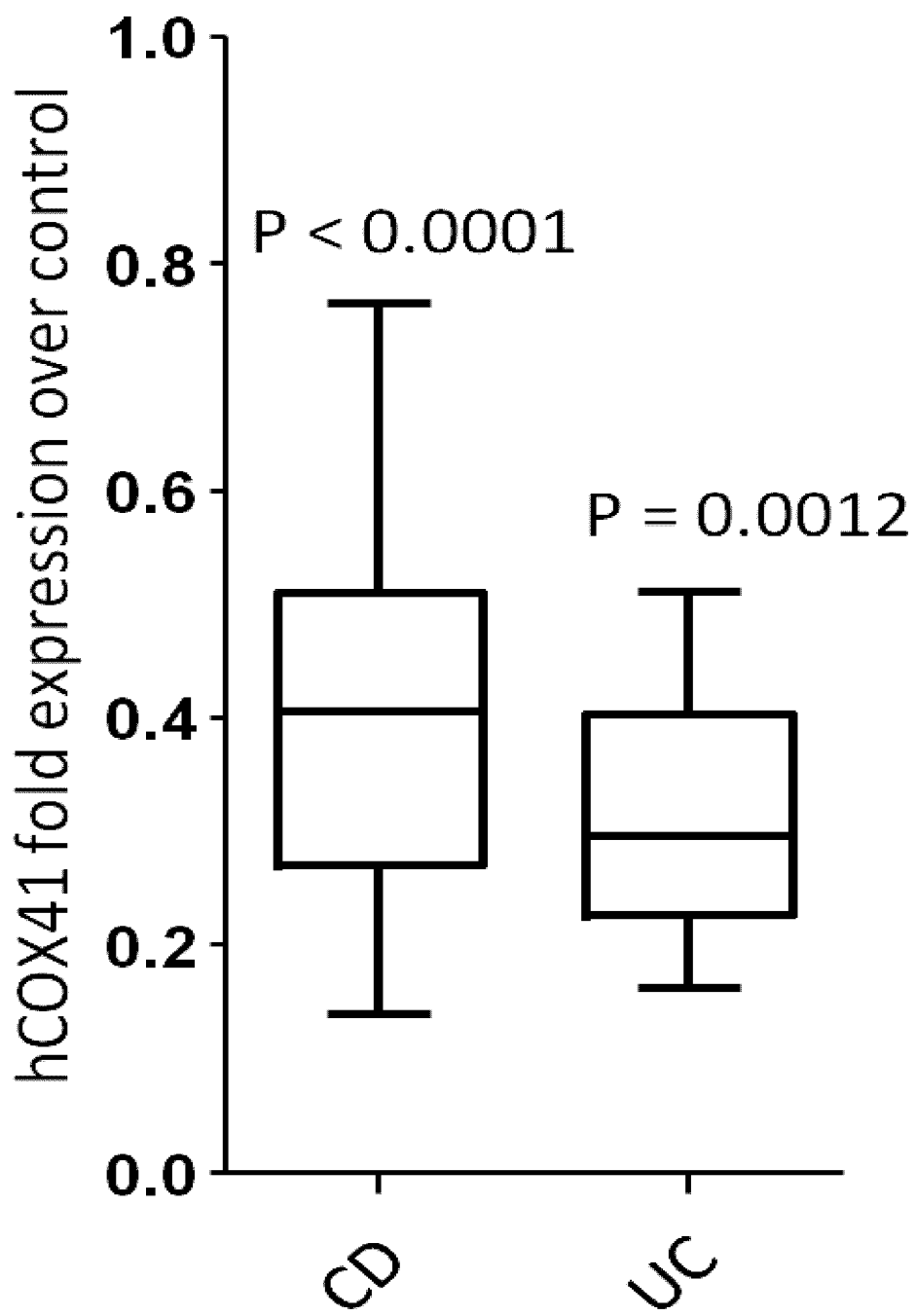
Figure 3E:
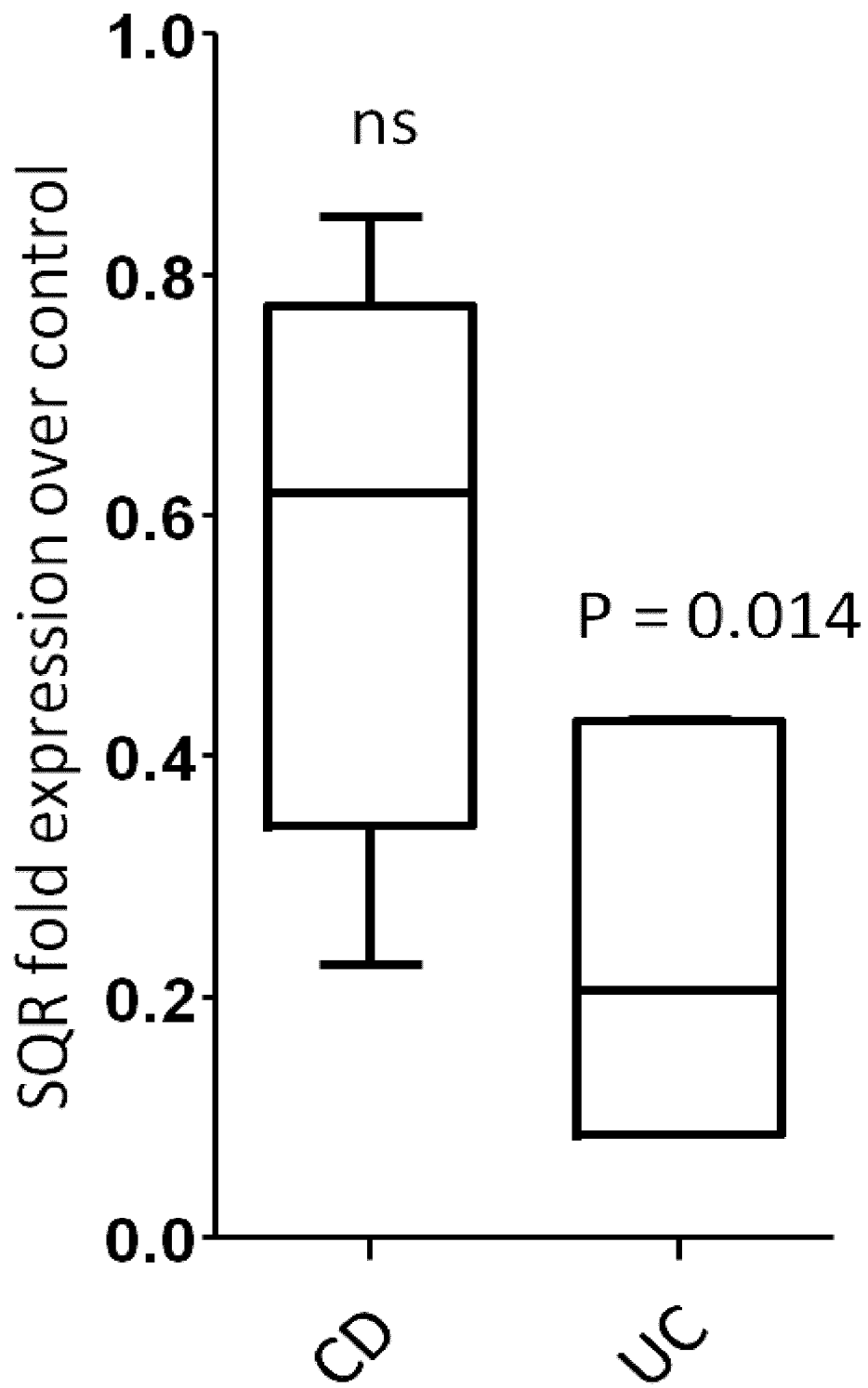
Figure 7A:
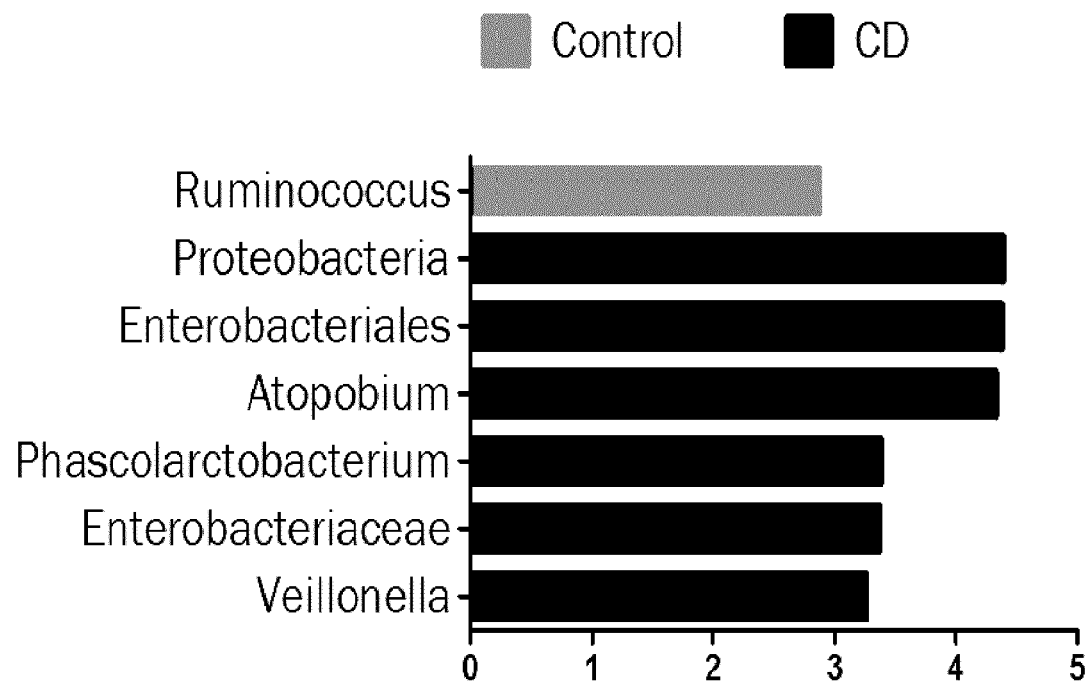
FIG. 7 A represents the relative abundances of the bacterial taxa obtained from the analysis of the 454 pyrosequencing reads were analysed by linear discrimination analysis (LDA) followed by a Wilcoxon Mann-Whitney test to assess the effect size using LEfSe; histogram of the LDA effect size score for CD-specific differentially abundant taxa (n=9 for CD and controls).
Figure 7B:
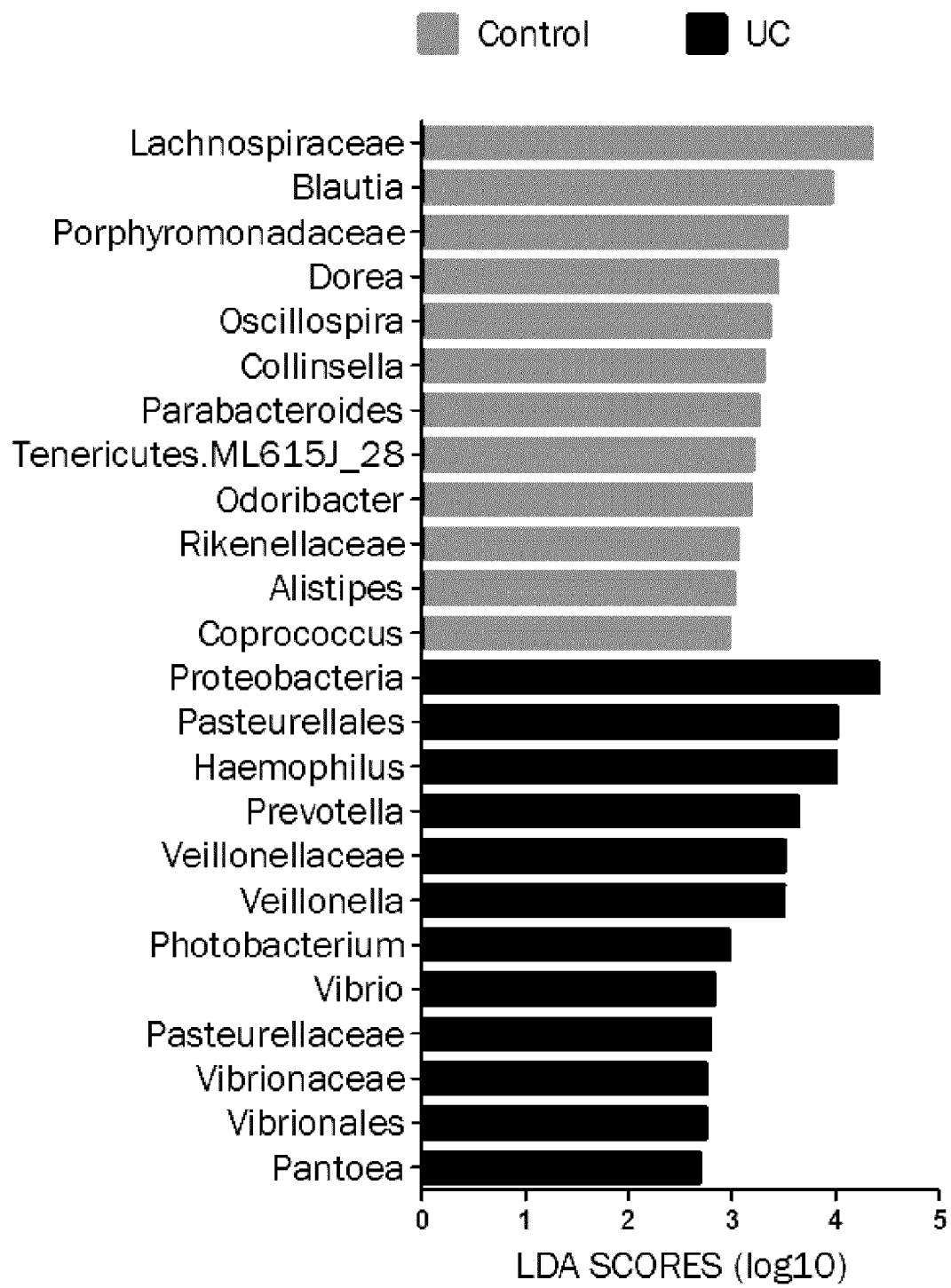
Figure 8A:
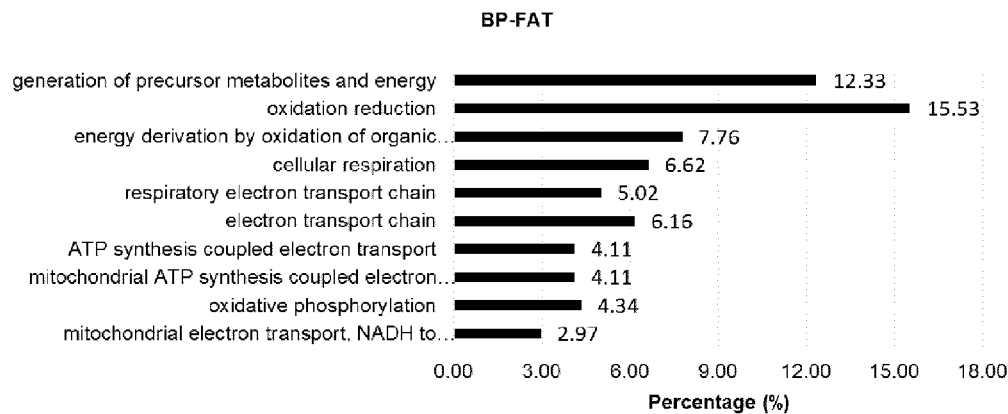
FIG. 8 A is a Functional annotation analysis of the differentially expressed proteins for BP: biological processes in which the 10 most significantly enriched functional groups (GO terms) are shown ($p<10^{-13}$); all classifications were significantly enriched compared to the whole proteomic dataset with $P<0.05$ (Fisher's exact test).
Figure 8B:
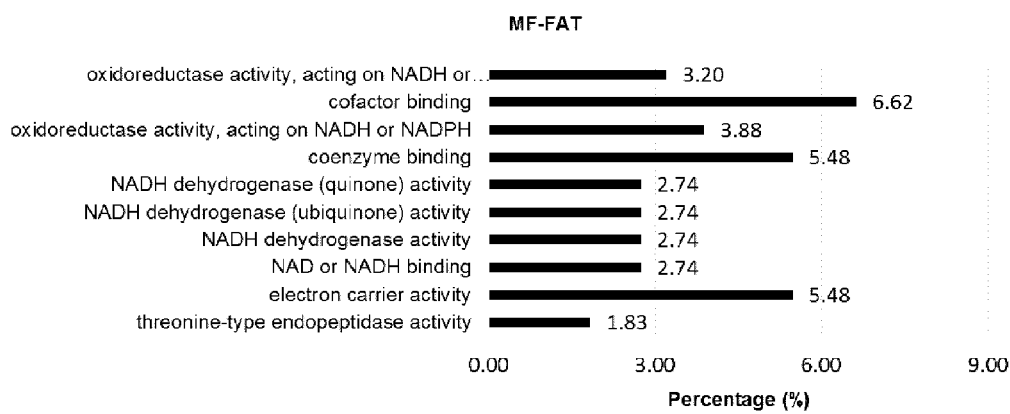
Figure 8C:
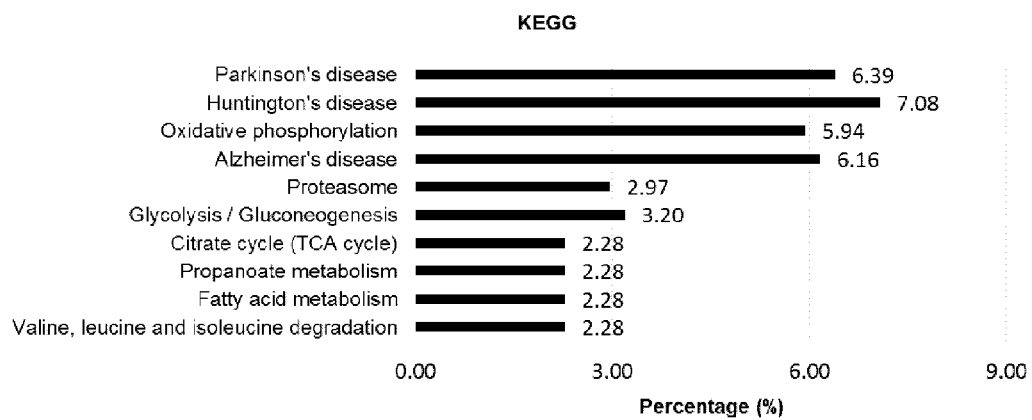
Figure 9A:
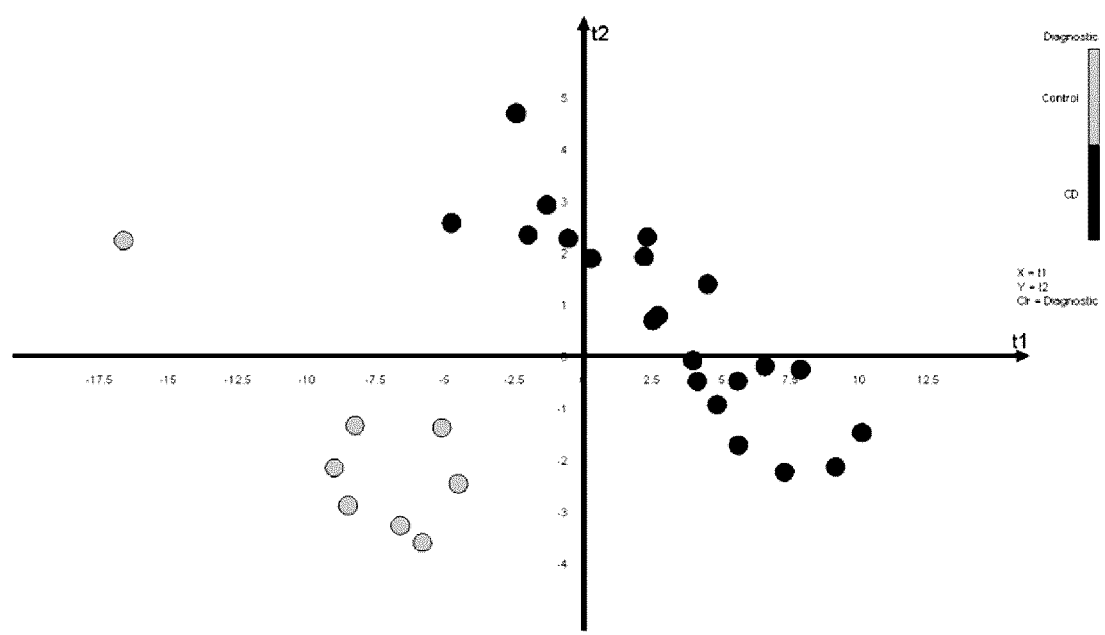
FIG. 9 A is a PLS-DA analysis of the mitochondrial protein profiles classified as CD patients (black) and control subjects (gray), the model was calculated based on the 95 differentially expressed mitochondrial proteins as determined by an ANOVA test and by selecting the proteins with the corresponding GO term (by using the DAVID functional GO annotation program), an acceptable PLS-DA model was obtained with 2 components (predictive ability parameter [$Q^2$ cum]=0.77, goodness-of-fit parameter [$R^2Y$ cum]= 0.92).
Figure 9B:
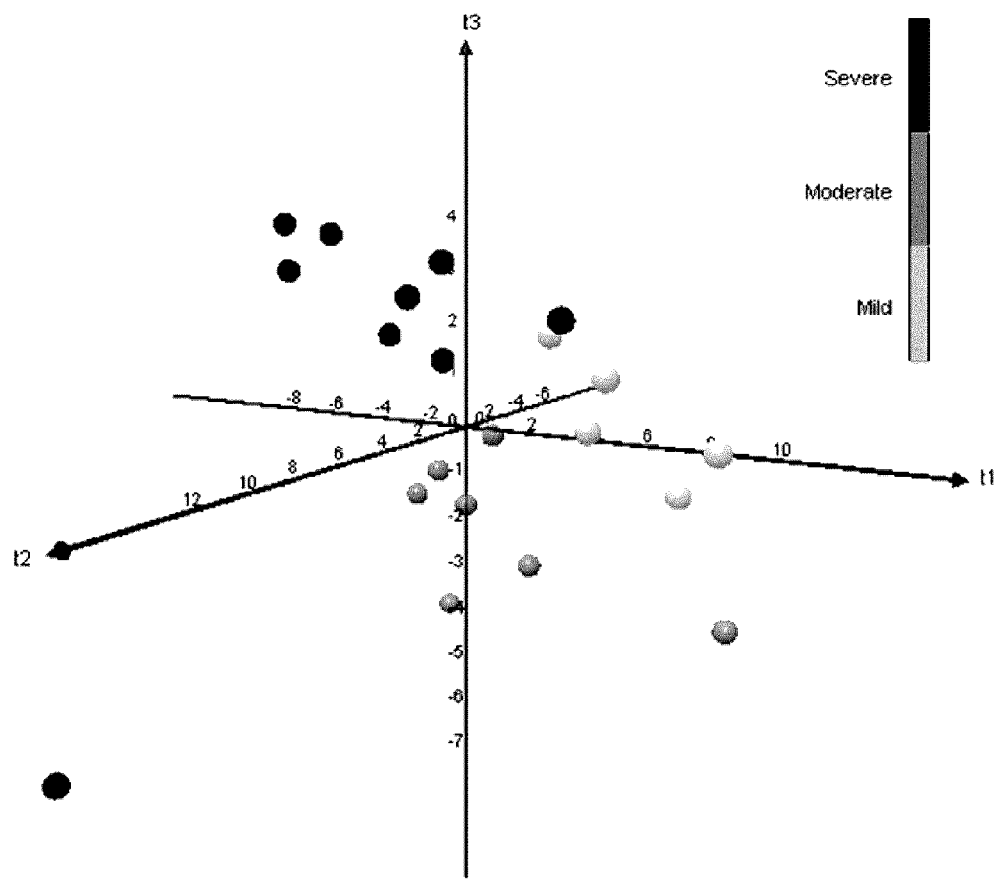
Figure 10:
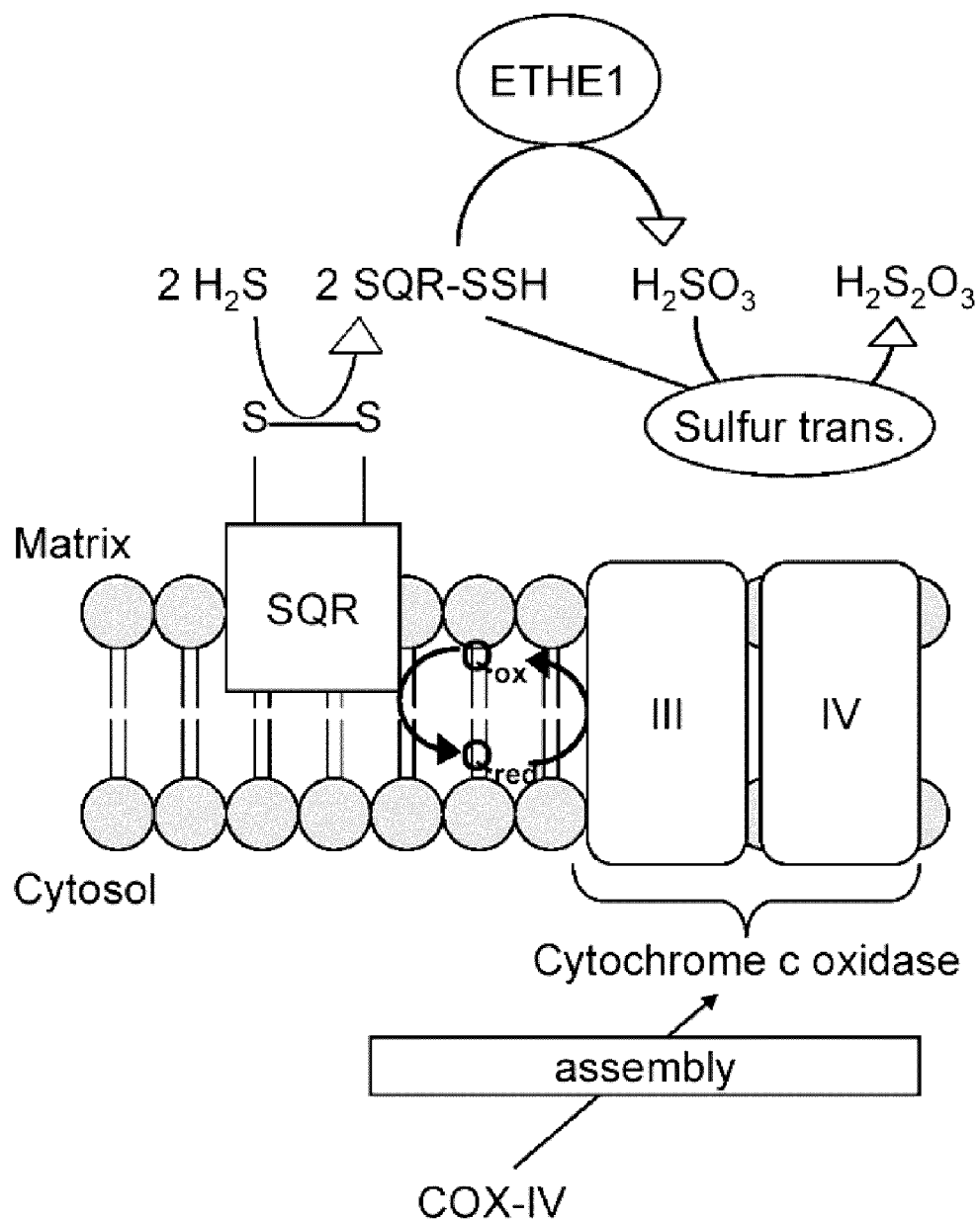
FIG. 10 is a model of mitochondrial $H_2S$ catabolism where the membrane bound sulfide dehydrogenase (SQR) oxidizes sulfide ($H_2S$) to persulfide (formed at one of the SQR's cysteines; SQR-SSH), the electrons are transferred to the mitochondrial respiratory chain (cytochrome c oxidase complex III and IV) via the quinone pool ($Q_{ox}/Q_{red}$) the sulfur dioxygenase, ETHE1, oxidizes persulfides to sulfites ($H_2SO_3$) in the mitochondrial matrix, rhodanese (sulfur trans.) catalyzes the final reaction, which produces thiosulfite ($H_2S_2O_3$) by transferring a second persulfide from the SQR to sulfite, the cytochrome c oxidase subunit IV (COX-IV) is required for the assembly of the cytochrome c oxidase, rhodanese comprises two iso-enzymes: thiosulfate sulfurtransferase (TST) and mercaptopyruvate sulfurtransferase (MST).
Figure 11A:
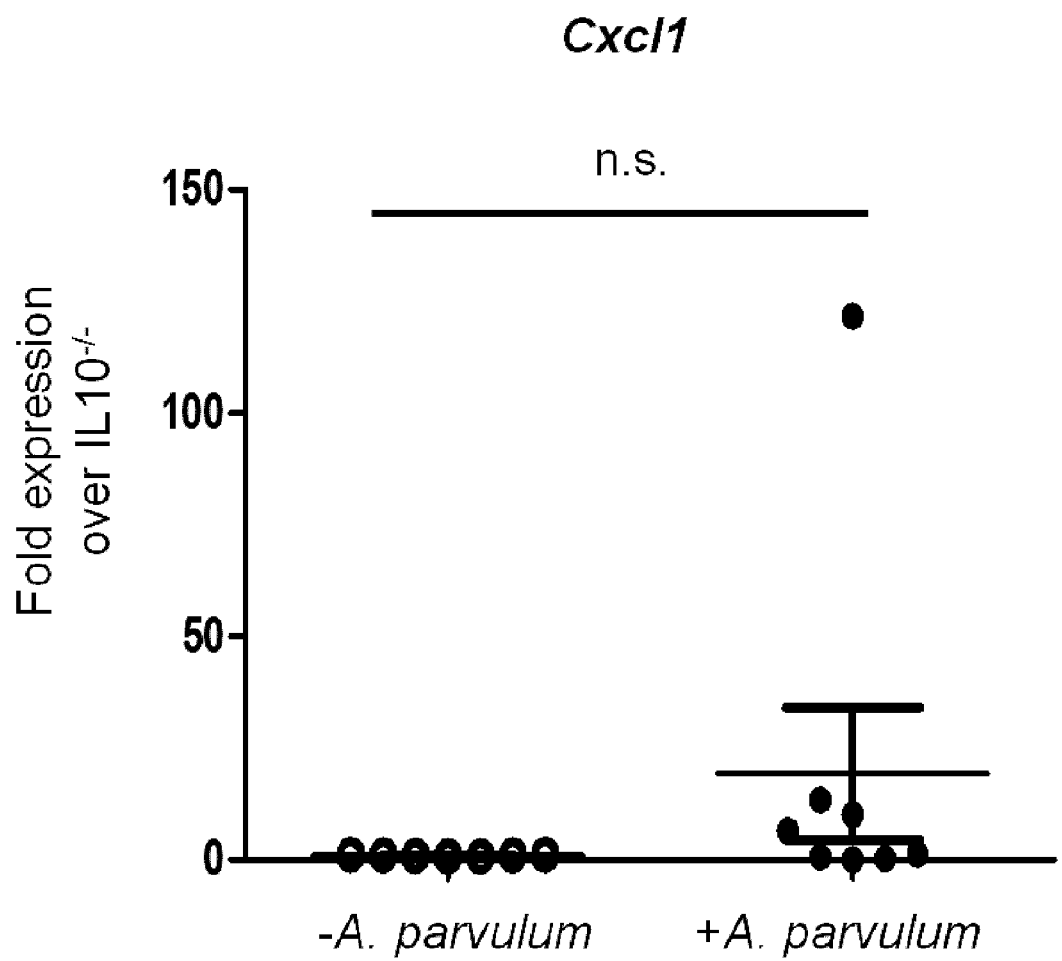
FIG. 11 A is a graph of Cxcl1 cytokine expression in conventionalized $Il10^{-/-}$ mice (129/SvEv $Il10^{-/-}$ mice), measured by qRT-PCR, which were associated or not with $A. parvulum$ and kept under SPF conditions (n=7 to 8 per group), total RNA was extracted from colonic intestinal tissues 6 weeks post-association and A Mann-Whitney U test was performed to assess statistical significance, the horizontal lines indicate the mean and error bars the SD, n.s., non-significant.
Figure 11B:
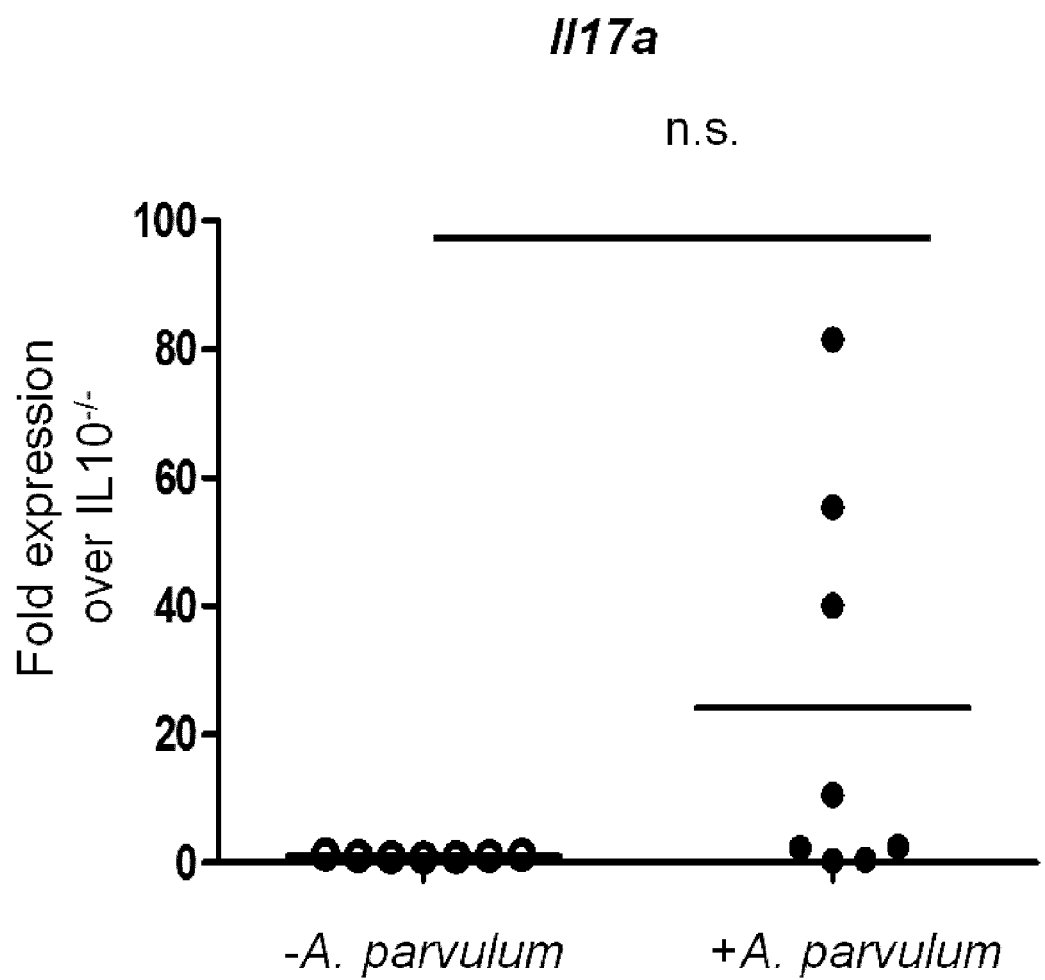
Figure 11C:
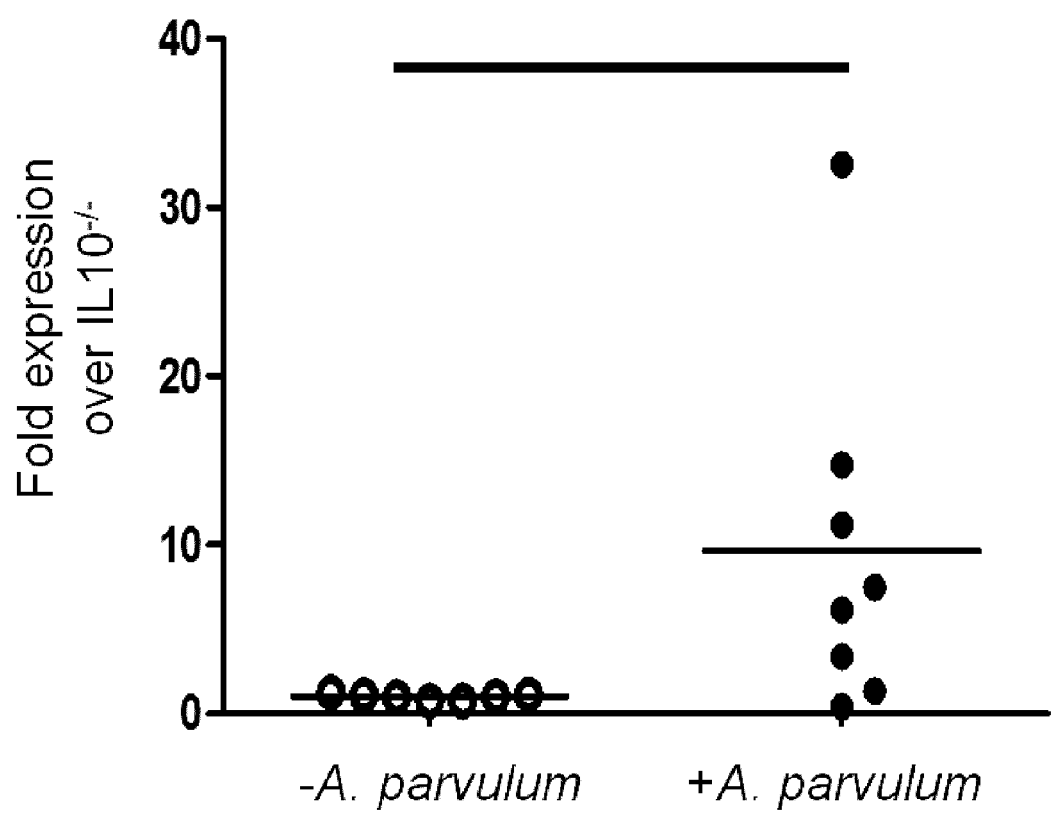
Figure 11D:
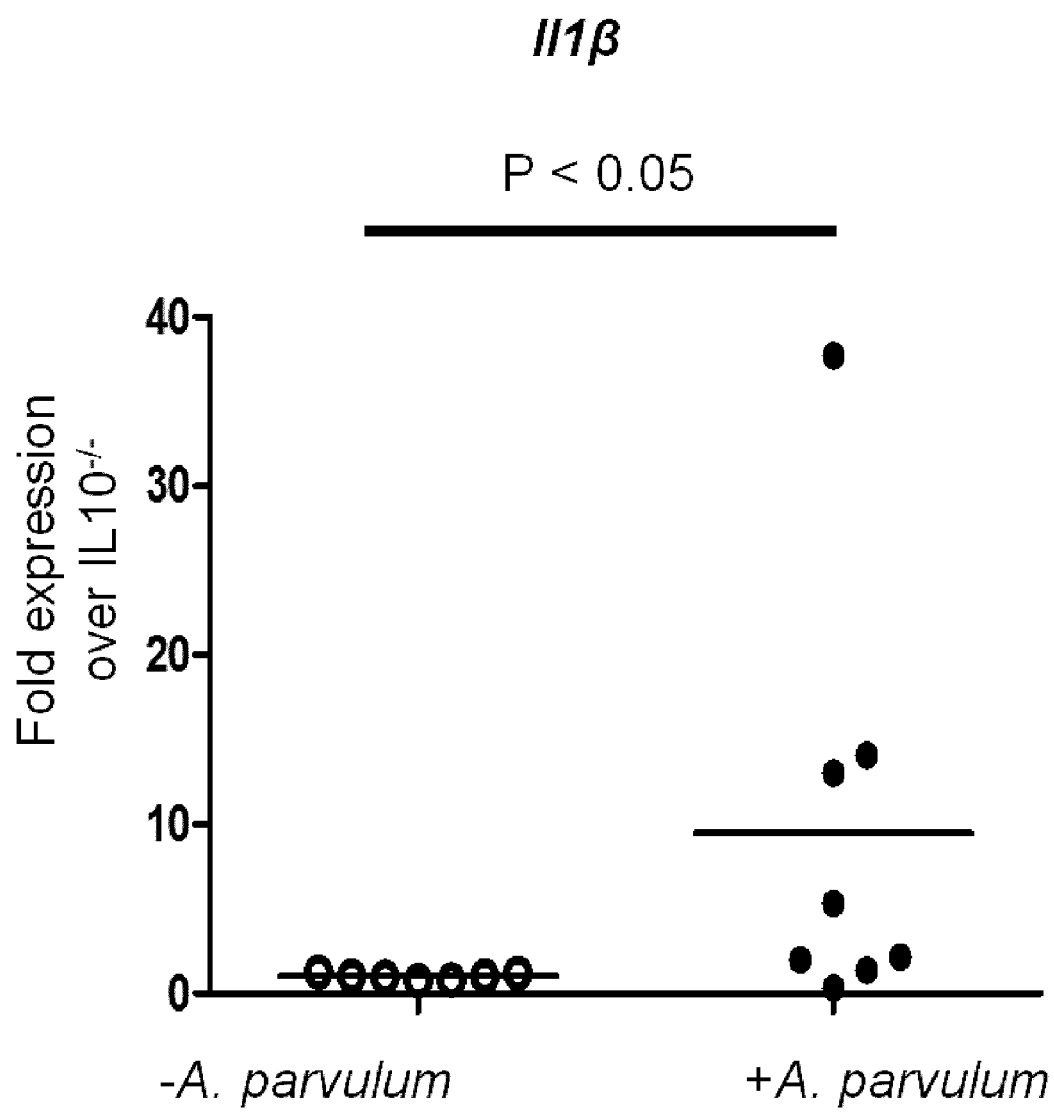

3A and FIGS. 8A, 8B and 8C). Proteins driving disease activity were identified by PLS-DA and the analysis of their variable importance projection (VIP) scores (Tables 4 and 5 and FIGS. 7B and 9A and 9B). Notably, components of the mitochondrial hydrogen sulfide detoxification complex ([9] and FIG. 10) were found to be the main proteins driving the separation based on disease severity (Table 5). These proteins, namely the sulfur dioxygenase (ETHE1), the thiosulfate sulfur transferase (TST), and the components of complexes III and IV of the mitochondrial respiratory chain, were down-regulated in CD patients compared to controls (P<0.05). Secondary validation by qRT-PCR confirmed the repression of the TST transcript (5 fold decrease, P=0.002) in CD and UC patients (FIG. 3C). Moreover, the expression levels of the cytochrome c oxidase subunit IV and the sulfide dehydrogenase genes (SQR), which also contribute to the detoxification of $H_2S$, were significantly down-regulated in CD and/or UC patients, as measured by qRT-PCR (FIG. 3D-E). These findings indicate that transcriptional regulation contributes to the observed change in protein abundance and that the decreased abundance of these $H_2S$-detoxification proteins is a hallmark of CD disease activity and possibly UC. Importantly, these results would explain the previously observed increase of fecal sulfide levels in IBD patients[14].

Figure 4A:
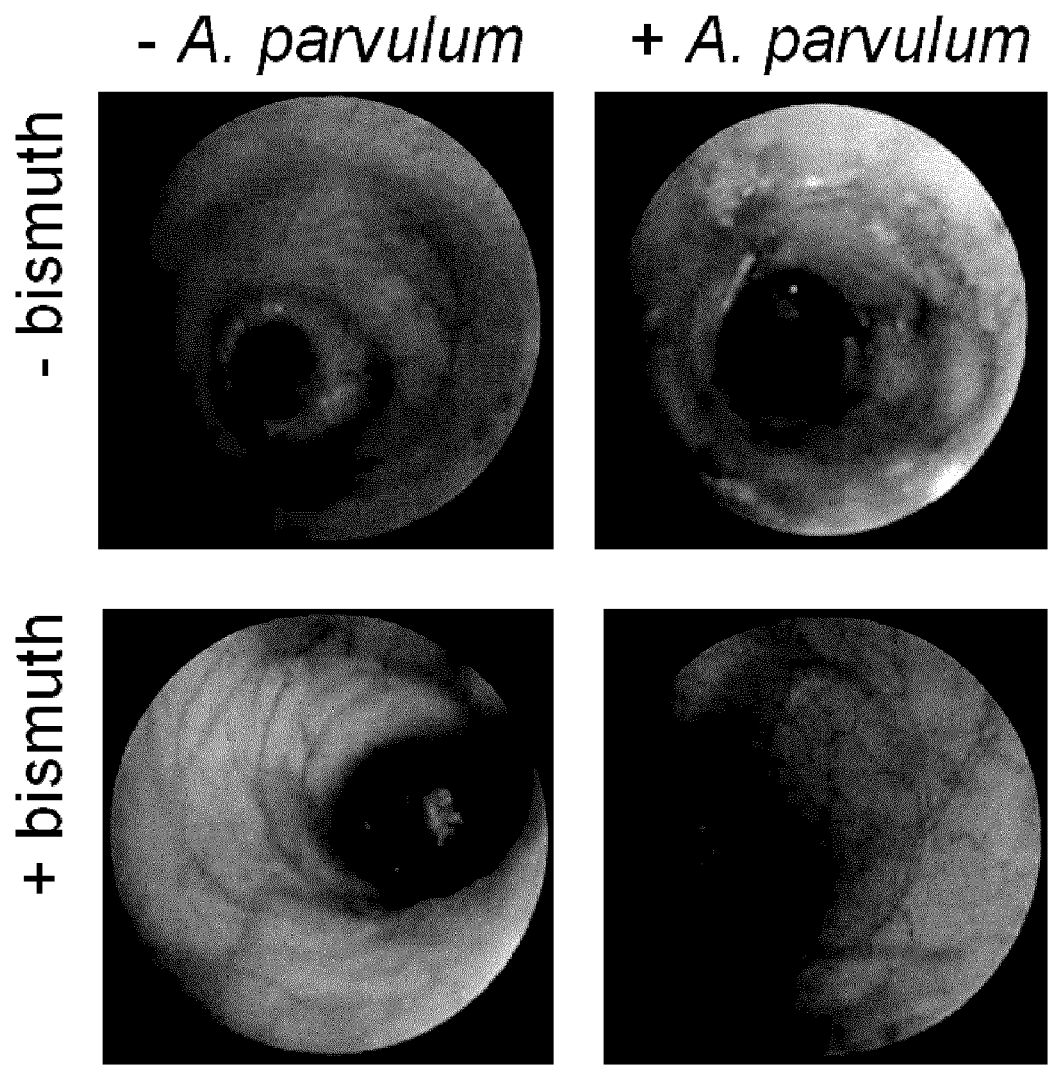
FIG. 4 A are representative murine endoscopies of Il10$^{-/-}$ mice associated or not with *A. parvulum*, treated or not with bismuth and kept under SPF conditions for 6 weeks.
Figure 4B:
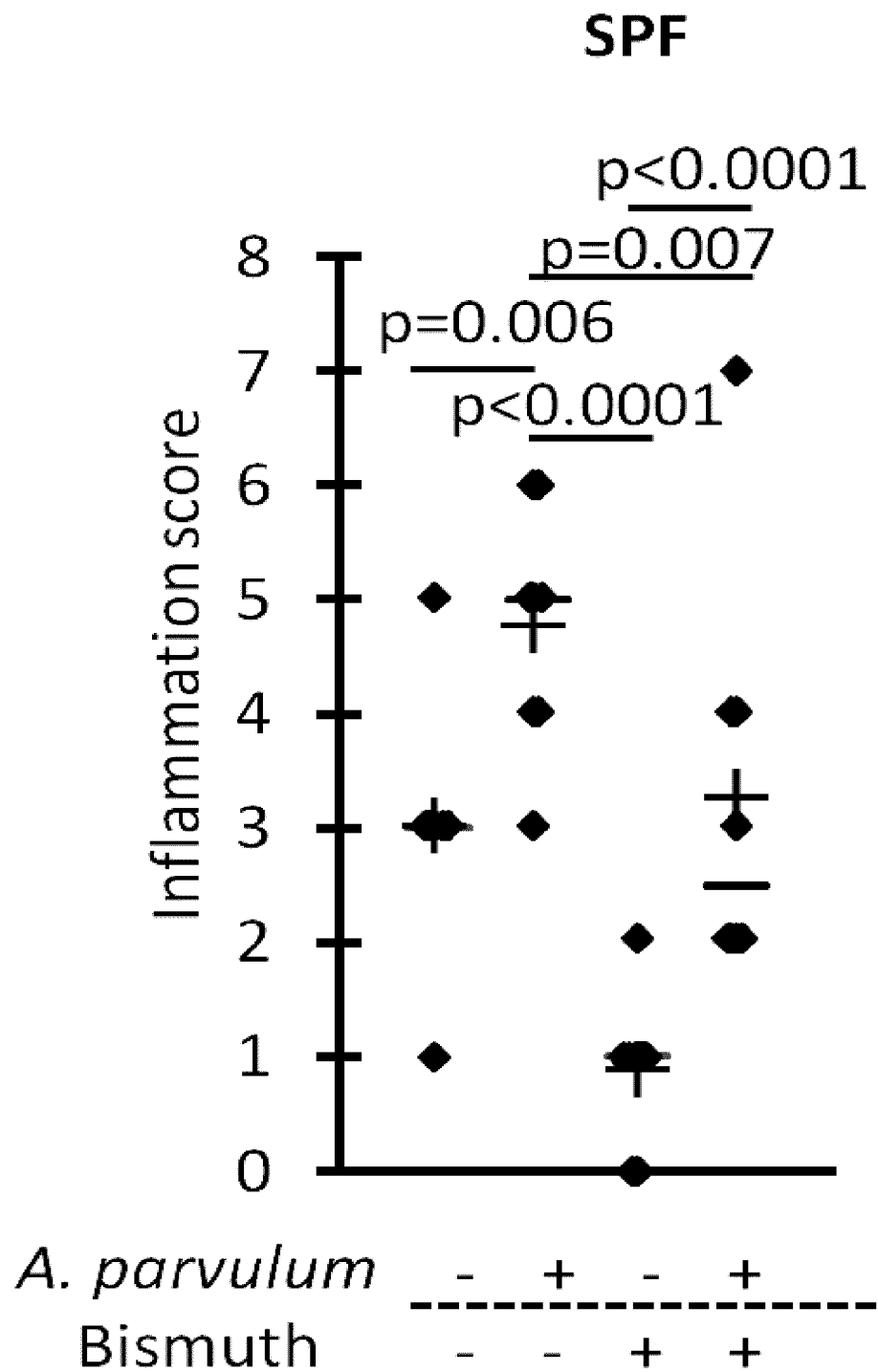
Figure 4C:
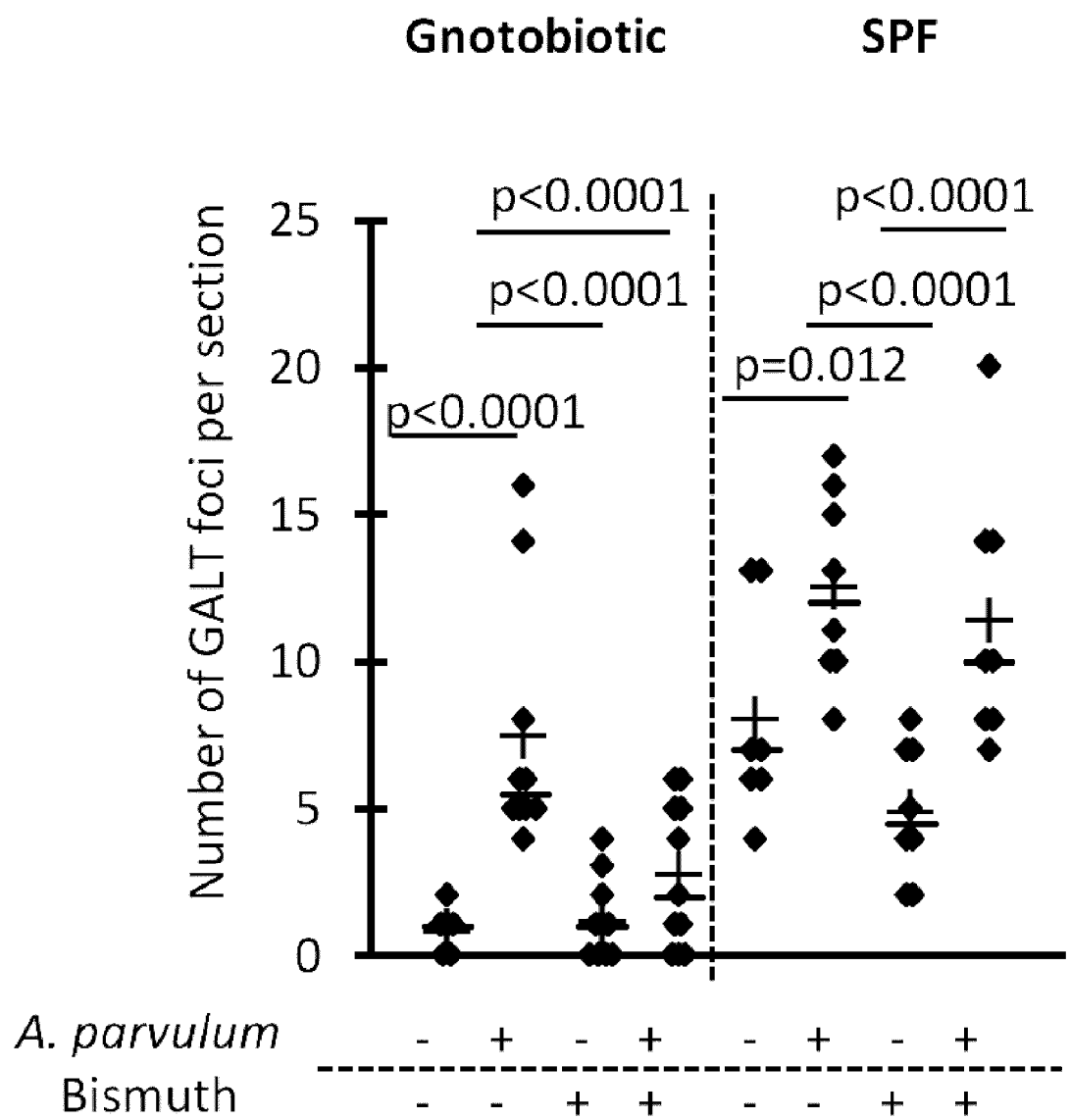
Figure 4E:
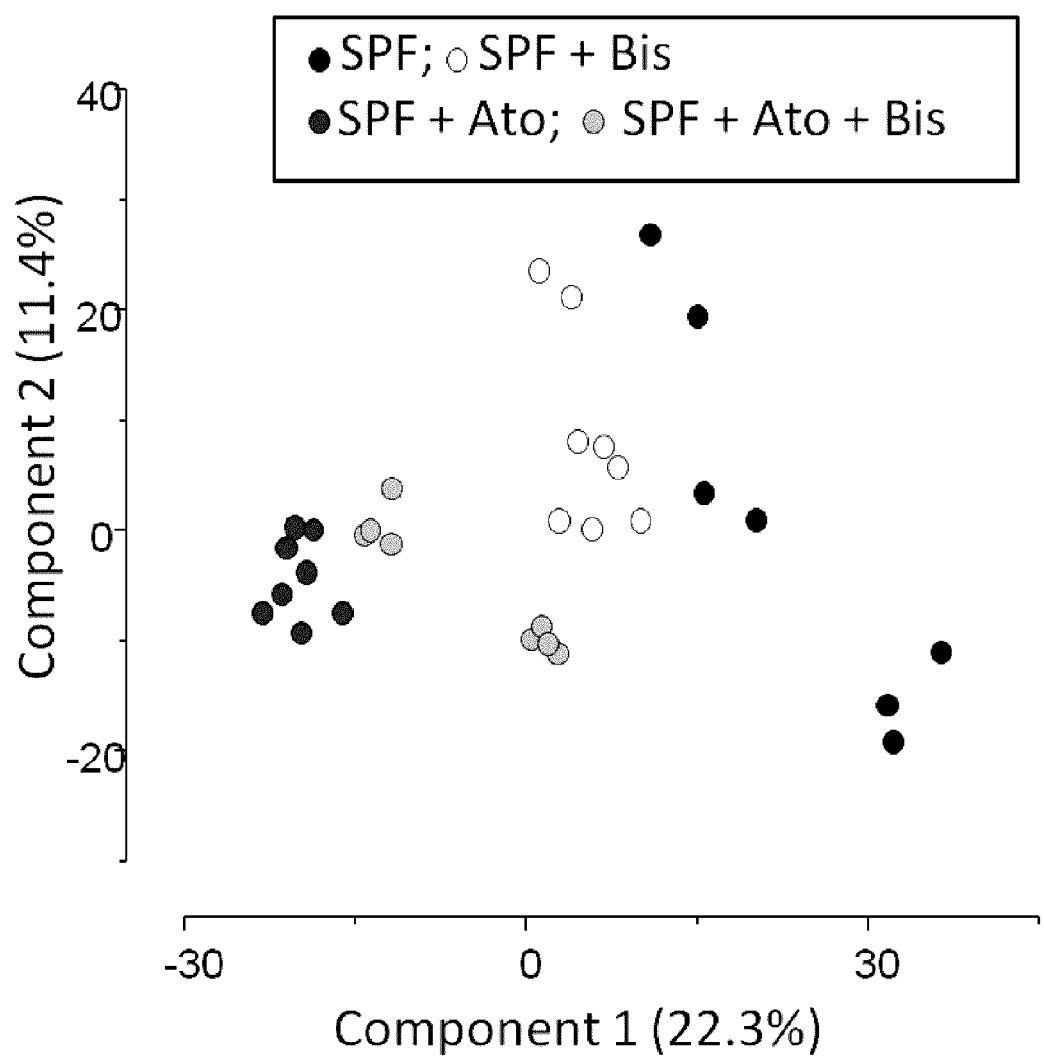
Figure 12A:
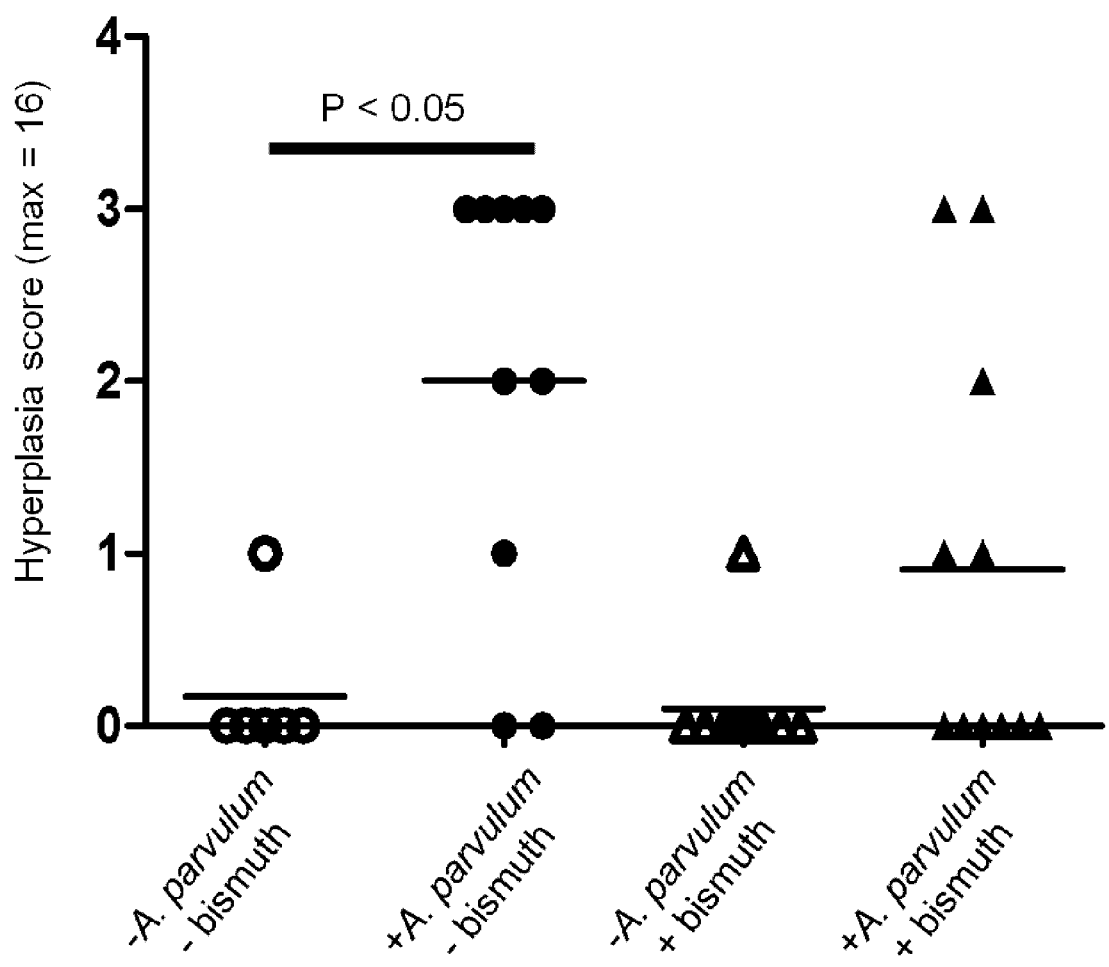
FIG. 12 A is a hyperplasia score of 129/SvEv $Il10^{-/-}$ mice mono-associated or not with $A. parvulum$ and treated or not with bismuth kept under gnotobiotic conditions (n=6 to 11 per group), error bars indicate SD.
Figure 12B:
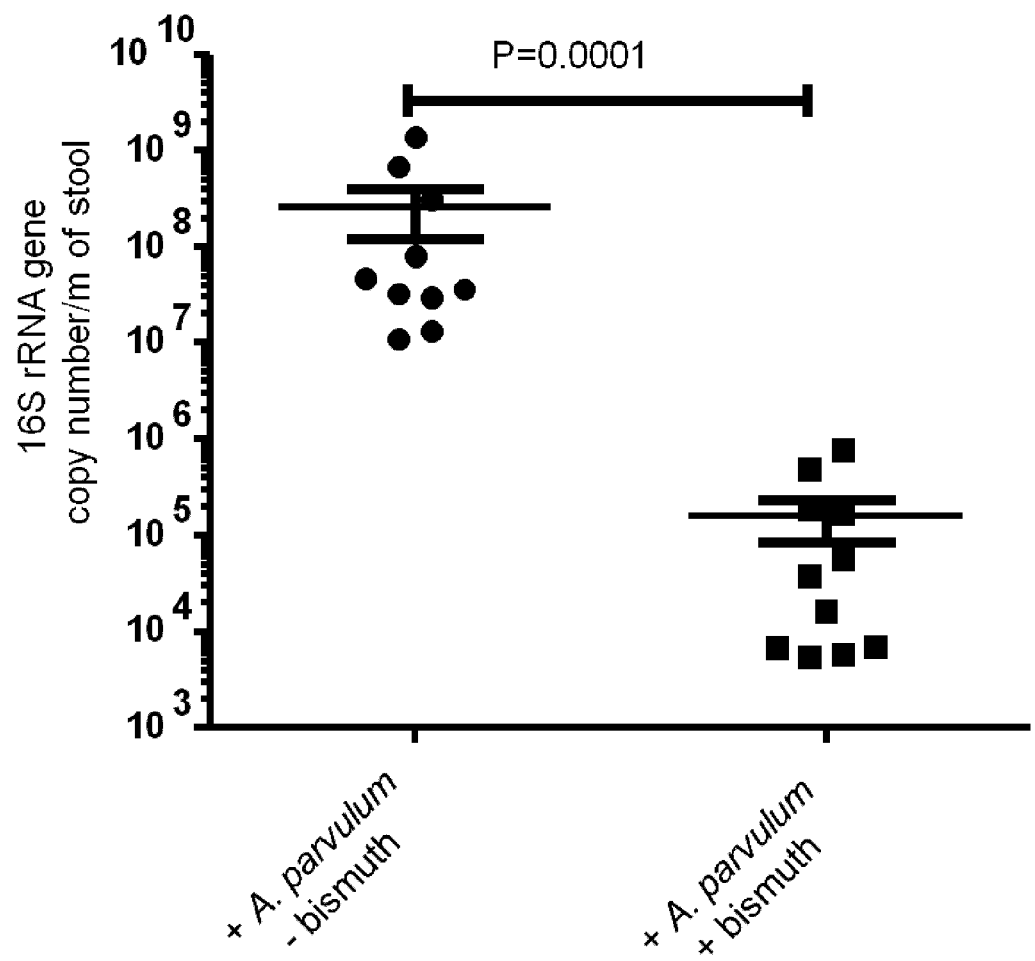

The findings demonstrate an alteration of the balance between bacterial-derived $H_2S$ production and host-mediated detoxification of $H_2S$ at the mucosal-luminal interface. To test the causative role of $H_2S$-producing microbes in colitis, we assessed whether an $H_2S$ scavenger (bismuth) could alleviate Atopobium-induced colitis in $II10^{-/-}$ mice. Consistent with the first cohort, Atopobium-associated SPF mice developed severe colitis (FIG. 4A-B) and exhibited significant increases of pro-inflammatory cytokine expression (FIG. 11A-D). Treatment with bismuth prevented colitis as evidenced by colonoscopy visualization (FIG. 4A) and by decrease inflammatory score (P=0.007; FIG. 4B). Atopobium-associated mice also exhibited an increased number of GALT (gut associated lymphoid tissue) foci as compared to non-associated mice (FIG. 4C; P=0.012). However bismuth treatment did not prevent GALT formation indicating that A. parvulum induces GALT neogenesis in $II10^{-/-}$ mice. It should be noted that the intestines of IBD patients also display a similar increased number of lymphoid follicles[15]. Interestingly, elimination of GALT with LTβR-Ig treatment protects mice from developing colitis suggesting a role for GALT formation in the development of chronic intestinal inflammation[16]. Increased GALT foci in Atopobium-associated mice could lead to an aberrant expression of lymphoid adhesion molecules and unwanted T cell activation towards commensal microbes. To assess the role of these commensal microbes in colitis development, germ-free mice were mono-associated with A. parvulum and kept under gnotobiotic conditions. While these mice showed crypt hyperplasia and increased GALT foci (FIG. 12A and FIG. 4C), they had no signs of ulcerations, goblet cell depletion or immune cell infiltration (FIG. 4D). This result indicates that the gut microbiota is required for the development of Atopobium-induced colitis. While bismuth treatment prevented GALT neogenesis in mice mono-associated with A. parvulum, the observed effect might not necessarily be due to $H_2S$ scavenging but instead due to a potential antimicrobial activity of bismuth on A. parvulum, as evidenced by a reduced colonization level (P=0.0001; FIG. 12B). Because both A. parvulum and the gut microbiota are required for colitis-development and because bismuth exhibits antimicrobial properties[17], we assessed the effect of bismuth on the gut microbiota composition of our SPF and Atopobium-associated mice. PCA analysis of the gut microbiota composition revealed a significant alteration in the microbial profile of the Atopobium-associated mice as compared to the SPF mice (FIG. 4E). Concomitantly to colitis prevention, bismuth administration altered the microbiota composition of these 2 groups of mice (Table 6). Altogether, these results indicate that (1) A. parvulum colonization altered the composition of the gut microbiota (with a significant decrease in abundance of the major butyrate-producers including Eubacterium and Faecalibacterium (P<0.02)) analogously to the microbiota composition of pediatric IBD patients; (2) the aberrant composition of the gut microbiota in Atopobium-associated mice is a major inducer of colitis; and (3) bismuth restores the microbiota of these mice toward a healthier community (with an increase abundance of butyrate-producers).

Collectively the findings shed light on the pathogenic mechanisms of early IBD onset. The emerging picture is that the pediatric IBD microbiota is characterized by a depletion in butyrate producing microbes together with an increased abundance of $H_2S$-generating bacteria, namely A. parvulum, Fusobacterium and Veillonella, which produce $H_2S$ by protein fermentation[18]. Because IBD patients exhibit increased levels of fecal $H_2S$[14], sulfate-reducing bacteria (SRB) have long been proposed to be involved in the etiology of IBD, although studies have failed to demonstrate a link between SRB and IBD[10]. Instead, our study demonstrates a key role for microbes producing $H_2S$ through protein fermentation in CD pathogenesis. Butyrate is known to activate the expression of the genes encoding the host mitochondrial $H_2S$ detoxification components[19] and our proteomic analyses indicate a diminished capacity for $H_2S$ detoxification by IBD patients. Therefore, we postulate that the depletion of butyrate-producing microbes from the gut microbiota would disable the host $H_2S$ defense systems. This "disarmed" host would be highly susceptible to further damage caused by enhanced $H_2S$ production, resulting in metabolic stress and subsequently increased mucosal inflammation. Interestingly, variants in mitochondrial DNA, which result in increased metabolic activities, protect mice from colitis[20]. This is in agreement with the important role of the mitochondria in modulating the mucosal barrier. More recently, excess $H_2S$ has been shown to act as an autocrine T-cell activator, potentially contributing to unwanted T-cell responses against commensal bacteria[21], consistent with our observation that the gut microbiota is required for A. parvulum-induced experimental colitis. Given the essential role of butyrate in regulating regulatory T cells ($T_{reg}$) homeostasis and the critical role of $T_{reg}$ in limiting intestinal inflammation[22], $H_2S$ production may also interfere with this process by impairing butyrate oxidation and thus might lead to increased colitis severity. This result emphasises the importance of the microbial community and its interaction with the host in the pathogenesis of IBD. Altogether, our findings provide new avenues for diagnostics as well as therapies to treat IBD.

Methods

Example 2

Colonic mucosal lavages and/or mucosal biopsies were collected from 157 pediatric subjects (84 Crohn's Disease, 20 Ulcerative Colitis, and 53 controls). All IBD cases were newly diagnosed with IBD and met the standard diagnostic criteria for either CD or UC. Metagenomic DNA from the intestinal lavages was extracted using the FastDNA SPIN Kit. Microbial communities were surveyed by deep sequencing the 16S rRNA V6 hypervariable region using Illumina HiSeq2500 and 454-Pyrosequencing. Reads were quality filtered and QIIME[23] was used to assign reads into operational taxonomic units (OTUs) against the Greengenes reference set. Several statistical approaches (Kruskal-Wallis tests, LEFSe, PCA, PLS-DA) were used to determine differentially abundant OTUs. The correlation between *A. parvulum* relative abundance and CD severity was confirmed by qPCR. Proteomic analysis of mucosal biopsies was conducted using super-SILAC-based HPLC-ESI-MS/MS. The generated raw data was processed and analyzed by MaxQuant against the decoy Uniport-human database with the protein-group file imported into Persus for statistical analysis. Pathway analysis was done using the DAVID Bioinformatics Resources. The transcript levels of TST, SQRDL and COX4-1 were quantified by RT-qPCR. Gnotobiotic and specific pathogen free Il10$^{-/-}$ mice were gavaged once weekly with *A. parvulum* ($10^8$ cfu) for 6 weeks. Bismuth (III) subsalicylate (7 g/kg) was added to the diet of the assigned groups one week before the gavage. Tissue samples from the colon were collected for RNA and histology as described previously[24] Mouse colonoscopies were performed and histological inflammation was blindly scored as previously described[25]. Mice mucosal cytokines (Cxcl1, Il12p40, Il1β and Il17a) were quantified by RT-qPCR.

Example 3

Patient Cohort and Study Design:

This study involved the enrollment, detailed assessment, and biological sampling of 157 pediatric subjects (84 CD, 20 UC, and 53 controls; Table 7). All patients under 18 years of age scheduled to undergo their first diagnostic colonoscopy at the Children's Hospital of Eastern Ontario (CHEO) were potentially eligible for recruitment to this study, with the following exclusions which are known to affect the gut microbiota composition: (1) body mass index (BMI) greater than 95$^{th}$ percentile for age; (2) diagnosis with diabetes mellitus; (3) diagnosis with infectious gastroenteritis within the preceding 2 months; and (4) use of any antibiotics or probiotics within the last 4 weeks. All cases were newly diagnosed with IBD (inception cohort prior to the initiation of treatment) and met the standard diagnostic criteria for either Ulcerative Colitis or Crohn's Disease following thorough clinical, microbiologic, endoscopic, histologic and radiologic evaluation[26]; most had active inflammatory luminal disease involving the terminal ileum and/or the colon+/− perianal disease. Phenotyping of disease was based on endoscopy and clinical disease activity scores. The Simplified-Endoscopy Score-Crohn's disease was used to record macroscopic activity in each segment of the intestinal tract in Crohn's disease[27], the site of involvement in CD was recorded utilizing the Paris IBD Classification[28] and clinical disease activity of CD was determined using the Pediatric Crohn's Disease Activity Index (PCDAI)[29]. For UC, the site of disease was recorded using the Paris Classification system[28], endoscopic activity was recorded using the Mayo Score Flexible Proctosigmoidoscopy Assessment in ulcerative colitis and clinical activity of UC was determined using and Pediatric Ulcerative Colitis Activity Index (PUCAI)[30]. The clinical activity scores are both validated for use in Pediatric IBD. All controls had a macroscopically and microscopically normal colon, and did not carry a diagnosis for any known inflammatory intestinal disorder and did not have a well-defined infectious etiology for the bowel inflammation. Data collected on all participants included: demographics (age, gender, BMI, country of birth, age of diagnosis), environmental exposures (cigarette smoke, diet, previous antibiotic exposure), and all clinical features. This study was performed in compliance with the protocol approved by the Research Ethic Board of the Children's Hospital of Eastern Ontario.

Example 4

Biopsies and Mucosa-Luminal Sample Collection:

Mucosal-luminal interface samples were collected from the right colon at the time of endoscopy. Colonoscopy preparation was done the day before the procedure as per standard protocol[31]. During endoscopy, once the correct position is reached, loose fluid and debris was aspirated. Thereafter sterile water was flushed onto the mucosa and the collection of water, mucus and intestinal cells of the colonic mucosa was aspirated into sterile container through the colonoscope. These samples were immediately place on ice in the endoscopy suite, promptly transferred to the lab to minimize delay for processing and then storing at −80° C. Up to 2 biopsies were collected from macroscopically involved area of the right colon. Biopsies were flash frozen on dry-ice in the endoscopy suite and immediately stored at −80° C. until further processing.

Example 5

Microbiota DNA Extraction and Sequencing of 16S rDNA Amplicons:

Metagenomic DNA was extracted from the mucosa-luminal samples using the Fast DNA SPIN Kit (MP Biomedicals) and the FastPrep machine (MP Biomedicals) with two mechanical lysis cycles at speed 6.0 for 40 seconds. Extracted DNA was then used for the construction of the sequencing libraries.

Two sequencing-by-synthesis platforms were used in this study: (1) pyrosequencing (Roche 454 GS-FLX) and (2) Illumina Hiseq 2500. Samples for both sequencing techniques were PCR amplified to target the same V6 hypervariable region. Samples for sequencing by Roche 454 were independently sequenced using the FLX chemistry on 12 lanes of a 16-lane sub-divided 454 FLX PicoTiter plate (70×75 mm) and using a total of 3 plates. The 454 amplicons libraries were constructed using the conserved V6 primers pair 16S-V6_907-F (5'-AAACTCAAAKGAATTGACGG-3') (SEQ ID NO. 16) and 16S-V6_1073-R (5'-ACGAGCT-GACGACARCCATG-3')[32] (SEQ ID NO. 17). The hypervariable V6 region of 16S rDNA gene was amplified using two successive PCR reactions to reduce PCR bias as previously described[33]. The first PCR used 16S-V6 specific primers and the 2nd PCR involved 454 fusion-tailed primers. In the first PCR, ten amplicons were generated from each extracted DNA sample. Each PCR reaction contained 2 μL DNA template, 17.5 μL molecular biology grade water, 2.5 μL 10× reaction buffer (200 mM Tris-HCl, 500 mM KCl, pH 8.4), 0.5 μL dNTPs (10 mM), 1 μl 50 mM MgCl$_2$, 1 μL of both forward and reverse primers (10 mM each) and 0.5 μL Invitrogen's Platinum Taq polymerase (5 U/μL) in total volume of 25 μL. The PCR conditions were initiated with heated lid at 95° C. for 5 min, followed by a total of 15 cycles of 94° C. for 40 sec, 48° C. for 1 min, and 72° C. for 30 sec, and a final extension at 72° C. for 5 min, and hold at 4° C. Amplicons generated from each sample were pooled and purified to remove the excess unused primers using Qiagen's MiniElute PCR purification columns and eluted in 30 μL molecular biology grade water. The purified amplicons from the first PCR were used as templates in a second PCR with the same amplification conditions used in the first PCR with the exception of using 454 fusion-tailed primers in a 30-cycle amplification regime. An Eppendorf Mastercycler ep gradient S thermalcycler was used in all PCRs. A negative control reaction (no DNA template) was included in all experiments. PCR success was checked by agarose gel electrophoresis. The 16S-V6 amplicon of each sample was quantified by fluorometer and purified with AMPure magnetic beads. The amplicon libraries were sequenced on a 454 Genome Sequencer FLX System (Roche Diagnostics GmbH) following the amplicon sequencing protocol. Amplicons of each sample was bi-directionally sequenced in 1/16th of full sequencing run (70×75 picotiter plate).

For samples to be sequenced by Illumina Hiseq 2500, the V6 hypervariable region of the 16S rDNA gene was amplified using two successive PCR reactions as described previously[34]. The universal 16S rDNA-V6 primers for the first PCR step were modified from Sundquist et al[32] to include the Illumina paired-end sequencing adapters, and a 4-6 nucleotide barcode sequence (Supplementary Table 10). Each PCR reaction was performed in a total volume of 50 µL using 50 ng of the extracted DNA, 1× Phusion HF PCR buffer, 0.5 µM of each primer, 0.2 mM dNTPs, and 1 U Phusion High-Fidelity DNA polymerase (Thermo Scientific). The PCR conditions included initial denaturation at 94° C. for 30 s, 10 cycles of 94° C. for 10 s, 61° C. for 10 s with a 1° C. drop each cycle and 72° C. for 15 s followed by an additional 15 cycles using an annealing temperature of 51° C. for 45 s, and a final extension at 72° C. for 2 min. The second PCR was carried out using 10 µL of the first PCR products in a final volume of 50 µL using the primers PCRFWD1/PCRRVS1 (Supplementary Table 10). The second PCR conditions were 30 s at 94° C., 15 cycles of 10 s at 94° C., 10 s at 65° C., and 15 s at 72° C. followed by a final extension step at 72° C. for 2 min. The amplicons of each sample were visualized on a 1.5% agarose gel and purified using the Montage $PCR_{96}$ Cleanup Kit (Millipore). Next, the DNA concentration in each reaction was quantified using the Qubit® dsDNA BR Assay Kit (Invitrogen) following the manufacturer instructions and 100 ng of amplicons from each sample were pooled. Finally, the library consisting of the pooled amplicons was gel purified using the QIAquick Gel Extraction Kit (Qiagen), quantified and subjected to Illumina HiSeq 2500 sequencing at The Center for Applied Genomics (TCAG, Toronto) generating paired-end reads of 2×100 bases.

Example 6

Microbiota Analysis:
454 Pyrosequencing Data Analysis:
A total of 346,160 reads were generated from 454 pyrosequencing of 16S rDNA-V6 region from 26 right colon samples. The generated reads were submitted to NCBI Sequence Read Archive under accession number SRP034632. The raw sequences were processed to remove low quality and short reads using Quantitative Insights Into Microbial Ecology pipeline release 1.4.0 (QIIME 1.4.0)[23] according to the following parameters: (1) Minimum read length of 100 bp, (2) Exact matching to the sequencing primers, (3) No ambiguous nucleotides, and (4) The minimum average quality score of 20. This resulted in a total of 266,006 high quality reads with an average of ~10,224 sequences per sample and a mean length of 169.58 bases including the primers. Next, sequences were clustered into operational taxonomic units (OTUs) using UCLUST based on average percentage of identity of 97%. The most abundant read from each OTU was picked as a representative sequence for that cluster, while singletons were discarded. PyNAST was used to align the representative sequences with a minimum alignment length of 100 and a minimum percentage identity of 75%, followed by identification of chimeric OTUs with the Blast Fragments Algorithm implemented in QIIME. Only 6 representative sequences were identified as chimeras and therefore were removed from the aligned representative set. Taxonomy assignments were made with BLAST by searching the representative sequences against the Greengenes database (release 4 Feb. 2011) with an e value of 1e-8 and a confidence score of ≥0.5. The resulting OTU table was used to determine the alpha and beta diversity within and between the samples using the default criteria of QIIME. Taxa significantly associated with disease status (CD, UC and control) or disease severity (mild, moderate and severe) were identified using the linear discriminant effect size (LEFSe) algorithm (http://huttenhower.org/galaxy/)[11]. To assign taxonomy at the species level, representative reads from OTUs of interest were retrieved from QIIME and aligned against the NCBI and RDB databases[35,36].

Illumina Sequencing Data Analysis:
Paired-end sequences obtained by Illumina HiSeq 2500 (2×101 nucleotides) were merged into longer reads (with an average length per sequence of 165 nucleotides) using Fast Length Adjustment of Short reads (FLASh) software avoiding any mismatch in the overlap region that ranges from 20 to 80 nucleotides[37]. More than 95% of the reads was merged successfully, while the sequences that failed to merge were discarded. The merged reads were then quality filtered with a minimum quality score of 20 using the fastq_quality_filter command from the Fastx toolkit (http://hannonlab.cshl.edu/). High quality reads were sorted according to the forward and the reverse barcode sequences with barcodes trimming using the NovoBarCode software (Novocraft-.com). Sequences with mismatched primers were excluded. The sorted reads were submitted to NCBI Sequence Read Archive under accession number SRP034595. Next, the reads were fed to QIIME 1.5.0[23] pipeline and clustered into OTUs using a closed-reference OTU picking workflow with UCLUST against the Greengenes reference set (release 4 Feb. 2011) based on average percentage of identity of 97%. The OTUs were assigned the taxonomy associated with the corresponding Greengenes reference sequence. Singletons and doubletons were removed and a table of OTU counts per sample was generated. Next, the OTU table was randomly subsampled to a total number of reads per sample of 500,000. The resulting rarefied OTU table was used to analyze the microbiota structure and diversity using the microbial ecology tools available in the QIIME package and for all other downstream analyses. For the identification of the core microbiota, OTUs detected in at least 75% of the samples within a clinical group (CD patients, UC patients or control subjects) were considered as members of the core microbiota for that particular group.

Multivariate Statistical Analysis:
Several statistical approaches were employed to identify taxa significantly associated with disease status and severity. A Kruskal-Wallis test with post hoc Dunn's test was performed to compare the relative abundance of taxa as a function of disease status (CD vs. UC vs. control) and disease severity (mild vs. moderate vs severe). A Bonferroni correction was employed to account for multiple hypotheses with a $P<0.05$ considered significant. The relative abundances of the taxa identified were also analyzed by principal component analysis (PCA) and partial least square discriminant analysis (PLS-DA). For PLS-DA calculation the data were log-transformed and scaled to unit variance as described in Durbin et al.[38]. The PLS-DA models were validated by cross-validation and permutation tests. The variable importance in projection (VIP) value was used to identify features which contribute the most to the clustering (taxa with VIP>1.0 were considered influential and with VIP>1.5 highly influential). All statistical analyses were performed using XLSTAT and/or R software package.

Example 7

*Atopobium parvulum* qPCR Quantification:

The relative abundance of *A. parvulum* was determined by conducting absolute quantitative PCR on the extracted metagenomic DNA using the Applied Biosystems 7300 DNA analyzer and *A. parvulum*-specific 16S rRNA primers developed for the current study; Aparv-711F 5'-GGGGAG-TATTTCTTCCGTGCCG-3' (SEQ ID NO. 1) and Aparv-881R 5'-CTTCACCTAAATGTCAA GCCCTGG-3' (SEQ ID NO. 2). Each sample was tested in duplicate in a total volume of 25 µL per reaction. 100 ng of template DNA was added to a reaction mixture containing 1 µM of each primer, and 1× QuantiFast SYBR Green PCR master mix (Qiagen). The amplification conditions were 5 min at 95° C. followed by 40 cycles of 95° C. for 10 sec and 66° C. for 1 min with data collection at the second step of each cycle. To normalize between samples, the total 16S rRNA in each sample was simultaneously quantified using the universal primers; 331F 5'-TCCTACGGGAGGCAGCAGT-3' (SEQ ID NO. 18) and 797R 5'-GGACTACCAGGGTATCTAATCCTGTT-3'[39] (SEQ ID NO. 19). The positive standards for *A. parvulum* and the total 16S rRNA quantification were prepared by conducting PCR on the DNA extracted from *A. parvulum* ATCC 33793 strain and one mucosal aspirate sample from a healthy subject, respectively. The amplicons were purified using PureLink™ PCR Purification Kit (Invitrogen) and quantified by Qubit® dsDNA BR Assay Kit (Invitrogen). Afterward, $10^6$, $10^7$, $10^8$ and $10^9$ copies from each gene fragment were prepared, assuming the average molecular weight of the base pair is 660, and the $C_t$ values were determined for each concentration by qPCR following the same conditions described above. The standard curves of both *A. parvulum* and the total 16S rRNA gene copy numbers against Ct values were established and the relative abundance of *A. parvulum* in each sample was calculated as *A. parvulum* 16S-rRNA divided by the total 16S-rRNA copy number. To validate the specificity of Apar-711F and Aparv-881R, fresh PCR amplicons from the total DNA extracted from two different mucosal aspirates was cloned using TOPO TA cloning kit (Invitrogen) according to the manufacturer's instructions, and then, the plasmid containing the 16S rRNA gene fragment was extracted from 6 different clones by QIAprep Spin Miniprep kit (Qiagen) using its standard protocol followed by Sanger sequencing using M13F and M13R primers.

Example 8

Stable Isotope Labeling by Amino Acids in Cell Culture (SILAC):

Human hepatic HuH7 cells (HuH-7), human embryonic kidney 293 cells (HEK-293) and human colorectal cancer 116 cells (HCT-116) were individually grown at 37° C. in a 5% $CO_2$ humidified incubator. SILAC medium was prepared as follows: DMEM lacking lysine, arginine and methionine was custom prepared by AthenaES (Baltimore, Md., USA) and supplemented with 30 mg/L methionine (Sigma Aldrich; Oakville, ON, CAN), 10% (v/v) dialyzed FBS (GIBCO-Invitrogen; Burlington, ON, CAN), 1 mM sodium pyruvate (Gibco-Invitrogen), 28 µg/mL gentamicin (Gibco-Invitrogen), and $[^{13}C_6, ^{15}N_2]$-L-lysine, $[^{13}C_6, ^{15}N_4]$-L-arginine (heavy form of amino acids; Heavy Media) from Sigma Aldrich (Oakville, ON, CAN) at final concentrations of 42 mg/L and 146 mg/L for arginine and lysine respectively. For HCT-116, the concentration of arginine was increased to 84 mg/L. Cells were grown for at least 10 doublings in SILAC media to allow for complete incorporation of the isotopically labeled amino acids into the cells.

Example 9

Determination of the Rate of SILAC Amino Acids Incorporation into HuH-7, HEK-293 and HCT-116 Cells:

Cells were grown to 80% confluency in SILAC medium ($5\times10^6$ cells were plated in 10-cm dish). Next, the cells were washed twice with ice-cold phosphate-buffered saline and lyzed by addition of 1 mL of 1×RIPA buffer (50 mM Tris (pH 7.6), 150 mM NaCl, 1% (v/v) NP-40, 0.5% (w/v) deoxycholate, 0.1% (w/v) SDS with protease inhibitor cocktail (Complete Mini Roche; Mississauga, ON,CAN) and phosphatase inhibitor (PhosStop Roche tablet). The lysates were then transferred to 15 mL conical tubes and the proteins were precipitated by addition of 5 mL ice-cold acetone followed by incubation at −20° C. overnight. Proteins were collected by centrifugation (3000×g, 10 min, 4° C.), washed with ice-cold acetone two times, and the protein pellets were resolubilized in 300 µL of a 50 mM $NH_4HCO_3$ solution containing 8 M urea. Protein concentrations were determined by the Bradford dye-binding method using Bio-Rad's Protein Assay Kit (Mississauga, ON, CAN). For the general in-solution digestion, 200 pg of protein lysates were reconstituted in 50 mM $NH_4HCO_3$ (200 µL) and proteins were reduced by mixing with 5 µL of 400 mM DTT at 56° C. for 15 min. The proteins were then subjected to alkylation by mixing with 20 µL of 400 mM iodoacetamide in darkness (15 min at room temperature) followed by addition of 800 µL of 50 mM $NH_4HCO_3$ to reduce the urea concentration to ~0.8 M. Next, the proteins were digested with TPCK-trypsin solution (final ratio of 1:20 (w/w, trypsin: protein) at 37° C. for 18 h. Finally, the digested peptides were desalted using $C_{18}$ Sep-Pack cartridges (Waters), dried down in a speed-vac, and reconstituted in 0.5% formic acid prior to mass spectrometric analysis (as described below) and the determination of labeling efficiency. The incorporation efficiency was calculated according to the following equation: (1−1/Ratio(H/L)); where H and L represents the intensity of heavy and light peptides detected by mass-spectrometry, respectively. Labeling was considered complete when values reached at least 95% for each cell type.

Example 10

Proteomic Analysis of Biopsies Using Super-SILAC-Based Quantitative Mass Spectrometry:

Biopsies were lysed in 4% SDS (sodium dodecyl sulfate), 50 mM Tris-HCl (pH 8.0) supplemented with proteinase inhibitor cocktail (Roche) and homogenized with a Pellet pestle. The lysates were sonicated 3 times with 10 s pulses each with at least 30 s on ice between each pulse. Protein concentrations were determined using the Bio-Rad DC Protein Assay. The proteins were processed using the Filter Aided Sample Preparation Method (FASP) as previously described with some modifications[40]. Colon tissue lysates (45 μg of proteins) and heavy SILAC-labeled cell lysates (15 μg from each HuH-7, HEK-293 and HCT-116 cells) were mixed at a 1:1 weight ratio and transferred into the filter. The samples were centrifuged (16,000×g, 10 min), followed by two washes of 200 μL 8 M urea, 50 mM Tris-HCl pH 8.0. Samples were then reduced by incubation in 200 μL of 8 M urea, 50 mM Tris-HCl (pH 8.0) supplemented with 20 mM dithiothreitol. After centrifugation, samples were subjected to alkylation by adding 200 μL of 8 M urea, 50 mM Tris-HCl pH 8.0, containing 20 mM iodoacetamide (30 min at room temperature protected from light). Samples were washed using 200 μL 8 M urea, 50 mM Tris-HCl pH 8.0 (twice) to remove excess SDS. To further dilute urea, two washes of 200 μL 50 mM Tris-HCl pH 8.0 were performed. For the trypsin digest, samples were incubated in 200 μL of 50 mM Tris-HCl pH 8.0, containing 5 μg of Trypsin (TPCK Treated, Worthington) on a shaker (250 rpm) at 37° C. overnight. Finally, 200 μL of 50 mM Tris-HCl pH 8.0 was added to elute the peptides by centrifugation (twice). Peptides were fractionated, using an in-house constructed SCX column with five pH fractions (pH 4.0, 6.0, 8.0, 10.0, 12.0). The buffer composition was 20 mM boric acid, 20 mM phosphoric acid, and 20 mM acetic acid, with the pH adjusted by using 1 M NaOH). Finally, the fractionated samples were desalted using in-house $C_{18}$ desalting cartridges and dried in a speed-vac prior to LC-MS analysis.

Mass-Spectrometry Analyses:

All resulting peptide mixtures were analyzed by high-performance liquid chromatography/electrospray ionization tandem mass spectrometry (HPLC-ESI-MS/MS). The HPLC-ESI-MS/MS consisted of an automated Ekspert™ nanoLC 400 system (Eksigent, Dublin, Calif., USA) coupled with an LTQ Velos Pro Orbitrap Elite mass spectrometer (ThermoFisher Scientific, San Jose, Calif.) equipped with a nano-electrospray interface operated in positive ion mode. Briefly, each peptide mixture was reconstituted in 20 μL of 0.5% (v/v) formic acid and 12 μL was loaded on a 200 μm×50 mm fritted fused silica pre-column packed in-house with reverse phase Magic $C_{18}$AQ resins (5 μm; 200 Å pore size; Dr. Maisch GmbH, Ammerbuch, Germany). The separation of peptides was performed on an analytical column (75 μm×10 cm) packed with reverse phase beads (3 μm; 120 Å pore size; Dr. Maisch GmbH, Ammerbuch, Germany) using a 120 min gradient of 5-30% acetonitrile (v/v) containing 0.1% formic acid (v/v) (JT Baker, Phillipsburg N.J., USA) at an eluent flow rate of 300 nL/min. The spray voltage was set to 2.2 kV and the temperature of heated capillary was 300° C. The instrument method consisted of one full MS scan from 400 to 2000 m/z followed by data-dependent MS/MS scan of the 20 most intense ions, a dynamic exclusion repeat count of 2, and a repeat duration of 90 s. The full mass was scanned in an Orbitrap analyzer with R=60,000 (defined at m/z 400), and the subsequent MS/MS analyses were performed in LTQ analyzer. To improve the mass accuracy, all the measurements in the Orbitrap mass analyzer were performed with on-the-fly internal recalibration ("Lock Mass"). The charge state rejection function was enabled with charge states "unassigned" and "single" states rejected. All data were recorded with Xcalibur software (ThermoFisher Scientific, San Jose, Calif.).

Database Search and Bioinformatic Analysis:

All raw files were processed and analyzed by MaxQuant, Version 1.2.2.5 against the decoy Uniport-human database (86,749 entries), including commonly observed contaminants. The following parameters were used: cysteine carbamidomethylation was selected as a fixed modification, with methionine oxidation, protein N-terminal acetylation and heavy proline set as variable modifications. Enzyme specificity was set to trypsin. Up to two missing cleavages of trypsin were allowed. SILAC double labeling (light: K0R0; heavy: K8R10) was set as the search parameter in order to assess the conversion efficiency. The precursor ion mass tolerances were 7 ppm and the fragment ion mass tolerance was 0.5 Da for MS/MS spectra. The false discovery rate (FDR) for peptides and proteins was set at 1% and a minimum length of six amino acids was used for peptide identification. The peptides file was imported into Persus (version 1.2.0.17) to extract the lysine- and arginine-containing peptides, respectively.

The protein-group file was imported into Persus (version 1.3.0.4) for data statistical analysis and an ANOVA—test was chosen for the protein profile with p values of less than 0.05 considered significant. Kyoto Encyclopedia of Genes and Genomes (KEGG) pathway analysis was achieved using the DAVID Bioinformatics Resources (http://david.abcc.ncifcrf.gov/). DAVID statistical analyses were performed against the whole genome. Proteomics has a tendency to oversample proteins from the cytosol and nucleus while under-sampling membrane-associated proteins. Therefore, the results from DAVID were retested against the set of proteins that were not changing in our dataset in order to eliminate any pathway/GO enrichment biases.

Example 11

Total RNA Extraction and qRT-PCR Quantification of Mitochondrial Genes Expression:

RNA integrity was preserved by adding the mucosal aspirates to an equal volume of RNAlater (Ambion) before freezing at −80° C. The frozen aliquot (2 mL) was thawed on ice and the total RNA was extracted following a hot phenol protocol as described previously[41]. Briefly, 4 mL of each sample in RNAlater was pelleted by centrifugation at 13,000×g for 5 min at 4° C. The pellets were washed once in 50% RNAlater/PBS buffer and resuspended with lysis in 2 mL of denaturing buffer (4 M guanidium thiocyanate, 25 mM sodium citrate, 0.5% N-laurylsarcosine, 1% N-acetyl cysteine, 0.1 M 2-mercaptoethanol). The lysate was divided into 500 μL aliquots, to which 4 μL of 1M sodium acetate (pH 5.2) was added. Each aliquot was then incubated with 500 μL of buffer saturated phenol (pH 4.3) at 64° C. for 10 minutes, with intermittent mixing. One ml of chloroform was added to the solution and incubated for 15 minutes on ice, followed by centrifugation at 18,000×g for 30 min at 4° C. Afterward, RNA was precipitated from the aqueous layer by adding 1/10 volume 3M sodium acetate, 500 mM DEPC treated EDTA and 2 volumes of cold ethanol followed by overnight incubation at −80° C. The RNA was then pelleted by centrifugation at 4° C., washed with 80% cold ethanol and resuspended in 100 μL of RNAse free $ddH_2O$. The extracted RNA was treated twice with DNase I (Epicentre) followed by PCR amplification using the 16S rRNA universal primers; Bact-8F and 1391-R; to confirm the absence of genomic DNA. The quality and the quantity of the extracted RNA was determined by NanoDrop 2000 spectrophotometer (Thermoscientific) and confirmed by BioRad's Experion StdSens RNA system according to the manufacturer's description and stored at −80° C. until use.

The quantification of the expression level of TST (Thiosulfate Sulfurtransferase), SQRDL (Sulfide Quinone Reductase Like) and COX4-1 (Cytochrome C oxidase subunit IV isoform 1) relative to GAPDH (Glyceraldehyde-3-Phosphate Dehydrogenase) genes was determined using the Applied Biosystems 7300 DNA analyzer and Quantitect SYBR Green RT-PCR kit (Qiagen). The primers used were either designed by NCBI Primer-BLAST tool[42] or extracted from a literature source as detailed in Supplementary Table 11. Each reaction contained 100 ng RNA template, 0.5 µM of each primer, 1× Quantitect SYBR Green RT-PCR master mix and 0.25 µL Quantitect RT-mix in a final volume of 25 µL. The one step RT-PCR conditions were 50° C. for 30 min, 95° C. for 15 min followed by 40 cycles of 15 sec at 94° C., 30 sec at 60° C. and 30 sec at 72° C. with data collection at the third step of each cycle. The amplification specificity was checked by the melting profile of the amplicon and 2% agarose gel electrophoresis. $C_t$ values were then extracted using the Applied Biosystems 7300 sequence detection software versions 1.3.1. $C_t$ values of TST, SQRDL, or COX4-1 were normalized to the $C_t$ values of GAPDH generating $\Delta C_t$. Next, $\Delta\Delta C_t$ was calculated by subtracting the average $\Delta C_t$ of the control group from the $\Delta C_t$ of each sample. The relative quantification were then calculated by $2^{-\Delta\Delta C_t}$, as mentioned previously[34].

Example 12

Il10$^{-/-}$ Mice Experiments and Tissue Processing:

Germ-free SvEv129/C57BL6 Il10$^{-/-}$; NF-κB$^{EGFP}$ mice (8-12 weeks old, n=12) were transferred to specific pathogen free (SPF) conditions and mice from one cohort (n=6) were gavaged once weekly with A. parvulum (1×10$^8$ CFUs) for 6 weeks. Atopobium parvulum ATCC 33793 was grown in fastidious anaerobic broth (FAB) (Lab M, Canada).

To investigate involvement of complex biota and H$_2$S in the development of colitis, we performed two subsequent experiments using 129/SvEv Il-10$^{-/-}$ mice. In the first experimental setting, gnotobiotic Il10$^{-/-}$ mice (n=37) were randomized into 4 groups; 1: GF only (n=6), 2: GF+bismuth (III) subsalicylate (n=10); 3: A. parvulum (1×10$^8$ CFUs) (n=10) and 4: A. parvulum+bismuth (III) subsalicylate (n=11). Mice were euthanized after 6 weeks of mono-association. Bismuth (III) subsalicylate (Sigma-Aldrich, Saint Louis, Mo.) was incorporated to the chow (Teklan Global 18% Protein Rodent Diet) at a concentration of 7 g/kg (Harlan Laboratories, Madison, Wis.) and then irradiated for gnotobiotic experiments. Mice were fed with this diet starting 1 week before the colonization with A. parvulum. In the second experimental setting, gnotobiotic Il10$^{-/-}$ mice (n=31) were transferred to SPF conditions and randomized into 4 groups; 1: SPF only (n=7), 2: SPF+bismuth (III) subsalicylate (n=8); 3: SPF plus A. parvulum (1×10$^8$ CFUs) (n=8) and 4: A. parvulum+bismuth (III) subsalicylate (n=8). Mice were euthanized after 6 weeks of weekly infection with A. parvulum. Bismuth (III) subsalicylate (Sigma-Aldrich, Saint Louis, Mo.) was incorporated to the chow (Teklan Global 18% Protein Rodent Diet) at a concentration of 7 g/kg (Harlan Laboratories, Madison, Wis.). Mice were fed with this diet starting 1 week before the colonization with A. parvulum.

All animal protocols were approved by the Institutional Animal Care and Use Committee of the University of North Carolina at Chapel Hill. Tissue samples from the colon were collected for RNA and histology as described previously[24]. Histological images were acquired using a DP71 camera and DP Controller 3.1.1.276 (Olympus), and intestinal inflammation was scored as previously described[12]. The tissue was divided into 4 quarters, a score was given to each quarter separately and then added to generate a final inflammation score on a scale of 0-16.

Example 13

Mouse Endoscopy:

Colonoscopy was performed using a "Coloview System" (Karl Storz Veterinary Endoscopy) as described previously[25]. Mice were anesthetized using 1.5% to 2% isoflurane and ~4 cm of the colon from the anal verge from the splenic flexure was visualized. The procedures were digitally recorded on an AIDA Compaq PC.

Example 14

Real Time RT-PCR on Mouse Intestinal Samples:

Total RNA from intestinal tissues was extracted using TRIzol (Invitrogen) following the manufacturers protocol. cDNA was reverse-transcribed using M-MLV (Invitrogen) and mRNA expression levels were measured using SYBR Green PCR Master mix (Applied Biosystems) on an ABI 7900HT Fast Real-Time PCR System and normalized to β-actin. The primers used were as follows: β-actin (5'-TGGAATCCTGTGGCATCCATGAAAC-3' (SEQ ID NO. 20) and 5'-TAAAACGCAGCTCAGTAACAGTCCG-3' (SEQ ID NO. 21)), cxcl1 (5'-GCTGGGATTCACCT-CAAGAA-3' (SEQ ID NO. 22) and 5'-TCTCCGTTACT-TGGGGACAC-3' (SEQ ID NO. 23)), tnf (5'-ATGAG-CACAGAAAGCATGATC-3' (SEQ ID NO. 24) and 5'-TACAGGCTTGTCACTCGAATT-3' (SEQ ID NO. 25)), il12p40 (5'-GGAAGCACGGCAGCAGCAGAATA-3' (SEQ ID NO. 26) and 5'-AACTTGAGGGAGAAGTAG-GAATGG-3' (SEQ ID NO. 27)), il1β (5'-GCCCATCCTCT-GTGACTCAT-3' (SEQ ID NO. 28) and 5'-AGGCCACAG-GTATTTTGTCG-3' (SEQ ID NO. 29)), il-17a (5'-TCCAGAAGGCCCTCAGACTA-3' (SEQ ID NO. 30) and 5'-ACACCCACCAGCATCTTCTC-3' (SEQ ID NO. 31)). The PCR reactions were performed for 40 cycles according to the manufacturer's recommendation, and RNA fold changes were calculated using the $\Delta\Delta C_t$ method.

Statistical Analyses Of Il10$^{-/-}$ Mice Results:

Unless specifically noted, statistical analyses were performed using GraphPad Prism version 5.0a (GraphPad, La Jolla, Calif.). Comparisons of mouse studies were made with a nonparametric analysis of variance, and then a Mann-Whitney U test. All graphs depict mean±SEM. Experiments were considered statistically significant if p<0.05.

Example 15

Sample Collection.

Mucosal aspirates (washings) were collected from the right colon of 40 control children, 41 crohn's disease (CD) and 20 ulcerative colitis (UC) patients aged 3-18 years old at initial diagnosis, at Children's Hospital of Eastern Ontario (CHEO), Ottawa, Canada, using a standardized protocol.[28] The right colon was selected in particular because it is thought to be the most active site for butyrate synthesis.[29,30] In addition, fresh stool samples were collected from a subset of patients (5 control and 10 CD) at least 24 h prior to the endoscopy procedure (Table S1 for participating patient information). Immediately following collection, samples were transported on ice to the lab where they were either processed for DNA extraction or stored at −80° C. until further use.

Extraction of Metagenomic DNA.

5 ml aliquots of the mucosal washes were spun at 20,000×g for 10 min at 4° C. Then, DNA was extracted from the sediments (or stool samples) using the FastDNA® Spin Kit (MP Biomedicals) utilizing two mechanical lysis cycles in a FastPrep® Instrument (MP Biomedicals) set at speed of 6.0 for 40 seconds. Extracted DNA was then stored at −20° C. until further use.

Characterize the Diversity of Butyrate-Producing Bacteria in Healthy and IBD Children Relative Quantification of BCoAT Gene from Mucosal-Washes Metagenomic DNA Using qPCR.

The overall abundance of butyrate-producing bacteria was determined by quantifying the amount of BCoAT gene utilizing the primers BCoATscrF/BCoATscrR as described elsewhere.[27] 50 ng of metagenomic DNA from each sample was used in a 25 µl qPCR reaction containing 1× QuantiTect SYBR Green PCR Master Mix (QIAGEN) and 0.5 µM of BCoATscrF/BCoATscrR primers. The amplification conditions were as follows: 1 cycle of 95° C. for 15 min; 40 cycles of 94° C. for 15 sec, 53° C., and 72° C. each for 30 sec with data acquisition at 72° C. For the melting curve analysis, a stepwise temperature increase from 55° C. to 95° C. was performed. Quantification standards were prepared by purifying and quantifying the BCoAT gene fragment from healthy subjects using PureLink™ PCR Purification Kit (Invitrogen) and Qubit® dsDNA BR Assay Kit (Invitrogen), respectively. Then, $10^6$, $10^7$, and $10^8$ gene copies were prepared assuming an average molecular weight of 660 per nucleotide. Simultaneously, the number of 16S rRNA gene copies was quantified in parallel to the BCoAT gene as described previously[31], and results were expressed as copy number of BCoAT genes per 16S rRNA gene.

Preparation of BCoAT Gene and 16S rRNA Libraries from Mucosal-Washes Metagenomic DNA for Deep Sequencing.

BCoAT library construction was carried out using a two-step PCR strategy. In the $1^{st}$ step, 50 ng of metagenomic DNA was used in a 50 µl PCR reaction containing 1.5 mM $MgCl_2$, 0.5 µM of BCoATscrF/BCoATscrR primers, 0.2 mM dNTPs, and 2.5 U HotStarTaq DNA polymerase (QIAGEN). Amplification started with an initial enzyme activation step at 95° C. for 15 min. Then, amplification was carried out using 25 cycles at 94° C., 53° C., and 72° C. (each for 30 sec), and a 10 min final extension at 72° C. For the second PCR, 13 fusion primers were designed (12 forward and one reverse, SEQ ID 3-15) following Roche's Amplicon Fusion Primer Design Guidelines for GS FLX Titanium Series Lib-L Chemistry. Briefly, the forward primers contain (from 5'-3') GS FLX Titanium Primer A, a four-base library key, 12 different Multiplex Identifiers (MIDs), and a BCoATscrF primer sequence. The reverse primer contains (from 5'-3') GS FLX Titanium Primer B, a four-base library key, and a BCoATscrR primer sequence (Table 9). 10 µl of product from the $1^{st}$ PCR was utilized in 50 µl for the second PCR reaction using a unique MID fusion primer for every 12 samples and the same concentration of PCR component as the $1^{st}$ PCR. A total of 15 amplification cycles were performed utilizing the same amplification conditions as the first PCR. For each sample, a total of 5 reaction tubes were prepared. Following amplification, PCR products from the same sample were pooled together, inspected on 1.5% agarose gel, and purified using Montage $PCR_{96}$ Cleanup Kit (Millipore). Finally, an equimolar amount of samples with unique MIDs (a total of 4 libraries) were pooled together and sequenced on a Roche 454 platform using a full plate of GS FLX Titanium chemistry (each library in ¼ plate) at The McGill University and Genome Quebec Innovation Centre, Montreal, QC, Canada. A 16S rRNA library was constructed. The 16S rRNA library was sequenced at The Centre for Applied Genomics (TCAG) at the Hospital for Sick Children in Toronto (Canada) using a HiSeq 2500 platform to generate paired-end reads of 2×100 bases.

TABLE 9

| Primer Name | Primer Sequence |
|---|---|
| $1^{st}$ PCR BCoATs crF | 5'-GCIGAICATTTCACITGGAAYWSITGGCAYATG-3' (SEQ ID NO. 32) |
| BCoATs crR | 5'-CCTGCCTTTGCAATRTCIACRAANGC-3' (SEQ ID NO. 33) |
| $2^{nd}$ PCR BCoAT-F-1 | 5'-CCATCTCATCCCTGCGTGTCTCCGACTCAG<u>ACGAGTGCGT</u>GCIGAICATTTCACITGGAAYWSITGGCAYATG-3' (SEQ ID NO. 3) |
| BCoAT-F-2 | 5'-CCATCTCATCCCTGCGTGTCTCCGACTCAG<u>ACGCTCGACA</u>GCIGAICATTTCACITGGAAYWSITGGCAYATG-3' (SEQ ID NO. 4) |
| BCoAT-F-3 | 5'-CCATCTCATCCCTGCGTGTCTCCGACTCAG<u>AGACGCACTC</u>GCIGAICATTTCACITGGAAYWSITGGCAYATG-3' (SEQ ID NO. 5) |
| BCoAT-F-4 | 5'-CCATCTCATCCCTGCGTGTCTCCGACTCAG<u>AGCACTGTAG</u>GCIGAICATTTCACITGGAAYWSITGGCAYATG-3' (SEQ ID NO. 6) |
| BCoAT-F-5 | 5'-CCATCTCATCCCTGCGTGTCTCCGACTCAG<u>ATCAGACACG</u>GCIGAICATTTCACITGGAAYWSITGGCAYATG-3' (SEQ ID NO. 7) |
| BCoAT-F-6 | 5'-CCATCTCATCCCTGCGTGTCTCCGACTCAG<u>ATATCGCGAG</u>GCIGAICATTTCACITGGAAYWSITGGCAYATG-3' (SEQ ID NO. 8) |

TABLE 9-continued

| Primer Name | Primer Sequence |
|---|---|
| BCoAT-F-7 | 5'-CCATCTCATCCCTGCGTGTCTCCGACTCAG<u>CGTGTCTCTA</u>GCIGAICATTTCACITGGAAYWSITGGCAYATG-3' (SEQ ID NO. 9) |
| BCoAT-F-8 | 5'-CCATCTCATCCCTGCGTGTCTCCGACTCAG<u>CTCGCGTGTC</u>GCIGAICATTTCACITGGAAYWSITGGCAYATG-3' (SEQ ID NO. 10) |
| BCoAT-F-10 | 5'-CCATCTCATCCCTGCGTGTCTCCGACTCAG<u>TCTCTATGCG</u>GCIGAICATTTCACITGGAAYWSITGGCAYATG-3' (SEQ ID NO. 11) |
| BCoAT-F-11 | 5'-CCATCTCATCCCTGCGTGTCTCCGACTCAG<u>TGATACGTCT</u>GCIGAICATTTCACITGGAAYWSITGGCAYATG-3' (SEQ ID NO. 12) |
| BCoAT-F-13 | 5'-CCATCTCATCCCTGCGTGTCTCCGACTCAG<u>CATAGTAGTG</u>GCIGAICATTTCACITGGAAYWSITGGCAYATG-3' (SEQ ID NO. 13) |
| BCoAT-F-14 | 5'-CCATCTCATCCCTGCGTGTCTCCGACTCAG<u>CGAGAGATAC</u>GCIGAICATTTCACITGGAAYWSITGGCAYATG-3' (SEQ ID NO. 14) |
| BCoAT-R | 5'-CCTATCCCTGTGTGCCTTGGCAGTCTCAGCCTGCCTTTGCAATRTCIACRAANGC-3' (SEQ ID NO. 15) |

Data Analysis.

For BCoAT sequencing, demultiplexed reads from each sample were filtered using RDP's Pyrosequencing Pipeline[32] based on a minimum quality score of 20 and 200 nucleotides read length cutoff. Operational Taxonomic Units (OTUs) clustering at 95% sequence similarity was achieved using a de novo UCLUST algorithm integrated in Quantitative Insights Into Microbial Ecology (QIIME) software package V 1.7.0,[33] after which, singleton OTUs were removed. QIIME was also used to compute alpha and beta diversity between samples using a fixed number of reads/sample of 4,600. The longest sequence from each OTU was then selected and used for taxonomy assignment as described previously.[23] Sequences with <75% identity to functional gene reference database were considered unclassified OTUs. Finally, the relative abundance (RA) of assigned species was calculated and differences in butyrate producing bacteria RA were analyzed.

16S rRNA paired-end sequences were merged using Fast Length Adjustment of SHort reads (FLASH) software.[34] During this step, most reads overlapped perfectly by about 10-80 nucleotides, and less than 5% of the reads failed to combine. Uncombined reads were discarded from further analysis. Subsequently, Novobarcode command from Novocraft Technologies was used to demultiplex merged reads according to the 5' and 3' barcode sequences and trim the barcode sequence from the corresponding read. Reads with minimum quality score of 20 were selected for further analysis using fastq_quality_filter command line from the Fastx-toolkit V 0.0.13. Taxonomy assignment to the genus level was done using QIIME V 1.5.0 aligning against Greengenes database (release 4 Feb. 2011) using UCLUST Reference-based OTU picking method at 97% sequence identity. Butyrate producers were selected from the overall micobiota using the list of bacteria that produce butyrate through BCoAT pathway found in reference[23]. Since each bacteria has a different copy number of the 16S rRNA gene and only one copy of the BCoAT gene, the copy number of 16S rRNA was normalized to 1 by dividing the number of reads of a given genus by its average 16S rRNA copy number obtained from rrnDB.[35] The RA of identified butyrate producer genera was then calculated. Finally, correlation between BCoAT and 16S rRNA datasets was analyzed.

For phylogenetic analysis, full nucleotide sequences of BCoAT genes for the assigned butyrate producer species were obtained from the National Center for Biotechnology Information (NCBI's) Reference Sequence Database and MUSCLE aligned with the unclassified OTUs sequences. Then, a phylogenetic tree of aligned sequences was constructed using a maximum-likelihood algorithm with Fast-Tree tool integrated into QIIME. Visual display of the rooted tree was achieved using Interactive Tree Of Life (iTOL) tool.[36] Using the same strategy, another phylogenetic tree was constructed from MUSCLE aligned unclassified OTU sequences and but nucleotide database sequences (a dataset of all predicted BCoAT gene sequences (4,041 sequences) obtained from the Functional Gene Pipeline/Repository.[26]

Confirmation of BCoAT Sequencing Results Using qPCR.

35 control, 37 CD and 19 UC mucosal aspirate samples were used to validate the sequencing result by qPCR. Primers specific to BCoAT gene of E. rectale and F. prausnitzii were used in the qPCR. In addition, primers targeting the 16S rRNA gene of Eubacterium rectale/Clostridium coccoides group (XIVa) (20-21), F. prausnitzii 22-23, and Roseburia 24-25 were used. For stool samples, 5 control and 10 CD subjects were used to determine the relative amount of F. prausnitzii using 16S rRNA specific primers only (table 10). The complete 16S rRNA gene was amplified using the universal primer UniF/UniR (18-19) adapted from reference[37]. Fifty ng of metagenomic DNA was used in a 25 μl PCR reaction using QuantiTect SYBR Green PCR Master Mix (QIAGEN) as described in the previous section using 55° C. instead of 53° C. annealing temperature. The assay was done in duplicate for each sample. Delta-Ct (ΔCt) for each target was calculated by subtracting the Ct of the total 16S rRNA from the target Ct. Then, the ΔCt values were compared between groups.

TABLE 10

| Target | Primer Name | Primer Sequence | Reference |
|---|---|---|---|
| 16S rRNA gene from all bacteria | UniF | 5'-GTGSTGCAYGGYYGTCGTCA-3' (SEQ ID NO. 34) | ISME J 2011; 5: 220-230 |
| | UniR | 5'-ACGTCRTCCMCNCCTTCCTC-3' (SEQ ID NO. 35) | |
| Eubacterium rectale/ Clostridium coccoides group 16S rRNA gene | UniF338 | 5'-ACTCCTACGGGAGGCAGC-3' (SEQ ID NO. 36) | Infect. Immun. 2008 |
| | C.cocR491 | 5'-GCTTCTTAGTCAGGTACCGTCAT-3' (SEQ ID NO. 37) | |
| Faecalibacterium prausnitzii 16S rRNA gene | Fprau 07 | 5'-CCATGAATTGCCTTCAAAACTGTT-3' (SEQ ID NO. 38) | FEMS Microbiol. Ecol. 2012; 79: 685-696 |
| | Fprau 02 | 5'-GAGCCTCAGCGTCAGTTGGT-3' (SEQ ID NO. 39) | |
| Roseburia spp. 16S rRNA gene | Ros-F1 | 5'-GCGGTRCGGCAAGTCTGA-3' (SEQ ID NO. 40) | FEMS Microbiol. Ecol. 2012; 79: 685-6964 |
| | Ros-R1 | 5'-CCTCCGACACTCTAGTMCGAC-3' (SEQ ID NO. 41) | |
| BCoAT gene from all bacteria | BCoATscrF | 5'-GCIGAICATTTCACITGGAAYWSITGGCAYATG-3' (SEQ ID NO. 42) | Appl. Environ. Microbiol. 2007; 73: 2009-2012. |
| | BCoATscrR | 5'-CCTGCCTTTGCAATRTCIACRAANGC-3' (SEQ ID NO. 43) | |
| Eubacterium rectale BCoAT gene | RosEub_F | 5'-TCAAATCMGGIGACTGGGTWGA-3' (SEQ ID NO. 44) | Microbiome 2013, 1:8 |
| | Eub_R | 5'-TCATAACCGCCCATATGCCATGAG-3' (SEQ ID NO. 45) | |
| Faecalibacterium prausnitzii BCoAT gene | Fprsn_F | 5'-GACAAGGGCCGTCAGGTCTA-3' (SEQ ID NO. 46) | Microbiome 2013, 1:8. |
| | Fprsn_R | 5'-GGACAGGCAGATRAAGCTCTTGC-3' (SEQ ID NO. 47) | |

Statistical Analysis.

Unless otherwise specified, result from the qPCR and sequencing was analyzed using two-tailed Mann-Whitney test comparing IBD subtypes to the control group. A P value less than 0.05 was considered significant. Correlation between BCoAT and 16S rRNA sequencing was done by calculating Spearman's rank correlation coefficient (r) of paired RA of bacterial taxa identified by the two approaches.

Butyrate Producers are Reduced in UC Patients with Colonic Inflammation.

Figure 13:
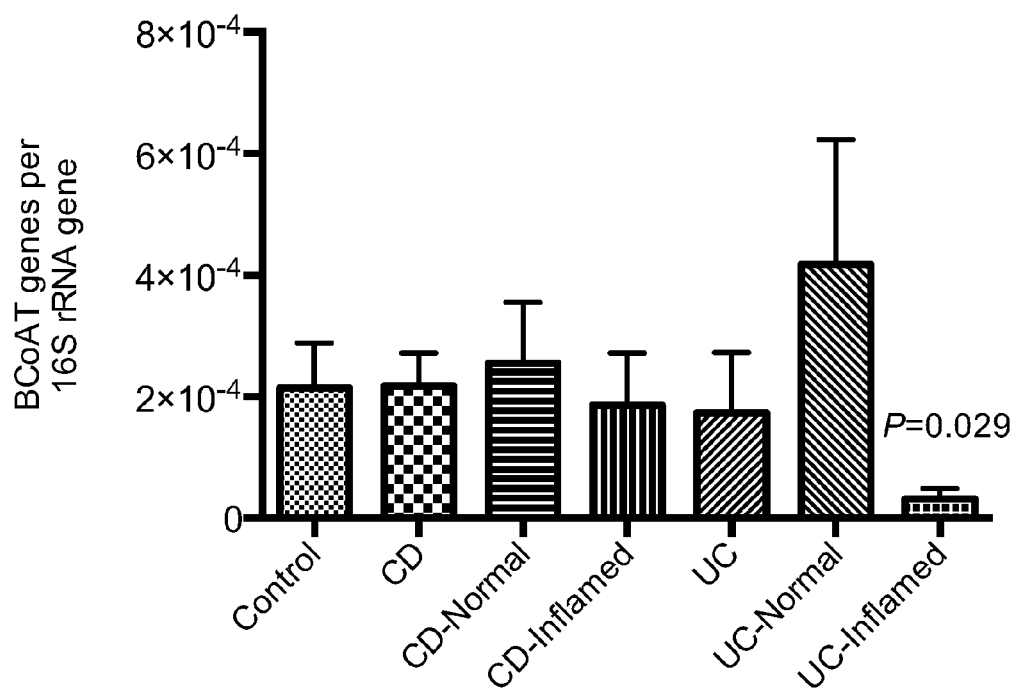
FIG. 13 shows the relative quantification of butyryl-CoA: CoA transferase (BCoAT) gene using qPCR. BCoAT was quantified from control and IBD samples. CD and UC samples were subclassified normal and inflamed based on colon appearance during sample collection. Result is expressed as number of BCoAT genes per 16S rRNA gene. Error bars represent the standard error of the mean.

In order to determine the relative amount of butyrate producers, the copy number of BCoAT genes to 16S rRNA was assayed. The difference in the relative number of BCoAT genes between control subjects ($2.15 \times 10^{-4} \pm 2.46 \times 10^{-4}$) and IBD subgroups (CD, $2.17 \times 10^{-4} \pm 1.97 \times 10^{-4}$; UC, $1.74 \times 10^{-4} \pm 2.78 \times 10^{-4}$) was not statistically significant (P>0.2) (FIG. 13). However, analyzing each IBD group based on macroscopic appearance during colonoscopy, revealed that UC patients with an inflamed colon had a lower number of butyrate producers ($3.13 \times 10^{-5} \pm 3.10 \times 10^{-5}$) compared to control subjects (P=0.029) (FIG. 13).

Diversity of Butyrate Producers is Different in IBD Patients Compared to Healthy Subjects.

Figure 14:
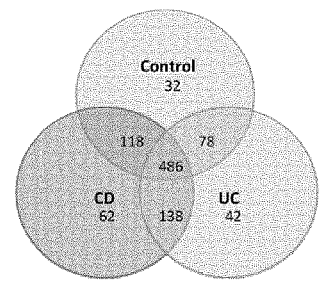
FIG. 14 A shows the diversity of butyrate-producing bacteria. Number of Observed Operational Taxonomic Units (OTUs) from BCoAT sequencing at 95% sequence similarity.
Figure 14:
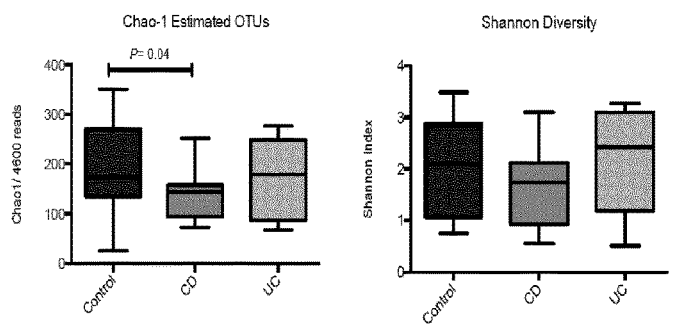
Figure 14:
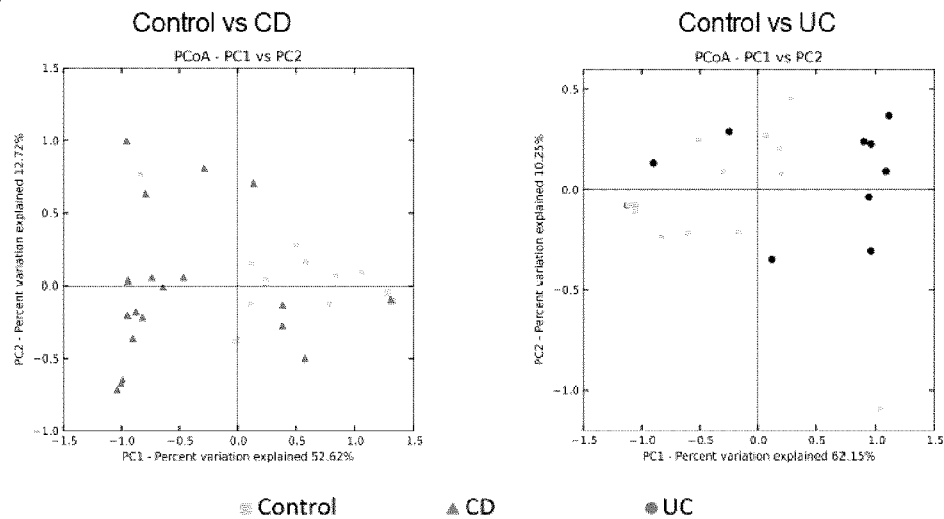

A total of 670,287 high quality reads were generated from 43 samples (13 control, 20 CD, and 10 UC) with an average of 15,570 reads per sample (range, 44,158-2,938) and an average read length of 465 nucleotides (summarized in Table S4). Clustering reads at a 0.05 distance resulted in a total of 965 OTUs from all samples with a total OTU number of 714 for controls, 804 for CD, and 744 for UC. The majority of observed OTUs were shared between the three groups (486 OTUs), and only a few were unique to each individual group (FIG. 14A). Comparing samples alpha diversity, using Chao1 estimated OTUs and the Shannon diversity index with equalized data sets to 4,600 reads, revealed that CD samples had significantly lower Chao1 estimated OTUs compared to controls (P=0.04) (FIG. 14B). In contrast, no difference was observed in the Shannon index (FIG. 14B). This signifies that IBD subjects have a similar evenness to controls, but CD patients show a lower richness.

Furthermore, multidimensional scaling analysis of UniFrac metrics, presented by principal coordinates analysis (PCoA) plot, indicates that the IBD group is different than controls. Although no separation was observed with unweighted UniFrac (data not shown), PCoA showed good separation of CD and UC samples from control with weighted UniFrac. When clustering CD samples with controls, most control and CD subjects were grouped into two distinct clusters with 52.6% of the variance accounted for by coordinate 1 (PCoA1) and an additional 12.7% of variance attributable to PCoA2 (FIG. 14C). Similar separation was observed when comparing UC against control, with 62.1% of variance explained by PCoA1 and 10.2% by PCoA2 (FIG. 14C).

Eubacterium Rectale is Depleted and Faecalibacterium prausnitzii Thrives in IBD Patients.

Figure 15:
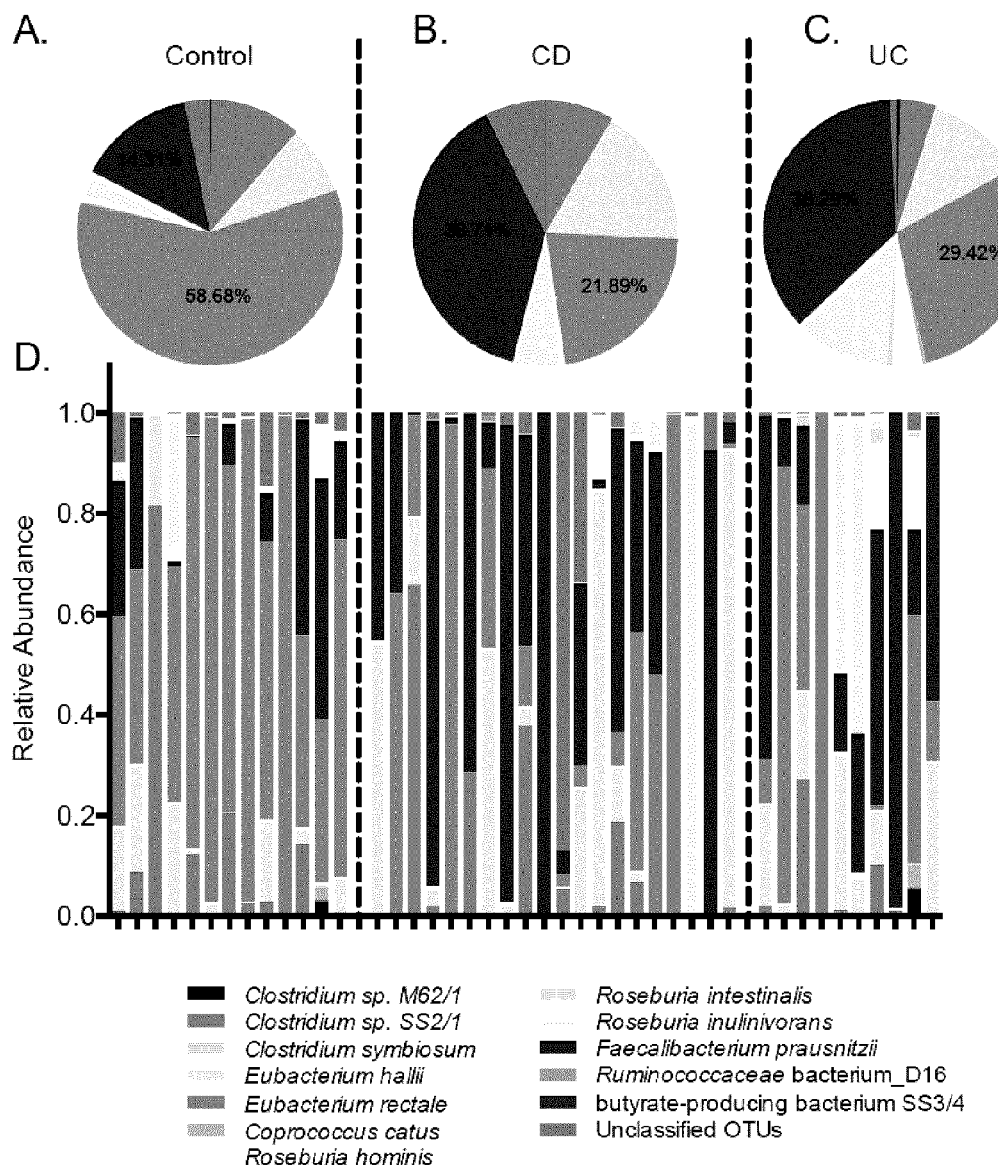
FIG. 15 A-D shows the identified butyrate-producing bacteria at the species level using BCoAT sequencing. (A-C) Pie charts of relative abundance of butyrate producers in each group combined. (A) Control group, (B) CD patients, and (C) UC patients. (D) Relative abundance of butyrate producers in individual samples. Each stacked bar represent one subject.

In order to take a more in depth look at butyrate producer diversity, we looked at the assigned bacterial taxa. Overall, OTUs from all samples were assigned to 12 classified bacterial species that belong to the Firmicutes phylum in addition to 67 unclassified OTUs (FIG. 15). In the control group, the majority of butyrate-producing bacteria belonged to Clostridium cluster XIVa. These included Eubacterium rectale (58.7%±29.7), Eubacterium hallii (8.5%±8.9), Roseburia inulinivorans (2.7%±7.2), Roseburia hominis (1%±2.9), Coprococcus catus (0.18%±0.65), Roseburia

Figure 16:
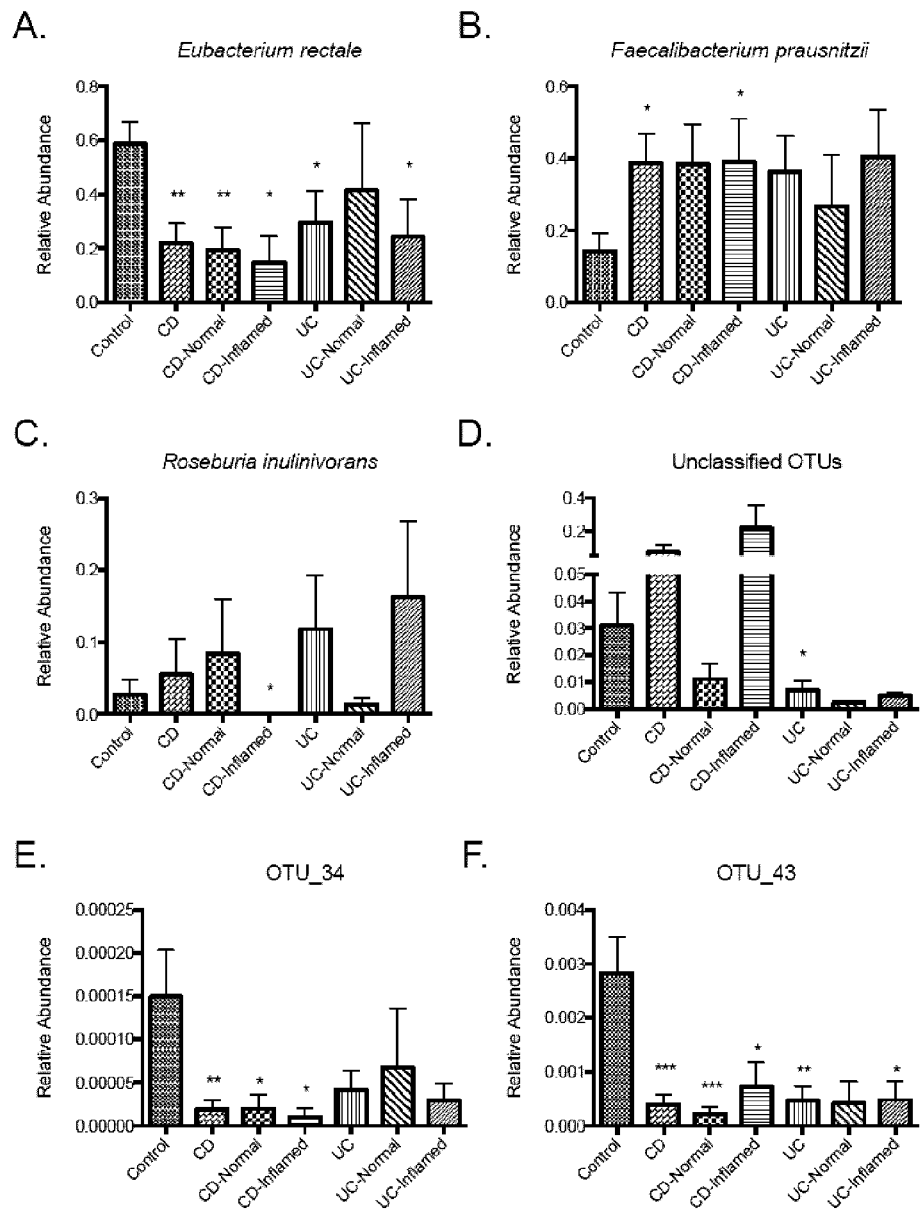
FIG. 16 A-F shows the butyrate-producers species with differential abundance in IBD. (A-F) The relative abundance of $Eubacterium\ rectale$, $Faecalibacterium\ prausnitzii$, $Roseburia\ inulinivorans$, total unclassified OTUs, unclassified OUT_34, and unclassified OUT_43; respectively. Each bar represents the average relative abundance in one group. Error bars represent the standard error of the mean. *, $P<0.05$; , $P<0.01$; *, $P<0.001$.

*intestinalis* (0.06%±0.17), and *Clostridium symbiosum* (8.4× $10^{-5}$%±2.8×$10^{-4}$). *Faecalibacterium prausnitzii*, a member of the *Clostridium* cluster IV, was also found to be a major contributor to healthy butyrate producers' consortium with an abundance of 14.3%±17.4. Other members of the healthy core of butyrate producers are *Clostridium* sp. SS2/1 (11.2%±22.1), butyrate-producing bacterium SS3/4 (0.03%±0.08), *Clostridium* sp. M62/1 (0.019%±0.068), *Ruminococcus bacterium* D16 (2.7×$10^{-6}$%±9.8×$10^{-6}$), and 49 different unclassified OTUs (3.1%±4.4).

a. Comparing the identified bacterial species RA of the control group to IBD patients (both CD or UC) revealed that the control group is characterized by a higher RA of *E. rectale* ($P<0.05$) (FIG. 16A). Subclassifying IBD patients based on endoscopic appearance showed that *E. rectale* was reduced in CD patients with either inflamed or non-inflamed colon ($P<0.02$). Conversely, only UC patients with an inflamed colon had reduced *E. rectale* RA ($P<0.05$) (FIG. 16A). Another butyrate producer with reduced RA in CD is *R. inulinivorans*. *R. inulinivorans* reduction was solely restricted to CD patients with an inflamed colon ($P=0.04$) (FIG. 16C). Unexpectedly, *F. prausnitzii*, which is one of the most abundant butyrate producers in the healthy human gut, was increased in CD, particularly CD patients with an inflamed colon ($P=0.04$) (FIG. 16B). Although *F. prausnitzii* RA was also high in UC patients compared to control, the difference did not reach statistical significance ($P=0.07$). In conclusion, this highlights the presence of a unique signature of butyrate producers that distinguishes IBD from controls. Comparison of bacterial RA was also carried-out for unclassified OTUs. In total, 61 unclassified OTUs were found in CD samples that represent 7.2%±20.2 of all reads and 39 for UC that represent 0.7%±1 of total reads. The overall number of unclassified OTUs was significantly lower in UC ($P<0.05$; FIG. 16D). Unclassified OTU_34, which shares 59% identity with *E. rectale*, was reduced in CD patients with either normal or inflamed colons (CD, $P=0.006$; CD_normal, $P=0.01$; CD_inflamed, $P=0.05$; FIG. 16E). Another unclassified OTU, OTU_43 that share 61% identity with *E. rectale*, was reduced in all IBD subsets ($P<0.01$). OTU_43 was reduced in both CD subtypes as well as UC patients with an inflamed colon (FIG. 16F).

b. In order to test the possibility that the unclassified OTUs could represent novel butyrate producers, the complete sequences of the BCoAT gene for the assigned bacterial species were MUSCLE aligned with the unclassified OTUs sequences. The aligned sequences were then used to construct a phylogeny tree using a maximum-likelihood algorithm. Twenty-five of the 67 unclassified OTUs were clustered with known butyrate producers. Among these, the unclassified OTUs 34 and 43, which were found to be deficient in IBD, clustered with *E. rectale*. Interestingly, 42 of the unclassified OTUs did not cluster with any of the assigned butyrate producers. In a second step, the sequences of unclassified OTUs were MUSCLE aligned with the but nucleotide database downloaded from the Functional Gene Pipeline/Repository. The but database contains all nucleotide sequences of probable BCoAT genes identified by Hidden Markov Model searches of the NCBI bacterial protein database. Subsequently the aligned sequences were subjected to phylogenetic tree construction. This time, only 4 of the 67 unclassified OTUs were clustered with classified bacteria. The remaining OTUs clustered only with partial BCoAT coding sequences isolated from human samples that belong to unclassified uncultured bacterium. Hence, this suggests that the 63 unclassified OTUs might belong to novel butyrate producers.

Figure 17:
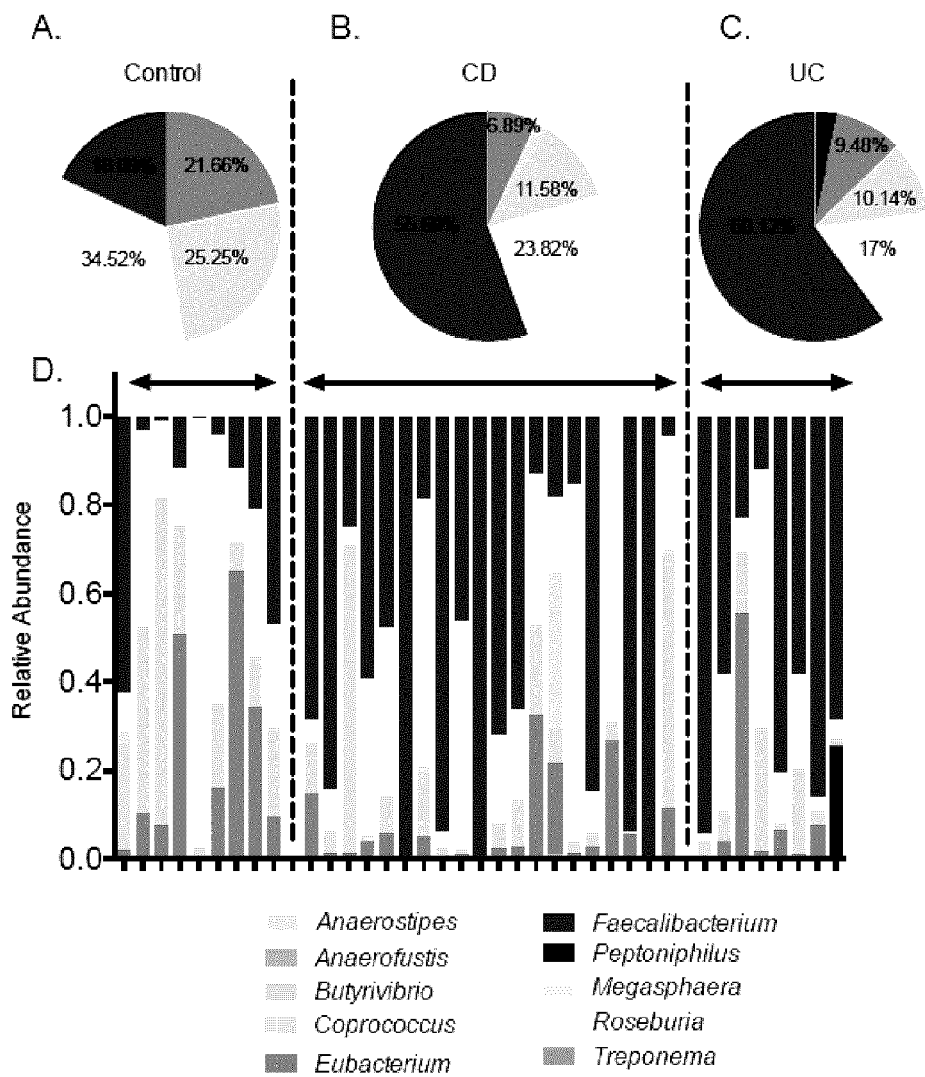
FIG. 17 A-D shows the butyrate producers' genera identified by V6 hypervariable region of 16S rRNA sequencing. (A-C) Pie charts of relative abundance of butyrate producers in each group combined. (A) Control group, (B) CD patients, and (C) UC patients. (D) Relative abundance of butyrate producers in individual samples. Each stacked bar represent one subject.

Diversity of Butyrate-Producing Bacteria Revealed by 16S rRNA Sequencing:

Analyzing the diversity of butyrate producing bacteria at the genus level using 16S rRNA sequencing reveals similar results to BCoAT sequencing with minor differences. In total, 10 genera of butyrate producers were identified with the 16S rRNA approach compared to 6 genera using a functional gene approach. The majority of reads were assigned to 4 genera: *Eubacterium*, *Faecalibacterium*, *Roseburia*, and *Coprococcus* (FIG. 17). In accordance with our functional gene findings, *Eubacterium* was higher in the control (21.66%±22.95) group compared to IBD (CD, 6.89%±9.47; UC, 9.48±18.72). Furthermore, *Faecalibacterium* dominated both CD (55.6%±35.56) and UC (60.12%±29.29) compared to controls (18.09%±22.13). In contrast to BCoAT data, *Roseburia* was the most abundant butyrate-producing bacteria in the control group (34.52%±28.55) and had a higher abundance compared to CD (23.82%±24.76) and UC (16.99%±19.3). This further supports a previous hypothesis that butyrate production is restricted to certain members of the same genus.[26] Similarly, *Coprococcus* abundance was higher in 16S rRNA data compared to the BCoAT approach (FIG. 17). However, it is worth noting that *Coprococcus* can produce butyrate not only via the BCoAT pathway but also via a butyrate kinase pathway.[26] This could explain the reduced abundance of *Coprococcus* in the BCoAT data. The 16S rRNA approach identified 6 low abundant butyrate producers (total abundance of the 6 genera<1%) that were missed by BCoAT sequencing. These include: *Peptoniphilus*, *Anaerofustis*, *Anaerostipes*, *Butyrivibrio*, *Megasphaera*, and *Treponema*. This could be attributed to the higher sequencing depth of the HiSeq2500 Illumina platform used for 16S rRNA that can generate up to 50 times more reads than 454 pyrosequencing, which was used for the BCoAT sequencing. Lack of species level resolution by the 16S rRNA data made it impossible to identify some important butyrate producers that were identified by the functional gene approach. These include: *Clostridium* sp. M62/1, *Clostridium* sp. SS2/1, and *Clostridium symbiosum*. Calculating paired Spearman's rank correlation coefficient (r) for the relative abundance of butyrate producers identified by 16S rRNA and BCoAT sequencing revealed a strong correlation between the two datasets ($r=0.73$).

Figure 18:
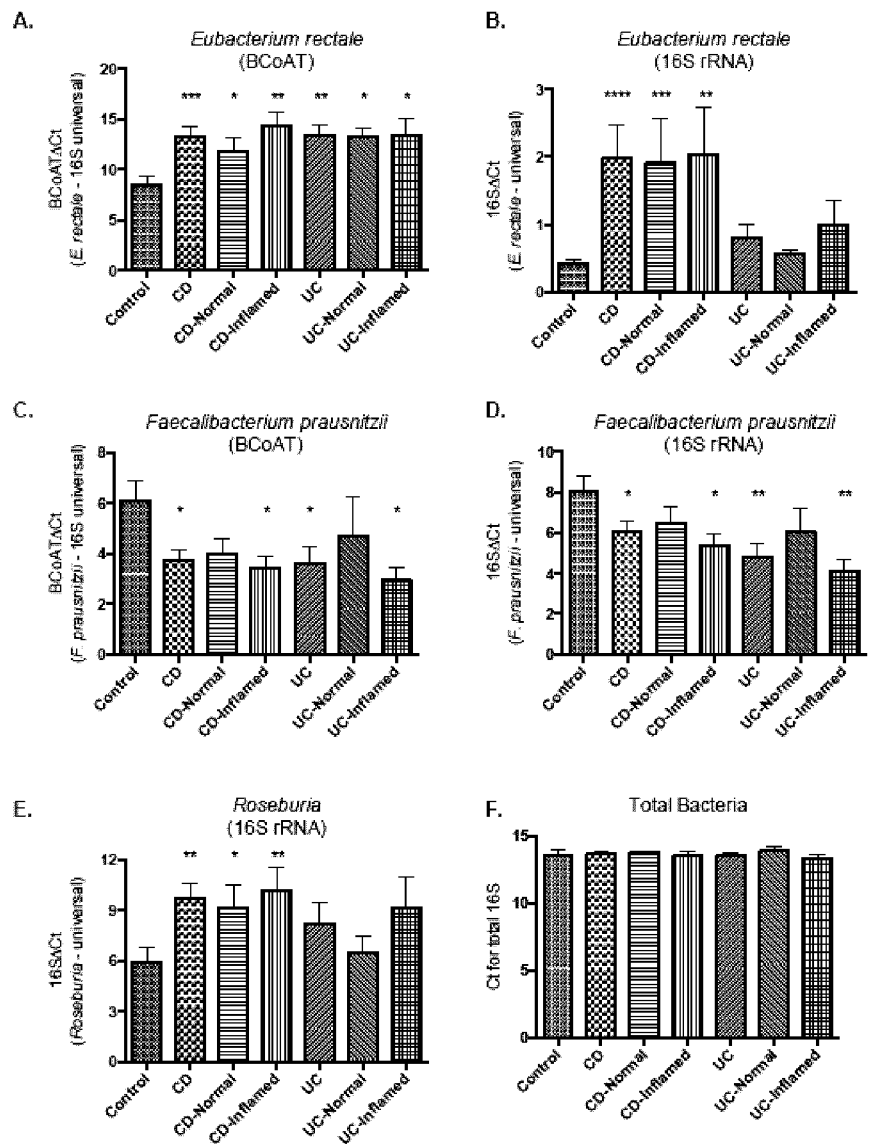
FIG. 18 A-F shows the quantitative PCR analysis of key butyrate producers. $Eubacterium\ rectale$ and $Faecalibacterium\ prausnitzii$ were quantified using BCoAT and 16S rRNA primers. $Roseburia$ was quantified using 16S rRNA primers. (A-E) represent the ΔCt of targeted butyrate producers relative to total bacteria 16S rRNA. (F) Ct for total bacteria 16S rRNA is similar between groups. Error bars represent the standard error of the mean. *, $P<0.05$; , $P<0.01$; *, $P<0.001$; ****, $P<0.0001$.

Relative Quantification of Key Butyrate Producers Revealed by qPCR:

BCoAT sequencing results were further validated using qPCR utilizing BCoAT and 16S rRNA specific primers. *Eubacterium rectale/Clostridium coccoides* group (XIVa), which is dominated by *E. rectale*, was reduced in both CD subtypes compared to controls. On the other hand, the UC group had similar levels of group XIVa compared to the controls (FIG. 18B). This finding in the UC group is not unexpected since *Clostridium* cluster XIVa harbors other major butyrate producers and non-butyrate producers, and an increase in other members of group XIVa could obscure the reduction of *E. rectale* in UC patients. Absence of species-specific, or even genus specific, primers to *E. rectale* 16S rRNA made it impossible to target this bacteria only using the 16S rRNA qPCR. When targeting the BCoAT gene of *E. rectale*, a clear reduction in all IBD subtypes compared to controls was observed ($P<0.02$; FIG. 18A). Nonetheless, BCoAT sequencing showed a decrease in *E. rectale* RA in UC patients with an inflamed colon only, and the reduction of *E. rectale* RA in UC patients with normal colon did not reach statistical significance (FIG. 16A). Although *F. prausnitzii* was high in CD with inflamed colons by sequencing, qPCR (using both BCoAT and 16S rRNA primers specific to *F. prausnitzii*) revealed that it is increased not only in CD but also in UC patients with an inflamed colon (FIGS. 18C and 18D). However, the slight difference in qPCR statistical significance compared to sequencing is due to higher sample numbers used in qPCR compared to sequencing. Finally, the reduction in *R. inulinivorans*, demonstrated by sequencing, was only validated at the genus level using 16S rRNA specific primers due to the lack of species-specific primers. qPCR shows that *Roseburia* is reduced in CD (both with normal and inflamed colon) (FIG. 8E), however, the statistical significance was higher in CD with inflamed colons (CD-normal, P<0.017; CD-inflamed, P<0.009). Taken together, the qPCR findings are in keeping with those of the BCoAT sequencing.

Figure 19:
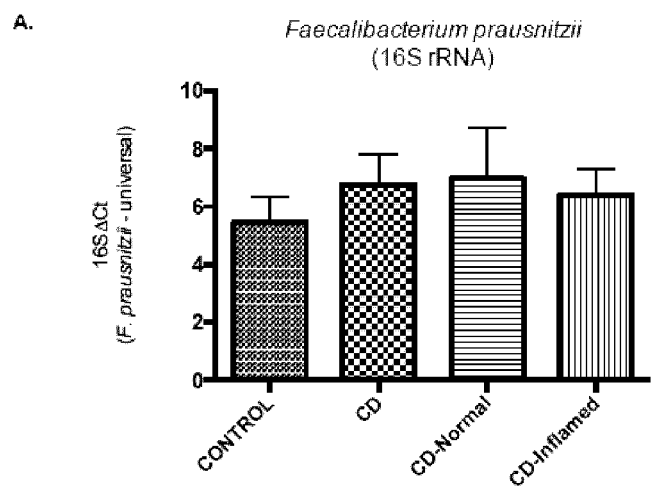
FIG. 19 A shows the quantitative PCR analysis of $Faecalibacterium\ prausnitzii$ from stool samples. $Faecalibacterium\ prausnitzii$ was quantified using 16S rRNA primers abd represents the ΔCt of $F.\ prausnitzii$ relative to total bacteria 16S rRNA.
Figure 19:
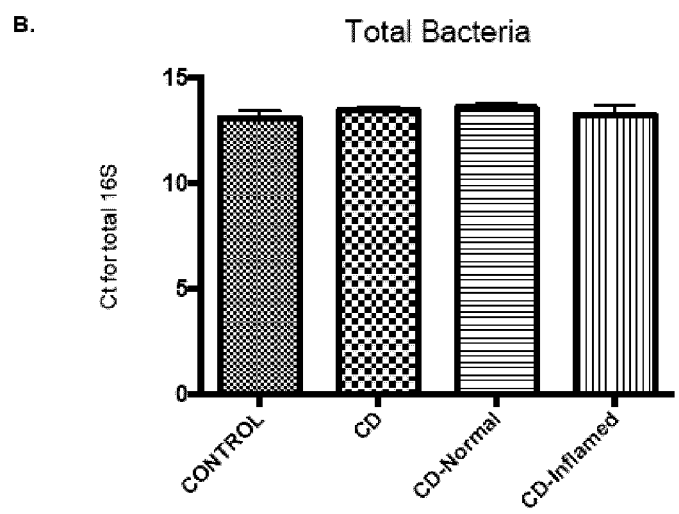

In order to investigate if sample type (stool versus mucosal aspirate) could affect the level of detected bacteria, stool collected from 5 control and 10 CD (6 with normal and 4 with inflamed colons, table S1) patients were subjected to qPCR using 16S rRNA specific primers to *F. prausnitzii*. Contrary to the mucosal aspirate finding, *F. prausnitzii* showed similar levels to the controls in both CD subtypes (FIG. 19).

REFERENCES

1 Cho, I. & Blaser, M. J. *Nature reviews. Genetics* 13, 260-270, doi:10.1038/nrg3182 (2012).

2 Manichanh, C., Borruel, N., Casellas, F. & Guarner, F. *Nature reviews. Gastroenterology & hepatology* 9, 599-608, doi:10.1038/nrgastro.2012.152 (2012).

3 Benchimol, E. I. et al. *Gut* 58, 1490-1497, doi:10.1136/gut.2009.188383 (2009).

4 Kostic, A. D. et al. *Cell host & microbe* 14, 207-215, doi:10.1016/j.chom.2013.07.007 (2013).

5 Rubinstein, M. R. et al. *Cell host & microbe* 14, 195-206, doi:10.1016/j.chom.2013.07.012 (2013).

6 Strauss, J. et al. *Inflammatory bowel diseases* 17, 1971-1978, doi:10.1002/ibd.21606 (2011).

7 Copeland, A. et al. *Standards in genomic sciences* 1, 166-173, doi:10.4056/sigs.29547 (2009).

8 Kazor, C. E. et al. *Journal of clinical microbiology* 41, 558-563 (2003).

9 Blachier, F. et al. *Amino acids* 39, 335-347, doi:10.1007/s00726-009-0445-2 (2010).

10 Linden, D. R. *Antioxidants & redox signaling*, doi: 10.1089/ars.2013.5312 (2013).

11 Segata, N. et al. Metagenomic biomarker discovery and explanation. *Genome biology* 12, R60, doi:10.1186/gb-2011-12-6-r60 (2011).

12 Karrasch, T., Kim, J. S., Muhlbauer, M., Magness, S. T. & Jobin, C. *Journal of immunology* 178, 6522-6532 (2007).

13 Kim, S. C., Tonkonogy, S. L., Karrasch, T., Jobin, C. & Sartor, R. B. *Inflammatory bowel diseases* 13, 1457-1466, doi: 10. 1002/ibd.20246 (2007).

14 Levine, J., Ellis, C. J., Furne, J. K., Springfield, J. & Levitt, M. D. *The American journal of gastroenterology* 93, 83-87, doi:10.1111/j.1572-0241.1998.083_c.x (1998).

15 Kaiserling, E. Newly-formed lymph nodes in the submucosa in chronic inflammatory bowel disease. *Lymphology* 34, 22-29 (2001).

16 Mackay, F. et al. Both the lymphotoxin and tumor necrosis factor pathways are involved in experimental murine models of colitis. *Gastroenterology* 115, 1464-1475 (1998).

17 Salvador, J. A., Figueiredo, S. A., Pinto, R. M. & Silvestre, S. M. *Future medicinal chemistry* 4, 1495-1523, doi:10.4155/fmc.12.95 (2012).

18 Rajilic-Stojanovic, M. *Clinical gastroenterology* 27, 5-16, doi:10.1016/j.bpg.2013.03.006 (2013).

19 Ramasamy, S., Singh, S., Taniere, P., Langman, M. J. & Eggo, M. C. *American journal of physiology. Gastrointestinal and liver physiology* 291, G288-296, doi:10.1152/ajpgi.00324.2005 (2006).

20 Bar, F. et al. *Gastroenterology* 145, 1055-1063 e1053, doi:10.1053/j.gastro.2013.07.015 (2013).

21 Miller, T. W. et al. *The Journal of biological chemistry* 287, 4211-4221, doi:10.1074/jbc.M 111.307819 (2012).

22 Smith, P. M. et al. *Science* 341, 569-573, doi:10.1126/science.1241165 (2013).

23 Caporaso, J. G. et al. *Nature methods* 7, 335-336, doi:10.1038/nmeth.f.303 (2010).

24 Sun, X., Threadgill, D. & Jobin, C. *Gastroenterology* 142, 86-95 e85, doi:10. 1053/j.gastro.2011.09.042 (2012).

25 Lippert, E. et al. *PloS one* 4, e7413, doi:10.1371/journal.pone.0007413 (2009).

26 Vital M, Penton C R, Wang Q, et al. 2013; 1:1.

27 Louis P, Flint HJ. Appl. Environ. Microbiol. 2007; 73:2009-2012. Available at: http://www.pubmedcentral.nih.gov/articlerender.fcgi?artid=1828812&tool=pmcentrez&rend ertype=abstract [Accessed Nov. 11, 2013].

28. Jimenez-Rivera C, Haas D, Boland M, et al. Gastroenterol Res Pr. 2009; 2009:1-4. Available at: http://www.pubmedcentral.nih.gov/articlerender.fcgi?artid=2796226&tool=pmcentrez&rendertype=abstract [Accessed Nov. 11, 2013].

29. Louis P, Flint H J. FEMS Microbiol. Lett. 2009; 294:1-8.

30. Duncan S H, Louis P, Thomson J M, et al. Environ. Microbiol. 2009; 11:2112-2122.

31. Bourne D G, Muirhead A, Sato Y. ISME J 2011; 5:559-564. Available at: http://www.pubmedcentral. nih.gov/articlerender.fcgi?artid=3105726&tool=pmcentrez&rend ertype=abstract [Accessed Nov. 11, 2013].

32. Cole J R, Wang Q, Cardenas E, et al. Nucleic Acids Res 2009; 37:D141-D145.

33. Caporaso J G, Kuczynski J, Stombaugh J, et al. Nat Methods 2010; 7:335-336.

34. Magoc T, Salzberg S L, Mago6 T. Bioinformatics 2011; 27:2957-2963. Available at: http://www.pubmedcentral.nih.gov/articlerender.fcgi?artid=3198573&tool=pmcentrez&rend ertype=abstract [Accessed Nov. 11, 2013].

35. Lee ZM-P, Bussema C, SchmidtT M rrnDB: Nucleic Acids Res 2009; 37:D489-93.

36. Letunic I, Bork P. Interactive Tree Of Life (iTOL): Bioinformatics 2007; 23:127-128. Available at: http://www.ncbi.nlm.nih.gov/pubmed/17050570 [Accessed Dec. 13, 2013].

What is claimed is:

1. A method for determining a severity of inflammatory bowel disease, Crohn's disease, or ulcerative colitis in a human subject, wherein the determining of the severity includes determining if there is an absence of inflammatory bowel disease, Crohn's disease, or ulcerative colitis, comprising:

measuring a level of *Atopobium parvulum* in a gut microbiota sample from the human subject using quantitative polymerase reaction, wherein the quantitative polymerase chain reaction uses a forward and reverse primer for targeting *A. parvulum* and wherein the forward primer is SEQ ID 1 and the reverse primer is SEQ ID 2, and comparing the measured level of *A. parvulum* to a predetermined level of *A. parvulum*, wherein the measured level of *A. parvulum* relative to the predetermined level is indicative of the severity of the disease.

2. A method for determining a severity of Crohn's disease, wherein a degree of inflammation is indicative of the severity of Crohn's disease, comprising: measuring a level of *Atopobium parvulum* in a gut microbiota sample from a human subject using quantitative polymerase chain reaction, wherein a level higher than a predetermined level of *A. parvulum* is indicative of moderate or severe inflammation, and wherein the quantitative polymerase chain reaction uses a forward and reverse primer for targeting *A. parvulum* and wherein the forward primer is SEQ ID 1 and the reverse primer is SEQ ID 2.

3. The method of claim 2 wherein the predetermined level is a level corresponding to mild inflammation.

4. The method of claim 2, wherein the predetermined level is an abundance of *A. parvulum* greater than about 0.005 relative abundance of total bacteria from the gut microbiota sample.

5. A method of treating inflammatory bowel disease in a patient comprising:

(1) performing an assay to determine the presence and severity of the inflammatory bowel disease of the patient, the assay comprising (i) measuring the level of *Atopobium parvulum* in a gut microbiota sample from the patient, wherein the measuring comprises using quantitative polymerase chain reaction, wherein the quantitative polymerase chain reaction uses a forward and reverse primer for targeting *A. parvulum*, and wherein the forward primer is SEQ ID 1 and the reverse primer is SEQ ID 2, and (ii) comparing the measured level of *A. parvulum* to a predetermined level of *A. parvulum* from gut microbiota samples of healthy human subjects, wherein the measured level of *A. parvulum* relative to the predetermined level is indicative of the presence and severity of the disease, and (2) administering to the patient a pharmaceutically effective amount of a compound selected from the group consisting of aminosalycylates, immunomodulators, anti-integrins, anti-cytokines, enteral feed programs, steroids, corticosteroids, antibiotics, anti-TNFa, and bismuth, or a combination thereof.

6. The method of claim 5, wherein bismuth is administered.

* * * * *